United States Patent [19]

Farge et al.

[11] 4,307,116
[45] Dec. 22, 1981

[54] 3-THIOVINYL-CEPHALOSPORINS

[75] Inventors: Daniel Farge, Thiais; Claude Moutonnier, Le Plessis Robinson; Pierre Le Roy, Thiais; Jean-François Peyronel, Palaisseau, all of France

[73] Assignee: Rhone-Poulenc Industries, Paris, France

[21] Appl. No.: 152,115

[22] Filed: May 21, 1980

[30] Foreign Application Priority Data

May 23, 1979 [FR] France ............ 79 13095
Nov. 9, 1979 [FR] France ............ 79 27687
Jan. 17, 1980 [FR] France ............ 80 00978
Feb. 12, 1980 [FR] France ............ 80 03057

[51] Int. Cl.³ ............... A61K 31/545; C07D 501/24
[52] U.S. Cl. ............... 424/246; 542/413; 544/27
[58] Field of Search ............ 424/246; 542/413; 544/27

[56] References Cited

U.S. PATENT DOCUMENTS

| | | | |
|---|---|---|---|
| 3,983,113 | 9/1976 | Beeby | 542/413 |
| 4,065,620 | 12/1977 | Webber | 424/246 |
| 4,098,888 | 7/1978 | Ochiai et al. | 424/246 |
| 4,166,115 | 8/1979 | Takaya et al. | 424/246 |
| 4,202,893 | 5/1980 | Heymes et al. | 424/246 |
| 4,264,595 | 4/1981 | Numata et al. | 424/246 |

*Primary Examiner*—Paul M. Coughlan, Jr.
*Attorney, Agent, or Firm*—Stevens, Davis, Miller & Mosher

[57] ABSTRACT

Novel cephalosporins of the general formula (I);

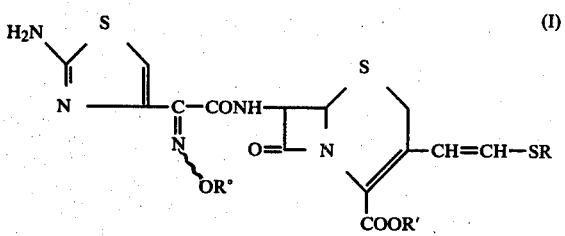

in which R is alkyl, L-2-amino-2-carboxy-ethyl, phenyl, pyridyl, pyridyl-N-oxide, pyrimidin-2-yl, substituted pyridazin-3-yl, 5,6-dioxo-1,4,5,6-tetrahydro-1,2,4-triazin-3-yl substituted in the 4-position, 1,3,4-triazol-5-yl or 2-alkoxycarbonyl-1,3,4-triazol-5-yl substituted in the 1-position, 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl, 2-alkyl-5,6-dioxo-1,2,5,6-tetrahydro-1,2,4-triazin-3-yl, triazol-5-yl, 1,3,4-thiadiazol-5-yl which is substituted or unsubstituted, 1,2,4-thiadiazol-5-yl which is substituted, 1,3,4-oxadiazol-5-yl which is substituted or unsubstituted, oxazol-2-yl which is substituted or unsubstituted or tetrazol-5-yl which is substituted or unsubstituted in the 1-position, R' is a hydrogen atom or a radical of the general formula (II);

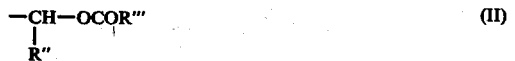

and R° is hydrogen, alkyl, vinyl or cyanomethyl, as well as their salts, are useful as anti-bacterial agents.

14 Claims, No Drawings

3-THIOVINYL-CEPHALOSPORINS

The present invention relates to novel 3-thiovinyl-cephalosporins of the general formula:

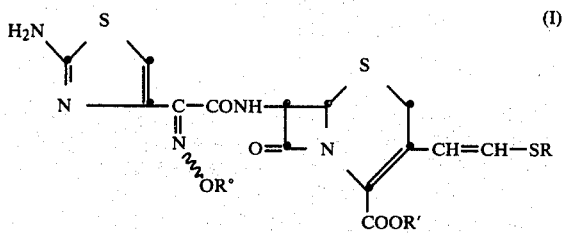

their salts, their preparation and the pharmaceutical compositions which contain these compounds.

In the general formula (I), the symbol R is chosen from amongst the following meanings:

(1) alkyl, L-2-amino-2-carboxy-ethyl and phenyl, (2) pyrid-2-yl, pyrid-3-yl or pyrid-4-yl and their N-oxides, (3) pyrimidin-2-yl; pyridazin-3-yl substituted in the 6-position (by an alkyl, methoxy, amino or acylamino radical), its N-oxide, and tetrazolo[4,5-b]pyridazin-6-yl, (4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl, in each case substituted in the 1-position (a) by an alkyl radical which is unsubstituted or substituted by an alkoxy, alkylthio, phenyl, formyl, carbamyl, alkylcarbamyl, dialkylcarbamyl, acyl, alkoxycarbonyl or thiazolidin-2-yl radical, (b) by an allyl, 2,3-dihydroxypropyl, 1,3-dihydroxyprop-2-yl, 2-formyl-2-hydroxy-ethyl, 3-formyloxy-2-hydroxypropyl, 2-3-bisformyloxypropyl or 1-3-bis-formyloxyprop-2-yl, (c) by an alkyl radical which contains 2 to 4 carbon atoms and is substituted by a hydroxyl, carbamyloxy, acyloxy (of which the acyl part can be substituted by an amino, alkylamino or dialkylamino radical), alkylsulphinyl, alkylsulphonyl, amino, alkylamino, dialkylamino, sulphoamino, alkylsulphonylamino, sulphamylamino, acylamino (of which the acyl part is optionally substituted by hydroxyl, amino, alkylamino or dialkylamino), alkoxycarbonylamino, ureido, alkylureido or dialkylureido radical, (d) by a radical corresponding to one of the general formulae:

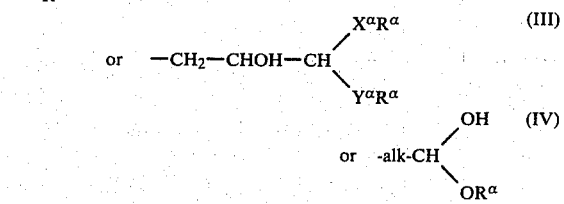

in which alk is an alkylene radical containing 1 to 4 carbon atoms, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) by an alkyl radical containing 1 to 5 carbon atoms, substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl, which is unsubstituted or substituted in the 3-position by alkoxycarbonyl, (7) a. 1,3,4-thiadiazol-5-yl which is unsubstituted or substituted by an alkyl, trifluoromethyl, alkoxy, alkylthio, hydroxyalkylthio, of which the alkyl part contains 2 to 4 carbon atoms, alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or b. 1,2,4-thiadiazol-5-yl substituted by an alkyl or alkoxy radical, (8) a. 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or b. oxazol-2-yl or 4-alkyl-oxazol-2-yl, or (9) tetrazol-5-yl which is unsubstituted or substituted in the 1-position by a. an alkyl radical which is unsubstituted or substituted by alkoxy, sulpho, carboxyl, formyl or sulphamyl, b. an alkyl radical which contains 2 to 4 carbon atoms and is substituted by hydroxyl, amino, alkylamino, dialkylamino, acylamino, carboxyalkylamino, sulphamylamino, sulphoamino, ureido, alkylureido or dialkylureido, c. an alkyl radical which contains 1 to 5 carbon atoms and is substituted by hydroxyimino or alkoxyimino, d. a phenyl, 2,3-dihydroxypropyl, 1,3-dihydroxyprop-2-yl, 2-formyl-2-hydroxy-ethyl, 3-formyloxy-2-hydroxy-propyl, 2-3-bisformyloxypropyl or 1-3-bisformyloxyprop-2-yl or e. a radical of the general formula (II), in which $R^\beta$ is a hydrogen atom or a radical of the general formula (III), the symbol $R^o$ represents a hydrogen atom or an alkyl, vinyl or cyanomethyl radical, and the symbol R' represents a hydrogen atom or an enzymatically easily removable radical of the general formula:

$$-\underset{\underset{R'''}{|}}{CH}-OCOR''' \qquad (V)$$

in which R'' represents a hydrogen atom or an alkyl radical and R''' represents an alkyl radical or the cyclohexyl radical.

It is to be understood that the alkyl or acyl portions or radicals mentioned above (or which will be mentioned later) are (unless stated to the contrary) straight or branched and contain 1 to 4 carbon atoms.

It is also to be understood that the substituent in the 3-position of the products of the general formula (I) can be in the cis- or trans-form or be a mixture of the cis- and trans-forms.

In the text which follows the trans-stereoisomerism will be referred to as E and the cis-stereoisomerism as Z.

Furthermore, it is to be understood that the group $OR^o$ can be in one of the syn- or anti-positions and that these isomers and their mixtures fall within the scope of the present invention.

The syn-form can be represented by the formula:

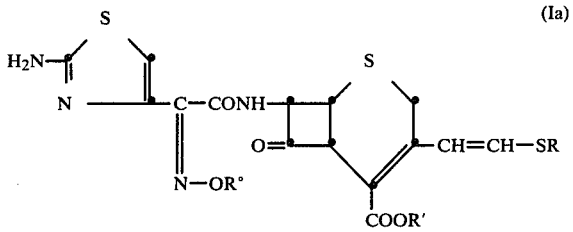
(Ia)

The anti-form can be represented by the formula:

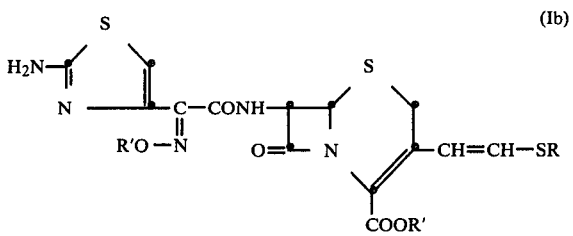
(Ib)

Equally, if the radical R contains a hydroxyiminoalkyl or alkoxyiminoalkyl substituent, this group can exhibit syn- and anti-isomerism, and these isomers and their mixtures also fall within the scope of the present invention.

If the radical R is a 1,4,5,6-tetrahydrotriazinyl radical substituted in the 1- or 4-position or a 1,2,5,6-tetrahydro-triazinyl radical substituted in the 2-position, it can be represented by the following tautomeric forms:

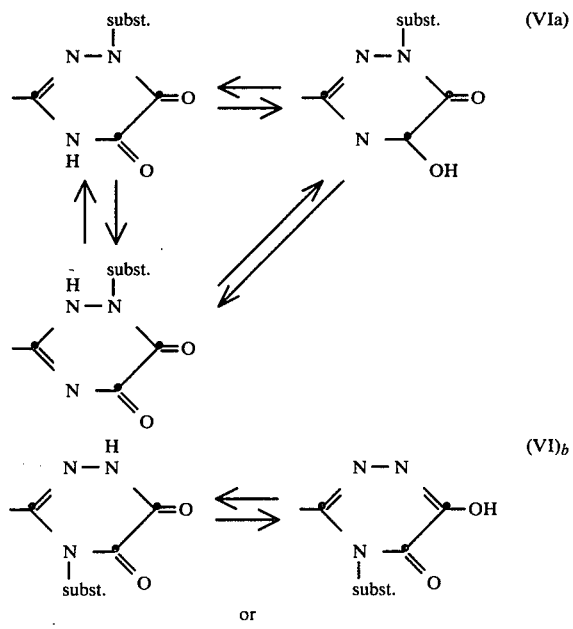
(VIa)

(VI)$_b$

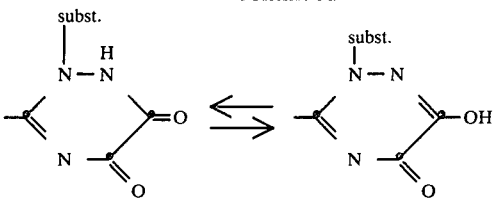
(VI)$_c$

If the radical R contains a formylalkyl substituent, it can be in its free aldehyde form or aldehyde hydrate form. In particular, these forms are encountered under the conditions described below.

Nuclear magnetic resonance studies show in particular that if R is 5,6-dioxo-4-formylmethyl-1,4,5,6-tetrahydro-1,2,4-triazin-3-yl, then:

in an acid solvent, such as (deuterated) formic or trifluoroacetic acid, in the presence or absence of (heavy) water, the product is principally in the free aldehyde form, in a basic solvent such as (heavy) water, to which sodium bicarbonate has been added, it is principally in the form of the aldehyde hydrate, and in a neutral solvent such as dimethylsulphoxide ($d_6$), the free aldehyde form and aldehyde hydrate form are present, and the addition of water results progressively in the conversion of the free aldehyde form to the aldehyde hydrate form.

In general, the products of the general formula (Ia) are preferred.

Amongst the meanings of the symbol R given above, there may in particular be mentioned methyl, ethyl, propyl, isopropyl, butyl, isobutyl, sec.-butyl and tert.-butyl, 1,3,4-thiadiazol-5-yl, 2-methyl-1,3,4-thiadiazol-5-yl, 2-ethyl, 1,3,4-thiadiazol-5-yl, 2-propyl-1,3,4-thiadiazol-5-yl, 2-isopropyl-1,3,4-thiadiazol-5-yl, 2-butyl-1,3,4-thiadiazol-5-yl, 2-isobutyl-1,3,4-thiadiazol-5-yl, 2-sec.-butyl-1,3,4-thiadiazol-5-yl, 2-t.-butyl-1,3,4-thiadiazol-5-yl, 2-hydroxymethyl-1,3,4-thiadiazol-5-yl, 2-(2-hydroxyethyl)-1,3,4-thiadiazol-5-yl, 2-aminomethyl-1,3,4-thiadiazol-5-yl, 2-methylaminomethyl-1,3,4-thiadiazol-5-yl, 2-dimethylaminomethyl-1,3,4-thiadiazol-5-yl, 2-(2-aminoethyl)-1,3,4-thiadiazol-5-yl, 2-(2-methylaminoethyl)-1,3,4-thiadiazol-5-yl, 2-(2-dimethylaminoethyl)-1,3,4-thiadiazol-5-yl, 2-carboxymethyl-1,3,4-thiadiazol-5-yl, 2-(2-carboxyethyl)-1,3,4-thiadiazol-5-yl, 2-methoxy-1,3,4-thiadiazol-5-yl, 2-methylthio-1,3,4-thiadiazol-5-yl, 2-methylthio-1,3,4-thiadiazol-5-yl, 2-methylsulphonyl-1,3,4-thiadiazol-5-yl, 2-amino-1,3,4-thiadiazol-5-yl, 2-methylamino-1,3,4-thiadiazol-5-yl, 2-dimethylamino-1,3,4-thiadiazol-5-yl, 2-acetylamino-1,3,4-thiadiazol-5-yl, 2-hydroxy-1,3,4-thiadiazol-5-yl, 2-acetamidomethyl-1,3,4-thiadiazol-5-yl, 2-(2-acetamidoethyl)-1,3,4-thiadiazol-5-yl, 3-methyl-1,2,4-thiadiazol-5-yl, 3-ethyl-1,2,4-thiadiazol-5-yl, 3-methoxy-1,2,4-thiadiazol-5-yl, 1,2,3-triazol-5-yl, 1,3,4-triazol-5-yl, 1-methyl-3-methoxycarbonyl-1,2,4-triazol-5-yl, 3-methoxycarbonyl-1-ethyl-1,2,4-triazol-5-yl, 1-methyl-3-ethoxycarbonyl-1,2,4-triazol-5-yl, 1-ethyl-3-ethoxycarbonyl-1,2,4-triazol-5-yl, 1H-tetrazol-5-yl, 1-methyl-tetrazol-5-yl, 1-ethyl-tetrazol-5-yl, 1-propyl-tetrazol-5-yl, 1-isopropyl-tetrazol-5-yl, 1-butyl-tetrazol-5-yl, 1-(2-hydroxyethyl)-tetrazol-5-yl, 1-(3-hydroxypropyl)-tetrazol-5-yl, 1-methoxymethyl-tetrazol-5-yl, 1-carboxymethyl-tetrazol-5-yl, 1-sulphomethyl-tetrazol-5-yl, 1-(2-methylaminoethyl)-tetrazol-5-yl, 1-(2-dimethylaminoethyl)-tetrazol-5-yl, 1-(2-diethylaminoethyl)-tetrazol-5-yl, 1-(3-dimethylaminopropyl)-tetrazol-5-yl, 1-(2-sulphamylaminoethyl)-tetrazol-5-yl, 1-(2-acetamidoethyl)-tetrazol-5-yl, pyrid-2-yl, pyrid-3-yl, pyrid-4-yl, pyrid-2-yl-1-oxide, 6-methyl-pyridazin-3-yl, 6-methyl-pyridazin-3-yl-1-oxide, 6-ethyl-pyridazin-3-yl, 6-ethyl-pyridazin-3-yl-1-oxide, 6-methoxy-pyridazin-3-yl, 6-amino-pyridazin-3-yl, 6-acetamido-pyridazin-3-yl, tetrazolo[4,5-b]pyridazin-6-yl, 5,6-dioxo-4-methyl-1,4,5,6-tetrahydro-1,2,4-triazin-3-yl, 5,6-dioxo-4-ethyl-1,4,5,6-tetrahydro-1,2,4-triazin-3-yl, 5,6-dioxo-4-propyl-1,4,5,6-tetrahydro-1,2,4-triazin-3-yl, 5,6-dioxo-4-isopropyl-1,4,5,6-tetrahydro-1,2,4-triazin-3-yl, 4-allyl-5,6-dioxo-1,4,5,6-tetrahydro-1,2,4-triazin-3-yl, 5,6-dioxo-4-(2-hydroxyethyl)-1,4,5,6-tetrahydro-1,2,4-triazin-3-yl, 5,6-dioxo-4-(3-hydroxypropyl)-1,4,5,6-tetrahydro-1,2,4-triazin-3-yl, 5,6-dioxo-4-methoxymethyl-1,4,5,6-tetrahydro-1,2,4-triazin-3-yl, 5,6-dioxo-4-(2-methoxyethyl)-1,4,5,6-tetrahydro-1,2,4-triazin-3-yl, 5,6-dioxo-4-ethoxymethyl-1,4,5,6-tetrahydro-1,2,4,-triazin-3-yl, 5,6-dioxo-4-(2-ethoxyethyl)-1,4,5,6-tetrahydro-1,2,4-triazin-3-yl, 4-(2-acetamidoethyl)-5,6-dioxo-1,4,5,6-tetrahydro-1,2,4-triazin-3-yl, 4-benzyl-5,6-dioxo-1,4,5,6-tetrahydro-1,2,4-triazin-3-yl, 5,6-dioxo-4-phenethyl-1,4,5,6-tetrahydro-1,2,4-triazin-3-yl, 5,6-dioxo-4-methylthiomethyl-1,4,5,6-tetrahydro-1,2,4-triazin-3-yl, 5,6-dioxo-4-methylthioethyl-1,4,5,6-tetrahydro-1,2,4-triazin-3-yl, 4-carbamylmethyl-5,6-dioxo-1,4,5,6-tetrahydro-1,2,4-triazin-3-yl, 4-(2-carbamylethyl)-5,6-dioxo-1,4,5,6-tetrahydro-1,2,4-triazin-3-yl, 4-(3-carbamylpropyl)-5,6-dioxo-1,4,5,6-tetrahydro-1,2,4-triazin-3-yl, 4-(2-carbamyloxyethyl)-5,6-dioxo-1,4,5,6-tetrahydro-1,2,4-triazin-3-yl, 4-(3-carbamyloxypropyl)-5,6-dioxo-1,4,5,6-tetrahydro-1,2,4-triazin-3-yl, 5,6-dioxo-4-methylsulphinylethyl-1,4,5,6-tetrahydro-1,2,4-triazin-3-yl, 5,6-dioxo-4-(2-formyloxyethyl)-1,4,5,6-tetrahydro-1,2,4-triazin-3-yl, 5,6-dioxo-4-(3-formyloxypropyl)-1,4,5,6-tetrahydro-1,2,4-triazin-3-yl, 4-(2-acetoxyethyl)-5,6-dioxo-1,4,5,6-tetrahydro-1,2,4-triazin-3-yl, 4-(3-acetoxypropyl)-5,6-dioxo-1,4,5,6-tetrahydro-1,2,4-triazin-3-yl, 5,6-dioxo-4-(2-glycyloxyethyl)-1,4,5,6-tetrahydro-1,2,4-triazin-3-yl, 5,6-dioxo-4-(3-glycyloxypropyl)-1,4,5,6-tetrahydro-1,2,4-triazin-3-yl, 5,6-dioxo-4-(2-propanyloxyethyl)-1,4,5,6-tetrahydro-1,2,4-triazin-3-yl, 4-(2,2-dimethoxyethyl)-5,6-dioxo-1,4,5,6-tetrahydro-1,2,4-triazin-3-yl, 4-(3,3-dimethoxypropyl)-5,6-dioxo-1,4,5,6-tetrahydro-1,2,4-triazin-3-yl, 4-(2,2-diethoxyethyl)-5,6-dioxo-1,4,5,6-tetrahydro-1,2,4-triazin-3-yl, 4-(3,3-diethoxypropyl)-5,6-dioxo-1,4,5,6-tetrahydro-1,2,4-triazin-3-yl, 4-(2,2-bis-methylthioethyl)-5,6-dioxo-1,4,5,6-tetrahydro-1,2,4-triazin-3-yl, 4-(3,3-bis-methylthiopropyl)-5,6-dioxo-1,4,5,6-tetrahydro-1,2,4-triazin-3-yl, 4-(2,2-bis-ethylthioethyl)-5,6-dioxo-1,4,5,6-tetrahydro-1,2,4-triazin-3-yl, 4-(3,3-bis-ethylthiopropyl)-5,6-dioxo-1,4,5,6-tetrahydro-1,2,4-triazin-3-yl, 5,6-dioxo-4-(1,3-dioxolan-2-yl)-methyl-1,4,5,6-tetrahydro-1,2,4,-triazin-3-yl, 5,6-dioxo-4-[2-(1,3-dioxolan-2-yl)-ethyl]-1,4,5,6-tetrahydro-1,2,4-triazin-3-yl, 5,6-dioxo-4-(1,3-dithiolan-2-yl)-methyl-1,4,5,6-tetrahydro-1,2,4-triazin-3-yl, 5,6-dioxo-4-[2-(1,3-dithiolan-2-yl)-ethyl]-1,4,5,6-tetrahydro-1,2,4-triazin-3-yl, 5,6-dioxo-4-(1,3-oxathiolan-2-yl)-methyl-1,4,5,6-tetrahydro-1,2,4-triazin-3-yl, 5,6-dioxo-4-[2-(1,3-oxathiolan-2-yl)-ethyl]-1,4,5,6-tetrahydro-1,2,4-triazin-3-yl, 5,6-dioxo-4-(1,3-dioxan-2-yl)-methyl-1,4,5,6-tetrahydro-1,2,4-triazin-3-yl, 5,6-dioxo-4-[2-(1,3-dioxan-2-yl)-ethyl]-1,4,5,6-tetrahydro-1,2,4-triazin-3-yl, 5,6-dioxo-4-(1,3-dithian-2-yl)-methyl-1,4,5,6-tetrahydro-1,2,4-triazin-3-yl, 5,6-dioxo-4-[2-(1,3-dithian-2-yl)-ethyl]-1,4,5,6-tetrahydro-1,2,4-triazin-3-yl, pyrimidin-2-yl, 5,6-dioxo-4-methylcarbamyl-methyl-1,4,5,6-tetrahydro-1,2,4-triazin-3-yl, 5,6-dioxo-4-(2-methylcarbamylethyl)-1,4,5,6-tetrahydro-1,2,4-triazin-3-yl, 5,6-dioxo-4-ethylcarbamylmethyl-1,4,5,6-tetrahydro-1,2,4-triazin-3-yl, 4-dimethylcarbamylmethyl-5,6-dioxo-1,4,5,6-tetrahydro-1,2,4-triazin-3-yl, 4-(2-dimethylcarbamylethyl)-5,6-dioxo-1,4,5,6-tetrahydro-1,2,4-triazin-3-yl, 4-diethylcarbamylmethyl-5,6-dioxo-1,4,5,6-tetrahydro-1,2,4-triazin-3-yl, 4-acetonyl-5,6-dioxo-1,4,5,6-tetrahydro-1,2,4-triazin-3-yl, 5,6-dioxo-4-(2-oxo-butyl)-1,4,5,6-tetrahydro-1,2,4-triazin-3-yl, 5,6-dioxo-4-(3-oxobutyl)-1,4,5,6-tetrahydro-1,2,4-triazin-3-yl, 5,6-dioxo-4-(methoxycarbonylmethyl)-1,4,5,6-tetrahydro-1,2,4-triazin-3-yl, 5,6-dioxo-4-(2-methoxycarbonylethyl)-1,4,5,6-tetrahydro-1,2,4-triazin-3-yl, 5,6-dioxo-4-ethoxycarbonylmethyl)-1,4,5,6-tetrahydro-1,2,4-triazin-3-yl, 5,6-dioxo-1,4,5,6-tetrahydro-4-(thiazolidin-2-yl)-methyl-1,2,4-triazin-3-yl, 4-(2,3-dihydroxypropyl)-5,6-dioxo-1,4,5,6-tetrahydro-1,2,4-triazin-3-yl, 4-(1,3-dihydroxyprop-2-yl)-5,6-dioxo-1,4,5,6-tetrahydro-1,2,4-triazin-3-yl, 5,6-dioxo-4-(2-formyl-2-hydroxyethyl)-1,4,5,6-tetrahydro-1,2,4-triazin-3-yl, 4-(2-aminoethyl)-5,6-dioxo-1,4,5,6-tetrahydro-1,2,4-triazin-3-yl, 4-(3-aminopropyl)-5,6-dioxo-1,4,5,6-tetrahydro-1,2,4-triazin-3-yl, 5,6-dioxo-4-(2-methylaminoethyl)-1,4,5,6-tetrahydro-1,2,4-triazin-3-yl, 5,6-dioxo-4-(3-methylaminopropyl)-1,4,5,6-tetrahydro-1,2,4-triazin-3-yl, 5,6-dioxo-4-(2-ethylaminoethyl)-1,4,5,6-tetrahydro-1,2,4-triazin-3-yl, 5,6-dioxo-4-(3-ethylaminopropyl)-1,4,5,6-tetrahydro-1,2,4-triazin-3-yl, 4-(2-dimethylaminoethyl)-5,6-dioxo-1,4,5,6-tetrahydro-1,2,4-triazin-3-yl, 4-(3-dimethylaminopropyl)-5,6-dioxo-1,4,5,6-tetrahydro-1,2,4-triazin-3-yl, 4-(2-diethylaminoethyl)-5,6-dioxo-1,4,5,6-tetrahydro-1,2,4-triazin-3-yl, 4-(3-diethylaminopropyl)-5,6-dioxo-1,4,5,6-tetrahydro-1,2,4-triazin-3-yl, 5,6-dioxo-4-(2-sulphoaminoethyl)-1,4,5,6-tetrahydro-1,2,4-triazin-3-yl, 5,6-dioxo-4-(2-methylsulphonylaminoethyl)-1,4,5,6-tetrahydro-1,2,4-triazin-3-yl, 5,6-dioxo-4-(3-methylsulphonylaminopropyl)-1,4,5,6-tetrahydro-1,2,4-triazin-3-yl, 5,6-dioxo-4-(2-sulphamylaminoethyl)-1,4,5,6-tetrahydro-1,2,4-triazin-3-yl, 5,6-dioxo-4-(3-sulphamylaminopropyl)-1,4,5,6-tetrahydro-1,2,4-triazin-3-yl, 5,6-dioxo-4-(2-glycolylaminoethyl)-1,4,5,6-tetrahydro-1,2,4-triazin-3-yl, 5,6-dioxo-4-[2-(2-hydroxypropionamido)-ethyl]-1,4,5,6-tetrahydro-1,2,4-triazin-3-yl, 5,6-dioxo-4-(2-glycylaminoethyl)-1,4,5,6-tetrahydro-1,2,4-triazin-3-yl, 4-[2-(L)-alanylaminoethyl]-5,6-dioxo-1,4,5,6-tetrahydro-1,2,4-triazin-3-yl, 5,6-dioxo-4-(3-glycylaminopropyl)-1,4,5,6-tetrahydro-1,2,4-triazin-3-yl, 5,6-dioxo-4-(2-methylaminoacetamidoethyl)-1,4,5,6-tetrahydro-1,2,4-triazin-3-yl, 4-(2-dimethylaminoacetamidoethyl)-5,6-dioxo-1,4,5,6-tetrahydro-1,2,4-triazin-3-yl, 4-(2-diethylaminoacetamidoethyl)-5,6-dioxo-1,4,5,6-tetrahydro-1,2,4-triazin-3-yl, 5,6-dioxo-4-(2-methoxycarbonylaminoethyl)-1,4,5,6-tetrahydro-1,2,4-triazin-3-yl, 5,6-dioxo-4-(2-ethoxycarbonylaminoethyl)-1,4,5,6-tetrahydro-1,2,4-triazin-3-yl, 5,6-dioxo-1,4,5,6-tetrahydro-4-(2-ureidoethyl)-1,2,4-triazin-3-yl, 5,6-dioxo-1,4,5,6-tetrahydro-4-(3-ureidopropyl)-1,2,4-triazin-3-yl, 5,6-dioxo-4-[2-(3-methylureido)-ethyl]-1,4,5,6-tetrahydro-1,2,4-triazin-3-yl, 5,6-dioxo-4-[3-(3-methylureido)-propyl]-1,4,5,6-tetrahydro-1,2,4-triazin-3-yl, 5,6-dioxo-4-[2-(3-ethylureido)-ethyl]-1,4,5,6-tetrahydro-1,2,4-triazin-3-yl, 4-[2-(3,3-dimethylureido)-ethyl]-5,6-dioxo-1,4,5,6-tetrahydro-1,2,4-triazin-3-yl, 4-[3-(3,3-dimethylureido)-propyl]-5,6-dioxo-1,4,5,6-tetrahydro-1,2,4-triazin-3-yl, 4-[2-(3,3-dimethylureido)-ethyl]-5,6-dioxo- 1,4,5,6-tetrahydro-1,2,4-triazin-3-yl, 4-(2,2-dimethoxypropyl)-5,6-dioxo-1,4,5,6-tetrahydro-1,2,4-triazin-3-yl, 4-(3,3-dimethoxy-2-hydroxypropyl)-5,6-dioxo-1,4,5,6-tetrahydro-1,2,4-triazin-3-yl, 5,6-dioxo-4-[3-(dioxolan-2-yl)-2-hydroxypropyl]-1,4,5,6-tetrahydro-1,2,4-triazin-3-yl, 5,6-dioxo-4-(2-hydroxy-2-methoxyethyl)-1,4,5,6-tetrahydro-1,2,4-triazin-3-yl, 5,6-dioxo-4-(3-hydroxy-3-methoxypropyl)-1,4,5,6-tetrahydro-1,2,4-triazin-3-yl, 5,6-dioxo-4-(2-ethoxy-2-hydroxyethyl)-1,4,5,6-tetrahydro-1,2,4-triazin-3-yl, 5,6-dioxo-4-(3-ethoxy-3-hydroxypropyl)-1,4,5,6-tetrahydro-1,2,4-triazin-3-yl, 5,6-dioxo-4-(2-hydroxy-2-propoxyethyl)-1,4,5,6-tetrahydro-1,2,4-triazin-3-yl, 5,6-dioxo-4-(2-hydroxyiminoethyl)-1,4,5,6-tetrahydro-1,2,4-triazin-3-yl, 5,6-dioxo-4-(2-hydroxyimino-propyl)-1,4,5,6-tetrahydro-1,2,4-triazin-3-yl, 5,6-dioxo-4-(2-methoxyiminoethyl)-1,4,5,6-tetrahydro-1,2,4-triazin-3-yl, 5,6-dioxo-4-(3-methoxyiminopropyl)-1,4,5,6-tetrahydro-1,2,4-triazin-3-yl, 5,6-dioxo-4-(2-ethoxyiminoethyl)-1,4,5,6-tetrahydro-1,2,4-triazin-3-yl, 1-(formylmethyl)-1,3,4-triazol-5-yl, 1-(2-formylethyl)-1,3,4-triazol-5-yl, 1-carbamylmethyl-1,3,4-triazol-5-yl, 1-(2-hydroxyethyl)-1,3,4-triazol-5-yl, 1-(2-carbamyloxyethyl)-1,3,4-triazol-5-yl, 1-(2-glycyloxyethyl)-1,3,4-triazol-5-yl, 1-(2-acetamidoethyl)-1,3,4-triazol-5-yl, 1-(2,2-dimethoxyethyl)-1,3,4-triazol-5-yl, 1-methylcarbamylmethyl-1,3,4-triazol-5-yl, 1-dimethylcarbamylmethyl-1,3,4-triazol-5-yl, 1-(2-dimethylcarbamylmethyl)-1,3,4-triazol-5-yl, 1-acetonyl-1,3,4-triazol-5-yl, 1-(thiazolidin-2-yl-methyl)-1,3,4-triazol-5yl, 1-(2,3-dihydroxypropyl)-1,3,4-triazol-5-yl, 1-(1,3-dihydroxy-2-propyl)-1,3,4-triazol-5-yl, 1-(2-formyl-2-hydroxyethyl)-1,3,4-triazol-5-yl, 1-(2-aminoethyl)-1,3,4-triazol-5-yl, 1-(2-methylaminoethyl)-1,3,4-triazol-5-yl, 1-(2-dimethylaminoethyl)-1,3,4-triazol-5-yl, 1-(2-methylsulphonylaminoethyl)-1,3,4-triazol-5-yl, 1-(2-sulphamylaminoethyl)-1,3,4-triazol-5-yl, 1-(2-glycolylaminoethyl)-1,3,4-triazol-5-yl, 1-(2-glycylaminoethyl)-1,3,4-triazol-5-yl, 1-(2-methoxycarbonylaminoethyl)-1,3,4-triazol-5-yl, 1-(2-ureidoethyl)-1,3,4-triazol-5-yl, 1-[2-(3-methylureido)-ethyl]-1,3,4-triazol-5-yl, 1-[2-(3,3-dimethylureido)-ethyl]-1,3,4-triazol-5-yl, 1-(3,3-dimethoxy-2-hydroxypropyl)-1,3,4-triazol-5-yl, 1-(2-hydroxy-2-methoxyethyl)-1,3,4-triazol-5-yl, 1-(2-hydroxyiminoethyl)-1,3,4-triazol-5-yl, 1-(2-methoxy-iminoethyl)-1,3,4-triazol-5-yl, 1-formylmethyl-2-methoxycarbonyl-1,3,4-triazol-5-yl, 2-ethoxycarbonyl-1-formylmethyl-1,3,4-triazol-5-yl, 1-(2-formylethyl)-2-methoxycarbonyl-1,3,4-triazol-5-yl, 1-(2-hydroxyethyl)-2-methoxycarbonyl-1,3,4-triazol-5-yl, 1-carbamylmethyl-2-methoxycarbonyl-1,3,4-triazol-5-yl, 1-(2-carbamylethyl)-2-methoxycarbonyl-1,3,4-triazol-5-yl, 1-(2-acet-amidoethyl)-2-methoxycarbonyl-1,3,4-triazol-5-yl, 1-(2,2-dimethoxyethyl)-2-methoxycarbonyl-1,3,4-triazol-5-yl, 1-(dimethylcarbamylmethyl)-2-methoxycarbonyl-1,3,4-triazol-5-yl, 1-acetonyl-2-methoxycarbonyl-1,3,4-triazol-5-yl, 1-(2,3-dihydroxypropyl)-2-methoxycarbonyl-1,3,4-triazol-5-yl, 1-(1,3-dihydroxyprop-2-yl)-2-methoxycarbonyl-1,3,4-triazol-5-yl, 1-(3-formyl-2-hydroxyethyl)-2-methoxycarbonyl-1,3,4-triazol-5-yl, 1-(2-dimethylaminoethyl)-2-methoxycarbonyl-1,3,4-triazol-5-yl, 2-methoxycarbonyl-1-(2-methylsulphonylaminoethyl)-1,3,4-triazol-5-yl, 2-methoxycarbonyl-1-(2-sulphamylaminoethyl)-1,3,4-triazol-5-yl, 2-methoxycarbonyl-1-(2-methoxycarbonylaminoethyl)-1,3,4-triazol-5-yl, 2-methoxycarbonyl-1-(2-ureidoethyl)-1,3,4-triazol-5-yl, 2-methoxycarbonyl-1-[2 -(3-methylureido)-ethyl]-1,3,4-triazol-5-yl, 1-[2-(3,3-dimethylureido)-ethyl]-2-methoxycarbonyl-1,3,4-triazol-5-yl, 1-(3,3-dimethoxy-2-hydroxypropyl)-2-methoxycarbonyl-1,3,4-triazol-5-yl, 1-(2-hydroxy-2-methoxyethyl)-2-methoxycarbonyl-1,3,4-triazol-5-yl, 1,4-dimethyl-5,6-dioxo-1,4,5,6-tetrahydro-1,2,4-triazol-3-yl, 1,4-diethyl-5,6-dioxo-1,4,5,6-tetrahydro-1,2,4-triazin-3-yl, 1-ethyl-4-methyl-5,6-dioxo-1,4,5,6-tetrahydro-1,2,4-triazin-3-yl, 4-ethyl-1-methyl-5,6-dioxo-1,4,5,6-tetrahydro-1,2,4-triazin-3-yl, 1-methyl-5,6-dioxo-1,4,5,6-tetrahydro-1,2,4-triazin-3-yl, 1-ethyl-5,6-dioxo-1,4,5,6-tetrahydro-1,2,4-triazin-3-yl, 2-methyl-5,6-dioxo-1,2,5,6-tetrahydro-1,2,4-triazin-3-yl, 2-ethyl-5,6-dioxo-1,4,5,6-tetrahydro-1,2,4-triazin-3-yl, 1-methyl-1,2,4-triazol-5-yl, 2-(2-hydroxyethylthio)-1,3,4-thiadiazol-5-yl, 1,3,4-oxadiazol-5-yl, 2-methyl-1,3,4-oxadiazol-5-yl, 2-phenyl-1,3,4-oxoadiazol-5-yl, 2-aminomethyl-1,3,4-oxadiazol-5-yl, 2-acetamidomethyl-1,3,4-oxadiazol-5-yl, 2-dimethylaminomethyl-1,3,4-oxadiazol-5-yl, oxazol-2-yl, 4-methyloxazol-2-yl, 1-formylmethyl-tetrazol-5-yl, 1-(2-formylethyl)-tetrazol-5-yl, 1-sulphamylmethyl-tetrazol-5-yl 1-(2-carboxymethyl-aminoethyl)-tetrazol-5-yl, 1-(2-sulphoaminoethyl)-tetrazol-5-yl, 1-(2-ureidoethyl)-tetrazol-5-yl, 1-[2-(3-methylureido)-ethyl]-tetrazol-5-yl, 1-[2-(3,3-dimethylureido)-ethyl]-tetrazol-5-yl, 1-(2-hydroxyiminoethyl)tetrazol-5-yl, 1-(3-hydroxyiminopropyl)-tetrazol-5-yl, 1-(2-methoxyiminoethyl)-tetrazol-5-yl, 1-(3-methoxyiminopropyl)-tetrazol-5-yl, 1-(2,3-dihydroxypropyl)-tetrazol-5-yl, 1-(1,3-dihydroxyprop-2-yl)-tetrazol-5-yl, 1-(2-formyl-2-hydroxyethyl)-tetrazol-5-yl, 1-(2,2-dimethoxyethyl)-tetrazol-5-yl, 1-(3,3-dimethoxypropyl)-tetrazol-5-yl, 1-(2-hydroxy-2-methoxyethyl)-tetrazol-5-yl, 1-(2-ethoxy-2-hydroxyethyl)-tetrazol-5-yl, 2-hydroxy-1-(2-propoxyethyl)-tetrazol-5-yl, 1-(3-hydroxy-3-methoxypropyl)-tetrazol-5-yl, 1-(3-ethoxy-3-hydroxypropyl)-tetrazol-5-yl and 1-(dioxolan-2-ylethyl)-tetrazol-5-yl.

Amongst the meanings of the symbol R° above, there may especially be mentioned hydrogen, methyl, ethyl, propyl, isopropyl, butyl, isobutyl, sec.-butyl, vinyl and cyanomethyl.

Amongst the meanings of the symbol R' above, there may especially be mentioned hydrogen, pivalyloxymethyl and acetoxymethyl.

A. According to the invention, the products of the general formula (I) in which R has a meaning other than a triazinyl or triazolyl radical substituted by a group of the general formula (IV) can be prepared by the action of an acid of the general formula:

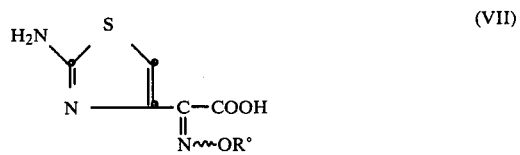

in which R° is defined as above, and in which the amine group has been protected beforehand (as has the oxime if R° represents hydrogen), or of a reactive derivative of this acid, on a 7-amino-cephalosporin of the general formula:

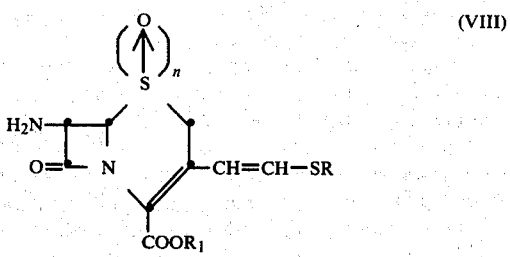

(VIII)

in which R is defined as above, except for the meanings of a triazolyl or triazinyl radical substituted by a group of the general formula (IV), $R_1$ represents a hydrogen atom, a radical of the general formula (V) or an easily removable protective radical, for example methoxymethyl, tert.-butyl, benzhydryl, p-nitrobenzyl or p-methoxybenzyl, and n represents 0 or 1, followed by reduction of the sulphoxide obtained if n=1, and then followed by removal of the protective radicals.

It is to be understood that the acid of the general formula (VII), in the syn- or anti-form, or mixtures thereof, respectively leads to the products of the general formula (I) in the syn- or anti-form, or mixtures thereof.

(a) If the product of the general formula (VII) is used in the acid form, its amino group is protected by any method which is in itself known for blocking an amino group without affecting the remainder of the molecule. It is necessary to use an easily removable group such as the t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxy-benzyloxycarbonyl, formyl or trifluoroacetyl group.

If $R^o$ represents a hydrogen atom, the oxime can be protected by any method which is known and which does not adversely affect the remainder of the molecule. In particular, a trityl, tetrahydropyranyl or 2-methoxy-prop-2-yl group is used.

In general, the condensation of the product of the general formula (VII), of which the acid group is free and of which the amine group has beforehand been protected, with the 7-amino-cephalosporin of the general formula (VIII), in which R and n are defined as above, and $R_1$ represents a radical of the general formula (V) or an easily removable protective radical such as methoxymethyl, tert.-butyl, benzhydryl, p-nitrobenzyl or p-methoxybenzyl, is carried out in an organic solvent such as dimethylformamide, acetonitrile, tetrahydrofurane, methylene chloride or chloroform, in the presence of a condensation agent such as a carbodiimide (for example dicyclohexylcarbodiimide), N,N'-carbonyldiimidazole or 2-ethoxy-1-ethoxycarbonyl-1,2-dihydroquinoline, at a temperature of between 31 20° and 40° C., after which the oxide obtained is reduced if a 7-amino-cephalosporin of the general formula (VIII), in which n=1, has been used, and the protective groups are removed from the amine group and, where necessary, from the acid group and the oxime group.

It is to be understood that the amino, alkylamino, carboxyl and hydroxyl groups which are present in certain radicals R are (or can be) protected by any protective groups which are usually employed for protecting amines, carboxylic acids or alcohols, and whose use does not adversely affect the remainder of the molecule.

By way of examples, the amino and alkylamino groups are protected by radicals such as tert.-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, formyl or trifluoroacetyl, the carboxyl groups can be protected by radicals such as methoxymethyl, tert.-butyl, benzhydryl, p-nitrobenzyl or p-methoxybenzyl, and the hydroxyl groups can be protected by radicals such as trityl, tetrahydropyranyl or 2-methoxy-prop-2-yl, or can be protected in the form of a 2,2-dimethyldioxolan-4-yl-methyl or 2,2-dimethyl-dioxolan-5-yl radical, if the protection of 2,3-dihydroxypropyl or 1,3-dihydroxyprop-2-yl radicals is involved.

It is also to be understood that if, in the general formula (VIII), the radical R contains a hydroxyl, sulpho, sulphinyl or sulphonyl group, it is preferable to employ a product in whose formula n=0.

If it is desired to obtain a product of the general formula (I) in which R contains a formylalkyl or acylalkyl radical, this radical can optionally be protected, as the acetal, in the form of a radical of the general formula (II) or (III) as defined above.

The removal of the protective radical from R is effected after the reduction of the oxide, before, simultaneously with, or after the removal of the other protective radicals.

The reduction of the S-oxide is effected, for example, under the conditions described in German Patent Application No. 2,637,176. The various protective radicals can be removed simultaneously or successively.

By way of example,

1. The removal of the protective groups of amines is effected as follows:

in the case of a tert.-butoxycarbonyl, trityl, p-methoxybenzyloxycarbonyl or formyl radical, by treatment in an acid medium. Preferably, trifluoroacetic acid is used and the process is carried out at a temperature of between 0° and 20° C., or anhydrous or aqueous formic acid, or para-toluenesulphonic or methanesulphonic acid, is used in acetone or acetonitrile at a temperature of between 20° C. and the reflux temperature of the reaction mixture. Under these conditions, the product of the general formula (I) can be obtained in the form of the trifluoroacetate, the solvate with formic acid, the methanesulphonate or the para-toluenesulphonate, and from these the amine group can be liberated by any method which is in itself known for obtaining an amine from one of its salts without affecting the remainder of the molecule. In particular, the process is carried out by bringing the compound into contact with an ion exchange resin or by the action of an organic base.

In the case of a 2,2,2-trichloro-ethoxycarbonyl or p-nitrobenzyloxycarbonyl radical, by reduction (especially by treatment with zinc in acetic acid).

In the case of a chloroacetyl or trichloroacetyl radical, by applying the method described in the French Patent published under French Pat. No. 2,243,199.

In the case of a benzyl, dibenzyl or benzyloxycarbonyl radical, by catalytic hydrogenation.

In the case of a trifluoroacetyl radical, by treatment in a basic medium.

2. The removal of the protective groups from the carboxyl radical is effected as follows:

in the case of a tert.-butyl, p-methoxybenzyl or benzhydryl radical, by treatment in an acid medium, under the conditions described above for the removal of the protective trityl radical from an amino group. In the case of the benzhydryl radical, the process can be carried out in the presence of anisole.

In the case of a methoxymethyl group, by treatment in a dilute acid medium.

In the case of a p-nitrobenzyl group, by reduction (especially by treatment with zinc in acetic acid, or by hydrogenolysis).

3. The removal of the protective groups from the oxime and/or the hydroxyl radicals is effected as follows:

in the case of a trityl or tetrahydropyranyl group, or of the 2,2-dimethyl-dioxolan-4-yl-methyl or 2,2-dimethyl-dioxan-5-yl radicals, by acidolysis, for example with trifluoroacetic acid, aqueous or non-aqueous formic acid or para-toluenesulphonic acid.

When aqueous or non-aqueous formic acid is used, the cleaving of cyclic acetal protecting hydroxy radicals may yield, at least partially, the corresponding mono or diesters; these latter can be separated, where necessary, by chromatography.

In the case of the 2-methoxy-prop-2-yl group, in accordance with the method described in Belgian Pat. No. 875,379.

4. The removal of the groups of the general formula (II) or (III) (if it is desired to obtain a product of the general formula (I) in which R contains a formylalkyl or acylalkyl radical) is effected:

in the presence of sulphonic acid (for example methanesulphonic acid or p-toluenesulphonic acid) in an organic solvent (for example acetonitrile or acetone), optionally in the presence of water and optionally in the presence of an acetalisable reactant such as acetone, glyoxylic acid, benzaldehyde or pyruvic acid, at a temperature of between 20° C. and the reflux temperature of the reaction mixture, or, if the radical R is a 5,6-dioxo-1,4,5,6-tetrahydrol,2,4-triazin-3-yl radical, by the action of aqueous formic acid (preferably containing less than 10% of water), in the presence or absence of silica, or by transacetalisation in the presence of an acetalisable reactant as defined above.

(b) If a derivative of the acid of the general formula (VII) is used, it is possible to employ the anhydride, a mixed anhydride or a reactive ester of the general formula:

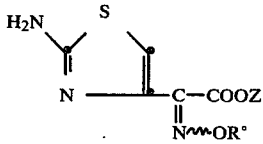
(IX)

in which R° is defined as above and Z represents a succinimido, benzotriazol-1-yl, 4-nitrophenyl, 2,4-dinitrophenyl, pentachlorophenyl or phthalimido radical, the amine group of such derivatives having been protected beforehand (for example as described in a).

It is also possible to employ reactive derivatives such as a thiolo-ester of the general formula (XIV), defined later, or an acid halide. In this latter case it is possible, for example, to react the hydrochloride of the acid chloride with the 7-amino-cephalosporin of the general formula (VIII).

If the anhydride, a mixed anhydride or an acid halide (which derivatives can be prepared in situ) are employed, the condensation is carried out in an inert organic solvent such as ether (for example tetrahydrofurane or dioxane), a chlorinated solvent (for example chloroform or methylene chloride), an amide (for example dimethylformamide or dimethylacetamide) or a ketone (for example acetone), or in mixtures of the above solvents, in the presence of an acid acceptor such as an epoxide (for example propylene oxide) or such as a nitrogen-containing organic base such as pyridine, dimethylaminopyridine, N-methylmorpholine or a trialkylamine (for example triethylamine), or in an aqueous organic medium in the presence of an alkaline condensation agent such as sodium bicarbonate, and the process is carried out at a temperature of between $-40°$ and $+40°$ C., after which, where necessary, the S-oxide obtained is reduced and, where relevant, the protective groups are replaced by hydrogen atoms.

If a reactive ester of the general formula (IX) or a thiolo-ester is employed, the process is generally carried out in the presence of a trialkylamine (for example triethylamine) in an organic solvent such as dimethylformamide, at a temperature of between 0° and 40° C., after which, where necessary, the S-oxide obtained is reduced, and the protective groups are replaced by hydrogen atoms.

B. According to the invention, the products of the general formula (I), in which R has a meaning other than a triazinyl or triazolyl radical substituted by a group of the general formula (IV) can also be prepared by the action of a thiol of the general formula:

$$R\text{—SH} \qquad (X)$$

(or of one of its alkali metal or alkalin earth metal salts) in which R, which is defined as above, is protected in the form of an acetal [as defined by the general formulae (II) and (III)] if it is desired to obtain a cephalosporin of the general formula (I) in which R contains a formyl or acylalkyl radical, on a cephalosporin derivative (or, where appropriate, on a mixture of the isomers of this derivative) of the general formula:

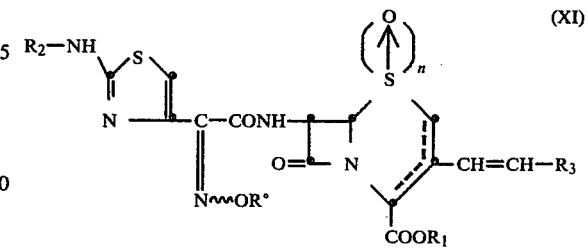
(XI)

in which, with R°, R₁ and n being defined as above, if n=0 the product is in the form of the bicyclooct-2-ene or bicyclooct-3-ene form, and if n=1, the product is in the bicyclooct-2-ene form (according to the Chemical Abstracts nomenclature), the substituent on the carbon atom in the 3-position of the bicyclooctene possesses the E or Z stereoisomeric configuration, R₂ represents a hydrogen atom or a protective radical for the amino group, as defined above in A. and R₃ represents a radical of the general formula:

$$-O-SO_2-R'_3 \qquad (XII)a$$

or

—O—CO—R''₃  (XII)ᵦ in which formulae R'₃ is an alkyl, trifluoromethyl or trichloromethyl radical or is a phenyl radical which is optionally substituted by a halogen atom or by an alkyl or nitro radical and R''₃ is defined like R'₃ or represents an acylmethyl, 2-acylethyl, 2-acylpropyl, alkoxycarbonylmethyl, 2-alkoxycarbonylethyl or 2-alkoxycarbonylpropyl radical, followed by reduction of the oxide obtained (if n=1) and then followed, where appropriate, by the removal of the protective radicals.

If it is to be understood that if the radical R of the product of the general formula (X) is prone to interfere with the reaction, it is preferable to protect this group under the conditions described above (especially if R contains an amino, alkylamino, hydroxyl or carboxyl radical).

It is also to be understood that if R⁰ represents hydrogen, it is preferable to protect the oxime under the conditions described above.

It is also to be understood that, if there is a danger of the radical R interfering with the reduction reaction, it is preferable to use a product of the general formula (XI) for which n=0 (especially if R contains a hydroxyl, sulpho, sulphinyl or sulphonyl group).

The process is in general carried out in the presence of an organic base, such as a pyridine or a tertiary organic base of the type:

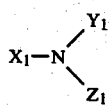  (XIII)

wherein X₁, Y₁ and Z₁ represent alkyl or phenyl radicals in which two of them may form a ring with the nitrogen atom to which they are attached. For example, diisopropylethylamine or diethylphenylamine are used.

If an alkali metal salt or alkaline earth metal salt of the thiol of the general formula (X) is used, it is not necessary to carry out the reaction in the presence of an organic base, as defined above.

The reaction is advantageously carried out in an organic solvent such as dimethylformamide, tetrahydrofurane or acetonitrile or in a mixture of the solvents mentioned above.

It is also possible to carry out the reaction in the presence of an alkali metal bicarbonate in a solvent such as mentioned above, optionally in the presence of water.

The reaction is carried out at a temperature of between −20° C. and the reflux temperature of the reaction mixture, the chosen temperature varying depending on the thiol employed. Equally, depending on the thiol employed, the reaction time can vary from 5 minutes to 48 hours.

The reaction is optionally carried out under nitrogen.

Preferably, if it is desired to use a bicyclooct-3-ene of the general formula (XI), a product of this type in which R₁ is other than hydrogen is employed.

The reduction of the oxide and the removal of the protective groups are carried out in accordance with the methods described above.

C. According to the invention, the products of the general formula (I), in which R has a meaning other than a triazinyl or triazolyl radical substituted by a group of the general formula (IV) can also be prepared by the action of a thiolo-ester of the general formula:

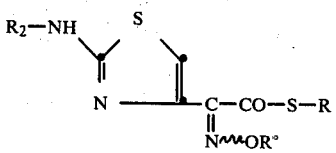  (XIV)

in which R⁰ and R₂ are defined as above and R is defined as above [it being understood that, if it contains an amino or alkylamino substituent, the latter is protected, if it contains a hydroxyl or carboxyl substituent the latter is free or protected and it is contains a formyl or acylalkyl substituent, the latter is protected, in the form of the acetal of the general formula (II) or (III)] on a 7-amino-caphalosporin of the general formula:

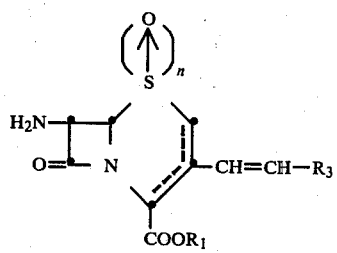  (XV)

in which R₁, R₃ and n are defined as above, and which exhibits the stereoisomerism defined above for the product of the general formula (XI), followed by reduction of the sulphoxide obtained, if n=1, and, where appropriate, by removal of the protective radicals.

In the same way as for process A., it is to be understood that the thiolo-esters, in the syn- or anti-form or their mixtures, respectively give the products of the general formula (I), in the syn- or anti-form or their mixtures.

It is also to be understood that the radicals R which contain a group which is prone to interfere with the reaction have been protected beforehand. The same is true of the oxime if R⁰ represents a hydrogen atom.

Equally, as for the processes described above, if R contains a hydroxyl, sulpho, sulphinyl or sulphonyl substituent, it is preferred to employ a product of the general formula (XV) in which n=0.

The protection, and the removal of the protective radicals, are carried out under the conditions described above.

The reaction of the thiolo-ester with the 7-aminocephalosporin of the general formula (XV) is in general carried out in the presence of an acid acceptor such as an organic base, more especially in the presence of a pyridine or of a tertiary organic base of the general formula (XIII), especially triethylamine, N,N-diisopropyl-N-ethylamine, diethylphenylamine or N-methylmorpholine.

The reaction is advantageously carried out in an organic solvent such as an amide (for example dimethylformamide or dimethylacetamide), an ether (for example tetrahydrofurane or dioxane), a chlorinated solvent (for example chloroform or methylene chloride), a ketone (for example acetone) or a nitrile (for example acetonitrile) or in a mixture of these solvents. It is also possible to carry out the reaction in the presence of an alkali metal bicarbonate in one of the abovementioned solvents, optionally in the presence of water.

The reaction is carried out at a temperature of between −20° C. and the reflux temperature of the reaction mixture. Optionally, the reaction is carried out under nitrogen.

amine, trimethylamine or pyridine), at a temperature of between −30° and 60° C.

If the reaction is carried out in the presence of a base, the intermediate of the general formula:

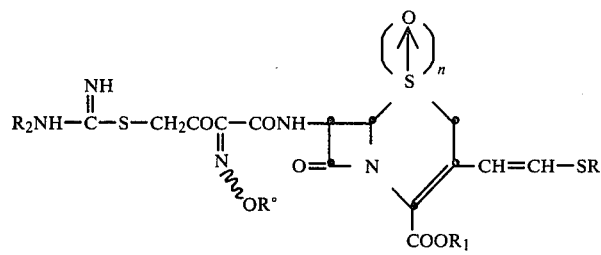

(XVIIA)

in which R°, R, R₁ and n are defined as above, may or may not be isolated, depending on the nature of the base and the amount introduced; the intermediate can subsequently be cyclised in an acid medium.

If it is desired to obtain a product of the general formula (I) in which R contains a formylalkyl or acylalkyl radical this radical can be protected, as the acetal, in the form of a radical of the general formula (II) or (III), as defined above.

The reduction of the sulphoxide and the removal of the protective radicals are effected under the conditions described above.

The reduction of the S-oxide is carried out under the conditions described above.

D. According to the invention, the products of the general formula (I), in which R° and R' are defined as above and R is defined as above except for being able to represent a triazinyl or triazolyl radical substituted by a group of the general formula (IV), can be prepared by the action of a thiourea of the general formula:

 (XVI)

(in which R₂ is defined as above in B., with the exception of representing chloroacetyl or trichloroacetyl) on a product of the general formula:

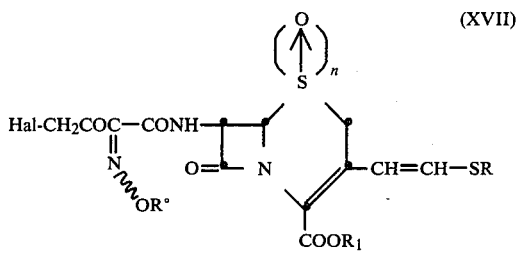

(XVII)

in which R°, R, R₁ and n are defined as above and Hal represents a chlorine or bromine atom, followed, if appropriate, by reduction of the sulphoxide and by E. According to the invention, the products of the general formula (I), in which R° and R' are defined as above and R represents a 5,6-dioxo-1,4,5,6-tetrahydro-1,2,4-triazin-3-yl radical substituted in the 4-position or a 1,3,4-triazol-5-yl or 2-alkoxycarbonyl-1,3,4-triazol-5-yl radical substituted in the 1-position by an alkyl radical containing 2 to 4 carbon atoms substituted by a carbamyloxy group or acyloxy group (of which the acyl part is optionally substituted by an amino, alkylamino or dialkylamino radical), which are functional derivatives of the corresponding product of the general formula (I) in which R° and R' are defined as above and R is a —Ⓡ—alk'—OH radical selected from amongst 5,6-dioxo-4-hydroxyalkyl-1,4,5,6-tetrahydro-1,2,4-triazin-3-yl or 1-hydroxyalkyl-1,3,4-triazol-5-yl or 2-alkoxycarbonyl-1-hydroxyalkyl-1,3,4-triazol-5-yl can be obtained from a product of the general formula:

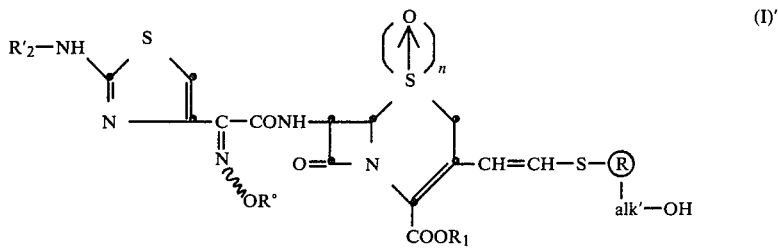

(I)' removal of the protective radicals.

The reaction is in generally carried out in an aqueous, organic or aqueous-organic medium, for example in solvents or mixtures of solvents such as alcohols (methanol or ethanol), ketones (acetone), chlorinated solvents (chloroform or ethylene chloride), nitriles (acetonitrile), amides (dimethylformamide or dimethylacetamide), ethers (tetrahydrofurane or dioxane), esters (ethyl acetate) or acids (acetic acid or formic acid) in the presence or absence of a base such as sodium hydroxide, potassium hydroxide, alkali metal carbonates and bicarbonates, alkali metal salts of carboxylic acids (sodium formate or sodium acetate) or tertiary amines (triethylin which R°, R₁, Ⓡ—alk'—OH and n are defined as above and R'₂ is defined like R₂ except for representing hydrogen, by any known method for obtaining an ester or a carbamate from an alcohol without affecting the remainder of the molecule followed, where appropriate, by reduction of the sulphoxide obtained, and removal of the protective radicals.

The esterification is carried out at a temperature of between −50° C. and the reflux temperature of the reaction mixture, especially by condensation of the acid anhydride (or of some other reactive derivative, for example a halide) in an inert organic solvent such as an ether (for example tetrahydrofurane), a chlorinated solvent (for example methylene chloride) or a mixture of these solvents, in the presence of a nitrogen-containing base such as pyridine, 4-dimethylaminopyridine or a trialkylamine (triethylamine) or of an alkaline condensation agent (for example sodium bicarbonate) followed, where appropriate, by reduction of the S-oxide obtained and removal of the protective groups in accordance with the methods described above.

The carbamate is obtained by any known method which does not adversely affect the remainder of the molecule. In particular, reaction with chlorosulphonyl isocyanate or trichloroacetyl isocyanate in an inert organic solvent, for example tetrahydrofurane or acetonitrile, at a temperature of between $-80°$ and $20°$ C., followed by removal of the protective groups, is employed.

The products of the general formula (I)' can be obtained in accordance with one or other of the processes described above.

F. According to the invention, the products of the general formula (I) in which $R^o$ and $R'$ are defined as above, and R represents a 5,6-dioxo-1,4,5,6-tetrahydro-1,2,4-triazin-3-yl radical substituted in the 4-position or a 1,3,4-triazol-5-yl or 2-alkoxycarbonyl-1,3,4-triazol-5-yl radical substituted in the 1-position, by an alkyl radical containing 2 to 4 carbon atoms substituted by a sulphoamino, alkylsulphonylamino, sulphamylamino, acylamino (of which the acyl part is optionally substituted by hydroxyl, amino, alkylamino or dialkylamino), alkoxycarbonylamino, ureido, alkylureido or dialkylureido radical, or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1-position by an alkyl radical containing 2 to 4 carbon atoms substituted by an acylamino, sulphamylamino, sulphoamino, ureido, alkylureido or dialkylureido group, which are all functional derivatives of the corresponding amine, can be obtained from a product of the general formula:

without affecting the remainder of the molecule, followed, where appropriate, by reduction of the sulphoxide and removal of the protective groups.

It is to be understood that the products which contain a sulpho, sulphonyl or sulphamyl group are preferably prepared from a product of the general formula (I)" in which $n=0$.

Furthermore, if it is desired to prepare a product of which the radical R contains an amino or hydroxyl group, it is necessary to protect these radicals in the reactant used. Equally, if $R^o$ represents a hydrogen atom, it is necessary to protect the oxime.

If it is desired to prepare a product of the general formula (I) in which the radical R contains an alkylsulphonylamino, sulphamylamino, substituted or unsubstituted acylamino, alkoxycarbonylamino or dialkylureido substituent, the reaction is advantageously carried out respectively by the action of the corresponding chlorosulphonyl derivative, acid chloride, chloroformate or dialkylcarbamyl chloride on the 7-aminocephalosporin of the general formula (VIII) under the conditions described above for the reaction of the acid chloride of the general formula (VII).

If it is desired to prepare a product of the general formula (I) in which the radical R contains a sulphoamino, alkylsulphonylamino or substituted or unsubstituted acylamino substituent, it is possible to carry out the reaction by means of the corresponding acid anhydride under the conditions described above for reacting the product of the general formula (VII) in the form of an anhydride, If it is desired to obtain a product of the general formula (I) in which R contains a substituted or unsubstituted acylamino radical, it is also possible to carry out the reaction with the corresponding acid under the working conditions described above for the use of the acid of the general formula (VII).

If it is desired to obtain a product of the general formula (I) in which R contains a ureido or alkylureido radical, an alkali metal isocyanate or alkyl isocyanate, respectively, is used to treat the corresponding product of the general formula (I)" in an aqueous-organic or organic medium (for example in tetrahydrofurane) at a temperature of between $-20°$ and $60°$ C.

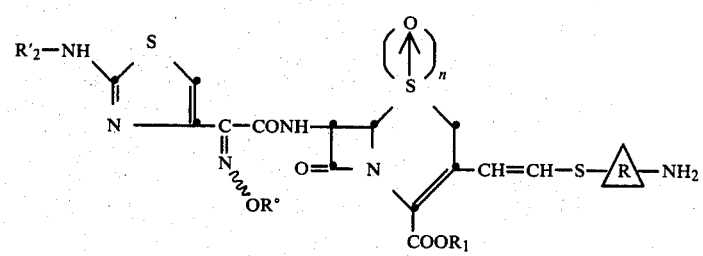

(I)"

in which $R^o$, $R_1$, $R'_2$ and n are defined as above, and $\underline{R}$—$NH_2$ represents a 5,6-dioxo-1,4,5,6-tetrahydro-1,2,4-triazin-3-yl radical substituted in the 4-position or 1,3,4-triazol-5-yl or 2-alkoxycarbonyl-1,3,4-triazol-5-yl radical substituted in the 1-position, by an aminoalkyl radical of which the alkyl part contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical of which the alkyl part contains 2 to 4 carbon atoms, by any method known in itself for forming an amide, sulphamide, carbamate or urea group The reduction, and the removal of the protected radicals, are carried out under the conditions described above.

G. According to the invention, the products of the general formula (I) in which $R^o$ and $R'$ are defined as above and R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by a thiazolidin-2-yl-alkyl radical, by a radical of the general formula (IV) or by a hydroxyiminoalkyl or alkoxyiminoalkyl radical of which the iminoalkyl part contains 1 to 5 carbon atoms, or represents a tetrazol-5-yl radical substituted in the 1-position by a hydroxyiminoalkyl or alkoxyiminoalkyl radical of which the iminoalkyl part contains 1 to 5 carbon atoms, which products are addition reaction derivatives of the product of the general formula (I), in which $R^o$ and $R'$ are defined as above and R is one of the heterocyclic structures metioned above, substituted by a formylalkyl radical (or its hydrate form), can be obtained from the product of the general formula:

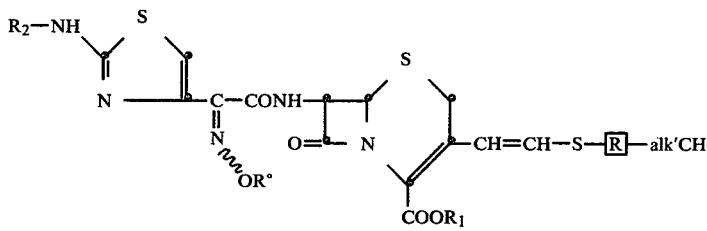

(I)''' in which $R^o$, $R_1$ and $R_2$ are defined as above and ℝ —alk'CHO represents a 5,6-dioxo-4-formylalkyl-1,4,5,6-tetrahydro-1,2,4-triazin-3-yl, or 1-formylalkyl-1,3,4-triazol-5-yl, 2-alkoxycarbonyl-1-formylalkyl-1,3,4-triazol-5-yl or 1-formylalkyl-tetrazol-5-yl radical, by respective addition reaction of cysteamine, of an alcohol, or hydroxylamine or of an alkoxyamine, in accordance with the known methods for forming the addition reaction derivatives of carbonyl groups, after which the protective radicals are removed.

The reaction is in general carried out in an organic solvent at a temperature of between 20° C. and the reflux temperature of the reaction mixture.

The organic solvents are chosen in accordance with the solubility of the products. If a product of the general formula (I)''', in which $R_1$ and $R_2$ are other than hydrogen, is employed, it is advantageous to use solvents such as tetrahydrofurane, acetonitrile, alcohols and ketones. If a product of the general formula (I)''' is employed, in which $R_1$ and $R_2$ are hydrogen atoms, the reaction is advantageously carried out in solvents such as pyridine, dimethylsulphoxide or dimethylformamide.

If it is desired to prepare a product of the general formula (I) in which the radical R contains a substituent of the general formula (IV), the reaction is carried out in an acid medium.

H. According to the invention, the products of the general formula (I), in which $R'$ represents a radical of the general formula (V), in which $R''$ and $R'''$ are defined as above, can also be obtained by esterification of a product of the general formula (I) in which $R'$ represents a hydrogen atom, and of which the amine group has been protected beforehand, by any method which is in itself known for the preparation of an ester from an acid without affecting the remainder of the molecule.

In general, an alkali metal salt or tertiary amine salt of a product of the general formula (I), as defined above, in which the amine group has beforehand been protected and in which, where appropriate, the radical R and the oxime have also been protected, is reacted with a product of the general formula:

$$Z_2-\underset{\underset{R''}{|}}{CH}-OCO-R''' \qquad (XVIII)$$

in which $R''$ and $R'''$ are defined as above and $Z_2$ represents a halogen atom, in an inert solvent such as dimethylformamide, at a temperature of between 0° and 30° C.

The products of the general formula (XVIII) can be prepared in accordance with the method described in German patent application No. 2,350,230.

The products of the general formula (VII) can be prepared in accordance with the method described in Belgian Pat. No. 850,662, or by application of the method described in Belgian Pat. No. 877,884.

The products of the general formula (VII) in which $R^o$ is a vinyl radical can be prepared in accordance with the method described in Belgian Pat. No. 869,079.

The products of the general formula (VII) in which $R^o$ is a cyanomethyl radical can be prepared in accordance with the method described in German patent application No. 2,812,625.

The products of the general formula (VIII) can be obtained from a product of the general formula:

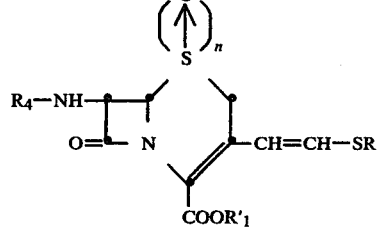

(XIX)

(in which R and n are defined as above, except for R representing a triazinyl or triazolyl radical substituted by a radical of the general formula (IV), $R'_1$ is defined like $R_1$, except for representing hydrogen and $R_4$ represents an easily removable radical) by removing the radical $R_4$ or, where appropriate, by successively or simultaneously moving the radicals $R_4$ and $R'_1$ if it is desired to obtain a product of the general formula (VIII) in which $R_1$ is a hydrogen atom.

By an easily removable radical $R_4$ there is understood a benzhydryl or trityl radical, a 2,2,2-trichloroethyl radical, an acyl radical of the general formula:

$$R_5-CO- \qquad (XX)a$$

(in which $R_5$ is a hydrogen atom or an alkyl radical [optionally substituted by one or more halogen atoms or by a phenyl or phenoxy radical] or is a phenyl radical), or a radical of the general formula:

$$R_6OCO- \qquad (XX)b$$

[in which $R_6$ is a branched unsubstituted alkyl radical, a straight or branched alkyl radical {carrying one or more substituents chosen from amongst halogen atoms and the cyano, trialkylsilyl, phenyl and substituted phenyl radicals (the substituents of the phenyl radical being one or more alkoxy, nitro or phenyl radicals)}, vinyl, allyl or quinolyl] or nitrophenylthio. Furthermore, the radical R₄NH— can be replaced by a methyleneimino radical in which the methylene radical is substituted by a dialkylamino or aryl group (the latter being optionally substituted by one or more methoxy or nitro radicals).

The following radicals may be mentioned as examples of radicals $R_4$ which can be used: formyl, acetyl, chloroacetyl, trichloroacetyl, phenylacetyl, phenoxyacetyl, benzoyl, tert.-butoxycarbonyl, 2-chloro-1,1-dimethyl-ethoxycarbonyl, 2,2,2-trichloro-ethoxycarbonyl, 2,2,2-trichloro-1,1-dimethyl-ethoxycarbonyl, 2-cyano-1,1-dimethyl-ethoxycarbonyl, 2-trimethylsilylethoxycarbonyl, benzyloxycarbonyl, p-methoxybenzyloxycarbonyl, 3,5-dimethoxy-benzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, quinol-8-yloxycarbonyl, o-nitrophenylthio and p-nitrophenylthio.

As examples of methyleneimino radicals there may be mentioned dimethylaminomethyleneimino, 3,4-dimethoxybenzylideneimino and 4-nitro-benzylideneimino.

The protective radical $R_4$ is removed by any known method for liberating an amine group without affecting the remainder of the molecule.

By way of example, the following methods may be mentioned:

if $R_4$ represents trityl, benzhydryl, trichloroacetyl, chloroacetyl, tert.-butoxycarbonyl, trichloroethoxycarbonyl, benzyloxycarbonyl, p-methoxybenzyloxycarbonyl and p-nitrobenzyloxycarbonyl: in accordance with the methods mentioned above for liberating the amino radical of the product of the general formula (I); advantageously this is carried out by using p-toluenesulphonic acid in acetonitrile at a temperature of between 0° and 50° C.;

if $R_4$ represents formyl, 2-chloro-1,1-dimethyl-ethoxycarbonyl, 2-cyano-1,1-dimethyl-ethoxycarbonyl, 3,5-dimethoxy-benzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, and if R₄NH— is replaced by dimethylaminomethyleneimino, 3,4-dimethoxy-benzylideneimino or 4-nitro-benzylideneimino: by hydrolysis in an acid medium;

if $R_4$ represents 2,2,2-trichloroethyl or 2,2,2-trichloro-1,1-dimethyl-ethoxycarbonyl: by treatment with zinc in acetic acid;

if $R_4$ represents acetyl, benzoyl, phenylacetyl or phenoxyacetyl: in accordance with the method described in Belgian Pat. No. 758,800;

if $R_4$ represents trimethylsilylethoxycarbonyl: in accordance with the method described by H. GERLACH, Helv. Chim. Acta 60 (8), 3039 (1977); and if $R_4$ represents p-nitrobenzyloxycarbonyl: by hydrogenolysis in the presence of palladium.

The products of the general formula (XIX) can be obtained by the action of a thiol of the general formula (X), of which the radical R is protected if appropriate, or of one of its alkali metal salts or alkaline earth metal salts, on a cephalosporin derivative or, where appropriate, on a mixture of isomers of a derivative of the general formula:

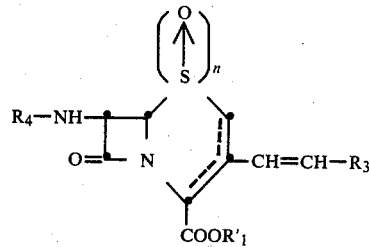

(XXI)

in which $R'_1$, $R_3$, $R_4$ and n are defined as above, if n=0, the product is in the bicyclooct-2-ene or bicyclooct-3-ene form, if n=1, the product is in the bicyclooct-2-ene form and the substituent on the carbon atom in the 3-position of the bicyclooctene exhibits the E- or Z-stereoisomeric configuration.

The reaction is generally carried out under the conditions described above for obtaining a 3-thiovinylcephalosporin of the general formula (I) from a thiol of the general formula (X) and from a product of the general formula (XI).

The thiols of the general formula (X) (which can be employed in their tautomeric form) can be prepared by application of one of the following methods, depending on the meaning of the radical R:

if R is a pyrid-3-yl radical: according to the method described by H. M. WUEST and E. H. SAKAL, J. Am. Chem. Soc., 73, 1210 (1951);

if R is a pyrid-3-yl-1-oxide radical: according to the method described by B. BLANK et al., J. Med. Chem. 17, 1065 (1974);

if R is a pyrid-4-yl-1-oxide radical: according to the method described by R. A. Y. JONES et al., J. Chem. Soc. 2937 (1960);

if R is a pyridazin-3-yl radical substituted by alkyl or methoxy, or a N-oxide derivative of such a radical: according to the method described in Belgian Pat. No. 787,635;

if R is a pyridazin-3-yl radical substituted by amino, or a N-oxide derivative of such a radical: according to the method described in Belgian Pat. No. 579,291;

if R is a pyridazin-3-yl radical substituted by acylamino, or a N-oxide derivative of such a radical: by application of the methods described by M. KUMAGAI and M. BANDO, Nippon Kagaku Zasshi, 84, 995 (1963) and by T. HORIE and T. UEDA, Chem. Pharm. Bull., 11, 114 (1963);

if R is a tetrazolo[4,5-b]pyridazin-6-yl radical: according to the method described in Belgian Pat. No. 804,251; and if R is a 5,6-dioxo-1,4,5,6-tetrahydro-1,2,4-triazin-3-yl radical substituted in the 4-position or a 2-alkoxycarbonyl-1,3,4-triazol-5-yl radical substituted in the 1-position by a radical $R^\gamma$ chosen from amongst:

(a) an allyl radical, or an alkyl radical (which has 1 to 4 carbon atoms and is itself optionally substituted by an alkoxy, alkylthio, phenyl, carbamyl, alkylcarbamyl, dialkylcarbamyl, acyl, alkoxycarbonyl or thiazolidin-2-yl radical), (b) a 2,3-dihydroxy-propyl radical or 1,3-dihydroxy-prop-2-yl radical (optionally protected in the form of the cyclic acetal), (c) an alkyl radical [which has 2 to 4 carbon atoms and is itself substituted by hydroxyl, carbamyloxy, dialkylamino, alkylsulphinyl, alkylsulphonyl, alkylsulphonylamino, sulphamylamino, acylamino (which is optionally substituted), alkoxycarbonylamino, ureido, alkylureido or dialkylureido], (d) a radical of the general formula (II) or (III), or (e) a hydroxyiminoalkyl or alkoxyiminoalkyl radical: by reacting an alkyl oxalate with a thiosemicarbazide of the general formula:

 (X)a (in which R$^\gamma$ is defined as above), in the presence of an alkali metal alcoholate, for example sodium ethylate or sodium methylate, or potassium tert.-butylate, by applying the method described by M. PESSON and M. ANTOINE, Bull. Soc. Chim. France (1970), 1590.

It is not absolutely necessary to purify the product obtained (nor to liberate the protected radicals) in order to employ the product for the preparation of the products of the general formula (I).

The thiosemicarbazide of the general formula (X)a can be prepared in accordance with one of the methods described by K. A. JENSSEN et al., Acta Chim. Scand., 22, 1 (1968), or by application of the method described by Y. KAZAROV and J. Y. POTOVSKII, Doklady Acad. Nauk. SSSR 134, 824 (1966), it being understood that if R$^\gamma$ contains an amino radical, the latter is protected.

The protection of the amino radical and the removal of the protective radical are carried out in accordance with the usual methods which do not adversely affect the remainder of the molecule. In particular, the tert.-butoxycarbonyl group, which can be removed by acid hydrolysis, is used.

If R is a 1,3,4-triazol-5-yl radical substituted in the 1-position by an alkyl, allyl or alkoxyalkyl radical, by an alkyl radical (having 1 to 4 carbon atoms) which is itself substituted as defined above in (a), with the exception of a thiazolidin-2-yl radical, by a radical as defined above in (c) or by an alkoxyiminoalkyl radical: by application of one of the methods described by M. PESSON and M. ANTOINE, Bull. Soc. Chim. France 1590 (1970).

If R is a 1,3,4-triazol-5-yl radical substituted in the 1-position by thiazolidin-2-yl-alkyl or hydroxyiminoalkyl: by the respective action of cysteamine or hydroxylamine on a 1-dialkoxyalkyl-5-mercapto-1,3,4-triazole, which can be obtained by application of the method described by M. KANAOKA, J. Pharm. Soc. Japan, 75, 1149 (1955), from a 4-dialkoxyalkyl-thiosemicarbazide.

If R is a 1,3,4-triazol-5-yl radical substituted in the 1-position by 2,3-dihydroxypropyl or 1,3-dihydroxyprop-2-yl (optionally protected in the form of a cyclic acetal), or R represents a radical of the general formula (II) or (III): by application of the method described by M. KANAOKA, J. Pharm. Soc. Japan, 75, 1149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by optionally substituted acyloxyalkyl: by acylation of, respectively, 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, of which the mercapto radical has beforehand been protected (for example according to the method of C. G. KRUSE et al., Tet. Lett. 1725 (1976)), by any method known for acylating an alcohol without affecting the remainder of the molecule, followed by liberation of the mercapto group in an acid medium.

If R is a 5,6-dioxo-1,4,5,6-tetrahydro-1,2,4-triazin-3-yl radical substituted in the 4-position or 2-alkoxycarbonyl-1,3,4-triazol-5-yl or 1,3,4-triazol-5-yl radical substituted in the 1-position by aminoalkyl or alkylaminoalkyl: by liberating the amine group of the corresponding product, protected, for example, by a tert.-butoxycarbonyl group.

If R is a 5,6-dioxo-1,4,5,6-tetrahydro-1,2,4-triazin-3-yl radical substituted in the 4-position or 2-alkoxycarbonyl-1,3,4-triazol-5-yl or 1,3,4-triazol-5-yl radical substituted in the 1-position by sulphoaminoalkyl: from the corresponding product substituted by a tert.-butoxycarbonylaminoalkyl radical, by analogy with the method described in Belgian Pat. No. 847,237.

If R is a 1,4-dialkyl-1,4,5,6-tetrahydro-1,2,4-triazin-3-yl radical or 1-alkyl-5,6-dioxo-1,4,5,6-tetrahydro-1,2,4-triazin-3-yl radical: according to the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: according to the method described by M. PESSON and M. ANTOINE, C.R. Acad Sci., Ser C, 267, 25, 1726 (1968).

If R is a 1,2,3-triazol-5-yl radical: according to the method described in French patent application 2,215,942.

If R is a 1,3,4-triazol-5-yl radical: according to the method described by M. KANAOKA, J. Pharm. Soc. Jap. 75, 1149 (1955).

If R is a 1,3,4-thiadiazol-5-yl radical optionally substituted by alkyl, alkoxy, alkylthio, alkylsulphonyl, amino, alkylamino, dialkylamino or acylamino: according to the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: according to the method described in German patent application No. 2,446,254.

If R is a 1,3,4-thiadiazol-5-yl radical substituted by a carboxyalkyl radical: by application of the method described in German patent application No. 1,953,861.

If R is a 1,3,4-thiadiazol-5-yl radical substituted by a trifluoromethyl radical: according to the method described in German patent application No. 2,162,575.

If R is a 1,3,4-thiadiazol-5-yl radical substituted by a carboxyl radical: according to the method described in Japanese patent application No. 77/48,666.

If R is a 1,3,4-thiadiazol-5-yl radical substituted by an acylaminoalkyl radical: according to the method described in Japanese patent application No. 76/80,857.

If R is a 1,3,4-thiadiazol-5-yl radical substituted by a hydroxyalkylthio radical: by application of the method described by G. NANNINI, Arz. Forsch. 27 (2), 343 (1977).

If R is a 1,2,4-thiadiazol-5-yl radical substituted by alkyl or alkoxy: according to the method described in German patent application No. 2,806,226 or according to Chem. Ber. 90, 184 (1957).

If R is a 1,3,4-oxadiazol-5-yl radical as defined above in 8 a.: by application of the method described by E. HOGGARTH, J. Chem. Soc. 4811 (1952).

If R is an oxazol-2-yl or 4-alkyl-oxazol-2-yl radical: by application of the method described previously by C. BRADSHER, J. Org. Chem. 32, 2079 (1967).

If R is a tetrazol-5-yl radical optionally substituted in the 1-position by alkyl, hydroxyalkyl or phenyl: according to the methods described in Belgian Pat. No. 830,821.

If R is a tetrazol-5-yl radical substituted in the 1-position by alkoxyalkyl: by addition reaction of sodium azide with an isothiocyanatoalkoxyalkyl derivative, in an organic solvent such as ethanol, at the reflux temperature of the reaction mixture.

The isothiocyanatoalkoxyalkyl derivative can be obtained by application of the method described by E. Schmidt et al., Chem. Ber. 73, 286 (1940).

If R is a tetrazol-5-yl radical substituted in the 1-position by a carboxyalkyl radical: according to the method described in Belgian Pat. No.858,112.

If R is a tetrazol-5-yl radical substituted in the 1-position by a sulphoalkyl radical: according to the method described in Belgian Pat. No. 856,498 or described by D. A. BERGES et al., J. Het. Chem. 15, 981 (1978).

If R is a tetrazol-5-yl radical substituted in the 1-position by an aminoalkyl, alkylaminoalkyl or dialkylaminoalkyl radical: by application of the method described in German patent application No. 2,738,711.

If R is a tetrazol-5-yl radical substituted in the 1-position by a sulphamylalkyl, sulphamylaminoalkyl or sulphoaminoalkyl radical: according to the method described in Belgian Pat. No. 856,636.

If R is a tetrazol-5-yl radical substituted by an acylaminoalkyl radical or a 1,3,4-thiadiazol-5-yl radical substituted by hydroxyl: according to the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (of which the mercapto radical has beforehand been protected), by treatment with an alkali metal isothiocyanate, with an alkyl isocyanate or with a dialkylcarbamyl halide, followed by liberation of the mercapto group under the conditions described in Belgian Pat. No. 847,237.

If R is a tetrazol-5-yl radical substituted in the 1-position by a carboxyalkylaminoalkyl radical: according to the method described in German patent application No. 2,715,597.

If R is a tetrazol-5-yl radical substituted in the 1-position by a 2,3-dihydroxypropyl radical: according to the method described in U.S. Pat. No. 4,064,242.

If R is a tetrazol-5-yl radical substituted in the 1-position by a 1,3-dihydroxy-prop-2-yl radical: by addition reaction of sodium azide with a 2,2-dimethyl-1,3-dioxolan-5-yl isothiocyanate (followed, where appropriate, by liberation of the hydroxyl groups).

If R is a tetrazol-5-yl radical substituted in the 1-position by a radical of the general formula (II) as defined above in 9e. or of the general formula (III), or a radical defined above in 9c.: by the action of sodium azide on the corresponding isothiocyanate, by analogy with the method described by R. E. ORTH, J. Pharm. Sci. 52 (9), 909 (1963), it being understood that where R contains a hydroxy or hydroxyiminoalkyl substituent, the alcohol or oxime function are protected, if appropriate, for example by a tetrahydropyranyl group.

The products of the general formulae (XI) and (XXI) can be prepared by the action of an activated derivative of the acids R'$_3$SO$_3$H and R"$_3$COOH [see formulae (XIIa) and (XIIb)] of the type:

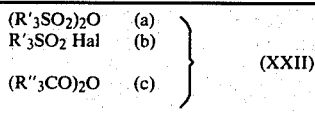

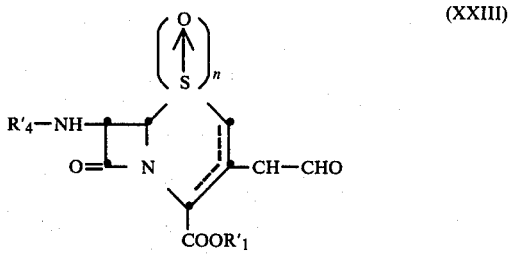

[in which formulae R'$_3$ and R"$_3$ are defined as above and Hal represents a halogen atom] on a product (or a mixture of the isomers) of the general formula:

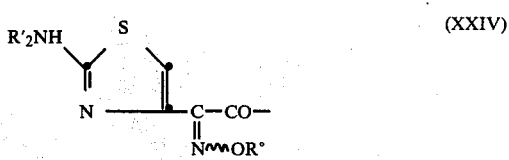

(in which, n and R'$_1$ being defined as above, the product is in the bicyclooct-2-ene or bicyclooct-3-ene or 3-oxoethylidene-bicyclooctane form, if n=0, and is in the bicyclooct-2-ene or 3-oxoethylidene-bicyclooctane form, if n=1, and R'$_4$ represents a radical of the general formula in which R$^o$ is defined as above and R'$_2$ is defined like R$_2$, with the exception of representing hydrogen, or R'$_4$ represents a radical R$_4$, as defined above), followed, where appropriate, by reduction of the sulphoxide obtained and, where appropriate, by the removal of the protective radicals from the amine group and from the acid group (if it is desired to obtain a product of the general formula (XI) in which R$_1$ and/or R$_2$ are hydrogen).

It is to be understood that if R'$_4$ is a radical of the general formula (XXIV) in which R$^o$ is hydrogen, it is necessary to protect the oxime. The protection, and liberation of the oxime are carried out in accordance with the methods described above.

The reaction is in general carried out in the presence of a tertiary base as defined by the general formula (XIII), for example triethylamine or N,N-dimethylaniline, in a chlorinated organic solvent (for example methylene chloride), an ester (ethyl acetate), an ether (for example dioxane or tetrahydrofurane), an amide (for example dimethylacetamide or dimethylformamide), acetonitrile or N-methylpyrrolidone, or directly in a basic solvent such as pyridine, or in an aqueous organic medium in the presence of an alkaline condensation agent (for example an alkali metal bicarbonate, sodium hydroxide or potassium hydroxide), at a temperature of between −78° C. and the reflux temperature of the reaction mixture.

Where appropriate, the reaction is carried out under nitrogen.

It is not absolutely necessary to purify the intermediate of the general formula (XXIII) before carrying out this reaction.

Where relevant, the removal of the protective radicals of the amine group and of the acid group is effected in accordance with the methods described above for obtaining the product of the general formula (I).

The products of the general formula (XI) can also be obtained by the action of an acid of the general formula (VII), of which the amine group has beforehand been protected, or by the action of one of its reactive derivatives, on a product of the general formula (XV), in which $R_1$, $R_3$ and n are defined as above, the product is in the bicyclooct-2-ene or bicyclooct-3-ene form if n=0, or is in the bicyclooct-2-ene form if n=1, and the substituent on the carbon atom in the 3-position of the bicyclooctene exhibits the E or Z stereoisomerism, or, where appropriate, on a mixture of the isomers of this product, followed, where appropriate, by the reduction of the oxide obtained and then, where appropriate, by the removal of the protective radicals.

The reaction is carried out under the conditions described above for the action of an acid of the general formula (VII) on a 7-amino-cephalosporin of the general formula (VIII).

Where relevant, the reduction of the oxide as well as the removal of the protective radicals can be carried out under the conditions described for obtaining the product of the general formula (I).

The product of the general formula (XV) can be obtained by removing the protective radical $R_4$ from a product of the general formula (XXI), or, where appropriate, by simultaneous removal of the radicals $R_4$ and $R'_1$, if it is desired to obtain a product of the general formula (XV) in which $R_1$ is hydrogen.

The process is generally carried out under the conditions described above for obtaining a product of the general formula (VIII) from a product of the general formula (XIX).

The products of the general formula (XXIII), in which n is 0, can be obtained by hydrolysis of the enamine (or of the mixture of isomeric enamines) of the general formula:

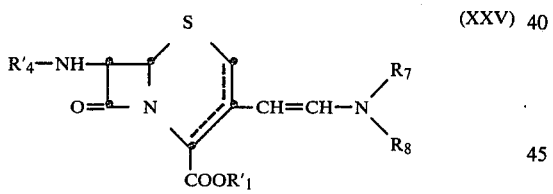

(XXV)

in which $R'_1$ and $R'_4$ are defined as above, the product is in the bicyclooct-2-ene or bicyclooct-3-ene form and the substituent on the carbon atom in the 3-position of the bicyclooctene exhibits E or Z stereoisomerism, and $R_7$ and $R_8$, which are identical or different, represent alkyl radicals (optionally substituted by a hydroxyl, alkoxy, amino, alkylamino or dialkylamino radical) or phenyl radicals, or form, together with the nitrogen atom to which they are attached, a saturated heterocyclic ring with 5 or 6 members, which optionally contains another hetero-atom chosen from amongst nitrogen, oxygen or sulphur, and which is optionally substituted by an alkyl radical.

Preferably, an enamine of the general formula (XXV), in which $R_7$ and $R_8$ each represent a methyl radical, is hydrolysed.

The reaction is generally carried out in an organic acid (for example formic acid or acetic acid) or an inorganic acid (for example hydrochloric acid or sulphuric acid) in the presence or absence of a solvent, in an aqueous or organic medium, at a temperature of between −20° C. and the reflux temperature of the reaction mixture. If the reaction is carried out in an organic medium, the hydrolysis is carried out by adding water to the reaction mixture and then treating it, if appropriate with an inorganic base (for example an alkali metal bicarbonate) or an organic base (for example a tertiary amine or pyridine).

If the reaction is carried out in the presence of a solvent, it is not necessary for the solvent to be miscible with the acid aqueous phase. If it is not miscible, contact is effected by vigorous stirring.

Amongst the solvents which can be used, there may be mentioned the chlorinated solvents, ethyl acetate, tetrahydrofurane, acetonitrile, dimethylformamide and the alcohols. It is not absolutely necessary, for carrying out this reaction, to have purified the intermediate of the general formula (XXV).

The products of the general formula (XXIII) in which n is 1 can be obtained by oxidising the products of the general formula (XXIII) in which n is 0, by application of the method described in German Patent Application No. 2,637,176.

Equally, the products of the general formulae (VIII), (XI), (XV), (XVII), (XIX) or (XXI), in which n is 1, can be obtained by oxidising, respectively, the products of the general formulae (VIII), (XI), (XV), (XVII), (XIX) or (XXI), in which n is 0, by application of the method described in German Patent Application No. 2,637,176.

The products of the general formula (XXV), in which $R_7$ and $R_8$ are defined as above, with the exception of representing alkyl substituted by hydroxyl, amino or alkylamino, can be obtained by the action of a product of the general formula:

(XXVI)

which may have been prepared in situ [and in which $R_7$ and $R_8$ are defined as above and $R_9$ and $R_{10}$, which are identical or different, either represent groups of the general formula:

$-X_2R_1$      (XXVII)a in which $X_2$ is an oxygen atom and $R_{11}$ represents an alkyl or phenyl radical, or one of $R_9$ and $R_{10}$ represents a radical of the general formula (XXVII)a (in which $X_2$ represents an oxygen or sulphur atom and $R_{11}$ is alkyl or phenyl) and the other represents an amino radical of the general formula

(XXVII)b in which $R_{12}$ and $R_{13}$ are defined like $R_7$ and $R_8$, or $R_9$ and $R_{10}$ each represent a radical of the general formula (XXVII)b] on a cephalosporin derivative of the general formula

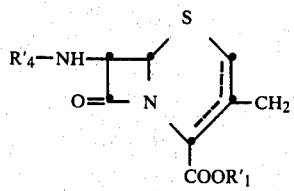 (XXVIII)

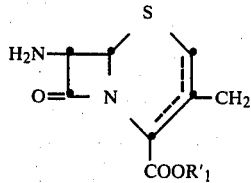 (XXX)

in which R'₁ and R'₄ are defined as above and the product is in the 3-methyl-bicyclooct-2-ene or 3-methyl-bicyclooct-3-ene or 3-methylene-bicyclooctane form.

If a product of the general formula (XXVI) in which the radical (XXVII)b is different from —NR₇R₈ is chosen, it is preferable to choose a product of this type in such a way that the amine HNR₁₂R₁₃ is more volatile than HNR₇R₈.

The reaction is generally carried out in an organic solvent such as dimethylformamide or hexamethylphosphorotriamide, or in a mixture of solvents (for example dimethylformamide/tetrahydrofurane, dimethylformamide/dimethylacetamide, dimethylformamide/ether or dimethylformamide/dioxane) at a temperature of between 20° C. and the reflux temperature of the reaction mixture.

It is to be understood that if R'₄ is a radical of the general formula (XXIV), in which R° is a hydrogen atom, it is preferable that the oxime should be protected under the conditions described above.

The products of the general formula (XXV) in which R'₁ and R'₄ are defined as above and R₇ and R₈ represent alkyl radicals substituted by hydroxyl, amino or alkylamino can be obtained by transenamination from a product of the general formula (XXV), in which R₇ and R₈ represent alkyl radicals, preferably methyl.

The reaction is carried out by the action of an amine of the general formula

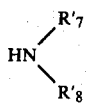 (XXIX)

in which R'₇ and R'₈, which are identical or different, represent alkyl radicals substituted by hydroxyl, amino or alkylamino, on the product of the general formula (XXV), under the conditions described above for the action of a product of the general formula (XXVI) on a derivative of the general formula (XXVIII).

The products of the general formula (XXVII) can be prepared in accordance with the methods described by H. BREDERECK et al., Chem. Ber. 101 41 (1968), Chem. Ber. 101, 3058 (1968) and Chem. Ber. 106, 3725 (1973).

The cephalosporin derivatives of the general formula (XXVIII), in which R'₄ represents a radical of the general formula (XXIV), can be prepared from the products of the general formula in which R'₁ is defined as above, by the action of an acid of the general formula (VII) or of one of its derivatives, under the conditions described above for obtaining products of the general formula (I).

The cephalosporin derivatives of the general formulae (XXVIII) and (XXX), in which R'₁ represents a radical of the general formula (V), can be obtained by esterification of the corresponding acids in accordance with the method described above for obtaining a product of the general formula (I), in which R₁ is a radical of the general formula (V), from a product of the general formula (I), in which R₁ is a hydrogen atom.

The protective groups R'₁ and R'₄ of the product of the general formula (XXVIII) {or (XXX) in the case of R'₁} can be introduced into a 7-amino-cephalosporin of the general formula

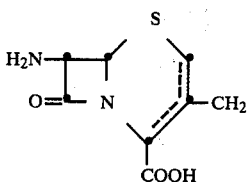 (XXXI)

in which the position of the double bond is defined as above, in accordance with methods which are known or are described in the literature:

If R'₄ is a formyl radical: according to J. C. SHEEHAN et al., J. Amer. Chem. Soc. 80 1156 (1958).

If R'₄ is acetyl, chloroacetyl, trichloroacetyl, phenylacetyl, phenoxyacetyl or benzoyl: according to E. H. FLYNN, Cephalosporins and Penicillins, Academic Press (1972).

If R'₄ is a tert.-butoxycarbonyl radical: according to L. MORODER and al., Hoppe Seyler's Z. Physiol. Chem. 357, 1651 (1976).

If R'₄ is 2,2,2-trichloro-1,1-dimethyl-ethoxycarbonyl: according to J. UGI et al., Angew. Chem. Int. Ed. Engl. 17(5), 361 (1978).

If R'₄ is 2,2,2-trichloro-ethoxycarbonyl, 2-chloro-1,1-dimethyl-ethoxycarbonyl, 2-cyano-1,1-dimethylethoxycarbonyl, 2-trimethylsilyl-ethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by the action of a chloroformate in an aqueous organic medium in the presence of an alkali metal bicarbonate, or in accordance with Belgian Patent 788,885.

If R'₄ is diphenylmethoxycarbonyl: by the action of the corresponding azidoformate in an aqueous organic medium, in the presence of an alkali metal bicarbonate.

If R'₄ is 2-(biphenyl-4-yl)-isopropoxycarbonyl: by analogy with the method described in Helv. Chim. Acta, 51, 924 (1968).

If R'₄ is quinol-8-yloxycarbonyl or allyloxycarbonyl: by the action of the corresponding carbonate in a basic aqueous organic medium.

If R′₄ is o-nitrophenylthio or p-nitrophenylthio: by analogy with the method described by L. ZERVAS et al., J. Amer. Chem. Soc. 85, 3660 (1963).

If R′₄NH— is replaced by dimethylaminomethyleneimino: by analogy with the method described by J. F. FITT, J. Org. Chem. 42(15), 2639 (1977).

If R′₄NH— is replaced by 4-nitro-benzylideneimino or 3,4-dimethoxy-benzylideneimino: according to the method described by R. A. SIRESTONE, Tetrahedron Lett., 33, 2915 (1977).

If R′₁ is methoxymethyl: according to S. SEKI et al., Tetrahedron Lett., 33, 2915 (1977).

If R′₁ is tert.-butyl: according to R. J. STEDMAN, J. Med. Chem., 9, 444 (1966).

If R′₁ is benzhydryl: according to Netherlands Patent Application No. 73/03,263.

If R′₁ is p-nitrobenzyl or p-methoxybenzyl: according to R. R. CHAUVETTE et al., J. Org. Chem. 38(17), 2994 (1973).

The products of the general formula (XI) can also be prepared from a product of the general formula:

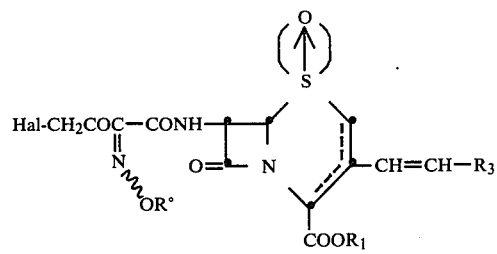

(XXXII)

in which R⁰, R₁, R₃ and n are defined as above and Hal is defined as in the general formula (XVIII), by analogy with the method described for the preparation of the products of the general formula (I) in process D.

The products of the general formula (XXXII) can be prepared from a product of the general formula (XV) by application of the methods described below for the preparation of the products of the general formula (XVII).

The thiolo-esters of the general formula (XIV) can be prepared by the action of an acid or of a reactive derivative of an acid of the general formula:

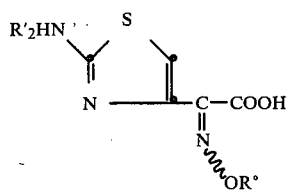

(VII)a

[in which R⁰ represents an alkyl, vinyl or cyanomethyl radical or a protective radical and in which R′₂ is defined like R₂ with the exception of representing a hydrogen atom (or can represent a hydrogen atom if the reactive derivative is the acid chloride)] on a thiol of the general formula (X) (in which R is defined as above in the case of the products of the general formula (XIV)), or of one of its alkali metal salts or alkaline earth metal salts, followed by removal of the R′₂ protective radical from the amino radical, if it is desired to obtain a product in which R₂ is a hydrogen atom, and followed, where appropriate, by removal of the other protective radicals.

If it is desired to obtain a product of the general formula (XIV) in which R⁰ is a hydrogen atom, the oxime can be protected by any known method which does not adversely affect the remainder of the molecule. In particular, the trityl group is used.

Furthermore, if it is desired to obtain a product of the general formula (XIV) in which R contains a carboxyl or sulpho radical, it is preferable to treat the corresponding thiol with a reactive derivative of the acid of the general formula (VII).

If it is desired to obtain a product in which R contains a hydroxyl radical, it is preferable to protect this radical beforehand, for example by a trityl group.

It is advantageous only to remove these protective groups after the reaction of the thiolo-esters of the general formula (XIV) with the products of the general formula (XV) or (VIII).

a. If the product of the general formula (VII)a is used in the acid form, the condensation is in general carried out in an organic solvent such as dimethylformamide, acetonitrile, tetrahydrofurane, methylene chloride, chloroform or ethyl acetate, in the presence of a condensation agent such as a carbodiimide (for example dicyclohexylcarbodiimide), N,N′-carbonyldiimidazole or 2-ethoxy-1-ethoxycarbonyl-1,2-dihydroquinoline, at a temperature of between −20° and 40° C., after which, if appropriate, the protective groups are removed.

b. If a reactive derivative of the acid of the general formula (VII)a is used, it is possible to employ the anhydride, a mixed anhydride, an acid halide or a reactive ester of the general formula:

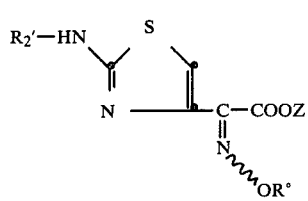

(IX)a in which R⁰ and R′₂ are defined as above and Z represents a radical such as succinimido, benzotriazol-1-yl, 4-nitrophenyl, 2,4-dinitrophenyl, pentachlorophenyl or phthalimido.

c. If it is desired to obtain a product of the general formula (XIV) in which R₂ is a hydrogen atom, it is also possible to employ an acid halide, for example the acid chloride, by reacting the hydrochloride of the acid chloride of the general formula (VII) with the thiol or with one of its salts.

If the anhydride, a mixed anhydride or an acid halide (all of which can be prepared in situ) is employed, the condensation is carried out in an inert organic solvent such as an ether (for example tetrahydrofurane or dioxane), a chlorinated solvent (for example chloroform or methylene chloride), an amide (for example dimethylformamide or dimethylacetamide) or a ketone (for example acetone), or in mixtures of the above solvents, in the presence of an acid acceptor, such as an epoxide (for example propylene oxide) or such as a nitrogen-containing organic base, such as pyridine, N-methylmorpholine or a trialkylamine (for example triethylamine), or in an aqueous-organic medium in the presence of an alkaline condensation agent such as sodium bicarbonate, the reactions being carried out at a temperature of between −40° and +40° C., and thereafter the protective group or groups are removed, if appropriate.

If a reactive ester of the general formula (IXa) is employed, the reaction is in general carried out in the presence of a trialkylamine (for example triethylamine) in an organic solvent such as dimethylformamide, at a temperature of between 0° and 60° C., after which, if appropriate, the protective group or groups are removed.

By way of example, the liberation of the various protected radicals can be carried out under the following conditions:

If it is desired to obtain a product of the general formula (XIV), in which $R_2$ is hydrogen, the tert.-butoxycarbonyl radical which protects the aminothiazole is removed by treatment in an anhydrous acid medium. In that case, the product is obtained either in the form of a salt or in the form of a solvate with the acid employed. Preferably, trifluoroacetic acid is used and the process is carried out at between 0° and 20° C. It is also possible to remove a protective benzyl radical from the aminothiazole by catalytic hydrogenation.

If it is desired to obtain a product of the general formula (XIV) in which the radical R contains a hydroxyl group and/or in which $R^o$ is a hydrogen atom, the trityl group or groups are removed by acidolysis with anhydrous trifluoroacetic acid. This removal is effected before, simultaneously with, or after the removal of the protective radical from the aminothiazole.

According to the invention, the thiolo-esters of the general formula (XIV) in which R contains a carbamyloxyalkyl or acyloxyalkyl radical (of which the acyl part is optionally substituted by a protected amino or alkylamino radical, or by a dialkylamino radical) can also be prepared from the corresponding thiolo-ester of the general formula (XIV), in which R contains a hydroxyalkyl radical and in which the radical $R_2$ and the radical $R^o$ are other than a hydrogen atom, by any known method for obtaining a carbamate or an ester from an alcohol without affecting the remainder of the molecule.

The reaction is in general carried out in accordance with the methods described for obtaining products of the general formula (I), containing such substituents, from a product of the general formula (I').

The products of the general formula (XVII) in which $R^o$ is other than a hydrogen atom, can be obtained by the action of an acid halide of the general formula:

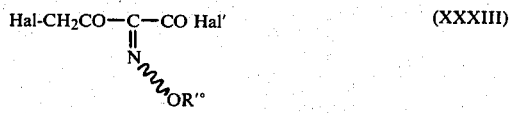 (XXXIII)

in which Hal is defined as above, $R'^o$ is defined like $R^o$ except for representing a hydrogen atom, and Hal' represents chlorine or bromine, on a 7-amino-cephalosporin of the general formula (VIII), followed, if appropriate, by the reduction of the sulphoxide obtained (if n=1) and by the removal of the protective radicals.

The reaction is in general carried out in an aqueous organic medium, for example water/ether (the ether being tetrahydrofurane or dioxane), water/ketone (the ketone being acetone) or water/chlorinated solvent (the chlorinated solvent being chloroform or methylene chloride), in the presence of an alkaline condensation agent, such as an alkali metal bicarbonate (for example sodium bicarbonate), at a temperature of between −40° and +40° C.

It is also possible to carry out the process by analogy with the method described in French Patent Application No. 2,399,418.

It is to be understood that if the radical R of the 7-amino-cephalosporin contains an amino or alkylamino radical, the latter is protected, and if the radical R contains a hydroxyl, carboxyl, formyl or acylalkyl radical, the latter is free or protected.

The protection, and removal, of the protective radicals are carried out under the conditions described above.

The products of the general formula (XXXIII) can be obtained by halogenation of a product of the general formula:

 (XXXIV)

in which $R'^o$ and Hal' are defined as above, by any method which is in itself known for the preparation of halogenated derivatives, which does not adversely affect the remainder of the molecule.

If it is desired to obtain a product of the general formula (XXXIII) in which Hal represents a bromine atom, the treatment with bromine is carried out in the presence of a catalyst, which may be an acid catalyt such as hydrobromic acid, hydrochloric acid or a sulphonic acid (methanesulphonic acid, anhydrous p-toluenesulphonic acid or benzenesulphuric acid), or in the presence of ultraviolet light.

If it is desired to obtain a product of the general formula (XXXIII) in which Hal is a chlorine atom, the treatment is carried out with chlorine in the presence of a catalyst such as those mentioned above, or with sulphuryl chloride.

The halogenation is carried out in an organic solvent such as the chlorinated solvents (for example methylene chloride, chloroform, carbon tetrachloride, dichloroethane or trichloroethane) or the ethers (for example ethyl ether or dioxane) or in a mixture of these solvents, at a temperature of between −40° C. and the reflux temperature of the reaction mixture.

The products of the general formula (XXXIV) can be prepared by the action of a halogenating agent on the acid, or on a salt or silyl ester of the acid, of the general formula:

 (XXXV)

in which $R'^o$ is defined as above, in the presence of a product of the general formula:

 (XIIIa)

in which $X_3$, $Y_3$ and $Z_3$ are identical or different and represent alkyl or phenyl radicals, or 2 of them, together with the atoms to which they are attached, form a heterocyclic ring with 5 or 6 ring members, which optionally contains another hetero-atom chosen from amongst oxygen, nitrogen or sulphur, or $X_3$ and $Y_3$ represent alkyl radicals such as those defined above and $Z_3$ represents a hydrogen atom or a dialkylamino radical.

The halogenating agent can be chosen from amongst phosphorus pentachloride, phosphorus oxychloride, oxalyl chloride or phosgene, if it is desired to obtain the acid chloride, or from amongst phosphorus pentabromide, phosphorus oxybromide or thionyl bromide if it is desired to obtain the acid bromide.

Amongst the products of the general formula (XIII)a it is advantageous to use dimethylacetamide, diethylacetamide, dimethylpropionamide, diethylpropionamide, dimethylformamide, N-acetylmorpholine, N-acetylpiperidine, N-acetyl-N-methylaniline, N-methylpyrrolidone or tetramethylurea.

If a salt of the acid of the general formula (XXXV) is employed, it is preferred to use an alkali metal salt or a tertiary amine salt (for example a triethylamine salt).

If a silyl ester is employed, it is advantageous to use a trimethylsilyl ester or tert-butyldimethylsilyl ester. This ester can advantageously be prepared by application of the method described by A. WISSNER et al., J. Org. Chem., 43 (20), 3972 (1978), or can be generated in situ.

The halogenation of the acid of the general formula (XXXV) is in general carried out in an organic solvent such as a chlorinated solvent (for example methylene chloride or chloroform), an ester (for example ethyl acetate), an aromatic hydrocarbon (for example toluene or xylene) or an ether (for example ethyl ether, isopropyl ether or tetrahydrofurane), at a temperature of between $-70°$ and $+30°$ C.

It is to be understood that the acids of the general formula (XXXV) in the syn-form lead to the acid halides in the syn-form and that the acids of the general formula (XXXV) in the anti-form lead to the acid halides of the general formula (XXXIV) in the anti-form.

The acids of the general formula (XXXV) can be obtained by acid hydrolysis or by saponification of an ester of the general formula:

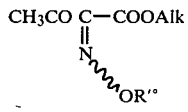

CH$_3$CO C—COOAlk   (XXXVI)
      ‖
      N
       OR'° in which $R'^o$ is defined as above and Alk represents an alkyl radical.

The reaction is in general carried out in the presence of sodium hydroxide in ethanol, at the reflux temperature of the reaction mixture.

The esters of the general formula (XXXVI) can be prepared by application of the method described by R. BUCOURT et al., Tetrahedron 34, 2233 (1978).

The products of the general formula (XVII) in which $R^o$ represents a hydrogen atom can be obtained from a product of the general formula:

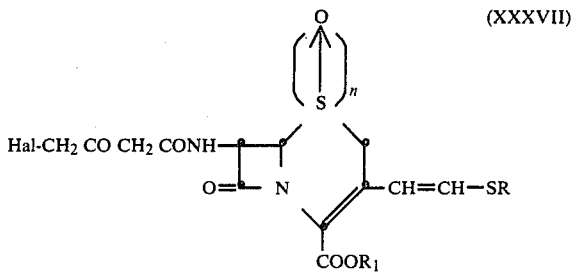

in which R, $R_1$, Hal and n are defined as above, by analogy with the method described in French Patent Application No. 2,399,418, followed, where appropriate, by reduction of the sulphoxide, and removal of the protective radicals.

It is to be understood that if the radical R of the product of the general formula (XXXVII) contains an amino, alkylamino or formyl radical, this radical is protected, and if the radical R contains a hydroxyl, carboxyl or acylalkyl substituent, this substituent is free or protected.

Where relevant, the reduction of the sulphoxide and the removal of the protective radicals are carried out under the conditions described above.

The products of the general formula (XXXVII) can be obtained from a 7-amino-cephalosporin of the general formula (VIII), by the action of a product of the general formula:

Hal-CH$_2$COCH$_2$-COHal   (XXXVIII)

in which Hal is defined as above (which compound may be formed in situ), using the conditions described above for condensing a product of the general formula (XXXIII) with a product of the general formula (VIII), or by analogy with the method described in French Patent Application No. 2,399,418.

The products of the general formula (XXXVIII) which can be prepared in situ are prepared as described in the above French application.

The isomers of the products of the general formulae (I), (VIII), (XI), (XIV), (XV), (XVII), (XIX), (XXI), (XXIII), (XXV), (XXVIII), (XXXII) or (XXXVII) can be separated by chromatography or crystallisation.

The novel products according to the invention can be converted to addition salts with acids. According to the processes of the present invention, the products can be obtained in the form of a trifluoroacetate, a solvate with formic acid or with water, or a para-toluenesulphonate. The products of the general formula (I), in which R is defined according to the present invention, which are obtained in the form of these salts can be liberated and converted to salts with other acids in accordance with the conventional methods.

The products according to the present invention can also be converted to metal salts or to addition salts with nitrogen-containing bases in accordance with methods which are in themselves known. These salts can be obtained by the action of a metal base (for example an alkali metal or alkaline earth metal base), or ammonia or of an amine on a product according to the invention in an appropriate solvent such as an alcohol, an ether or water, or by an exchange reaction with a salt of an organic acid. The salt formed precipitates, if necessary after concentrating its solution, and is separated off by filtration, decantation or lyophilisation.

As examples of pharmaceutically acceptable salts there may be mentioned the addition salts with inorganic acids (hydrochlorides, hydrobromides, sulphates, nitrates or phosphates) or with organic acids (succinates, fumarates, maleates and p-toluenesulphonates), the alkali metal (sodium, potassium or lithium) salts or alkaline earth metal (magnesium or calcium) salts, the ammonium salt and the salts with nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N′-dibenzylethylenediamine, diphenylenediamine, benzhydrylamine, quinine, choline, arginine, lysine, leucine or dibenzylamine).

The novel products according to the present invention can optionally be purified by physical methods such as crystallisation or chromatography.

The novel cephalosporin derivatives according to the present invention and their pharmaceutically acceptable salts exhibit particularly valuable anti-bacterial properties. They display a remarkable activity, in vitro and in vivo, against Gram-positive and Gram-negative germs.

In vitro, the products of the general formula (I) have proved active at a concentration of between 0.5 and 15 μg/cc against strains of staphylococci which are sensitive to penicillin G (Staphylococcus aureus Smith), at a concentration of between 1 and 30 μg/cc against strains of staphylococci resistant to penicillin G (*Staphylococcus aureus* MB 9), at a concentration of between 0.001 and 1 μg/cc against *Escherichia coli*, Monod strain, and at a concentration of between 0.06 and 30 μg/cc against *Klebsiella pneumoniae*. Furthermore, some of them have proved active at a concentration of between 0.01 and 30 μg/cc against *Proteus morganii* and at a concentration of between 0.1 and 30 μg/cc against *Enterobacter aerogenes*.

In vivo, the products of the general formula (I) have proved active against experimental infections of mice with *Staphylococcus aureus* Smith (sensitive to penicillin G) at a dose of between 0.2 and 15 mg/kg per day, administered subcutaneously, and against *Escherichia coli* (Monod strain) at doses of between 0.001 and 10 mg/kg per day, administered subcutaneously.

Furthermore, the $LD_{50}$ of the products of the general formula (I) is between 1.5 g/kg and doses greater than 2.5 g/kg, for subcutaneous administration to mice.

Compounds of particular interest are the products of the general formula (I)$_a$ in which:
the symbol R is chosen from amongst the following meanings:

(1) methyl, L-2-amino-2-carboxyethyl or phenyl, (2) pyrid-2-yl or pyrid-2-yl-N-oxide, (3) pyrimidin-2-yl or pyridazin-3-yl substituted in the 6-position by a methyl or acetamido radical, or the N-oxides of these, (4) 5,6-dioxo-1,4,5,6-tetrahydro-1,2,4-triazin-3-yl substituted in the 4-position by (a) an alkyl radical containing 1 to 3 carbon atoms, an alkyl radical containing 1 or 2 carbon atoms substituted by an alkoxy, alkylthio, phenyl, formyl, carbamyl, alkylcarbamyl, dialkylcarbamyl, alkoxycarbonyl or thiazolidin-2-yl radical, (b) an allyl or 2,3-dihydroxypropyl radical, (c) an alkyl radical containing 2 or 3 carbon atoms, substituted by hydroxyl, carbamyloxy, acyloxy (which is unsubstituted or substituted by amino), amino, alkylsulphonylamino, acylamino (which is unsubstituted or substituted by amino), alkoxycarbonylamino, ureido or alkylureido, (d) a radical of the general formula (II) in which alk is alkylene containing 1 or 2 carbon atoms, $X^α$ and $Y^α$ represent oxygen atoms, $R^α$ represents alkyl radicals and $R^β$ represents a hydrogen atom, (e) an alkyl radical containing 1 to 3 carbon atoms, substituted by an alkoxyimino or hydroxyimino radical, (4′) 1,3,4-triazol-5-yl or 2-alkoxycarbonyl-1,3,4-triazol-5-yl substituted in the 1-position by a radical of the general formula (II) such as defined above or by a formylalkyl or 2,3-dihydroxypropyl radical, (5) 1,4-dialkyl-5,6-dioxo-1,4,5,6-tetrahydro-1,2,4-triazin-3-yl; 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1-alkyl-3-alkoxycarbonyl-1,2,4-triazol-5-yl.

(7) (a) 1,3,4-thiadiazol-5-yl which is unsubstituted or substituted by an alkyl, amino, aminoalkyl, alkylaminoalkyl, dialkylaminoalkyl or acylaminoalkyl radical, (b) 1,2,4-thiadiazol-5-yl substituted by an alkyl radical, (8) (a) 1,3,4-oxadiazol-5-yl substituted by alkyl or phenyl, (b) 4-alkyl-oxazol-2-yl, (9) tetrazol-5-yl substituted in the 1-position by (a) an alkyl radical which is unsubstituted or substituted by formyl, (b) an alkyl radical containing 2 or 3 carbon atoms substituted by hydroxyl, amino, alkylamino, dialkylamino or acylamino or (c) a radical of the general formula (II) as defined above;

the symbol $R^o$ represents a hydrogen atom or a methyl, vinyl or cyanomethyl radical, and the symbol R′ represents a hydrogen atom, it being understood that the alkyl or acyl portions or radicals mentioned above contain, unless stated otherwise, 1 or 2 carbon atoms.

Amongst these products, substances which are more especially active are the products of the general formula (Ia) in which:

$R^o$ is methyl, vinyl or cyanomethyl,

R′ is hydrogen and

R is chosen from amongst (1) pyrid-2-yl and its N-oxide (2) 6-methyl-pyridazin-3-yl-N-oxide (3) 5,6-dioxo-1,4,5,6-tetrahydro-1,2,4-triazin-3-yl substituted in the 4-position by an alkyl radical containing 1 or 2 carbon atoms, substituted by an alkoxy, alkylthio, phenyl or formyl radical, an allyl or 2,3-dihydroxypropyl radical, an alkyl radical containing 2 or 3 carbon atoms, substituted by hydroxyl, carbamyloxy, acyloxy (which is unsubstituted or substituted by amino), alkylsulphonylamino, acylamino (which is unsubstituted or substituted by amino), alkoxycarbonylamino or alkylureido, or an alkyl radical containing 1 to 3 carbon atoms, substituted by an alkoxyimino or hydroxyimino radical (4) 2-alkoxycarbonyl-1,3,4-triazol-5-yl substituted in the 1-position by a dimethoxyalkyl radical, (5) 1,4-dialkyl-5,6-dioxo-1,4,5,6-tetrahydro-1,2,4-triazin-3-yl, (6) 1-alkyl-3-alkoxycarbonyl-1,2,4-triazol-5-yl, (7) 1,3,4-thiadiazol-5-yl substituted by an alkyl, dialkylaminoalkyl or acylaminoalkyl radical, or 1,2,4-thiadiazol-5-yl substituted by an alkyl radical, (8) phenyl-1,3,4-oxadiazol-5-yl and 4-alkyl-oxazol-2-yl, (9) tetrazol-5-yl substituted in the 1-position by
an alkyl radical,
an alkyl radical containing 2 or 3 carbon atoms substituted by hydroxyl, dialkylamino or acylamino or
a dimethoxyalkyl radical, it being understood that the alkyl or acyl radicals and portions mentioned above contain (unless mentioned otherwise) 1 or 2 carbon atoms.

Amongst these products, the preferred products are the products of the general formula (Ia) for which
$R^o$ is methyl,
R' is hydrogen and
R is chosen from amongst the following meanings:
(1) pyrid-2-yl-N-oxide,
(2) 6-methyl-pyridazin-3-yl-1-oxide,
(3) 5,6-dioxo-1,4,5,6-tetrahydro-1,2,4-triazin-3-yl substituted in the 4-position by
(a) an alkyl radical containing 1 or 2 carbon atoms, substituted by alkoxy, alkylthio or formyl,
(b) an allyl or 2,3-dihydroxypropyl radical or
(c) an alkyl radical containing 2 or 3 carbon atoms, substituted by hydroxyl, carbamyloxy, acyloxy or acylamino (of which the acyl portions are unsubstituted or substituted by amino), alkylsulphonylamino or alkylureido,
(4) 1-alkyl-3-alkoxycarbonyl-1,2,4-triazol-5-yl,
(5) 1,3,4-thiadiazol-5-yl substituted by dialkylaminoalkyl or acylaminoalkyl or
(6) tetrazol-5-yl substituted in the 1-position by
(a) an alkyl radical or
(b) an alkyl radical containing 2 or 3 carbon atoms substituted by hydroxyl or acylamino, it being understood that the alkyl or acyl radicals and portions mentioned above contain (unless stated otherwise) 1 or 2 carbon atoms.

The following products, in particular, are of interest:
7-[2-(2-amino-thiazol-4-yl)-2-methoxyiminoacetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-aza-bicyclo[4.2.0]oct-2-ene, syn-isomer, E-form, 7-[2-(2-amino-thiazol-4-yl)-2-methoxyiminoacetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]oct-2-ene, synisomer, E-form, 7-[2-(2-amino-thiazol-4-yl)-2-methoxyiminoacetamido]-2-carboxy-3-{2-[5,6-dioxo-4-(formylmethyl)-1,4,5,6-tetrahydro-1,2,4-triazin-3-yl]-thiovinyl}-8-oxo-5-thia-1-aza-bicyclo[4.2.0]oct-2-ene, syn-isomer, E-form, 3-{2-[4-(2-acetamido-ethyl)-5,6-dioxo-1,4,5,6-tetrahydro-1,2,4-triazin-3-yl]-thiovinyl}-7-[2-(2-aminothiazol-4-yl)-2-methoxyimino-acetamido]-2-carboxy-8-oxo-5-thia-1-aza-bicyclo[4.2.0]oct-2-ene, syn-isomer, E-form,
and
7-[2-(2-amino-thiazol-4-yl)-2-methoxyimino-acetamido]-2-carboxy-3-{2-[4-(2-methoxyethyl)-5,6-dioxo-1,4,5,6-tetrahydro-1,2,4-triazin-3-yl]-thiovinyl}-8-oxo-5-thia-1-aza-bicyclo[4.2.0]oct-2-ene, syn-isomer, E-form.

The examples which follow and are given without implying a limitation, show how the invention can be put into practice.

In these examples, the products are described in accordance with the Chemical Abstracts nomenclature. It is to be understood that all the cephalosporin derivatives which are mentioned exhibit the stereochemistry indicated by the partial general formula

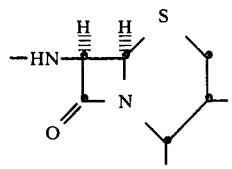

EXAMPLE 1

A mixture 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.-0]oct-2-ene (syn-isomer, mixture of the E- and Z-forms) (8.03 g), dimethylformamide (80 cc), methylmercaptan (1.59 g) and N-ethyl-N,N-diisopropylamine (1.53 cc) is heated at 40° C. for 5 hours in an autoclave. The mixture is diluted with ethyl acetate (500 cc) washed with water (3×250 cc), 0.1 N hydrochloric acid (100 cc), a 1% strength sodium bicarbonate solution (100 cc) and a half-saturated sodium chloride solution (2×200 cc), dried over sodium sulphate and concentrated to dryness under reduced pressure (20 mm Hg) at 20° C.

The residue is dissolved in a 50:50 (by volume) mixture of cyclohexane and ethyl acetate (100 cc) and the solution is chromatographed over a column of Merck silica gel (0.04–0.06 mm) (300 g) (column diameter: 6 cm, height: 36 cm). Elution is carried out with a 50:50 (by volume) mixture of cyclohexane and ethyl acetate (8 liters) under a pressure of 40 kPa, and 125 cc fractions are collected. Fractions 25 to 57 are combined and evaporated to dryness under reduced pressure (20 mm Hg) at 20° C. 2-Benzhydryloxycarbonyl-7-[2-methoxyimino-2-(2-tritylamino-thiazol-4-yl)-acetamido]-3-(2-methylthiovinyl)-8-oxo-5-oxide-5-thia-1-aza-bicyclo[4.2.0]oct-2-ene (syn isomer, mixture of the E- and Z-forms) (3.7 g) is collected in the form of a cream-coloured froth.

Infrared spectrum (CHBr$_3$): characteristic bands (cm$^{-1}$) at 3380, 1800, 1720, 1680, 1515, 1370, 1205, 1045, 835, 750 and 740.

Proton nuclear magnetic resonance spectrum (350 MHz, CDCl$_3$, δ in ppm, J in Hz): 2.17 (s, 3H, —CH$_3$ E-form); 2.35 (s, 3H, —CH$_3$ Z-form); 3.23 and 3.98 (AB, J=18, 2H, —SCH$_2$— E-form); 3.44 and 4.3 (AB, J=18, 2H, —SCH$_2$— Z-form); 4.09 (s, 3H, —OCH$_3$); 4.58 (d, J=9, 1H, H in the 6-position); 6.12 (dd, J=4 and 9, 1H, H in the 7-position); 6.17 (d, J=10, 1H, —C<u>H</u>=CH—S—CH$_3$, Z-form); 6.65 (d, J=15, 1H, —C<u>H</u>=CH—S—CH$_3$, E-form); 6.88 (d, J=10, 1H, =CH—S—CH$_3$, Z-form); 7.15 (d, J=15, 1H, =C<u>H</u>—S—CH$_3$, E-form); 6.72 (s, 1H, H in the 5-position of the thiazole); 0.98 (s, 1H, —COOCH); 7.07 (s broad, 1H, (C$_6$H$_5$)$_3$CN<u>H</u>—).

A solution of 2-benzhydryloxycarbonyl-7-[2-methoxyimino-2-(2-tritylamino-thiazol-4-yl)-acetamido]-3-(2-methylthiovinyl)-8-oxo-5-oxide-5-thia-1-aza-bicyclo[4.2.0]-oct-2-ene (syn isomer, mixture of E- and Z-forms) (2.30 g) in methylene chloride (25 cc) and dimethylacetamide (1.04 cc) is treated with phosphorus trichloride (0.46 cc) at −10° C. for 30 minutes. The mixture is diluted with ethyl acetate (500 cc), washed with a 2% strength sodium bicarbonate solution (2×100 cc) and a half-saturated sodium chloride solution (2×100 cc), dried over sodium sulphate, filtered and concentrated to dryness under reduced pressure (20 mm Hg) at 20° C.

The residue is dissolved in methylene chloride (10 cc) and the solution is chromatographed on a column of Merck silica gel (0.04–0.06 mm) (150 g) (column diameter: 4 cm, height: 20 cm). Elution is carried out with a 60:40 (by volume) mixture of cyclohexane and ethyl acetate (2 liters) under a pressure of 40 kPa, and 125 cc fractions are collected. Fractions 4 to 8 are concentrated under reduced pressure (20 mm Hg) at 20° C.; 2-benzhydryloxycarbonyl-7-[2-methoxyimino-2-(2-tritylaminothiazol-4-yl)-acetamido]-3-(2-methylthiovinyl)-8-oxo-5-thia-1-aza-bicyclo[4.2.0]oct-2-ene (syn isomer, mixture of the E- and Z-forms) (1.32 g) is obtained in the form of a cream-coloured froth.

Infra-red spectrum (CHBr$_3$): characteristic bands (cm$^{-1}$) at 3390, 1780, 1715, 1680, 1515, 1370, 1200, 1050, 1035, 750 and 740.

Proton nuclear magnetic resonance spectrum (350 MHz, CDCl$_3$, δ in ppm, J in Hz): 2.18 (s, 3H,—CH$_3$ E-form); 2.31 (s, 3H, —CH$_3$ Z-form); 3.44 (AB, J=18, 2H, —SCH$_2$— E-form); 3.80 (AB, J=18, 2H, —SCH$_2$— Z-form); 4.08 (s, 3H, —OCH$_3$); 5.06 (d, J=4, 1H, H in the 6-position); 5.80 (dd, J=4 and 9, 1H, H in the 7-position E-form); 5.90 (dd, J=4 and 9, 1H, H in the 7-position, Z-form); 6.14 (d, J=11, 1H, —CH=CHS— Z-form); 6.64 (d, J=16, 1H, —CH=CHS—, E-form); 6.70 (d, J=11, 1H, =CHS—, Z-form); 6.79 (s, 1H, H in the 5-position of the thiazole);

6.93 (s, 1H, —COOCH—);

6.98 (d, J=16, 1H, =CHS—, E-form).

2-Benzhydryloxycarbonyl-7-[2-methoxyimino-(2-tritylamino-thiazol-4-yl)-acetamido]-3-(2-methylthiovinyl)-8-oxo-5-thia-1-aza-bicyclo[4.2.0]oct-2-ene (syn isomer, mixture of the E- and Z-forms) (1.26 g) is dissolved in formic acid (35 cc), water (13 cc) is added and the mixture is heated for 15 minutes at 50° C. It is allowed to cool and is filtered and concentrated to dryness under reduced pressure (20 mm Hg at 20° C.). The residue is triturated in diethyl ether (20 cc), filtered off, washed with ether (20 cc) and dried. 7-[2-(2-Aminothiazol-4-yl)-2-methoxyimino-acetamido]-2-carboxy-3-(2-methylthiovinyl)-8-oxo-5-thia-1-aza-bicyclo-[4.2.0]oct-2-ene (syn isomer, mixture of the E- and Z-forms) (0.63 g) is obtained as the solvate with formic acid, in the form of a cream-coloured powder.

Rf=0.34 and 0.48 [silica gel chromatographic plate, solvent: ethyl acetate/acetone/formic acid/water, 60:20:1:1 (by volume)].

Infra-red spectrum (KBr): characteristic bands (cm$^{-1}$) at 3320, 1770, 1675, 1530 and 1035.

Proton nuclear magnetic resonance spectrum (350 MHz, DMSO d$_6$, δ in ppm, J in Hz) E-form: 2.34 (s, 3H, —SCH$_3$); 3.61 and 3.77 (AB, J=18, 2H, —SCH$_2$—); 3.86 (s, 3H, —OCH$_3$); 5.14 (d, J=4, 1H, H in the 6-position); 5.62 (dd, J=4 and 9, 1H, H in the 7-position); 6.77 (s, 1H, H in the 5-position of the thiazole); 6.85 (d, J=16, 1H, —CH=CH—S—); 7.04 (d, J=16, 1H, =CH—S—); 9.57 (d, J=9, 1H, —CONH—) Z-form: in particular, the following signals are observed: 2.25 (s, 3H, —SCH$_3$), 6.74 (d, J=13, 1H, —CH=CH—S—CH$_3$) and 6.83 (d, J=13, 1H, =CHS—).

2-Benzhydryloxycarbonyl-7-[2-methoxyimino-2-(2-tritylamino-thiazol-4-yl)-acetamido]-8-oxo-5-oxide-3-(2-tosyloxy-vinyl)-5-thia-1-aza-bicyclo[4.2.0]oct-2-ene (syn isomer, a mixture of the E- and Z-forms) can be prepared as follows:

bis-(Dimethylamino)-ethoxymethane (0.91 g) is added to a solution of 2-benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene (syn isomer) (2.5 g) in dimethylformamide (50 cc), which has been heated to 80° C. The solution becomes brownish green. It is left at 80° C. for 20 minutes and then cooled rapidly and poured into ethyl acetate (200 cc) and the mixture is washed with water (three×80 cc) and with a saturated sodium chloride solution (50 cc). The ethyl acetate phase is then stirred at 20° C. for one hour in the presence of 1 N hydrochloric acid (37.5 cc). The aqueous phase is removed, and the organic phase is washed with a saturated sodium bicarbonate solution (20 cc) and then with a saturated sodium chloride solution (20 cc). The organic phase is dried over magnesium sulphate, filtered in the presence of decolorising charcoal and then concentrated to dryness under reduced pressure (20 mm Hg) at 40° C. The residue is dissolved in anhydrous pyridine (10 cc). The solution is cooled to 5° C. in an ice bath, tosyl chloride (0.87 g) is added and the reaction mixture is allowed to return to 20° C. After 1½ hours, the mixture is poured onto iced water (200 cc). The precipitated formed is filtered off, washed with water (2×20 cc) and then dissolved in ethyl acetate (50 cc). This solution is washed with a saturated sodium bicarbonate solution (20 cc) and a saturated sodium chloride solution (20 cc), dried over magnesium sulphate, filtered in the presence of decolorising charcoal and concentrated to dryness under reduced pressure (20 mm Hg) at 40° C. The residue is dissolved in methylene chloride (13 cc) and the solution obtained is cooled to −10° C. in an ice/methanol bath. A solution of 85% pure m-chloroperbenzoic acid (0.226 g) in methylene chloride (10 cc) is added in the course of 15 minutes. The reaction mixture is left at between −10° C. and +5° C. for 20 minutes and is then washed twice with a saturated sodium bicarbonate solution (20 cc), dried over magnesium sulphate, filtered in the presence of decolorising charcoal and concentrated to dryness under reduced pressure (20 mm Hg) at 40° C.

The residue is chromatographed over a column (diameter: 1.7 cm, height: 21 cm) containing silica gel (26 g). Elution is carried out with ethyl acetate/cyclohexane mixtures (120, 240, 200 and 120 cc, with respective compositions of 20:80, 30:70, 40:60 and 60:40 by volume), and 20 cc fractions of eluate are collected. Fractions 17 to 34 are evaporated and 2-benzhydryloxycarbonyl-7-[2-methoxyimino-2-(2-tritylaminothiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (0.88 g) is isolated.

2-Benzhydryloxycarbonyl-3-methyl-8-oxo-7-[2-methoxyimino-2-(2-tritylamino-thiazol-4-yl)-acetamido]-5-thia-1-aza-bicyclo[4.2.0]-oct-2-ene, syn isomer, can be prepared as follows:

A solution of the anhydride of 2-(2-tritylamino-thiazol-4-yl)-2-methoxyimino-acetic acid (syn isomer)(7.2 g) in methylene chloride (22.5 cc) is added in a single shot to a solution of 7-amino-2-benzhydryloxycarbonyl-3-methyl-8-oxo-5-thia-1-aza-bicyclo[4.2.0]oct-2-ene (3.15 g) in methylene chloride (31.5 cc). The temperature rises from 8° to 14° C. The mixture is kept stirred for one hour 15 minutes, during which the temperature returns to 20° C., and is then washed with 0.5 N hydrochloric acid (10 cc), distilled water (10 cc) and a saturated sodium bicarbonate solution (20 cc). The insoluble matter formed is filtered off, and the organic phase is washed again with distilled water (two×20 cc), dried over magnesium sulphate, filtered and concentrated to dryness under reduced pressure (20 mm Hg) at 40° C. The residue is chromatographed over a column (diameter: 3 cm, height: 33 cm) containing silica gel (125 g), and elution is carried out with ethyl acetate/cyclohexane mixtures (1.2 and 1 liter, of respective composition 20:80 and 40:60 by volume), 50 cc fractions of eluate being collected. Fractions 31 to 44 are evaporated and 2-benzhydryloxycarbonyl-3-methyl-8-oxo-7-[2-methoxyimino-2-(2-tritylamino-thiazol-4-yl)-acetamido]-5-thia-1-aza-bicyclo[4.2.0]-oct-2-ene, syn isomer (2.8 g) is obtained in the form of a pale yellow solid.

7-Amino-2-benzhydryloxycarbonyl-3-methyl-8-oxo-5-thia-1-aza-bicyclo[4.2.0]oct-2-ene can be prepared in accordance with the method described in Netherlands Patent Application No. 73/03,263.

EXAMPLE 2

Thiophenol (0.90 cc), followed by N-ethyl-N,N-diisopropylamine (1.53 cc) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (8.03 g) in dimethylformamide (80 cc) cooled to +2° C., under nitrogen. The mixture is stirred for 2 hours at 20° C. and is then diluted with ethyl acetate (320 cc), washed with water (3×200 cc), 0.1 N hydrochloric acid (100 cc), a 5% strength sodium bicarbonate solution (150 cc) and a saturated sodium chloride solution (2×150 cc), dried over sodium sulphate and concentrated to dryness under reduced pressure (20 mm Hg) at 20° C. The product is dissolved in methylene chloride (35 cc) and chromatographed over a column (diameter: 6 cm, height: 30 cm) of Merck silica gel (0.04–0.06 mm) (250 g). Elution is carried out with a 55:45 (by volume) mixture of cyclohexane and ethyl acetate (4 liters) under a pressure of 40 kPa, 100 cc fractions being collected. Fractions 12 to 32 are evaporated under reduced pressure (20 mm Hg) at 20° C. and 2-benzhydryloxycarbonyl-7-[2-methoxyimino2-(2-tritylamino-thiazol-4-yl)-acetamido]-8-oxo-5-oxide3-(2-phenylthiovinyl)-5-thia-1-aza-bicyclo[4.2.0]oct-2-ene (syn isomer, mixture of the E- and Z-forms) (4.8 g) is obtained in the form of a yellow froth.

Infra-red spectrum (CHBr$_3$): characteristic bands (cm$^{-1}$) at 3380, 2820, 1795, 1720, 1680, 1580, 1475, 1445 and 1440.

Proton nuclear magnetic resonance spectrum (350 MHz, CDCl$_3$, δ in ppm, J in Hz): 3.93 and 3.13 (AB, J=19, 2H, —SCH$_2$—, E-form); 4.32 and 5.0 (AB, J=19, 2H, —SCH$_2$—, Z-form); 4.05 (s, 3H, —OCH$_3$, E-form); 4.07 (s, 3H, —OCH$_3$, Z-form); 4.51 (d, 1H, J=4, H in the 6-position, E-form); 4.56 (d, 1H, J=4, H in the 6-position, Z-form); 6.10 (dd, J=4 and 9, 1H, H in the 7-position, E-form); 6.14 (dd, J=4 and 9, 1H, H in the 7-position, Z-form); 6.41 (d, J=11, 1H, —CH=CH—S—, Z-form); 6.6 (d, J=16, 1H, CH=CH—S, E-form); 6.71 (s, 1H, H in the 5-position of the thiazole, E-form); 6.72 (s, 1H, H in the 5-position of the thiazole, Z-form); 6.93 (s, CO$_2$CH); 7.09 (s, —NH— thiazole).

Phosphorus trichloride (0.98 cc) is added to a solution, cooled to −10° C., of 2-benzhydryloxycarbonyl7-[2-methoxyimino-2-(2-tritylamino-thiazol-4-yl)-acetamido]-8-oxo-5-oxide-3-(2-phenylthiovinyl)-5-thia-1-aza-bicyclo[4.2.0]oct-2-ene (syn isomer, mixture of the E- and Z-forms) (4.8 g) in methylene chloride (51 cc) and dimethylacetamide (2.02 cc). The mixture is stirred for 1 hour at −10° C. and is then taken up in ethyl acetate (300 cc), and this solution is washed with a 5% strength sodium bicarbonate solution (2×150 cc) and a saturated sodium chloride solution (150 cc), dried over sodium sulphate and concentrated to dryness under reduced pressure (20 mm Hg at 20° C.). The product is dissolved in methylene chloride (30 cc) and the solution is chromatographed over a column (column diameter: 5 cm, height: 30 cm) containing Merck silica gel (0.02–0.06 mm) (250 g). Elution is carried out with a 65:35 (by volume) mixture of cyclohexane and ethyl acetate (2 liters) under a pressure of 0.4 bar, 100 cc fractions being collected. Fractions 10 to 16 are evaporated; 2-benzhydryloxycarbonyl-7-[2-methoxyimino-2-(2-tritylamino-thiazol-4-yl)-acetamido]-8-oxo-3-(2-phenylthiovinyl)-5-thia-1-aza-bicyclo[4.2.0]oct-2-ene (syn isomer, mixture of the E- and Z-forms) (2.6 g) is obtained in the form of a cream-coloured froth.

Proton nuclear magnetic resonance spectrum (350 MHz, CDCl$_3$, δ in ppm, J in Hz): 3.42 and 3.52 (AB, J=19, 2H, —SCH$_2$—, E-form); 3.50 and 3.88 (AB, J=19, 2H, —SCH$_2$—, Z-form); 4.07 (s, 3H, —OCH$_3$, E-form); 4.09 (s, 3H, —OCH$_3$, Z-form); 5.07 (d, J=4, 1H, H in the 6-position, E-form); 5.10 (d, J=4, 1H, H in the 6-position, Z-form); 5.87 (dd, J=4 and 9, 1H, H in the 7-position, E-form); 5.93 (dd, J=4 and 9, 1H, H in the 7-position Z-form); 6.41 (d, J=11, 1H, —CH=CH—S—, Z-form); 6.70 (d, J=16, 1H, —CH=CH—S—, E-form); 6.76 (s, H in the 5-position of the thiazole);

6.95 (s, —CO$_2$CH—);

6.95 (d, J=11, 1H, —CH=CH—S—, Z-form); 7.22 (d, J=16, 1H, —CH=CH—S, E-form); 7.01 (s broad, —NH— thiazole).

2-Benzhydryloxycarbonyl-7-[2-methoxyimino-2-(2-tritylamino-thiazol-4-yl)-acetamido]-8-oxo-3-(2-phenylthiovinyl)-5-thia-1-aza-bicyclo[4.2.0]oct-2-ene (syn isomer, mixture of the E- and Z-forms) (2.6 g) is dissolved in formic acid (40 cc) and the solution is diluted with water (12.5 cc) and heated at 50° C. for 20 minutes. It is then cooled, the insoluble matter is removed by filtration and the filtrate is evaporated to dryness at 20° C. under reduced pressure (0.05 mm Hg). The residue is triturated in ethyl ether (50 cc), filtered off, washed with ether (50 cc) and dried. 7-[2-(2-aminothiazol-4-yl)-2-methoxyimino-acetamido]-2-carboxy-3-(2-phenylthiovinyl)-8-oxo-5-thia-1-aza-bicyclo[4.2.0]oct-2-ene (syn isomer, mixture of the E- and Z-forms) (1.3 g) is obtained as a solvate with formic acid in the form of a yellow powder.

Infra-red spectrum (KBr): characteristic bands (cm$^{-1}$) at 3320, 1775, 1680, 1530, 1380, 1045, 945, 745 and 690.

Proton nuclear magnetic resonance spectrum (DMSO d$_6$, 350 MHz, δ in ppm, J in Hz): 3.65 and 3.94 (AB, J=18, 2H, —SCH$_2$—, E-form); 3.84 (s, 3H, —OCH$_3$); 5.17 (d, J=4, 1H, H in the 6-position, E-form); 5.22 (d, J=4, 1H, H in the 6-position, Z-form); 5.73 (dd, J=4 and 9, 1H, H in the 7-position, E-form); 6.61 (d, J=11, 1H, —C$\underline{H}$=CH—S—, Z-form); 6.80 (d, J=11, 1H, —CH=C$\underline{H}$—S—, Z-form); 6.98 (d, J=15, 1H, —C$\underline{H}$=CH—S—, E-form); 7.06 (d, J=15, 1H, —CH=C$\underline{H}$—S—, E-form); 6.74 (s, H in the 5-position of the thiazole), 7.18 (broad signal, —NH$_3$+ and —CO$_2$H); 8.11 (s, $\underline{H}$CO$_2$−); 9.58 (d, J=9, 1H, —CON$\underline{H}$—).

EXAMPLE 3

A solution of the solvate of 7-[2-(2-aminothiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) with formic acid (0.1 g) and of thiophenol (0.02 g) in anhydrous N,N-dimethylformamide (1 cc) is cooled to 0° C. A solution of N,N-diisopropyl-N-ethylamine (0.069 g) in N,N-dimethylformamide (3 cc) is added dropwise. The reaction mixture is warmed up again and stirred for 1 hour at 25° C. Evaporation of the solvent under reduced pressure (10 mm Hg) at 30° C. gives a residue (0.19 g), of which the chromatographic examination [silica gel chromatographic plate; eluant: a 50:20:10:10 (by volume) mixture of ethyl acetate/acetone/water/acetic acid] shows the formation of 7-[2-(2-amino-thiazol-4-yl)-2-methoxyiminoacetamido]-2-carboxy-8-oxo-3-(2-phenylthiovinyl)-5-thia1-aza-bicyclo[4.2.0]oct-2-ene (syn isomer, E-form): Rf=0.62.

The solvate of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) with formic acid can be obtained as follows:

2-Benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (1.5 g) is dissolved in a mixture of formic acid (30 cc) and distilled water (10 cc). The solution is heated at 50° C. for 30 minutes. After it has cooled, the precipitate is filtered off and the filtrate is concentrated to dryness under reduced pressure (10 mm Hg) at 30° C. The residue is triturated with diethyl ether (50 cc). The solidified product is filtered off, washed with diethyl ether (two×25 cc) and then dried under reduced pressure (5 mm Hg) at 25° C. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.75 g) is obtained as a solvate with formic acid.

Rf=0.57; silica gel chromatographic plate; eluant: a 50:20:10:10 mixture (by volume) of ethyl acetate/acetone/water/acetic acid.

IR spectrum (KBr): characteristic bands (cm$^{-1}$) at 3400, 3340, 3000, 2820, 2200, 1775, 1720, 1670, 1630, 1370, 1190, 1165 and 1070.

Proton nuclear magnetic resonance spectrum (350 MHz, DMSO d$_6$, δ in ppm, J in Hz): 2.42 (s, 3H, —CH$_3$ tosyl); 3.55 and 3.78 (AB, J=19, 2H, —SCH$_2$—); 3.83 (s, 3H, —OCH$_3$); 5.14 (d, J=4, 1H, H in the 6-position); 5.75 (dd, J=4 and 9, 1H, H in the 7-position); 6.65 (d, J=12, 1H, —C$\underline{H}$=CH—OSO$_2$—); 6.73 (s, 1H, H in the 5-position of the thiazole); 7.18 (s broad, —NH$_3$+); 9.58 (d, J=9, 1H, —CON$\underline{H}$—).

2-Benzhydryloxycarbonyl-7-[2-methoxyimino-2-(2-tritylamino-thiazol-4-yl)-acetamido]-3-(2-tosyloxyvinyl)8-oxo-5-thia-1-aza-bicyclo[4.2.]-oct-2-ene (syn isomer, E-form) can be prepared as follows:

2-Benzhydryloxycarbonyl-7-[2-methoxyimino-2-(2-tritylamino-thiazol-4-yl)-acetamido]-3-(2-tosyloxyvinyl)8-oxo-5-oxide-5-thia-1-aza-bicyclo[4.2.0]oct-2-ene (syn isomer, E-form) (3 g) is dissolved in methylene chloride (30 cc); N,N-dimethylacetamide (1.2 cc) is added. The solution is placed under an atmosphere of dry nitrogen, cooled to −10° C. and treated with phosphorus trichloride (0.9 g). The reaction mixture is stirred for 90 minutes at between −10° and −5° C., then diluted with ethyl acetate (250 cc) and washed with an aqueous saturated sodium bicarbonate solution (150 cc) and a saturated sodium chloride solution (two×100 cc). After drying over magnesium sulphate, and filtering, the organic solution is concentrated to dryness under reduced pressure (20 mm Hg) at 30° C.; the residue is taken up in methylene chloride (20 cc) and the solution is chromatographed over a column (height: 25 cm, diameter: 5 cm) containing silica (0.04–0.063 mm) (240 g). Elution is carried out with a 60:40 (by volume) mixture of cyclohexane and ethyl acetate (2 liters), 100 cc fractions being collected. Fractions 8 to 13 are concentrated to dryness under reduced pressure (20 mm Hg) at 30° C. 2-Benzhydryloxycarbonyl-7-[2-methoxyimino2-(2-tritylamino-thiazol-4-yl)-acetamido]-3-(2-tosyloxyvinyl)-8-oxo-5-thia-1-aza-bicyclo[4.2.0]oct-2-ene (syn isomer, E-form) (1.7 g) is obtained.

Rf=0.52; silica gel chromatographic plate; eluant: 50:50 (by volume) cyclohexane/ethyl acetate.

Infra-red spectrum (CHBr$_3$): characteristic bands (cm$^{-1}$) at 3400, 1790, 1725, 1685, 1520, 1375, 1190, 1180, 1075, 1050, 755 and 740.

Proton nuclear magnetic resonance spectrum (350 MHz, CDCl$_3$, δ in ppm, J in Hz): 2.42 (s, 3H, —CH$_3$, tosyl); 3.33 and 3.42 (AB, J=19, 2H, —SCH$_2$—); 4.07 (s, 3H, —OCH$_3$); 5.03 (d, J=4, 1H, H in the 6-position); 5.87 (dd, J=4 and 9, 1H, H in the 7-position); 6.71 (s, 1H, H in the 5-position of the thiazole);

6.87 (s, 1H, —CO$_2$C$\underline{H}$—);

6.87 (d, J=10, 1H, —C$\underline{H}$=CH—OSO$_2$—); 7.0 (s broad, 1H, —NH— thiazole); 7.78 (d, J=9, 1H, —CON$\underline{H}$—).

2-Benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form and Z-form) can be prepared as follows:

Dicyclohexylcarbodiimide (1.85 g) is added, with stirring, to a solution, cooled to +4° C., of syn-2-methoxyimino-2-(2-tritylamino-triazol-4-yl)-acetic acid (7.97 g) in methylene chloride (100 cc). The solution is stirred for 40 minutes at +4° C. and then for 30 minutes at 20° C., and is filtered.

To this filtered solution, cooled at −30° C., is added rapidly a solution of crude 7-amino-2-benzhydryloxycarbonyl-8-oxo-5-oxide-3-(2-tosyloxyvinyl)-5-thia-1-aza-bicyclo[4.2.0]oct-2-ene (mixture of the E- and Z-forms) (3.47 g) in methylene chloride (30 cc) containing triethylamine (0.84 cc). The cooling bath is removed at the end of the addition, and the reaction mixture is stirred for 1 hour 50 minutes at 20° C. It is then concentrated to dryness at 20° C. under reduced pressure (20 mm Hg) and the residue is taken up in ethyl acetate (250 cc). The organic phase is washed with water (3×100 cc), 0.05 N hydrochloric acid (100 cc), a 1% strength sodium bicarbonate solution (100 cc) and a half-saturated aqueous sodium chloride solution (2×100 cc), dried over sodium sulphate, filtered and concentrated to dryness under reduced pressure (20 mm Hg at 20° C.). The residue is taken up in ethyl acetate (20 cc), cyclohexane (20 cc) is added, and the solution is filtered and chromatographed on a column (column diameter: 6 cm, height: 30 cm) of Merck silica gel (0.04–0.06 mm) (300 g). Elution is carried out with a 40:60 (by volume) mixture of cyclohexane and ethyl acetate (4 liters) under a pressure of 40 kPa, 125 cc fractions being collected. Fractions 6 to 25 are concentrated under reduced pressure (20 mm Hg) at 20° C.; 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, mixture of the E- and Z-forms) (4.8 g) is obtained in the form of a cream-coloured froth.

On carrying out a second chromatographic separation identical to the above, the Z-form (1.21 g) is isolated from fractions 12 to 16 and 1.49 g of the E.form from fractions 22 to 40; fractions 17 to 21 contain a mixture of the E- and Z-forms (0.8 g).

Z-form:
Infra-red spectrum (CHBr₃): characteristic bands (cm⁻¹) at 3380, 1800, 1720, 1680, 1510, 1375, 1190, 1175, 1045, 1000 and 735.

Proton nuclear magnetic resonance spectrum (350 MHz, CDCl₃, δ in ppm, J in Hz): 2.03 (s, 3H, —C₆H₄—CH₃); 3.36 and 4.07 (2 d, J=19, 2H, —SCH₂—); 4.09 (s, 3H, —OCH₃); 4.52 (d, J=4, 1H, H in the 6-position); 6.16 (dd, J=4 and 9, 1H, H in the 7-position); 6.43 (AB, J=8, 2H, —CH=CH—);

6.86 (s, 1H, —CH—OCO—);
|

6.71 (s, 1H, H in the 5-position of the thiazole); 7.75 (d, J=9, 2H, H in the ortho-position of the tosyl group).

E-form:
Infra-red spectrum (CHBr₃): characteristic bands (cm⁻¹) at 3380, 1800, 1725, 1685, 1515, 1380, 1190, 1180, 1070, 1050, 755 and 735.

Proton nuclear magnetic resonance spectrum (350 MHz, CDCl₃, δ in ppm, J in Hz): 2.45 (s, 3H, —C₆H₄CH₃); 3.19 and 3.77 (2 d, J=18, 2H, —SCH₂—); 4.08 (s, 3H, —OCH₃); 4.6 (d, J=4, H in the 6-position); 6.18 (dd, J=4 and 9, H in the 7-position); 6.72 (s, 1H, H in the 5-position of the thiazole); 6.93 (d, J=12, 1H, —CH=CH—OSO₂—); 7.11 (d, J=12, 1H, —CH=CH OSO₂—);

6.90 (s, 1H, —COOCH—);
|

7.73 (d, J=9, 2H, H in the ortho-position of the tosyl group).

7-Amino-2-benzhydryloxycarbonyl-8-oxo-5-oxide3-(2-tosyloxyvinyl)-5-thia-1-aza-bicyclo[4.2.0]oct-2-ene (mixture of the E- and Z-forms) can be prepared as follows:

A solution of 2-benzhydryloxycarbonyl-7-tert.-butoxycarbonylamino-8-oxo-5-oxide-3-(2-tosyloxyvinyl)5-thia-1-aza-bicyclo[4.2.0]oct-2-ene (mixture of the E- and Z-forms) (4.06 g) in acetonitrile (150 cc) is stirred for 16 hours at 20° C. with p-toluenesulphonic acid monohydrate (2.28 g). The mixture is then concentrated under reduced pressure (20 mm Hg) at 20° C. to a volume of 10 cc, and this is diluted with ethyl acetate (150 cc), washed with a 2% strength sodium bicarbonate solution (100 cc) and then with a saturated aqueous sodium chloride solution (2×150 cc), dried over sodium sulphate and concentrated to dryness under reduced pressure (20 mm Hg) at 20° C. 7-Amino-2-benzhydryloxycarbonyl-8-oxo-5-oxide-3-(2-tosyloxyvinyl)-5-thia-1-aza-bicyclo[4.2.0]oct-2-ene (a mixture of the E- and Z-forms) (3.5 g) is obtained in the form of a crude brown solid.

Infra-red spectrum (KBr): characteristic bands (cm⁻¹) at 3430, 3360, 1780, 1725, 1370, 1170, 1180, 1070, 745 and 700.

Proton nuclear magnetic resonance spectrum (350 MHz, CDCl₃, δ in ppm, J in Hz): 2.43 (s, 3H, —CH₃); 3.12 and 3.75 (2 d, J=18, 2H, —SCH₂—); 4.36 (d, J=4, 1H, H in the 6-position); 4.75 (d, J=4, 1H, H in the 7-position); 6.87 (d, J=12, 1H, —CH=CH OSO₂—);

6.90 (s, 1H, —COOCH—);
|

6.99 (d, J=12, 1H, =CH OSO₂—); 7.40 and 7.71 (2 d, J=9, —C₆H₄—).

2-Benzhydryloxycarbon-7-tert.-butoxycarbonylamino-8-oxo-5-oxide-3-(2-tosyloxyvinyl)-5-thia-1-aza-bicyclo]4.2.0]oct-2-ene (mixture of the E- and Z-forms) can be obtained as described below (Example 47).

EXAMPLE 4

A mixture of 2-benzhydryloxycarbonyl-7-[2methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.02 g), dimethylformamide (75 cc), N-tert.-butoxycarbonyl-L-cysteine (2.21 g) and N,N-diisopropylethylamine (2.61 cc) is stirred at 60° C., under nitrogen, for 2 hours 30 minutes. After cooling, the mixture is diluted with ethyl acetate (500 cc) and the organic phase is washed with water (2×400 cc), 0.1 N hydrochloric acid (250 cc) and a half-saturated aqueous sodium chloride solution (250 cc), dried over sodium sulphate, filtered and concentrated to dryness at 20° C. under reduced pressure (20 mm Hg).

The residue is dissolved in acetonitrile (50 cc). A solution of diphenyldiazomethane (0.97 g) in acetonitrile (25 cc) is added, at 20° C., whilst stirring, and the mixture is then stirred for 2 hours at 20° C. and diluted with ethyl acetate (500 cc). It is then washed, in a separating funnel, with 0.05 N hydrochloric acid (100 cc), a 1% strength sodium bicarbonate solution (100 cc) and a half-saturated sodium chloride solution (2×100 cc), dried over sodium sulphate, filtered and concentrated to dryness at 20° C. under reduced pressure (20 mm Hg). The residue is taken up in a 60:40 (by volume) mixture of cyclohexane and ethyl acetate (50 cc) and the solution is chromatographed over a column (column diameter: 6 cm, height: 30 cm) of Merck silica gel (0.04–0.06 mm) (300 g). Elution is carried out with the preceding mixture (4 liters) under a pressure of 40 kPa, 115 cc fractions being collected. Fractions 11 to 23 are combined and concentrated to dryness at 20° C. under reduced pressure (20 mm Hg). 2-Benzhydryloxycarbonyl-3-[2-(2-L-benzhydryloxycarbonyl-2-tert.-butoxycarbonylamino-ethyl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.57 g) is obtained.

Infra-red spectrum (CHBr$_3$): characteristic bands (cm$^{-1}$) at 3380, 1795, 1710, 1690, 1510, 1495, 1445, 1365, 1045, 940, 750 and 740.

Proton nuclear magnetic resonance spectrum (350 MHz, CDCl$_3$, δ in ppm, J in Hz): 1.48 (s, 9H, —C(CH$_3$)$_3$); 2.95 and 3.75 (2d, J=18, 2H, —S CH$_2$—); 3.20 (d, J=7, 2H, —SCH$_2$—); 4.08 (s, 3H, —OCH$_3$); 4.48 (d, J=4, 1H, H in the 6-position);

4.67 (mt, 1H, —CH—COO—);
|

6.10 (dd, J=4 and 9, 1H, H in the 7-position); 6.39 (d, J=7, 1H, —NH COO—); 6.41 (d, J=16, 1H, =CHS—); 6.71 (s, 1H, H of the thiazole);

6.85 (s, 1H, —COOCH—); 6.93 (s, 1H, —COOCH—);
|                              |

7.10 (s, 1H, —NH—C(C$_6$H$_5$)$_3$).

Dimethylacetamide (1.35 cc) followed, with stirring, by phosphorus trichloride (0.59 cc) are added to a solution, cooled to −10° C., of 2-benzhydryloxycarbonyl-3-[2-(2-L-benzhydryloxycarbonyl-2-tert.-butoxycarbonylamino-ethyl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (4.14 g) in methylene chloride (45 cc). The mixture is stirred for 1 hour at −10° C., diluted with ethyl acetate (600 cc), washed with 2% strength sodium bicarbonate solution (2×100 cc) and a half-saturated sodium chloride solution (2×100 cc), dried over sodium sulphate, filtered and concentrated to dryness at 20° C. under reduced pressure (20 mm Hg). The residue is dissolved in a 65:35 (by volume) mixture of cyclohexane and ethyl acetate (60 cc) and the solution is chromatographed over a column (column diameter: 5 cm) of Merck silica gel (0.04–0.06 mm) (250 g). Elution is carried out with a 65:35 (by volume) mixture of cyclohexane and ethyl acetate (2 liters) under a pressure of 40 kPa, 130 cc fractions being collected. Fractions 5 to 8 are combined and concentrated to dryness at 20° C. under reduced pressure (20 mm Hg), and 2-benzhydryloxycarbonyl-3-[2-(2-L-benzhydryloxycarbonyl-2-tert.-butoxycarbonylamino-ethyl)thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.78 g) is thus obtained in the form of a yellow froth.

Infra-red spectrum (CHBr$_3$), characteristic bands (cm$^{-1}$) at 3400, 1780, 1710, 1690, 1515, 1495, 1450, 1390, 1370, 1050, 945, 755 and 745.

Proton nuclear magnetic resonance spectrum (350 MHz, CDCl$_3$, δ in ppm, J in Hz): 1.43 (s, 9H, (CH$_3$)$_3$C—); 3.22 (2 AB limit, 4H, —S CH$_2$—); 4.10 (s, 3H, —OCH$_3$); 4.70 (m, 1H, <CH NH—); 5.36 (s broad, 1H, —NH COO—); 5.04 (d, J=4, 1H, H in the 6-position); 5.85 (dd, J=4 and 9, 1H, H in the 7-position); 6.41 (d, J=16, 1H, =CHS—); 6.8 (s, 1H, H of the thiazole);

6.88 (s, 1H, —CH—COO—CH—);
|                    |

6.93 (s, 1H, —COOCH—);
|

7.03 (s, 1H, —NHC(C$_6$H$_5$)$_3$); 7.08 (d, J=16, 1H, —CH=CHS—).

2-Benzhydryloxycarbonyl-3-[2-(2-L-benzhydryloxycarbonyl-2-tert.-butoxycarbonylamino-ethyl)-thiovinyl]-7-[2-methoxyimino-2-(2-tritylamino-1,3-thiazol-4-yl)-acetamido]-8-oxo-5-thia-1-aza-bicyclo[4.2.0]oct-2-ene (syn isomer, E-form) (2.71 g) is dissolved in formic acid (40 cc) and the solution is diluted with water (40 cc) and stirred at 50° C. for 30 minutes. The mixture is then cooled to 20° C., filtered and concentrated to dryness at 30° C. under reduced pressure (0.05 mm Hg). The residue is taken up 3 times in succession in ethanol (using 75 cc each time) and the solution is in each case evaporated to dryness at 20° C. under reduced pressure (20 mm Hg). The solid residue is treated with ethanol (200 cc) under reflux, and the cooled suspension is filtered. After washing with diethyl ether (3×25 cc) and drying, the formate of 3-[2-(2-L-amino-2-carboxyethyl)-thiovinyl]-7-[2-(2-amino-1,3-thiazol-4-yl)-2-methoxyimino-acetamido]-2-carboxy-8-oxo-5-thia-1-aza-bicyclo[4.2.0]oct-2-ene (syn isomer, E-form) (1.34 g) is obtained.

Infra-red spectrum (KBr), characteristic bands (cm$^{-1}$) at 3500, 2000, 1750, 1660, 1530, 1035 and 940.

Proton nuclear magnetic resonance spectrum (350 MHz, DMSO d$_6$, δ in ppm, J in Hz): 3 to 3.70 (hump, 4H, —SCH$_2$— cephalosporin and side chain); 3.87 (s, 3H, —O CH$_3$); 5.15 (d, J=4, 1H, H in the 6-position); 5.65 to 5.72 (hump, 2H, H in the 7-position and <CH COOH); 6.77 (s, 1H, H of the thiazole); 6.92 (AB, 2H, —CH=CH—); 7.20 (s, 3H, —NH$_3$+); 9.58 (d, J=9, 1H, —CONH—).

EXAMPLE 5

A solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (6.0 g) and 2-mercaptopyridine (1.33 g) in dimethylformamide (60 cc) and N,N-diisopropylethylamine (2.1 cc) is stirred at 20° C. for 2 hours under nitrogen. The mixture is diluted with ethyl acetate (400 cc) and the organic phase is washed with distilled water (2×500 cc), then with a half-saturated sodium bicarbonate solution (300 cc) and thereafter with a half-saturated sodium chloride solution (300 cc). It is dried over magnesium sulphate, filtered and concentrated to dryness under reduced pressure (20 mm Hg) at 20° C. The residue, dissolved in methylene chloride (25 cc), is chromatographed over a column (column diameter: 5 cm) of MERCK silica (0.04–0.06 mm) (300 g), elution being carried out with an 80:20 (by volume) mixture of methylene chloride and ethyl acetate (4 liters), and 100 cc fractions being collected. Fractions 17 to 34 are combined and concentrated to dryness under reduced pressure (20 mm Hg) at 35° C. The residue is dried for 15 hours under reduced pressure (0.2 mm Hg) at 20° C. This gives 2-benzhydryloxycarbonyl-7-[2-methoxyimino-2-(2-tritylaminothiazol-4-yl)-acetamido]-8-oxo-5-oxide-3-[2-(pyrid-2-yl)-thiovinyl]-5-thia-1-aza-bicyclo[4.2.0]oct-2-ene (syn isomer, E-form) (3.9 g) in the form of a yellow froth.

A mixture of 2-benzhydryloxycarbonyl-7-[2-methoxyimino-2-(2-tritylamino-thiazol-4-yl)-acetamido]-8-oxo-5-oxide-3-[2-(pyrid-2-yl)-thiovinyl]-5-thia-1-aza-bicyclo[4.2.0]oct-2-ene (syn isomer, E-form) (3.9 g), dimethylformamide (1.6 cc), methylene chloride (40 cc) and phosphorus trichloride (0.7 cc) is stirred for 1 hour at −15° C. The solution obtained is poured into ethyl acetate (600 cc) and the organic phase is washed with a half-saturated sodium bicarbonate solution (2×200 cc) and then with a half-saturated sodium chloride solution (2×200 cc). It is dried over sodium sulphate and filtered, the filter cake is washed with ethyl acetate (100 cc) and the combined filtrates are concentrated under reduced pressure (20 mm Hg) at 35° C. The residue is taken up in methylene chloride (30 cc) and is chromatographed over a column (column diameter: 4 cm) of MERCK silica (0.04–0.06 mm) (150 g), elution being carried out with a 95:5 (by volume) mixture of methylene chloride and ethyl acetate (4.5 liters). 100 cc fractions are collected. Fractions 10 to 40 are combined and concentrated to dryness under reduced pressure (20 mm Hg) at 35° C. The residue is dried for 15 hours under reduced pressure (0.2 mm Hg) at 20° C. This gives 2-benzhydryloxycarbonyl-7-[2-methoxyimino-2-(2-tritylamino-thiazol-4-yl)-acetamido]-8-oxo-3-[2-(pyrid-2-yl)-thiovinyl]-5-thia-1-aza-bicyclo[4.2.0]oct-2-ene (syn isomer, E-form) (2.4 g).

A solution of 2-benzhydryloxycarbonyl-7-[2-methoxyimino-2-(2-tritylamino-thiazol-4-yl)-acetamido]-8-oxo-3-[2-(pyrid-2-yl)-thiovinyl]-5-thia-1-aza-bicyclo[4.2.0]oct-2-ene (syn isomer, E-form) (2.40 g) in formic acid (21 cc) and distilled water (13 cc) is stirred at 50° C. for 1 hour. After it has cooled, the suspension is filtered and the filter cake is washed with distilled water (20 cc). The combined filtrates are concentrated under reduced pressure (0.2 mm Hg) at 35° C. The residue is taken up in ethanol (100 cc) and is concentrated under reduced pressure (20 mm Hg). The solid obtained is disintegrated in distilled water (20 cc) at 20° C., the mixture is filtered and the filter cake is washed successively with distilled water (15 cc), ethanol (12 cc) and ether (20 cc). It is dried under reduced pressure (0.2 mm Hg) at 20° C. for 15 hours. 7-[2-(2-amino-thiazol-4-yl)-2-methoxyimino-acetamido]-2-carboxy-8-oxo-3-[2-(pyrid-2-yl)-thiovinyl]-5-thia-1-aza-bicyclo[4.2.0]oct-2-ene (syn isomer, E-form) (1.05 g) is thus obtained.

Infra-red spectrum (KBr): characteristic bands (cm$^{-1}$) at 3500, 2820, 2600, 1775, 1670, 1650, 1630, 1575, 1450, 1415, 1380, 1040, 940 and 765.

Proton nuclear magnetic resonance spectrum (350 MHz, DMSO, δ in ppm, J in Hz): 3.72 and 3.95 (2d, J=18, 2H, H in the 4-position); 3.85 (s, 3H, —OCH$_3$); 5.20 (d, J=4, 1H, H in the 6-position); 5.77 (dd, J=4 and 9, 1H, H in the 7-position); 6.76 (s, 1H, H of the thiazole); 7.15 (d, J=17, 1H, —C$\underline{H}$=CHS—); 7.18 (s, 2H, amino); 7.44 (d, J=16, 17, —CH=C$\underline{H}$S—); 7.75 and 8.2 (dt, 1H, J=8, H in the 4-position of the pyridine); 8.50 (t, 1H, J=4, H$_2$ of the pyridine); 9.50 (d, J=9, 1H, —CON$\underline{H}$—).

EXAMPLE 6

2-Mercapto-pyridine-N-oxide (0.43 g) and N,N-diisopropylethylamine (0.6 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (3.4 g) in dry N,N-dimethylformamide (85 cc) and the mixture is stirred for 30 minutes at 25° C. A further amount of 2-mercaptopyridine-N-oxide (0.43 g) and of N,N-diisopropylethylamine (0.6 cc) is added and the mixture is stirred for a further 10 minutes at 25° C., after which it is diluted with ethyl acetate (250 cc). The mixture is washed with water (2×200 cc) followed by 0.1 N hydrochloric acid (200 cc) and a saturated sodium chloride solution (200 cc); after drying over magnesium sulphate, the solvent is evaporated under reduced pressure (30 mm Hg) at 40° C. The residue (3.5 g) is added to a further amount (0.5 g) of product obtained in the same way and the mixture is chromatographed over Merck silica gel (0.04–0.06 mm) (column diameter: 5 cm), elution being carried out with 10 liters of a 98:2 (by volume) mixture of ethyl acetate and methanol under a pressure of 50 kPa, and 120 cc fractions being collected. Unchanged starting material (1.1 g) is recovered from fractions 2 to 4. Fractions 45 to 75 are concentrated to dryness under reduced pressure (30 mm Hg) at 40° C. and 2-benzhydryloxycarbonyl-7-[2-methoxyimino-2-(2-tritylamino-thiazol-4-yl)-acetamido]-8-oxo-3-(2-(pyrid-2-yl-1-oxide)-thiovinyl]-5-thia-1-aza-bicyclo[4.2.0]oct-2-ene (syn isomer, E-form) (1.6 g) is obtained in the form of a grey froth.

Infra-red spectrum (CHBr$_3$): characteristic bands (cm$^{-1}$) at 3390, 1780, 1720, 1680, 1585, 1510, 1465, 1420, 1040, 945 and 750.

Proton nuclear magnetic resonance spectrum (350 MHz, CDCl$_3$, δ in ppm, J in Hz): 3.60 and 3.69 (AB, J=18, 2H, —SCH$_2$—); 4.08 (s, 3H, =NOCH$_3$); 5.12 (d, J=4, 1H, H in the 6-position); 5.97 (dd, J=4 and 9, 1H, H in the 7-position); 6.57 (d, J=16, 1H, —C$\underline{H}$=CHS—); 6.76 (s, 1H, H of the thiazole); 7.0 (s, 2H, —C$\underline{H}$(C$_6$H$_5$)$_2$ and (C$_6$H$_5$)$_3$CN$\underline{H}$—); 7.1 to 7.5 (hump, aromatic); 8.25 (d, J=9, 1H, —CONH—).

2-Benzhydryloxycarbonyl-7-[2-methoxyimino-2-(2-tritylamino-thiazol-4-yl)-acetamido]-8-oxo-3-[2-(pyrid-2-yl-1-oxide)-thiovinyl]-5-thia-1-aza-bicyclo[4.2.0]oct-2-ene (syn isomer, E-form) (2.3 g) is dissolved in formic acid (54 cc). The solution is diluted with distilled water (21 cc) and stirred for 20 minutes at 50° C. It is then filtered hot and the solvents are evaporated under reduced pressure (10 mm Hg) at 40° C. The residue is triturated with ethanol (50 cc). The mixture is evaporated to dryness under reduced pressure (30 mm Hg) at 40° C. The operation is repeated once. The residue is taken up in ethanol (50 cc) and the solid is filtered off, washed with ethanol (15 cc) and then with ethyl ether (2×25 cc) and is dried under reduced pressure (10 mm Hg) at 25° C. 7-[2-(2-Amino-thiazol-4-yl)-acetamido]-2-carboxy-8-oxo-3-[2-(pyrid-2-yl-1-oxide)-thiovinyl]-5-thia-1-aza-bicyclo[4.2.0]oct-2-ene (syn isomer, E-form) (0.98 g) is obtained in the form of a grey powder.

Infra-red spectrum (KBr), characteristic bands (cm$^{-1}$) at 3330, 1770, 1670, 1540, 1470, 1420, 1040, 950 and 760.

Proton nuclear magnetic resonance spectrum (350 MHz, DMSO d$_6$, δ in ppm, J in Hz): 3.75 and 4.16 (AB, J=18, 2H, —SCH$_2$—); 3.88 (s, 3H, =NOCH$_3$); 5.24 (d, J=4, 1H, H in the 6-position); 5.73 (dd, J=4 and 9, 1H, H in the 7-position); 6.78 (s, 1H, H of the thiazole); 7.05 and 7.32 (AB, J=16, 2H, —CH=CH—S—); 7.63 (d, J=7, 1H, H in the 3-position of the pyridine group); 7.1 to 7.5 (hump, 4H, H in the 4- and 5-position of pyridine+—NH$_2$); 7.63 (d, J=7, 1H, H in the 3-position of pyridine); 8.32 (d, J=6, 1H, H in the 6-position of pyridine); 9.64 (d, J=9, 1H, —CONH—).

EXAMPLE 7

2-Mercapto-pyrimidine (1.12 g) and N,N-diisopropylethylamine (1.75 cc) are added to a solution of 2-benzhydryloxycarbonyl-7-[2-methoxyimino-2-(2-tritylaminothiazol-4-yl)-acetamido]-8-oxo-3-(2-tosyloxyvinyl)-5-thia-1-aza-bicyclo[4.2.0]oct-2-ene (syn isomer, E-form) (5.0 g) in dry N,N-dimethylformamide (50 cc). The reaction mixture is stirred for 15 minutes at 20° C. under nitrogen and is then diluted with ethyl acetate (250 cc). The organic solution is washed successively with distilled water (250 cc), a half-saturated sodium bicarbonate solution (250 cc) and finally a saturated sodium chloride solution (250 cc). After drying the organic solution over magnesium sulphate and filtering, the solvent is evaporated under reduced pressure (25 mm Hg; 3.3 kPa) at 40° C. This gives a crude product (5 g) which is chromatographed on a column (column diameter 4 cm, height 30 cm) of MERCK silica gel (0.04–0.06 mm), elution being carried out under a pressure of 60.3 kPa with a 95:5 (by volume) mixture of methylene choride and ethyl acetate (2.5 liters) and 100 cc fractions being collected. Fractions 15 to 24 are combined and concentrated under reduced pressure (25 mm Hg; 3.3 kPa) at 40° C. This gives 2-benzhydryloxycarbonyl-7-[2-methoxyimino-2-(2-tritylamino-thiazol-4-yl)-acetamido]8-oxo-3-[2-(pyrimidin-2-yl)-thiovinyl]-5-thia-1-aza-bicyclo[4.2.0]oct-2-ene (syn isomer, E-form) (3.0 g).

Infra-red spectrum (KBr), chracteristic bands (cm$^{-1}$) at 3400, 2820, 1785, 1730, 1685, 1595, 1585, 1575, 1550, 1495, 1450, 1420, 1190, 1045, 945, 770 and 750.

Proton nuclear magnetic resonance spectrum (350 MHz, CDCl$_3$, δ in ppm, J in Hz): 3.63 and 3.77 (2d, J=18, 2H, —SCH$_2$— in the 4-position); 4.06 (s, 3H, =NOCH$_3$); 5.08 (d, J=4, 1H, —H in the 6-position); 5.90 (d, J=4, 1H, —H in the 7-position); 6.75 (s, 1H, —H in the thiazole ring); 6.94 (s, 1H, —CH< of the benzhydryl); 6.98 and 7.63 (2d, J=16, 2H, trans vinyl protons); 7.0 (t, J=5, 1H, —H in the 5-position of the pyrimidine ring); 7.0 to 7.4 (Mt, 25 H, aromatic); 8.52 (d, J=5, 2H, —H in the 4- and 6-position of the pyrimidine ring); 9.0 (d, J=9, 1H, —CONH—).

2-Benzhydryloxycarbonyl-7-[2-methoxyimino-2-(2-tritylamino-thiazol-4-yl)-acetamido]-8-oxo-3-[2-(pyrimidin-2yl)-thiovinyl]-5-thia-1-aza-bicyclo[4.2.-0]oct-2-ene (syn isomer, E-form) (2.9 g) is dissolved in formic acid (30 cc). Distilled water (13 cc) is added and the mixture is heated at 50° C. for 30 minutes. After cooling, it is filtered and the filter is washed with distilled water (5 cc). The filtrate is concentrated under reduced pressure (1 mm Hg; 0.13 kPa) at 30° C. The residue is taken up successively in 4 portions of absolute ethanol (30 cc each) and the suspension is evaporated each time, as described above. The dry residue is taken up in distilled water (30 cc), the mixture is filtered and the filter cake is washed successively with water (15 cc), ethanol (30 cc) and finally ether (30 cc). It is dried under reduced pressure (0.2 mm Hg; 0.027 kPa) at 20° C. This gives 7-[2-(2-amino-thiazol-4-yl)-2-methoxyimino-acetamido]-2-carboxy-8-oxo-3-[2-(pyrimidin-2-yl)-thiovinyl]-5-thia-1-aza-bicyclo[4.2.0]oct-2-ene (syn isomer, E-form) (1.4 g) in the form of a beige powder.

Infra-red spectrum (KBr), characteristic bands (cm$^{-1}$) at 3320, 3200, 3100 to 2100, 1770, 1665, 1560, 1550, 1040, 945, 770 and 750.

Proton nuclear magnetic resonance spectrum (350 MHz, DMSO d$_6$, δ in ppm, J in Hz): 3.72 and 3.90 (2d, J=18, 2H, —SCH$_2$— in the 4-position); 3.86 (s, 3H, =NOCH$_3$); 5.20 (d, J=4, 1H, —H in the 6-position); 5.77 (dd, J=4 and 9, 1H, —H in the 7-position); 6.74 (s, 1H, —H in the thiazole ring) 7.12 and 7.46 (2d, J=16, 2H, trans vinyl protons); 7.14 (s, 2H, —NH$_2$ on the thiazole ring); 7.27 (broad, 1H, —H in the 5-position of the pyrimidine ring); 8.66 (d, J=5, 2H, —H in the 4- and 6-positions of the pyrimidine ring); 9.60 (d, J=9, 1H, —CONH—).

EXAMPLE 8

3-Mercapto-6-methyl-pyridazine-1-oxide (0.738 g) and N,N-diisopropylethylamine (0.89 cc) are added successively at 22° C., under a nitrogen atmosphere and with stirring, to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form), (4.9 g) in dimethylformamide (40 cc). The mixture is stirred for 15 minutes at 25° C. and is then diluted with ethyl acetate (600 cc), washed successively with water (2×120 cc), 0.1 N hydrochloric acid (120 cc), a 2% strength sodium bicarbonate solution (2×120 cc) and a half-saturated sodium chloride solution (2×120 cc), dried over sodium sulphate, filtered and concentrated to dryness at 20° C. under reduced pressure (20 mm Hg). The residue is taken up in ethyl acetate (10 cc) and the solution is filtered over a column ( column diameter: 2.4 cm) of Merck silica gel (0.05–0.2 mm) (50 g). Elution is carried out with ethyl acetate (500 cc), successively collecting a colourless fraction 1 (100 cc), a pale yellow fraction 2 (20 cc) and a fraction 3 (360 cc). The latter is concentrated to dryness at 20° C. under reduced pressure (20 mm Hg). This gives 2-benzhydryloxycarbonyl-7-[2-methoxyimino-2-(2-tritylaminothiazol-4-yl)-acetamido]-3-[2-(6-methyl-pyridazin-3-yl-1-oxide)-thiovinyl]-8-oxo-5-thia-1-aza-bicyclo[4.2.0]-oct-2-ene (syn isomer, E-form) (4 g) in the form of a brownish-orange froth.

Infra-red spectrum (KBr): characteristic bands (cm$^{-1}$) at 3400, 1780, 1720, 1680, 1530, 1495, 1450, 1330, 1210, 1050, 1040, 1000, 945, 810, 755 and 700.

Proton nuclear magnetic resonance spectrum (350 MHz, CDCl$_3$, δ in ppm, J in Hz): 2.45 (s, 3H, —CH$_3$); 3.62 and 3.77 (2d, J=18, 2H, —SCH$_2$—); 4.09 (s, 3H, —OCH$_3$); 5.08 (d, J=4, 1H, H in the 6-position); 5.93 (dd, J=4 and 9, 1H, H in the 7-position); 6.03 (s, 1H, (C$_6$H$_5$)$_3$CN$\underline{\text{H}}$—); 6.76 (s, 1H, H of the thiazole);

6.95 (s, 1H, —COOC$\underline{\text{H}}$—).

A solution of 2-benzhydryloxycarbonyl-7-[2-methoxyimino-2-(2-tritylamino-thiazol-4-yl)-acetamido]-3-[2-(6-methyl-pyridazin-3-yl-1-oxide)-thiovinyl]-8-oxo-5-thia-1-aza-bicyclo[4.2.0]oct-2-ene (syn isomer, E-form) (3.9 g) in a mixture of formic acid (60 cc) and distilled water (25 cc) is stirred at 50° C. for 30 minutes. The mixture is then cooled to about 20° C. and filtered, and the filtrate is concentrated to dryness at 30° C. under reduced pressure (0.05 mm Hg). The residue is taken up in ethanol (50 cc), the mixture is concentrated to dryness at 20° C. under reduced pressure (20 mm Hg) and this operation is repeated twice. The solid which remains is treated with ethanol (40 cc) under reflux for 5 minutes and the suspension is then cooled to about 20° C. and filtered. After drying, 7-[2-(2-amino-thiazol-4-yl)-2-methoxyimino-acetamido]-2-carboxy-3-[2-(6-methyl-pyridazin-3-yl-1-oxide)-thiovinyl]-8-oxo-5-thia-1-aza-bicyclo[4.2.0]oct-2-ene (syn isomer, E-form) (1.96 g) is obtained in the form of a yellow powder.

Infra-red spectrum (KBr): characteristic bands (cm$^{-1}$) at 3420, 3320, 3230, 1765, 1675, 1655, 1620, 1535, 1325, 1210, 1040, 1000 and 810.

Proton nuclear magnetic resonance spectrum (350 MHz, DMSO d$_6$, δ in ppm, J in Hz): 2.33 (s, 3H, —CH$_3$); 3.70 and 3.97 (2d, J=18, 2H, —SCH$_2$—); 3.86 (s, 3H, —OCH$_3$); 5.23 (d, J=4, 1H, H in the 6-position); 5.81 (dd, J=4 and 9, 1H, H in the 7-position); 6.76 (s, 1H, H of the thiazole); 7.18 to 7.20 (hump, 5H, —CH═CH— and —NH$_3$+); 7.31 and 7.86 (2d, J=7, H of the pyridazine); 9.62 (d, J=9, 1H, —CONH—).

3-Mercapto-6-methyl-pyridazine-1-oxide is prepared in accordance with Belgian Pat. No. 787,635.

EXAMPLE 9

A solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5 g) and of 6-acetamido-3-mercapto-pyridazine (1.05 g) in dry N,N-dimethylformamide (50 cc) is treated with N,N-diisopropylethylamine (1.1 cc) and the reaction mixture is heated for 1 hour 40 minutes at 60° C. It is then diluted with ethyl acetate (300 cc) and washed with distilled water (3×200 cc) and with a saturated sodium chloride solution (250 cc). After drying over magnesium sulphate, the organic phase is concentrated to dryness under reduced pressure (30 mm Hg) at 40° C. and the residue is chromatographed over a column (column diameter: 5 cm) of silica gel (0.06–0.04 mm), elution being carried out under a pressure of 50 kPa with a 25:75 (by volume) mixture of cyclohexane and ethyl acetate. Fractions of about 100 cc are collected. Fractions 10 to 22, containing the pure product, are concentrated under reduced pressure (30 mm Hg) at 40° C. 3-[2-(6-Acetamido-pyridazin-3-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.2 g) is obtained in the form of a brown froth.

Rf=0.48; silica gel chromatographic plate; eluant: 20:80 (by volume) cyclohexane/ethyl acetate.

Infra-red spectrum (CHBr$_3$): characteristic bands (cm$^{-1}$) at 3380, 3220, 1785, 1715, 1700, 1680, 1450, 1370, 1040, 935 and 750.

Proton nuclear magnetic resonance spectrum (350 MHz, CDCl$_3$, δ in ppm, J in Hz): 2.05 (s, 3H, CH$_3$CONH—); 3.26 and 4.8 (2d, J=18, 2H, —S(O)CH$_2$—); 4.08 (s, 3H, ═NOCH$_3$); 4.62 (d, J=4, 1H, H in the 6-position); 6.12 (dd, J=4 and 9, 1H, H in the 7-position); 6.75 (s, 1H, H of the thiazole); 7.0 (s, 1H, —CH(C$_6$H$_5$)$_2$; 7.09 (s, 1H, (C$_6$H$_5$)$_3$CNH—); 7.18 (d, J=4, 1H, H in the 5-position of the pyridazine); 7.12 (d, J=16, 1H, —CH═CH—S—); 7.25 to 7.5 (mt, aromatic+—CH═CHS+H in the 4-position of the pyridazine); 8.30 (d, J=9, 1H, —CONH—); 9.50 (s, 1H, CH$_3$CONH—).

A solution of 3-[2-(6-acetamido-pyridazin-3-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.2 g) in methylene chloride (12 cc) containing N,N-dimethylacetamide (0.47 cc) is cooled to −10° C. and treated with phosphorus trichloride (0.23 cc). The reaction mixture is stirred for 2 hours at about −10° C. A further amount of N,N-dimethylacetamide (0.47 cc) and of phosphorus trichloride (0.23 cc) is added and the mixture is stirred for 1 hour at about −10° C., after which it is diluted with a saturated sodium bicarbonate solution (150 cc) and ethyl acetate (150 cc); the aqueous phase is extracted with ethyl acetate (100 cc). The combined organic extracts are washed with a saturated sodium chloride solution (2×50 cc) and dried over magnesium sulphate. The solution is evaporated to dryness under reduced pressure (30 mm Hg) at 40° C. and the residue is chromatographed over a column (column diameter: 4 cm) of silica gel (0.04–0.06 mm), elution being carried out with a 40:60 (by volume) mixture of cyclohexane and ethyl acetate (1.5 liters) under a pressure of 40 kPa. Fractions of about 100 cc are collected. Fractions 3 to 10, containing the pure product, are concentrated to dryness under reduced pressure (30 mm Hg) at 40° C. 3-[2-(6-Acetamido-pyridazin-3-yl)-thiovinyl]-2-benzhydryloxycarbonyl-7-[2-methoxyimino-2-(2-tritylaminothiazol-4-yl)-acetamido]-8-oxo-5-thia-1-aza-bicyclo[4.2.0]oct-2-ene (syn isomer, E-form) (1 g) is obtained in the form of a yellow froth.

Rf=0.58; silica gel chromatographic plate; eluant 30:70 (by volume) cyclohexane/ethyl acetate.

Infra-red spectrum (CHBr$_3$): characteristic bands (cm$^{-1}$) at 3400, 3360, 2820, 1780, 1715, 1705, 1680, 1580, 1510, 1490, 1445, 1400, 1040, 940, 840 and 755.

3-[2-(6-Acetamido-pyridazin-3-yl)-thiovinyl]-2-benzhydryloxycarbonyl-7-[2-methoxyimino-2-(2-tritylamino-1,3-thiazol-4-yl)-acetamido]-8-oxo-5-thia-1-aza-bicyclo[4.2.0]oct-2-ene (syn isomer, E-form) (1 g) is dissolved in formic acid (23.5 cc) and distilled water (9 cc) is added, after which the mixture is heated for 25 minutes at 50° C. The precipitate is filtered off and the filtrate is concentrated under reduced pressure (10 mm Hg) at 40° C. The residue is triturated in ethanol (50 cc) and the latter is evaporated under reduced pressure (30 mm Hg) at 40° C. This operation is repeated, the residue is taken up in ethanol (50 cc) and the insoluble matter is filtered off and washed with ethyl ether (30 cc). 3-[2-(6-Acetamido-pyridazin-3-yl)-thiovinyl]-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form) (0.51 g) is obtained in the form of a cream-coloured solid.

Infra-red spectrum (KBr): characteristic bands (cm$^{-1}$) at 3300, 1760, 1660, 1550, 1510, 1035 and 940.

Proton nuclear magnetic resonance spectrum (350 MHz, DMSO d$_6$, δ in ppm, J in Hz): 2.10 (s, 3H, CH$_3$CONH—); 3.72 and 3.98 (AB, J=17, 2H, —SCH$_2$—); 3.86 (s, 3H, ═NOCH$_3$); 5.2 (d, J=4, 1H, H in the 6-position); 5.78 (dd, J=4 and 9, 1H, H in the 7-position); 6.76 (s, 1H, H of the thiazole); 7.20 (s, 2H, —NH$_2$); 7.19 (d, J=10, 1H, —CH═CH—S—); 7.33 (d, J=10, 1H, —CH═CH—S—); 7.78 (d, J=9, 1H, H in the 5-position on the pyridazine); 8.12 (s, 1H, CH$_3$CONH—); 9.65 (d, J=9, 1H, —CONH—); 8.27 (d, J=9, 1H, H in the 4-position on the pyridazine); 11.1 (s broad, 1H, —CO$_2$H).

3-Acetamido-6-mercapto-pyridazine can be prepared in accordance with the method described by M. KUMAGAI and M. BANDO, Nippon Kagaku Zasshi 84, 995 (1963).

EXAMPLE 10

5,6-Dioxo-4-methyl-3-thioxo-perhydro-1,2,4-triazine (0.7 g) and N,N-diisopropylethylamine (0.77 cc) are added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4 g) in N,N-dimethylformamide (40 cc). The reaction mixture is heated for 90 minutes at 60° C. and is then diluted with ethyl acetate (200 cc) and washed with distilled water (4×100 cc). After drying over magnesium sulphate, filtering and evaporating to dryness under reduced pressure (30 mm Hg) at 40° C., the residue is chromatographed over Merck silica gel (0.04–0.06 mm) (column diameter: 4 cm), elution being carried out under 50 kPa with ethyl acetate (3 liters) and 100 cc fractions being collected; fractions 11 to 29 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-Form) (2.8 g) is obtained.

Infra-red spectrum (CHBr$_3$): characteristic bands (cm$^{-1}$) at 3360, 3200, 2820, 1795, 1710, 1680, 1590, 1515, 1490, 1450, 1040 and 760.

Proton nuclear magnetic resonance spectrum (350 MHz, CDCl$_3$, δ in ppm, J in Hz): 3.30 (s, 3H, —CH$_3$ of the triazine); 3.30 and 4.0 (AB, J=18, —S(O)CH$_2$—); 3.88 (s, 3H, =NOCH$_3$); 4.65 (d, J=4, 1H, H in the 6-position); 6.02 (dd, J=4 and 9, 1H, H in the 7-position); 6.32 (d, J=16, 1H, —C$\underline{H}$=CH—S—); 6.68 (s, 1H, H of the thiazole); 6.92 (s, 1H, —C$\underline{H}$(C$_6$H$_5$)$_2$); 7.15 to 7.55 (hump, aromatic+—CONH—+(C$_6$H$_5$)$_3$C$\underline{N}$—+—CH=C$\underline{H}$S—).

Phosphorus trichloride (0.53 cc) is added to a solution, cooled to −30° C., of 2-benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylaminothiazol-4-yl)-acetamido]-8-oxo-5-oxide-5thia-1-aza-bicyclo[4.2.0]oct-2-ene (syn isomer, E-form) (2.8 g) in methylene chloride (30 cc) and N,N-dimethylacetamide (1.1 cc) and the reaction mixture is stirred for 2 hours at between −15° and −10° C., after which it is diluted with ethyl acetate (250 cc). It is washed with a saturated sodium bicarbonate solution (2×100 cc) and then with a saturated sodium chloride solution (250 cc), dried over magnesium sulphate and filtered, and the solvent is evaporated under reduced pressure (30 mm Hg) at 40° C. The residue is chromatographed over silica gel (0.04–0.06 mm) (120 g) (column diameter: 4 cm, height: 20 cm), elution being carried out with a 20:80 (by volume) mixture of cyclohexane and ethyl acetate (2 liters) under a pressure of 50 kPa, and 100 cc fractions being collected. Fractions 4 to 16 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.75 g) is obtained in the form of a cream-coloured solid.

Infra-red spectrum (CHBr$_3$): characteristic bands (cm$^{-1}$) at 3380, 1785, 1710, 1680, 1515, 1490, 1445, 1040, 940, 755 and 740.

Proton nuclear magnetic resonance spectrum (350 MHz, CDCl$_3$, δ in ppm, J in Hz): 3.41 (s, 3H, —CH$_3$ of the triazine); 3.58 and 3.68 (AB, J=18, 2H, —SCH$_2$—); 4.04 (s, 3H, =NOCH$_3$); 5.10 (d, J=4, 1H, H in the 6-position); 5.95 (dd, J=4 and 9, 1H, H in the 7-position); 6.74 (s, 1H, H of the thiazole); 6.84 (d, J=17, 1H, —C$\underline{H}$=CH—S—); 6.96 (s, 1H, —CH(C$_6$H$_5$)$_2$); 7.03 (d, J=9, 1H, —CONH—); 7.15 to 7.55 (hump, aromatics+(C$_6$H$_5$)$_3$CNH—+—CH=C$\underline{H}$S—); 10.8 (s, 1H, —NH— of the triazine).

2-Benzhydryloxycarbonyl-3-[2-(-5,6-dioxo-4-methyl-1,4,5,6-tétrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.7 g) is dissolved in formic acid (24 cc); after addition of distilled water (16 cc), the reaction mixture is heated for 25 minutes at 50° C. and is then filtered hot and concentrated to dryness under reduced pressure (10 mm Hg) at 40° C. The solid is triturated with ethanol (40 cc) and the mixture is evaporated to dryness under reduced pressure (30 mm Hg) at 40° C.; this operation is repeated once, and the residue obtained is then taken up in ethanol (30 cc). The insoluble matter is filtered off, washed with ethanol (10 cc) and ether (2×50 cc) and dried under reduced pressure (10 mm Hg) at 25° C. 7-[2-(2-Aminothiazol-4-yl)-2-methoxyimino-acetamido]-2-carboxy-3-[2-(5,6-dioxo-4-methyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.85 g) is obtained in the form of a cream-coloured solid.

Rf=0.37; silica gel chromatographic plate; eluant: 3:2:2 (by volume) ethyl acetate/water/acetic acid.

Infra-red spectrum (KBr): characteristic bands (cm$^{-1}$) at 3300, 3260, 2600, 1770, 1705, 1680, 1630, 1585, 1530, 1375, 1040 and 950.

Proton nuclear magnetic resonance spectrum (350 MHz, DMSO d$_6$, δ in ppm, J in Hz): 3.35 (s, 3H, —CH$_3$ of the triazine); 3.65 and 3.88 (AB, J=18, 2H, —SCH$_2$—); 3.87 (s, 3H, =NOCH$_3$); 5.22 (d, J=4, 1H, H in the 6-position); 5.80 (dd, J=4 and 9, 1H, H in the 7-position); 6.75 (s, 1H, H of the thiazole); 6.83 (d, J=16, —CH=C$\underline{H}$—S—); 7.11 (d, J=16, 1H, —C$\underline{H}$=CH—S—); 7.20 (s broad, 3H, —NH$_3$+); 9.58 (d, J=9, 1H, —CONH—).

5,6-Dioxo-4-methyl-3-thioxo-perhydro-1,2,4-triazine can be prepared in accordance with M. PESSON and M. ANTOINE, Bull. Soc. Chim. Fr., 1590 (1970).

EXAMPLE 11

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (7.02 g), dimethylformamide (50 cc), diisopropylethylamine (1.34 cc) and 5,6-dioxo-4-ethyl-3-thioxo-perhydro-1,2,4-triazine (1.33 g) is stirred for 2 hours at 60° C. under nitrogen. The cooled mixture is diluted with ethyl acetate (600 cc) and the organic phase is washed with water (2×125 cc), 0.5 N hydrochloric acid (150 cc), a half-saturated sodium bicarbonate solution (2×125 cc) and a saturated aqueous sodium chloride solution (2×125 cc), and is dried over magnesium sulphate and concentrated to dryness at 30° C. under reduced pressure (20 mm Hg). The residue is dissolved in ethyl acetate (150 cc) and the solution is chromatographed over a column (column diameter: 7 cm) of Merck silica gel (0.04–0.06 mm). Elution is carried out with ethyl acetate (3 liters) under a pressure of 40 kPa, 100 cc fractions being collected. Fractions 10 to 23 are concentrated to dryness at 20° C.

under reduced pressure (20 mm Hg). This gives 2-benzhydryloxycarbonyl-3-[2-(5,6-dioxo-4--ethyl-1,4,5,6-tetrahydro-1,2,4-triazin-3-yl)-thiovinyl]7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (5.3 g) in the form of a light brown solid.

Infra-red spectrum (KBr): characteristic bands ($cm^{-1}$) at 3500, 2000, 1785, 1710, 1685, 1520, 1495, 1450, 1040, 945, 755 and 700.

Proton nuclear magnetic resonance spectrum (350 MHz, $CDCl_3$, δ in ppm, J in Hz): 1.27 (t, J=7, 3H, —$CH_3$); 3.40 and 4.12 (2d, J=18, 2H, —$SCH_2$—); 3.86 (q, J=7, 2H, >$NCH_2$—); 4.0 (s, 3H, —$OCH_3$); 4.68 (d, J=4, 1H, H in the 6-position); 6.04 (dd, J=4 and 9, 1H, H in the 7-position); 6.70 (s, 1H, H of the thiazole);

6.85 (d, J = 16, —C$\underline{H}$=CHS—); 6.97 (s, 1H, —COOCH—).

Dimethylacetamide (1.95 cc) and phosphorus trichloride (1 cc) are added successively to a solution, cooled to −14° C., of 2-benzhydryloycarbonyl-3-[2--(5,6-dioxo-4-ethyl-1,4,5,6-tetrahydro-1,2,4-triazin-3-yl)thiovinyl]-7-[2-methoxyimino-2(2-tritylamino-thiazol-4-yl)-8-oxo-5-oxide-5-thia-1-aza-bicyclo[4.2.-0]oct-2-ene (syn isomer, E-form) (5.2 g) in methylene chloride (100 cc). The mixture is stirred for 1 hour 20 minutes at a temperature of about −12° C., a further amount of phosphorus trichloride (0.5 cc) is then added and stirring is continued at −12° C. for 15 minutes. The mixture, diluted with ethyl acetate (600 cc) is washed with a 2% strength sodium bicarbonate solution (2×250 cc) and a half-saturated sodium chloride solution (2×250 cc). The organic phase is dried over sodium sulphate, filtered and concentrated to dryness under reduced pressure (20 mm Hg) at 20° C. The oil which remains is purified by chromatography over a column (column diameter: 4.5 cm) of Merck silica gel (0.05–0.2 mm) (100 g), the product being fixed beforehand on silica gel (25 g). Elution is carried out with ethyl acetate (500 cc), 50 cc fractions being collected. Fractions 5 to 9 are concentrated to dryness at 20° C. under reduced pressure (20 mm Hg) and 2-benzhydryloxycarbonyl-3-[2-(5,6-dioxo-4-ethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-azabicyclo[4.2.0]oct-2-ene (syn isomer, E-form) (5.3 g) is obtained ,in the form of an orange-coloured froth.

Infra-red spectrum ($CHBr_3$): characteristic bands ($cm^{-1}$) at 3385, 1785, 1710, 1680, 1515, 1490, 1445, 1040, 940, 755 and 740.

Proton nuclear magnetic resonance spectrum (350 MHz, $CDCl_3$, δ in ppm, J in Hz): 1.34 (t, J=7, 3H, —$CH_3$); 3.60 and 3.70 (2d, J=18, 2H, —$SCH_2$—); 3.95 (q, J=7, 2H, >$NCH_2$—); 4.05 (s, 3H, —$OCH_3$); 5.12 (d, J=4, 1H, H in the 6-position); 5.94 (dd, J=4 and 9, 1H, H in the 7-position); 6.77 (s, 1H, H of the thiazole); 6.87 (d, J=16, 1H, —C$\underline{H}$=CHS—); 6.97 (d, J=9, 1H, —CONH—); 6.96 (s, 1H, —COOCH<);

8.20 (s, 1H, =NNH CO— or =NN—C—).
                                        |
                                        OH

2-Benzhydryloxycarbonyl-3-[2-(5,6-dioxo-4-ethyl-1,4,5,6-tetrahydro-1,2,4-triazin-3-yl)-thiovinyl]-7-[2-methoxyimino-2-(2-tritylamino-thiazol-4-yl)-acetamido]8-oxo-5-thia-1-aza-bicyclo[4.2.0]oct-2-ene (syn isomer, E-form) (3 g) is dissolved in formic acid (30 cc) and the solution is diluted with water (14 cc) and heated at 50° C. for 30 minutes, whilst stirring. The mixture is cooled to 20° C. and filtered, and the filtrate is concentrated to dryness at 30° C. under reduced pressure (0.05 mm Hg). The solid is taken up in ethanol (100 cc) and the mixture is concentrated to dryness at 20° C. under reduced pressure (20 mm Hg); this operation is repeated 3 times, and the solid is then treated with ethanol (500 cc) at 60° C. After removing a slight amount of insoluble matter, the solution is concentrated to 40 cc (at 30° C. under 20 mm Hg) and cooled to +4° C. After filtering and drying the insoluble material, 7-[2-(2-aminothiazol-4-yl)-2-methoxyimino-acetamido]-2-carboxy-3-[2-(5,6-dioxo-4-ethyl-1,4,5,6-tetrahydro-1,2,4-tri-azin-3-yl)-thiovinyl]-8-oxo-5-thia-1-aza-bicyclo[4.2.-0]oct-2-ene (syn isomer, E-form) (1.49 g) is obtained.

Infra-red spectrum (KBr): characteristic bands ($cm^{-1}$) at 3500, 2200, 1770, 1700, 1680, 1530, 1040 and 940.

Proton nuclear magnetic resonance spectrum (350 MHz, DMSO, $d_6$, δ in ppm, J in Hz): 1.22 (t, J=7, 3H, —$CH_3$); 3.65 and 3.80 (2d, J=18, 2H, —$SCH_2$—); 3.80 (q, J=7, 2H, >$NCH_2$—); 3.86 (s, 3H, —$OCH_3$); 5.20 (d, J=4, 1H, H in the 6-position); 5.78 (dd, J=4 and 9, 1H, H in the 7-position); 6.75 (s, 1H, H of the thiazole); 6.95 (d, J=16, 1H, —C$\underline{H}$=CHS—); 7.13 (d, J=16, 1H, =CHS—); 7.18 (s, 3H, —$NH_3^+$); 9.63 (d, J=9, 1H, —CONH—).

5,6-Dioxo-4-ethyl-3-thioxo-perhydro-1,2,4-triazine can be prepared in accordance with the method described in Belgian Pat. No. 830,455.

EXAMPLE 12

A mixture of 2-benzhydryloxycarbonyl-7-[2-methoxyimino-2-(2-tritylamino-thiazol-4-yl)-acetamido]8-oxo-5-oxide-3-(2-tosyloxyvinyl)-5-thia-1-aza-bicyclo[4.2.-0]oct-2-ene (syn isomer, E-form) (9.79 g), dimethylformamide (50 cc), 5,6-dioxo-4-isopropyl-3-thioxo-perhydro-1,2,4-triazine (2.28 g) and N,N-diisopropylethylamine (2.12 cc) is stirred at 60° C. under nitrogen for 1 hour 40 minutes. The mixture is diluted with ethyl acetate (600 cc), washed with water (2×150 cc), 1 N hydrochloric acid (100 cc), a 2% strength sodium bicarbonate solution (2×150 cc) and a half-saturated sodium chloride solution (2×150 cc), dried over sodium sulphate, filtered and concentrated to dryness at 20° C. under 20 mm Hg. Purification is effected by chromatography on a column (column diameter: 5 cm) of Merck silica gel (0.05–0.2 mm) (300 g). Elution is carried out with a 40:60 (by volume) mixture of cyclohexane and ethyl acetate (15 liters), 1 liter fractions being collected. Fractions 9 to 14 are concentrated to dryness at 20° C. under 20 mm Hg. 2-Benzhydryloxycarbonyl-3-[2-(5,6-dioxo-4-isopropyl-1,4,5,6-tetrahydro-1,2,4-triazin-3-yl)-thiovinyl]-7-[2-methoxyimino-2-(2-tritylaminothiazol-4-yl)-acetamido]-8-oxo-5-oxide-5-thia-1-azabicyclo[4.2.0]oct-2-ene (syn isomer, E-form) (7.4 g) is obtained in the form of a yellow-orange froth.

Proton nuclear magnetic resonance spectrum (350 MHz, DMSO, $d_6$, δ in ppm, J in Hz): 1.45 (d, J=7, 6H, —CH($CH_3$)$_2$); 3.68 and 4.29 (2d, J=19, 2H, —$SCH_2$—); 3.84 (s, 3H, —$OCH_3$), 4.35 (mt, 1H, —C$\underline{H}$($CH_3$)$_2$); 5.05 (d, J=4, 1H, H in the 6-position); 5.86 (dd, J=4 and 9, 1H, H in the 7-position); 6.78 (s, 1H, H of the thiazole); 6.97 (s, 1H, —COOCH<); 6.96 (d, J=16, 1H, —C$\underline{\text{H}}$=CHS—); 7.11 (d, J=16, 1H, =CHS—); 8.74 (s, 1H, —N$\underline{\text{H}}$—C(C$_6$H$_5$)$_3$); 9.05 (d, J=9, 1H, —CONH—);

12.53 (s, 1H, =NNH—CO— or =N—N=C—).
                                    |
                                    OH

A solution of 2-benzhydryloxycarbonyl-3-[2-(5,6-dioxo-4-isopropyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]-oct-2-ene (syn isomer, E-form) (7.3 g) and dimethylacetamide (2.73 cc) in methylene chloride (100 cc) is treated with phosphorus trichloride (1.25 cc) at −10° C. for 1 hour 30 minutes, whilst stirring. The mixture is diluted with ethyl acetate (600 cc), washed with a 2% strength sodium bicarbonate solution (2×150 cc) and a half-saturated sodium chloride solution (2×150 cc), dried over sodium sulphate, filtered and concentrated to dryness at 20° C. under reduced pressure (20 mm Hg). The residue is fixed to Merck silica gel (0.05–0.2 mm) (50 g) and the powder is deposited on a column (column diameter: 4 cm) of silica gel (200 g). Elution is carried out with an 80:20 (by volume) mixture of ethyl acetate and cyclohexane, 200 cc fractions being collected. Fractions 3 and 4 are concentrated to dryness at 20° C. under a pressure of 20 mm Hg and 2-benzhydryloxycarbonyl-3-[2-(5,6-dioxo-4-isopropyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.3 g) is obtained in the form of a yellow-orange froth.

Infra-red spectrum (CHBr$_3$): characteristic bands (cm$^{-1}$) at 3400, 1790, 1720, 1685, 1520, 1495, 1450, 1045, 945, 760 and 740.

Proton nuclear magnetic resonance spectrum (350 MHz, DMSO, d$_6$, δ in ppm, J in Hz): 1.46 (d, J=7, 6H, —CH(C$\underline{\text{H}}_3$)$_2$); 3.64 and 3.84 (2d, J=18, 2H, —SCH$_2$—); 3.82 (s, 3H, —OCH$_3$); 4.36 (mt, 1H, —C$\underline{\text{H}}$(CH$_3$)$_2$); 5.24 (d, J=4, 1H, H in the 6-position); 5.76 (dd, J=4 and 9, 1H, H in the 7-position); 6.72 (s, 1H, H of the thiazole); 6.94 (d, J=16, 1H, —C$\underline{\text{H}}$=CHS—); 6.94 (s, 1H, —COOCH<); 7.0 (d, J=16, 1H, =CHS—); 8.78 (s, 1H, —NHC(C$_6$H$_5$)$_3$); 9.58 (d, J=9, 1H, —CONH—);

12.53 (s, 1H, =NNHCO— or =N—N=C—).
                                  |
                                  OH

2-Benzhydryloxycarbonyl-3-[2-(5,6-dioxo-4-isopropyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.25 g) is dissolved in formic acid (50 cc) and the solution is diluted with water (20 cc) and heated at 50° C. for 30 minutes, whilst stirring. After it has cooled to 20° C., the mixture is filtered and the solution is concentrated to dryness at 30° C. under reduced pressure (0.05 mm Hg). The residue is taken up in ethanol (25 cc), the solvent is driven off at 20° C. under a pressure of 20 mm Hg and these operations are repeated 3 times. The solid is treated with ethanol (600 cc) under reflux, and the mixture is filtered and concentrated to 50 cc at 20° C. under 20 mm Hg. After filtering off and drying the insoluble material, 7-[2-(2-amino-thiazol-4-yl)-2-methoxyimino-acetamido]-2-carboxy-3-[2-(5,6-dioxo-4-isopropyl-1,4,5,6-tetrahydro-1,2,4-triazin-3-yl)-thiovinyl]-8-oxo-5-thia-1-aza-bicyclo[4.2.0]oct-2-ene (syn isomer, E-form) (2 g) is obtained in the form of a yellow powder.

Infra-red spectrum (KBr): characteristic bands (cm$^{-1}$) at 3500, 2200, 1775, 1705, 1680, 1530, 1050 and 950.

Proton nuclear magnetic resonance spectrum (350 MHz, DMSO, d$_6$, δ in ppm, J in Hz); 1.48 (d, J=7, 6H, —CH(C$\underline{\text{H}}_3$)$_2$); 3.64 and 3.82 (2d, J=18, 2H, —SCH$_2$—); 3.85 (s, 3H, —OCH$_3$); 4.42 (mt, 1H, —C$\underline{\text{H}}$(CH$_3$)$_2$); 5.22 (d, J=4, 1H, H in the 6-position); 5.78 (dd, J=4 and 9, 1H, H in the 7-position); 6.74 (s, 1H, H of the thiazole); 6.93 (d, J=16, 1H, —C$\underline{\text{H}}$=CHS—); 7.07 (d, J=16, 1H, =CHS—); 7.18 (s, 3H, —NH$_{13}^+$); 9.62 (d, J=9, 1H, —CONH—);

12.55 (s, 1H, =NNHCO— or =N—N=C—OH).
                                  |

5,6-Dioxo-4-isopropyl-3-thioxo-perhydro-1,2,4-triazine can be prepared in accordance with the method described in Belgian Pat. No. 830,455.

EXAMPLE 13

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.8 g), dimethylformamide (58 cc), 4-(2-methoxyethyl)-5,6-dioxo-3-thioxoperhydro-1,2,4-triazine (1.3 g) and diisopropylethylamine (0.819 mg) is stirred at 60° C. for 80 minutes, under nitrogen. The mixture is cooled to 20° C. and diluted with ethyl acetate (300 cc), and the organic phase is washed 4 times with water (a total of 100 cc), dried over magnesium sulphate, filtered and concentrated to dryness at 20° C. under reduced pressure (20 mm Hg). The residue, dissolved in ethyl acetate (250 cc) is filtered over a column of silica gel (32 g) and eluted with ethyl acetate (500 cc). The eluate is evaporated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]8-oxo-5-oxide-5-thia-1-aza-bicyclo[4.2.0-]-oct-2-ene (syn isomer, E-form) (5.4 g) in the form of a beige solid.

Infra-red spectrum (KBr): characteristic bands (cm$^{-1}$) at 3400, 2830, 1800, 1720, 1690, 1590, 1525, 1495, 1450, 1370, 1210, 1110, 1040, 945, 755 and 700.

Proton nuclear magnetic resonance spectrum (350 MHz, CDCl$_3$, δ in ppm, J in Hz): 3.32 (s, 3H, —CH$_2$OC$\underline{\text{H}}_3$); 3.60 (t, J=5, 2H, —CH$_2$O—); 4.05 (t, J=5, 2H, —CH$_2$N<); 3.34 and 4.1 (dd, J=18, 2H, —S(O)CH$_2$—); 4.00 (s, 3H, =NOCH$_3$); 4.66 (d, J=4, 1H, H in the 6-position); 6.08 (dd, J=4 and 9, 1H, H in the 7-position); 6.71 (s, 1H, H of the thiazole); 6.85 (d, J=16, 1H, —C$\underline{\text{H}}$=CHS—);

6.97 (s, 1H, —COOCH—).
                      |

Dimethylacetamide (2.06 cc), followed by phosphorus trichloride (0.91 cc) is added to a solution cooled to −10° C., of 2-benzhydryloxycarbonyl-3-{2-[5,6-dioxo-4-(2-methoxyethyl)-1,4,5,6-tetrahydro-1,2,4-triazin-3- yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (5.3 g) is methylene chloride (53 cc). The solution is stirred for 2 hours at $-10°$ C. and is then diluted with ethyl acetate (750 cc); this solution is washed with a saturated sodium bicarbonate solution ($2 \times 100$ cc), and a saturated sodium chloride solution ($2 \times 100$ cc), dried over magnesium sulphate and concentrated to 50 cc under reduced pressure (20 mm Hg) at 20° C., and isopropyl ether (200 cc) is added. The solid formed is isolated by filtration, washed with isopropyl ether (20 cc) and dried. This gives a cream-coloured solid (4.2 g). This solid, dissolved in a 70:30 (by volume) mixture of ethyl acetate and cyclohexane, is chromatographed over a column (column diameter 6 cm, height 20 cm) of Merck silica gel (0.04–0.06 mm). Elution is carried out with a 70:30 (by volume) mixture of ethyl acetate and cyclohexane (1,500 cc) under a pressure of 40 kPa, 75 cc fractions being collected. Fractions 9 to 19 are concentrated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.9 g) in the form of a cream-coloured solid.

Infra-red spectrum (KBr): characteristic bands (cm$^{-1}$) at 3400, 2820, 1785, 1720, 1690, 1590, 1525, 1495, 1450, 1370, 1210, 1110, 1040, 945, 755 and 705.

Proton nuclear magnetic resonance spectrum (350 MHz, CDCl$_3$, δ in ppm, J in Hz): 3.34 (s, 3H, —CH$_2$OCH$_3$); 3.65 (t, J=5, 2H, —CH$_2$O—); 4.11 (t, J=5, 2H, —CH$_2$N<); 3.60 and 3.68 (2d, J=18, 2H, —SC-H$_2$—); 4.06 (s, 3H, =NOCH$_3$); 5.11 (d, J=4, 1H, H in the 6-position); 5.95 (dd, J=4 and 9, 1H, H in the 7-position); 6.76 (s, 1H, H of the thiazole); 6.86 (d, J=16, 1H, —CH=CHS—); 6.93 (d, J=9, 1H, —CONH—);

6.97 (s, 1H, —COOCH<).

2-Benzyhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.8 g) is dissolved in formic acid (50 cc), water (25 cc) is added and the mixture is heated for 15 minutes at 50° C., with stirring. The mixture is then diluted with water (25 cc), cooled, filtered and concentrated to dryness at 40° C. under 0.05 mm Hg. The residue is taken up three times in ethanol (50 cc), and each time the mixture is evaporated to dryness under reduced pressure (0.05 mm Hg). The residue is taken up in ethanol (200 cc) under reflux, the mixture is filtered hot on a glass frit, the residue is again taken up in ethanol (100 cc) under reflux and the mixture again filtered hot, the two combined filtrates are concentrated to 20 cc and cooled to 0° C., and the solid obtained is filtered off and dried. This gives 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (1.45 g), in the form of a yellow solid.

Infra-red spectrum (KBr): characteristic bands (cm$^{-1}$) at 3480, 2830, 1775, 1710, 1680, 1635, 1590, 1535, 1380, 1110, 1040 and 940.

Proton nuclear magnetic resonance spectrum (350 MHz, DMSO d$_6$, δ in ppm, J in Hz): 3.36 (s, 3H, —CH$_2$OCH$_3$); 3.56 (t, J=5, 2H, —CH$_2$O—); 4.10 (t, J=5, 2H, —CH$_2$N<); 3.62 and 3.73 (2d, J=18, 2H, —SC-H$_2$—); 3.96 (s, 3H, =NOCH$_3$); 5.18 (d, J=4, 1H, H in the 6-position); 5.81 (dd, J=4 and 9, 1H, H in the 7-position); 6.78 (s, 1H, H of the thiazole); 6.87 (d, J=15, 1H, —CH=CH—S—); 7.29 (d, J=15, 1H, —CH=CH—S—); 6.70 (s, broad, 3H, —NH$_3^+$); 9.55 (d, J=9, 1H, —CONH—);

12.64 (s, 1H, =N NHCO— or =N N=C—).
                                                                        |
                                                                        OH 4-(2-Methoxyethyl)-5,6-dioxo-3-thioxo-perhydro-1,2,4-triazine can be prepared in accordance with Belgian Pat. No. 830,455.

EXAMPLE 14

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl-5-thia-1-aza-bicyclo[4.2.0]oct-2-ene (syn isomer, E-form) (8.03 g), dimethylformamide (150 cc), 5,6-dioxo-4-(2-methylthioethyl)-3-thioxo-perhydro-1,2,4-triazine (2.19 g) and diisopropylethylamine (1.7 cc) is stirred at 60° C. for 4 hours. The mixture is poured into ethyl acetate (300 cc), and this mixture is washed with water ($3 \times 200$ cc) and a saturated sodium chloride solution (200 cc), dried over sodium sulphate, filtered and concentrated to dryness at 20° C. under 20 mm Hg (2.7 kPa). The product, which is first fixed to Merck silica gel (0.05–0.2 mm) (20 g) is then chromatographed on silica gel (200 g) (column diameter: 3.4 cm, height: 40 cm). Elution is carried out successively with the following mixture of cyclohexane and ethyl acetate: 40:60 by volume (500 cc), 30:70 by volume (500 cc), 20:80 by volume (500 cc) and 10:90 by volume (500 cc), and finally with pure ethyl acetate (2 liters), 120 cc fractions being collected. Fractions 22 to 32 are concentrated to dryness and 2-benzhydryloxycarbonyl-3-{2-[5,6-dioxo-4-(2-methylthioethyl)-1,4,5,6-tetrahydro-1,2,4-triazin-3yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2ene (syn isomer, E-form) (5.66 g) is obtained in the form of a cream-coloured froth.

Infra-red spectrum (KBr): characteristic bands in cm$^{-1}$ at 1795, 1715, 1670, 1525, 1495, 1455, 1040, 945, 755 and 700.

A solution of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylamino-thiazol-4-yl)-acetamido[-8-oxo-5-oxide-5-thia-1-aza-bicyclo[4.2.0]oct-2-ene (syn isomer, E-form) (5.6 g) in a mixture of methylene chloride (53.8 cc) and dimethylacetamide (1.99 cc) is treated with phosphorus trichloride (0.941 cc) at $-10°$ C. for 30 minutes, with stirring. The mixture is diluted with ethyl acetate (200 cc) and this mixture is washed successively with a saturated sodium bicarbonate solution (100 cc), water ($2 \times 100$ cc) and a saturated sodium chloride solution (100 cc), dried over sodium sulphate, filtered and concentrated to dryness at 20° C. under 20 mm Hg (2.7 kPa).

droxy-4-propyl-5,6-dioxo-1,4,5,6-tetrahydro-1,2,4-triazin-3-yl)-thiovinyl]-8-oxo-5-thia-1-aza-bicyclo[4.2.0]oct-2-ene (syn isomer, E-form), 3-{2-[4-(2-acetamido-ethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form), 7-[2-(2-aminothiazol-4-yl)-2-methoxyimino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form), or 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form).

* * * * *

(6) 1-alkyl-3-alkoxycarbonyl-1,2,4-triazol-5-yl,
(7a) 1,3,4-thiadiazol-5-yl which is unsubstituted or substituted by an alkyl, amino, aminoalkyl, alkylaminoalkyl, dialkylaminoalkyl or acylaminoalkyl radical,
  (b) 1,2,4-thiadiazol-5-yl substituted by an alkyl radical,
(8a) 1,3,4-oxadiazol-5-yl substituted by alkyl or phenyl,
  (b) 4-alkyl-oxazol-2-yl,
(9) tetrazol-5-yl substituted in the 1-position by
  (a) an alkyl radical which is unsubstituted or substituted by formyl,
  (b) an alkyl radical containing 2 or 3 carbon atoms substituted by hydroxyl, amino, alkylamino, dialkylamino or acylamino or
  (c) a radical of the general formula (II) as defined above; the symbol R⁰ represents a hydrogen atom or a methyl, vinyl or cyanomethyl radical, and the symbol R' represents a hydrogen atom, it being understood that the alkyl or acyl portions or radicals mentioned above contain, unless stated otherwise, 1 or 2 carbon atoms, in its syn- or anti-forms and E- or Z-forms, and in the form of mixtures of these, as well as its addition salts with acids, its metal salts and its addition salts with nitrogen-containing bases.

3. 7-[2-(2-Amino-thiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]-oct-2-ene (syn isomer, E-form).

4. The lysine salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene(syn isomer, E-form), as the aldehyde hydrate.

5. 7-[2-(2-Amino-thiazol-4-yl)-2-methoxyimino-acetamido]-2-carboxy-3-[2-(2,3-dihydroxy-4-propyl-5,6-dioxo-1,4,5,6-tetrahydro-1,2,4-triazin-3-yl)-thiovinyl]-8-oxo-5-thia-1-aza-bicyclo[4.2.0]oct-2-ene (syn isomer, E-form).

6. 3-{2-[4-(2-Acetamido-ethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form).

7. 7-[2-(2-Aminothiazol-4-yl)-2-methoxyimino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form).

8. 7-[2-(2-Amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2ene (syn isomer, E-form).

9. A pharmaceutical composition which comprises a compound according to claim 1 together with one or more compatible and pharmaceutically acceptable diluents or adjuvants.

10. A composition according to claim 9 in which the active ingredient is 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.]oct-2-ene (syn isomer, E-form), the lysine salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thio-vinyl]-8-oxo-5-thia-1-aza-bicyclo[4.2.0]oct-2-ene (syn isomer, E-form), as the aldehyde hydrate, 7-[2-(2-amino-thiazol-4-yl)-2-methoxyimino-acetamido]-2-carboxy-3-[2-(2,3-dihydroxy-4-propyl-5,6-dioxo-1,4,5,6-tetrahydro-1,2,4-triazin-3-yl)-thiovinyl]-8-oxo-5-thia-1-aza-bicyclo[4.2.0]oct-2-ene (syn isomer, E-form), 3-{2-[4-(2-acetamido-ethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form), 7-[2-(2-aminothiazol-4-yl)-2-methoxyimino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form), or 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form).

11. Method of killing bacteria which comprises exposing said bacteria to the action of a compound as claimed in claim 1.

12. Method according to claim 11 in which the said compound is 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form), the lysine salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form, as the aldehyde hydrate, 7-[2-(2-amino-thiazol-4-yl)-2-methoxyimino-acetamido]-2-carboxy-3-[2-(2,3-dihydroxy-4-propyl-5,6-dioxo-1,4,5,6-tetrahydro-1,2,4-triazin-3-yl)-thiovinyl]-8-oxo-5-thia-1-aza-bicyclo[4.2.0]oct-2-ene (syn isomer, E-form), 3-{2-[4-(2-acetamido-ethyl)-5,6-dioxo-1,4,5,6-tetrahydro-1,2,4-triazin-3-yl]-thiovinyl}-7-[2-(2-aminothiazol-4-yl)-2-methoxyimino-acetamido]-2-carboxy-8-oxo-5-thia-1-aza-bicyclo[4.2.0]oct-2-ene (syn isomer, E-form, 7-[2-(2-aminothiazol-4-yl)-2-methoxyimino-acetamido]-2-carboxy-3-{2-[5,6-dioxo-4-(2-formyloxy-ethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) or 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]-oct-2-ene (syn isomer, E-form).

13. Method of treating or preventing a bacterial infection which comprises administering to a subject suffering therefrom or subject thereto a compound as claimed in claim 1.

14. Method according to claim 13 in which the said compound is 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form), the lysine salt of 7-[2-(2-aminothiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2ene (syn isomer, E-form), as the aldehyde hydrate, 7-[2-(2-amino-thiazol-4-yl)-2-methoxyimino-acetamido]-2-carboxy-3-[2-(2,3-dihyalkylamino or dialkylamino), alkoxycarbonylamino, ureido, alkylureido or dialkylureido radical, (d) by a radical corresponding to one of the general formulae:

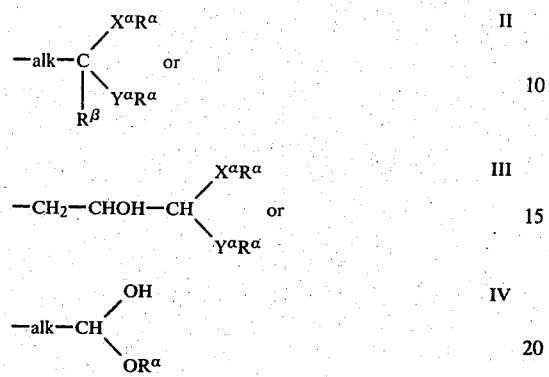

in which alk is an alkylene radical containing 1 to 4 carbon atoms, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) by an alkyl radical containing 1 to 5 carbon atoms, substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl, which is unsubstituted or substituted in the 3-position by alkoxycarbonyl, (7a) 1,3,4-thiadiazol-5-yl which is unsubstituted or substituted by an alkyl, trifluoromethyl, alkoxy, alkylthio, hydroxyalkylthio, of which the alkyl part contains 2 to 4 carbon atoms, alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or (b) 1,2,4-thiadiazol-5-yl substituted by an alkyl or alkoxy radical, (8a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or (b) oxazol-2-yl or 4-alkyl-oxazol-2-yl, or (9) tetrazol-5-yl which is unsubstituted or substituted in the 1-position by (a) an alkyl radical which is unsubstituted or substituted by alkoxy, sulpho, carboxyl, formyl or sulphamyl, (b) an alkyl radical which contains 2 to 4 carbon atoms and is substituted by hydroxyl, amino, alkylamino, dialkylamino, acylamino, carboxyalkylamino, sulphamylamino, sulphonylamino, ureido, alkylureido or dialkylureido, (c) an alkyl radical which contains 1 to 5 carbon atoms and is substituted by hydroxyimino or alkoxyimino, (d) a phenyl, 2,3-dihydroxypropyl, 1,3-dihydroxyprop-2-yl, 2-formyl-2-hydroxy-ethyl, 3-formyloxy-2-hydroxypropyl, 2,3-bisformyloxy-propyl, or 1,3-bisformyloxy-prop-2-yl radical or (e) a radical of the general formula (II), in which $R^\beta$ is a hydrogen atom or a radical of the general formula (III), the symbol $R^o$ represents a hydrogen atom or an alkyl, vinyl or cyanomethyl radical, and the symbol $R'$ represents a hydrogen atom or an enzymatically easily removable radical of the general formula:

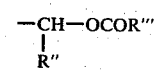

in which R" represents a hydrogen atom or an alkyl radical and R''' represents an alkyl radical or the cyclohexyl radical, it being understood that the alkyl or acyl portions or radicals mentioned above are (unless stated to the contrary) straight or branched and contain 1 to 4 carbon atoms, in its syn- or anti- and E- or Z-forms, and in the form of mixtures of these, as well as its addition salts with acids, its metal salts and its addition salts with nitrogen-containing bases.

2. A 3-thiovinyl-cephalosporin according to claim 1, wherein the symbol R is chosen from amongst the following meanings:

(1) methyl, L-2-amino-2-carboxyethyl or phenyl, (2) pyrid-2-yl or pyrid-2-yl-N-oxide, (3) pyrimidin-2-yl or pyridazin-3-yl substituted in the 6-position by a methyl or acetamido radical, or the N-oxides of these, (4) 5,6-dioxo-1,4,5,6-tetrahydro-1,2,4-triazin-3-yl substituted in the 4-position by (a) an alkyl radical containing 1 to 3 carbon atoms, or an alkyl radical containing 1 or 2 carbon atoms substituted by an alkoxy, alkylthio, phenyl, formyl, carbamyl, alkylcarbamyl, dialkylcarbamyl, alkoxycarbonyl or thiazolidin-2-yl radical, (b) an allyl or 2,3-dihydroxypropyl radical, (c) an alkyl radical containing 2 or 3 carbon atoms, substituted by hydroxyl, carbamyloxy, acyloxy (which is unsubstituted or substituted by amino), amino, alkylsulphonylamino, acylamino (which is unsubstituted or substituted by amino), alkoxycarbonylamino, ureido or alkylureido, (d) a radical of the general formula (II) in which alk is alkylene containing 1 or 2 carbon atoms, $X^\alpha$ and $Y^\alpha$ represent oxygen atoms, $R^\alpha$ represents alkyl radicals and $R^\beta$ represents a hydrogen atom, (e) an alkyl radical containing 1 to 3 carbon atoms, substituted by an alkoxyimino or hydroximino radical, (4') 1,3,4-triazol-5-yl or 2-alkoxycarbonyl-1,3,4-triazol-5-yl substituted in the 1-position by a radical of the general formula (II) as defined above or by a formylalkyl or 2,3-dihydroxypropyl radical, (5) 1,4-dialkyl-5,6-dioxo-1,4,5,6-tetrahydro-1,2,4-triazin-3-yl; 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, 1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (mixture of the syn, E, syn and anti, E, syn isomers) (0.85 g) in formic acid (20 cc) and water (15 cc) is stirred for 30 minutes at 50° C. It is then concentrated to dryness under 0.05 mm Hg (0.007 kPa) at 45° C., the residue is taken up in ethanol (40 cc), the mixture is evaporated to dryness under 20 mm Hg (2.7 kPa) at 20° C., and this operation is repeated twice. The yellow solid obtained is triturated in ethanol (20 cc) at 50° C., the mixture is allowed to cool and the product is filtered off. 7-[2-(2-Amino-thiazol-4-yl)-2-methoxyimino-acetamido]-2-carboxy-3-{2-[5,6-dioxo-4-(2-methoxyiminoethyl)-1,4,5,6-tetrahydro-1,2,4-triazin-3-yl]-thiovinyl}-8-oxo-5-thia-1-aza-bicyclo[4.2.0]oct-2-ene (mixture of the syn, syn, E and syn, anti, E isomers) (0.44 g) is obtained in the form of a yellow powder.

Infra-red spectrum (KBr): characteristc bands in cm$^{-1}$ at 3700 to 2000, 1775, 1710, 1690, 1630, 1585, 1550, 1050 and 945.

Proton nuclear magnetic resonance spectrum (350 MHz, DMSO d$_6$, δ in ppm, J in Hz):5.24 (d, J=4, 1H, H in the 6-position); 5.80 (dd, J=4 and 9, 1H, H in the 7-position); 6.95 and 7.10 (2d, J=16, 2H, —CH═CH—); 9.77 (d, J=9, 1H, —CONH—).

The present invention also relates to the medicaments which contain, as the active product, at least one product of the general formula (I) in the pure state (in the free form or in the form of a salt) or in the form of a composition in combination with one or more pharmaceutically acceptable adjuvants. These medicaments can be used orally, parenterally or rectally.

Tablets, pills, powders or granules can be used as solid compositions for oral administration. In these compositions, the active product according to the invention is mixed with one or more inert diluents or adjuvants such as sucrose, lactose or starch. These compositions can also contain substances other than the diluents, e.g. a lubricant such as magnesium stearate.

Pharmaceutically acceptable emulsions, solutions, suspensions, syrups and elixirs containing inert diluents such as water or paraffin oil can be used as liquid compositions for oral administration. These compounds can also contain substances other than diluents, e.g. wetting agents, sweeteners or flavourings.

The compositions for parenteral administration can be aqueous or non-aqueous sterile solutions, or suspensions or emulsions. Propylene glycol, a polyethylene glycol, vegetable oils, in particular olive oil, and injectable organic esters, e.g. ethyl oleate, can be used as the solvent or vehicle. These compositions can also contain adjuvants, in particular wetting agents, emulsifiers or dispersing agents. Sterilisation can be carried out in several ways, e.g. by using a bacteriological filter, by incorporating sterilising agents into the composition, by irradiation or by heating. The compositions can also be prepared in the form of sterile solid compositions which can be dissolved, at the time of use, in sterile water or in any other injectable sterile medium.

The compositions for rectal administration are suppositories which can contain excipients, such as cacao butter or suppository wax, in addition to the active product.

In human therapy, the medicaments according to the present invention are particularly useful in the treatment of infections of bacterial origin.

In general, the physician will decide the posology which he considers to be most appropriate, in accordance with the age, the weight, the severity of the infection and other factors peculiar to the subject to be treated. In general, the doses are between 1 and 10 g of active product per day, administered orally, intramuscularly or intravenously, for an adult.

The example which follows and which is given without implying a limitation illustrates a composition according to the present invention.

EXAMPLE

An injectable solution having the following composition is prepared:

| | |
|---|---|
| sodium salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form), as the aldehyde hydrate | 267 mg |
| sodium chloride | 1.5 mg |
| injectable base solution | 2 cm$^3$ |

This solution contains 250 mg of active product, calculated as free acid aldehyde.

We claim:

1. A 3-thiovinyl-cephalosporin which corresponds to the general formula:

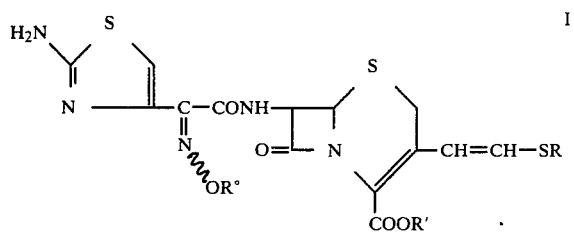

in which the symbol R is chosen from amongst the following meanings:

(1) alkyl, L-2-amino-2-carboxy-ethyl and phenyl, (2) pyrid-2-yl, pyrid-3-yl or pyrid-4-yl and their N-oxides, (3) pyrimidin-2-yl; pyridazin-3-yl substituted in the 6-position (by an alkyl, methoxy, amino or acylamino radical), its N-oxide, and tetrazolo[4,5-b]pyridazin-6-yl, (4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl, in each case substituted in the 1-position (a) by an alkyl radical which is unsubstituted or substituted by an alkoxy, alkylthio, phenyl, formyl, carbamyl, alkylcarbamyl, dialkylcarbamyl, acyl, alkoxycarbonyl or thiazolidin-2-yl radical, (b) by an allyl, 2,3-dihydroxypropyl, 1,3-dihydroxyprop-2-yl, 2-formyl-2-hydroxy-ethyl, 3-formyloxy-2-hydroxypropyl, 2,3-bisformyloxypropyl, or 1,3-bisformyloxyprop-2-yl radical, (c) by an alkyl radical which contains 2 to 4 carbon atoms and is substituted by a hydroxyl, carbamyloxy, acyloxy (of which the acyl part can be substituted by an amino, alkylamino or dialkylamino radical), alkylsulphinyl, alkylsulphonyl, amino, alkylamino, dialkylamino, sulphoamino, alkylsulphonylamino, sulphamylamino, acylamino (of which the acyl part is optionally substituted by hydroxyl, amino, mm Hg (2.7 kPa) at 20° C. 2-Benzhydryloxycarbonyl-3-{2-[[5,6-dioxo-4-[2-(3-methylureido)-ethyl]-1,4,5,6-tetrahydro-1,2,4-triazin-3-yl]]-thiovinyl}-7-[methoxyimino-2-(2-tritylamino-thiazol-4-yl)-acetamido]-8-oxo-5-thia-1-aza-bicyclo[4.2.0]oct-2-ene (syn isomer, E-form) (0.5 g) is obtained in the form of a yellow powder.

Infra-red spectrum (KBr): characteristic bands in cm$^{-1}$ at 3400, 1785, 1710, 1685, 1585, 1535, 1495, 1445, 1030, 940, 760 and 700.

A mixture of 2-benzhydryloxycarbonyl-3-{2-[[5,6-dioxo-4-[2-(3-methylureido)-ethyl]-1,4,5,6-tetrahydro-1,2,4-triazin-3-yl]]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.5 g), formic acid (8 cc) and water (4 cc) is treated at 50° C. for 40 minutes. It is then filtered and concentrated to dryness under 0.05 mm Hg (0.007 kPa) at 30° C., the residue is taken up in ethanol (4×50 cc), the mixture being concentrated to dryness each time under 20 mm Hg (2.7 kPa) at 20° C., and thereafter the residue is triturated in ethanol (40 cc), filtered off, washed with diethyl ether (2×10 cc) and dried.

7-[2-(2-Amino-thiazol-4-yl)-2-methoxyiminoacetamido]-2-carboxy-3-{2-[[5,6-dioxo-4-[2-(3-methylureido)-ethyl]-1,4,5,6-tetrahydro-1,2,4-triazin-3-yl]]thiovinyl}-8-oxo-5-thia-1-aza-bicyclo[4.2.0]oct-2-ene (syn isomer, E-form) (0.3 g) is obtained in the form of a yellow powder.

Infra-red spectrum (KBr): characteristic bands in cm$^{-1}$ at 3320, 3200, 1775, 1710, 1680, 1635, 1585, 1535, 1040 and 945.

Proton nuclear magnetic resonance spectrum (350 MHz, DMSO d$_6$, δ in ppm, J in Hz): 3.30 (m, 5H, CH$_2$NH— and >NCH$_3$); 3.60 and 3.78 (2 d, J=18, 2H, —SCH$_2$—); 3.85 (s broad, 5H, =NOCH$_3$ and >NCH$_2$—); 5.18 (d, J=4, 1H, H$_6$); 5.74 (dd, J=4 and 9, 1H, H$_7$); 6.09 (t, J=6, 1H, —NH—CH$_2$—); 6.74 (s, 1H, H of the thiazole); 6.82 and 7.12 (2d, J=16, 2H, —CH=CH—); 9.58 (d, J=9, 1H, —CONH—); 12.52 (s, 1H, —NH— of the triazine).

EXAMPLE 66

A solution of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1.19 g) and cysteamine hydrochloride (0.247 g) in pyridine (30 cc) is stirred at 50° C. for 30 minutes. It is then concentrated to dryness under 0.05 mm Hg (0.007 kPa) at 30° C., the residue is taken up in ethanol (20 cc), and the product is filtered off, and washed with ethanol (2×20 cc) and diethyl ether (2×20 cc). The pyridine salt of 7-[2-(2-amino-thiazol-4-yl)-2-methoxyimino-acetamido]-2-carboxy-3-{2-[5,6-dioxo-1,4,5,6-tetrahydro-4-[2-(thiazolidin-2-yl)-ethyl]-1,2,4-triazin-3-yl]-thiovinyl}-8-oxo-5-thia-1-aza-bicyclo[4.2.0]oct-2-ene (syn isomer, E-form) (1.3 g) is obtained in the form of a yellow powder.

Infra-red spectrum (KBr): characteristic bands in cm$^{-1}$ at 3400, 3280, 3200, 2000, 1775, 1710, 1680, 1610, 1380, 1035, 750 and 685.

Proton nuclear magnetic resonance spectrum (350 MHz, CF$_3$COOD, δ in ppm, J in Hz): 4.32 (s, 3H, —OCH$_3$); 5.40 (d, J=4, 1H, H in the 6-position); 6.04 (d, J=4, H in the 7-position); 7.25 and 7.78 (2d, J=16, 2H, —CH=CH—); 7.50 (s, 1H, H of the thiazole).

EXAMPLE 67

A mixture of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1.78 g), pyridine (50 cc) and hydroxylamine hydrochloride (0.42 g) is heated at 50° C. for 20 minutes. It is then concentrated to dryness under 0.05 mm Hg (0.007 kPa) at 30° C., the residue is taken up in ethanol (20 cc) and the product is filtered off, washed with ether (2×20 cc) and dried. The solid obtained (1.3 g) is heated in water (20 cc) at 60° C., a small amount of insoluble matter is filtered off, the filtrate is allowed to cool, the pH is brought to 3 by adding acetic acid (3 cc) and the mixture is heated to 70° C. to effect dissolution. It is then filtered, allowed to return to 20° C. and thereafter kept at 4° C. for 2 hours. After filtration and drying, 7-[2-(2-aminothiazol-4-yl)-2-methoxyimino-acetamido]-2-carboxy-3-{2-[5,6-dioxo-4-(2-hydroxyimino-ethyl)-1,4,5,6-tetrahydro-1,2,4-triazin-3-yl]-thiovinyl}-8-oxo-5-thia-1-aza-bicyclo[4.2.0]oct-2-ene (a mixture of the syn, syn, E and syn, anti, E isomers) (0.8 g) is obtained in the form of a cream-coloured powder.

Infra-red spectrum (KBr): characteristic bands in cm$^{-1}$ at 3700 to 3200, 1770, 1710, 1680, 1585, 1530, 1040 and 940.

Proton nuclear magnetic resonance spectrum (350 MHz, CF$_3$COOD, δ in ppm, J in Hz): 3.89 (s, 2H, —SCH$_2$—); 4.30 (s, 3H, —OCH$_3$); 5.39 (d, J=4, 1H, H in the 6-position); 6.04 (d, J=4, 1H, H in the 7-position); 7.28 and 7.77 (2d, J=16, 2H, —CH=CHS—); 7.50 (s, 1H, H of the thiazole).

EXAMPLE 68

A mixture of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.9 g), tetrahydrofurane (50 cc) and methoxyamine hydrochloride (0.49 g) is heated under reflux for 24 hours. It is then concentrated to dryness under 20 mm Hg (2.7 kPa) at 30° C., the residue is triturated in water (20 cc) and the product is filtered off, washed with ethanol (2×10 cc) and dried. 2-Benzhydryloxycarbonyl-3-{2-[5,6-dioxo-4-(2-methoxyiminoethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-aza-bicyclo[4.2.0]oct-2-ene (mixture of the syn, E, syn and anti, E, syn isomers) (0.92 g) is obtained.

Infra-red spectrum (KBr): characteristic bands in cm$^{-1}$ at 3700 to 2500, 1785, 1715, 1685, 1585, 1550, 1495, 1450, 1050, 950, 745 and 700.

Proton nuclear magnetic resonance spectrum (350 MHz, DMSO d$_6$, δ in ppm, J in Hz): 3.35 (s, 3H, —CH=N—O—CH$_3$); 3.70 and 3.90 (2d, J=18, 2H, —SCH$_2$—); 3.95 (s, 3H, =NOCH$_3$); 5.30 (d, J=4, 1H, H in the 6-position); 5.88 (dd, J=4 and 9, 1H, H in the 7-position); 6.95 and 7.05 (2d, J=16, 2H, —CH=CH—); 9.84 (d, J=9, 1H, —CONH—);

12.70 (s, 1H, =N NH CO— or =N N=C—).
                                            |
                                            OH

A solution of 2-benzhydryloxycarbonyl-3-{2-[5,6-dioxo-4-(2-methoxyiminoethyl)-1,4,5,6-tetrahydro- C. and is then allowed to cool. A half-saturated sodium bicarbonate solution (100 cc) is introduced, and the batch is stirred vigorously for 1 hour and then filtered. After drying, 3-{2-[4-(2-aminoethyl)-5,6-dioxo-1,4,5,6-tetrahydro-1,2,4-triazin-3-yl]-thiovinyl}2-benzhydryloxycarbonyl-7-[2-methoxyimino-2-(2-tritylaminothiazol-4-yl)-acetamido]-8-oxo-5-oxide-5-thia-1-azabicyclo[4.2.0]oct-2-ene (syn isomer, E-form) (2.73 g) is obtained in the form of a brown powder.

Infra-red spectrum (KBr): characteristic bands in cm$^{-1}$ at 3250 to 2300, 1800, 1715, 1685, 1595, 1520, 1500, 1450, 1215, 1180, 1040, 945, 755 and 700.

Proton nuclear magnetic resonance spectrum (350 MHz, DMSO d$_6$, δ in ppm, J in Hz): 3.08 (m, 2H, >N—CH$_2$CH$_2$—NH$_2$); 3.63 and 4.30 (2d, J=18, 2H, —SCH$_2$—); 3.85 (s, 3H, =NOCH$_3$); 4.09 (t, J=6, 2H, >NCH$_2$CH$_2$NH$_2$); 5.07 (d, J=4, H$_6$); 5.87 (dd, J=4 and 9, H$_7$); 6.80 (s, H of the thiazole); 6.95 (s, —COO-CH<); 7.07 and 7.13 (2d, J=16, —CH=CH—); 9.0 (d, J=9, —NHCO—); 12.62 (s broad, —NH— of the triazine).

EXAMPLE 64

A solution of potassium bicarbonate (0.5 g) in water (1.5 cc) and methyl chloroformate (0.16 cc) is added to a solution of 3-{2-[4-(2-aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylaminothiazol-4-yl)-acetamido]-8-oxo-5-thia-1-aza-bicyclo[4.2.0]oct-2-ene (syn isomer, E-form) (2 g) in tetrahydrofurane (60 cc) at 20° C., with stirring. The mixture is stirred for 1 hour 30 minutes at 20° C. and methyl chloroformate (0.32 cc) is then added. After 1 hour 30 minutes, the mixture is diluted with tetrahydrofurane (100 cc) and this mixture is dried over sodium sulphate, filtered and concentrated to dryness under 20 mm Hg (2.7 kPa) at 30° C. The product is fixed on Merck silica gel (0.06–0.2 mm) (5 g) and is chromatographed on a column (column diameter: 1.5 cm, height: 15 cm) of Merck silica gel (0.06–0.2 mm) (25 g). Elution is carried out with a 40:60 (by volume) mixture of cyclohexane and ethyl acetate (500 cc), and a 20:80 mixture (500 cc), and with ethyl acetate (500 cc), 25 cc fractions being collected. Fractions 19 to 32 are evaporated to dryness at 20° C. under 20 mm Hg (2.7 kPa) and 2-benzhydryloxycarbonyl-3-{2-[5,6-dioxo-4-(2-methoxycarbonylaminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.7 g) is obtained in the form of a yellow powder.

Infra-red spectrum (KBr): characteristic bands in cm$^{-1}$ at 3400, 3300, 1790, 1720, 1690, 1590, 1525, 1495, 1450, 1040, 755, 740 and 700.

A mixture of 2-benzhydryloxycarbonyl-3-{2-[5,6-dioxo-4-(2-methoxycarbonylaminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.7 g), formic acid (10 cc) and water (5 cc) is treated at 50° C. for 40 minutes. It is then filtered and concentrated to dryness at 30° C. under 0.05 mm Hg (0.007 kPa), the residue is taken up in ethanol (4×50 cc), the mixture being concentrated to dryness each time (under 20 mm Hg (2.7 kPa) at 20° C.), thereafter the residue is again triturated in ethanol (30 cc), and the product is filtered off, washed with diethyl ether (2×20 cc) and dried. 7-[2-(2-Amino-thiazol-4-yl)-2-methoxyiminoacetamido]-2-carboxy-3-{2-[5,6-dioxo-4-(2-methoxycarbonylaminoethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.35 g) is obtained in the form of a yellow powder.

Infra-red spectrum (KBr): characteristic bands in cm$^{-1}$ at 3340, 3210, 3100, 2200, 1770, 1685, 1625, 1590, 1530, 1035 and 945.

Proton nuclear magnetic resonance spectrum (350 MHz, DMSO d$_6$, δ in ppm, J in Hz): 3.55 (s, 3H, —COOCH$_3$), 3.62 and 3.79 (2d, J=18, 2H, —SCH$_2$—); 3.85 to 3.93 (mt, 5H, =NOCH$_3$ and >N CH$_2$—); 5.19 (d, J=4, 1H, H in the 6-position); 5.75 (dd, J=4 and 9, 1H, H in the 7-position); 6.74 (s, 1H, H of the thiazole); 9.58 (d, J=9, 1H, —CONH—);

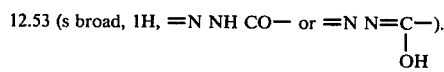

12.53 (s broad, 1H, =N NH CO— or =N N=C—).
　　　　　　　　　　　　　　　　　　　　　　|
　　　　　　　　　　　　　　　　　　　　　　OH 3-{2-[4-(2-Aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) can be prepared in the following manner:

A solution of 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiadiazol-4-yl)-acetamido]-8-oxo-5-thia-1-aza-bicyclo[4.2.0]oct-2-ene (syn isomer, E-form) (25 g) (obtained as described above, in Example 28) in acetonitrile (170 cc) is treated with a solution of p-toluenesulphonic acid (8.4 g) in acetonitrile (100 cc) at 40° C. for 1 hour. The gummy precipitate formed is isolated by decanting the supernatant phase and is treated with a saturated sodium bicarbonate solution (800 cc), with very vigorous stirring. The product is filtered off, washed with water (2×50 cc) and dried in air. 3-{2-[4-(2-Aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (15.3 g) is obtained in the form of a yellow powder.

Infra-red spectrum (KBr): characteristic bands in cm$^{-1}$ at 3400, 3150-2200, 1785, 1715, 1690, 1585, 1520, 1495, 1445, 1205, 1180, 1160, 1030, 940, 750 and 700.

EXAMPLE 65

A solution of 3-{2-[4-(2-aminoethyl-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2 g) in tetrahydrofurane (25 cc) is treated with methyl isocyanate (0.35 cc) at 4° C. The mixture is stirred for 2 hours at 5° C. and 2 hours at 20° C. It is then concentrated to dryness under 20 mm Hg (2.7 kPa) at 20° C. and the residue is taken up in diethyl ether (20 cc) and filtered off. A yellow powder (1.4 g) is obtained, which is fixed on Merck silica gel (0.06–0.2 mm) (10 g) and chromatographed on a column (column diameter: 1.5 cm, height: 15 cm) of Merck silica gel (0.06–0.2 mm) (20 g).

Elution is carried out with a 20:80 (by volume) mixture of cyclohexane and ethyl acetate (200 cc) and with ethyl acetate (500 cc), 25 cc fractions being collected. Fractions 15 to 25 are evaporated to dryness under 20

EXAMPLE 63

A solution of N,N'-dicyclohexylurea (0.5 g) in methylene chloride (10 cc) is added dropwise, in the course of 10 minutes, to a solution, cooled to +5° C., of N-tert.-butoxycarbonylglycine (0.84 g) in methylene chloride (20 cc). The mixture is stirred for 30 minutes at 5° C. and is filtered, and the filtrate is poured dropwise, in the course of 20 minutes, into a solution, cooled to 5° C., of 3-{2-[4-(2-aminoethyl-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (2.04 g), triethylamine (0.34 cc) and dimethylaminopyridine (50 mg) in methylene chloride (100 cc). The temperature is allowed to rise to 20° C. whilst stirring, and after 1 hour the mixture is concentrated to about 30 cc under 20 mm Hg (2.7 kPa) at 20° C. The residue is diluted with ethyl acetate (70 cc) and this mixture is washed with a saturated sodium bicarbonate solution (2×50 cc) and water (3×50 cc), dried over sodium sulphate, filtered and concentrated to dryness under 20 mm Hg (2.7 kPa) at 20° C. The residue is taken up in tetrahydrofurane (10 cc) and the mixture is left at 4° C. for 48 hours. It is then filtered and the filtrate is concentrated to dryness under 20 mm Hg (2.7 kPa) at 20° C.; the residue is triturated in diethyl ether (50 cc), filtered off and dried. 2-Benzhydryloxycarbonyl-3-{2-[4-(2-tert.-butoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (1.72 g) is obtained in the form of a brown powder.

Infra-red spectrum (KBr): characteristic bands in cm$^{-1}$ at 3380, 1800, 1710, 1690, 1590, 1515, 1495, 1450, 1210, 1165, 1050, 1040, 945, 755 and 700.

Proton nuclear magnetic resonance spectrum (350 MHz, DMSO d$_6$, δ in ppm, J in Hz): 1.35 (s, 9H, —C(CH$_3$)$_3$); 3.33 (m, 2H, >N—CH$_2$C$\underline{H}_2$NH—); 3.54 (t, J=5, 2H, >NC$\underline{H}_2$CH$_2$NH—); 3.63 (d, J=5, 2H, —COCH$_2$NH—); 3.6 and 4.3 (2d, J=18, 2H, —SCH$_2$—); 3.86 (s, 3H, =NOCH$_3$); 5.06 (d, J=4, 1H, H$_6$); 5.86 (dd, J=4 and 9, 1H, H$_7$); 6.78 (s, 1H, H of the thiazole); 6.85 and 7.12 (2d, J=16, 2H, —CH=CH—); 6.97 (s, 1H, —COOC$\underline{H}$<); 7.18 (s, 1H, N$\underline{H}$ of the thiazole); 8.0 (t, J=5, 1H, —COCH$_2$N$\underline{H}$—); 8.75 (s broad, 1H, NCH$_2$CH$_2$N$\underline{H}$—); 9.03 (d, J=9, 1H, —CONH—); 12.6 (s, 1H, —NH of the triazine).

A solution of 2-benzhydryloxycarbonyl-3-{2-[4-(2-tert.-butoxycarbonylglycylamino-ethyl)-5,6-dioxo-1,4,5,6-tetrahydro-1,2,4-triazin-3-yl]-thiovinyl}-2-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (1.65 g) in methylene chloride (30 cc) and dimethylacetamide (0.56 cc) is treated with phosphorus trichloride (0.5 cc) at −10° C. for 1 hour 30 minutes. The mixture is diluted with methylene chloride (150 cc), washed with a half-saturated sodium bicarbonate solution (2×100 cc) and a half-saturated sodium chloride solution (2×200 cc), dried over sodium sulphate, filtered and concentrated to dryness under 20 mm Hg (2.7 kPa) at 20° C.

The product is chromatographed on a column (column diameter: 2 cm, height: 34 cm) of Merck silica gel (0.06–0.2 mm) (50 g). Elution is carried out with a 50:50 (by volume) mixture of cyclohexane and ethyl acetate (250 cc) and with a 25:75 (by volume) mixture (500 cc), and with ethyl acetate (1.5 liters), 60 cc fractions being collected. Fractions 9 to 24 are concentrated to dryness and 2-benzhydryloxycarbonyl-3-{2-[4-tert.-butoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.78 g) is obtained in the form of a cream-coloured froth.

Infra-red spectrum (KBr): characteristic bands in cm$^{-1}$ at 3400, 3300, 1785, 1710, 1680, 1590, 1530, 1495, 1450, 1200, 1165, 1050, 950, 755 and 700.

Proton nuclear magnetic resonance spectrum (350 MHz, DMSO d$_6$, δ in ppm, J in Hz): 1.38 (s, 9H, —C(CH$_3$)$_3$); 3.30 (m, 2H, >NCH$_2$C$\underline{H}_2$NH—); 3.45 (d, J=5, —COCH$_2$NH—); 3.65 and 3.88 (2d, J=16, 2H, —SCH$_2$—); 3.85 (t, J=6, 2H, >NC$\underline{H}_2$CH$_2$NH—); 3.85 (s, 3H, =NOCH$_3$); 5.24 (d, J=4, H$_6$); 5.76 (dd, J=4 and 9, H$_7$); 6.92 and 7.00 (2d, J=16, —C$\underline{H}$=C$\underline{H}$—); 6.93 (s, —COOCH<); 7.79 (t, J=5, 1H, —CH$_2$N$\underline{H}$CO—); 8.80 (s, NH— of the thiazole); 9.59 (d, J=9, —CONH—); 12.53 (s, —NH— of the triazine).

A solution of 2-benzhydryloxycarbonyl-3-{2-[4-(2-tert.-butoxycarbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.73 g) in a mixture of formic acid (15 cc) and water (15 cc) is treated at 50° C. for 30 minutes. It is then concentrated to dryness under 0.05 mm Hg (0.007 kPa) at 50° C., and the residue is taken up in ethanol (3×150 cc), the mixture being evaporated each time under 20 mm Hg (2.7 kPa) at 20° C. Thereafter, the solid is taken up in ethanol (25 cc) at 45° C., and the mixture is stirred for 30 minutes, allowed to cool and filtered. After drying, 7-[2-(2-amino-thiazol-4-yl)-2-methoxyimino-acetamido]-2-carboxy-3-{2[5,6-dioxo-4-(2-glycylaminoethyl)-1,4,5,6-tetrahydro-1,2,4-triazin-3-yl]-thiovinyl}-8-oxo-5-thia-1-aza-bicyclo[4.2.0]oct-2ene (syn isomer, E-form) formate (0.39 g) is obtained in the form of a yellow powder.

Infra-red spectrum (KBr): characteristic bands in cm$^{-1}$ at 3700 to 2200, 1765, 1705, 1675, 1610, 1585, 1530, 1035 and 930.

Proton nuclear magnetic resonance spectrum (350 MHz, DMSO d$_6$, δ in ppm, J in Hz): 3.2 to 3.6 (m, 8H, —SCH$_2$—, >NCH$_2$CH$_2$N< and —COCH$_2$N<); 3.85 (s, =NOCH$_3$); 5.12 (d, J=4, H$_6$); 5.67 (dd, J=4 and 9, H$_7$); 6.35 (d, J=16, =C$\underline{H}$=CHS—); 6.73 (s, H of the thiazole); 7.15 (s broad, —NH$_2$); 8.2 (s, H of the formate); 8.6 (m, —CH$_2$N$\underline{h}$CO—); 9.54 (d, J=9, —NHCO—).

3-{2-[4-(2-Aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) can be obtained in the following manner:

A solution of hydrated p-toluenesulphonic acid (1.14 g) in acetonitrile (15 cc) is added dropwise, in the course of 10 minutes, to a solution, at 40° C., of 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo-[4.2.0]oct-2-ene (syn isomer, E-form) (3.36 g) (prepared as described in Example 28) in acetonitrile (45 cc). The mixture is stirred for 2 hours at 40° then with phosphorus trichloride (0.6 cc). After 1 hour 30 minutes at −10° C., the reaction mixture is diluted with ethyl acetate (600 cc) and washed successively with a saturated sodium bicarbonate solution (100 cc), distilled water (2×100 cc) and a saturated sodium chloride solution (2×200 cc). After drying over sodium sulphate and filtering, the organic solution is concentrated to dryness under reduced pressure (30 mm Hg; 4 kPa) at 40° C. The residue is chromatographed on a column (column diameter: 4 cm, height: 30 cm) of Merck silica gel (0.04–0.062 mm), elution being carried out under a pressure of 40 kPa with a 10:90 (by volume) mixture of cyclohexane and ethyl acetate (1.5 liters) and 50 cc fractions being collected. Fractions 7 to 22 are combined and concentrated to dryness under reduced pressure (30 mm Hg; 4 kPa) at 30° C. 2-Benzhydrylo xycarbonyl-3-{2-[4-(N-2-tert.-butoxycarbonylglycylo xyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.44 g) is obtained in the form of a yellow powder.

Infra-red spectrum (KBr): characteristic bands in cm⁻¹ at 1785, 1715, 1685, 1530, 1495, 1445, 1160, 1030, 945, 755 and 700.

Proton nuclear magnetic resonance spectrum (350 MHz, DMSO d$_6$, δ in ppm, J in Hz): 1.36 (s, 9H, (CH$_3$)$_3$CO—); 3.25 and 3.86 (2d, J=18, 1H, —SCH$_2$—); 3.65 (d, J=9, 2H, —COC$\underline{H}_2$NH—); 3.84 (s, 3H, =NOCH$_3$); 4.05 and 4.26 (2t, J=5, 2×2H, >NCH$_2$CH$_2$OCO—); 5.23 (d, J=4, 1H, H in the 6-position); 5.50 (d, J=9, 1H, —CH$_2$N$\underline{H}$CO—); 5.76 (dd, J=4 and 9, 1H, H in the 7-position); 6.71 (s, 1H, H of the thiazole); 6.91 (s, 1H, —C$\underline{H}$(C$_6$H$_5$)$_2$); 6.90 and 7 (2d, J=16, 2H, —CH=CH—S—); 7.15 to 7.5 (mt, 25H, aromatics); 8.78 (s broad, 1H, (C$_6$H$_5$)$_3$CN$\underline{H}$—); 9.60 (d, J=9, 1H, —CONH—);

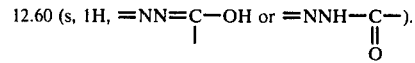

A solution of 2-benzhydryloxycarbonyl-3-{2-[4-(N--2-tert.-butoxycarbonylglycyloxy-ethyl)-5,6-dioxo -1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.5 g) in formic acid (15 cc) is diluted with distilled water (4 cc) and heated at 50° C. for 30 minutes, after which it is diluted with distilled water (11 cc). After filtering off the insoluble matter, the filtrate is evaporated to dryness under reduced pressure (5 mm Hg; 0.67 kPa) at 30° C. The residue is triturated with dry ethanol (60 cc), which is then evaporated under reduced pressure (30 mm Hg; 4 kPa) at 40° C. This latter operation is repeated 3 times in total, after which the solid residue is taken up in isopropyl ether (50 cc), filtered off, washed with ethyl ether (3×20 cc) and dried. The formate of 7-[2-(2-amino-thiazol-4-yl)-2-met hoxyimino-acetamido]-2-carboxy-3-{2-[5,6-dioxo-4-(2-glycyloxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.8 g) is obtained in the form of a light yellow powder.

Infra-red spectrum (KBr): characteristic bands in cm⁻¹ at 3550, 2200, 1755, 1705, 1675, 1580, 1530 and 1035.

Proton nuclear magnetic resonance spectrum (350 MHz, DMSO d$_6$, δ in ppm, J in Hz): 3.51 and 3.62 (AB, J=18, 2H, —SCH$_2$—); 3.72 (mt, 2H, —COC$\underline{H}_2$NH$_2$); 3.82 (s, 3H, =NOCH$_3$); 4.12 and 4.40 (2 Mt, 2×2H, >NCH$_2$CH$_2$OCO—); 5.10 (d, J=4, 1H, H in the 6-position); 5.67 (dd, J=4 and 9, 1H, H in the 7-position); 6.44 (d, J=16, 1H, —C$\underline{H}$=CH—S—); 6.72 (s, 1H, H of the thiazole); 7.18 (s broad, 3H, —NH$_3$⁺ of the thiazole); 8.12 (s, 1H, HCO$_2$—); 9.56 (d, J=9, 1H, —CONH—C$_7$).

EXAMPLE 62

Methylsulphonyl chloride (0.28 cc) and triethylamine (0.2 cc) are added, at −20° C., to a solution of 3-{2-[4--(2-aminoethyl)-5,6-dioxo-1,4,5,6-tetrahydro-1,2,4-triaz in-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2 g), prepared as described in Example 28, in tetrahydrofurane (25 cc), after which the temperature is allowed to rise to −5° C. in the course of 1 hour 30 minutes. The mixture is poured into water (500 cc), with vigorous stirring, and is filtered, and the solid is washed with ethanol (30 cc) and diethyl ether (10 cc) and dried; the product, fixed beforehand to Merck silica gel (0.06–0.2 mm) (5 g), is chromatographed on a column (column diameter: 0.5 cm, height: 10 cm) of Merck silica gel (0.06–0.2 mm) (10 g). Elution is carried out with ethyl acetate (200 cc), 15 cc fractions being collected. Fractions 5 to 11 are evaporated to dryness and 2-benzhydryloxycarbonyl-3-{2-[5,6-diox o-2-methylsulphonylaminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.3 g) is obtained in the form of a yellow powder.

Infra-red spectrum (KBr): characteristic bands (cm⁻¹) at 3300, 1790, 1715, 1695, 1590, 1525, 1495, 1450, 1320, 1160, 1035, 945, 755 and 700.

2-Benzhydryloxycarbonyl-3-{2-[5,6-dioxo-4-(2-m ethylsulphonylaminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.7 g) is treated with a mixture of formic acid (10 cc) and water (5 cc) for 30 minutes at 50° C. The mixture is filtered, the filtrate is concentrated to dryness under 20 mm Hg (2.7 kPa) at 50° C., and the residue is taken up in ethanol (4×50 cc), the mixture being evaporated to dryness each time under 20 mm Hg (2.7 kPa) at 20° C. The solid obtained is triturated in ethanol (50 cc), filtered off and washed with diethyl ether (2×10 cc). 7-[2-(2-Amino-t hiazol-4-yl)-2-methoxyimino-acetamido]-2-carboxy-3-{2-[5,6-dioxo-4-(2-methylsulphonylaminoethyl)-1,4,5,6-tetrahydro-1,2,4-triazin-3-yl]-thiovinyl}-8-oxo-5-thia-1-aza-bicyclo[4.2.0]oct-2-ene syn isomer, E-form) (0.4 g) is obtained in the form of a yellow powder.

Infra-red spectrum (KBr): characteristic bands (cm⁻¹) at 3400, 3300, 3200, 1775, 1710, 1680, 1590, 1530, 1320, 1150, 1140 and 945.

Proton nuclear magnetic resonance spectrum (350 MHz, DMSO d$_6$, δ in ppm, J in Hz): 2.90 (s, 3H, —SO$_2$CH$_3$); 3.20 (mt, 2H, —CH$_2$NH—); 3.61 and 3.78 (2 d, J=18, 2H, —SCH$_2$—); 3.96 (s, 3H, =NOCH$_3$); 3.96 (t, J=5, 2H, >N—CH$_2$—); 5.17 (d, J=4, 1H, H in the 6-position); 5.73 (dd, J=4 and 9, 1H, H in the 7-position); 6.74 (s, 1H, H of the thiazole); 6.79 (d, J=16, 1H, —C$\underline{H}$=CHS—); 7.17 (s, 2H, —NH$_2$); 9.60 (d, J=9, 1H, —CONH—).

6.96 (s, 1H, —CH(C6H5)2); 6.96 and 7.09 (AB, J=16, 2×1H, —CH=CH—S—); 7.15 to 7.60 (Mt, 25H, aromatics);

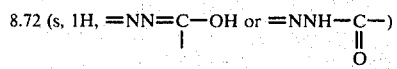
8.72 (s, 1H, =NN=C—OH or =NNH—C—)
                              |         ||
                                         O

EXAMPLE 60

Sodium bicarbonate (0.64 g) is added to a solution of 2-benzhydryloxycarbonyl-3-{2-[4-(2-hydroxyethyl)-5,6-siozo-1,4,5,6-tetrahydro-1,2,4triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.05 g) in dry tetrahydrofurane (25 cc) at 22° C., after which a solution of acetic anhydride (0.4 cc) in dry tetrahydrofurane (5 cc) is introduced dropwise in the course of 15 minutes. 4-Dimethylaminopyridine (0.05 g) dissolved in dry tetrahydrofurane (1 cc) is then added and the reaction mixture is stirred for 10 minutes at 25° C. It is then diluted with distilled water (50 cc) and ethyl acetate (120 cc). The organic phase is decanted and washed successively with 0.5 N hydrochloric acid (80 cc), a saturated sodium bicarbonate solution (80 cc) and a saturated sodium chloride solution (100 cc). After drying over magnesium sulphate and filtering, the solution is concentrated to dryness under reduced pressure (30 mm Hg. 4 kPa) at 40° C. A crude product (2.05 g) is obtained in the form of a yellow powder.

The crude product (2.5 g) obtained as above is chromatographed on a column (column diameter: 4 cm, height: 30 cm) of Merck silica (0.04–0.06 mm), elution being carried out with a 40:60 (by volume) mixture of cyclohexane and ethyl acetate (3 liters) under a pressure of 40 kPa, and 100 cc fractions being collected. Fractions 11 to 26 are concentrated to dryness under reduced pressure (30 mm Hg; 4 kPa) at 40° C. 3-55 2-[4-(2-Acetoxyethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.84 g) is obtained in the form of a light yellow froth.

Infra-red spectrum (CHBr3): characteristic bands in cm$^{-1}$ at 3400, 2820, 1790, 1720, 1685, 1590, 1495, 1450, 1050, 940, 760 and 740.

Proton nuclear magnetic resonance spectrum (350 MHz, DMSO d6, δ in ppm, J in Hz): 1.97 (s, 3H, CH3CO2—); 3.63 and 3.88 (AB, J=18, 2H, —SCH2—); 3.83 (s, 3H, =NOCH3); 4.06 (t, J=5, 2H, >N—CH2CH2OCOCH3); 4.23 (t, J=5, 2H, >NCH2—CH2OCOCH3); 5.21 (d, J=4, 1H, H in the 6-position); 5.76 (dd, J=4 and 9, 1H, H in the 7-position); 6.71 (s, 1H, H of the thiazole); 6.91 (d, J=16, 1H, —CH=CH—S—); 6.93 (s, 1H, —CH(C6H5)2); 7.0 (d, J=16, 1H, —CH=CH—S—); 7.2 to 7.5 (mt, 25H, aromatics); 9.60 (d, J=9, 1H, —CONH—); 12.58

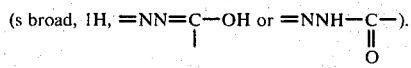
(s broad, 1H, =NN=C—OH or =NNH—C—).
              |              ||
                              O 3-{2-[4-(2-Acetoxyethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.8 g) is dissolved in formic acid (40 cc). After addition of distilled water (15 cc), the reaction mixture is heated at 60° C. for 30 minutes and then filtered and concentrated to dryness under reduced pressure (5 mm Hg; 0.67 kPa) at 40° C. The residue is triturated in ethanol (50 cc), which is then evaporated under reduced pressure (30 mm Hg; 4 kPa) at 40° C. This operation is repeated twice more. The residue is dissolved in boiling ethanol (150 cc); after filtering the hot solution, the filtrate is allowed to cool and is kept for 2 days at 5° C. The solid is filtered off, washed with diethyl ether (20 cc) and then dried. 3-{2-[4-(2-Acetoxyethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-8-oxo-5-thia-1-aza-bicyclo[4.2.0]oct-2-ene (syn isomer, E-form) (0.65 g) is obtained in the form of a pale yellow powder.

Infra-red spectrum (KBr): characteristic bands in cm$^{-1}$ at 3320, 3220, 3150, 2300, 1780, 1740, 1720, 1680, 1635, 1590, 1535, 1375, 1210, 1040 and 950.

Proton nuclear magnetic resonance spectrum (350 MHz, DMSO d6, δ in ppm, J in Hz): 2.0 (s, 3H, CH3CO2—); 3.63 and 3.82 (AB, J=18, 2H, —SCH2—); 3.85 (s, 3H, =NOCH3); 4.08 (t, J=5, 2H, >NCH2CH2OCOCH3); 4.25 (t, J=5, 2H, >NCH2CH2OCOCH3); 5.20 (d, J=4, 1H, H in the 6-position); 5.78 (dd, J=4 and 9, 1H, H in the 7-position); 6.73 (s, 1H, H of the thiazole); 6.90 (d, J=16, 1H, —CH=CH—S—); 7.12 (d, J=16, 1H, —CH=CHS—); 7.18 (s broad, 2H, —NH2); 9.60 (s, J=9, 1H, —CONH—C7);

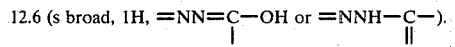
12.6 (s broad, 1H, =NN=C—OH or =NNH—C—).
                    |             ||
                                   O

EXAMPLE 61

A solution of N,N'-dicyclohexylcarbodiimide (0.72 g) in methylene chloride (20 cc) is added, in the course of 5 minutes, to N-tert.-butoxycarbonylglycine (1.12 g), dissolved in dry methylene chloride (30 cc), at 0° C. The reaction mixture is stirred for 30 minutes at a temperature of between 0° and 5° C. and is then filtered rapidly. The filtrate is added dropwise, in the course of 10 minutes, to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) in dry tetrahydrofurane (70 cc), which is cooled to 0° C. The reaction mixture is stirred for 45 minutes at 20° C. and is then diluted with ethyl acetate (500 cc) and washed successively with distilled water (200 cc), a saturated sodium bicarbonate solution (100 cc), distilled water (100 cc) and a saturated sodium chloride solution (50 cc). The organic phase is dried over sodium sulphate, filtered and concentrated under reduced pressure (30 mm Hg; 4 kPa) at 40° C. Crude 2-benzhydryloxycarbonyl-3-{2-[2-(2-N-tert.-butoxycarbonylglycyloxy-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.45 g) is obtained in the form of a brown powder.

This crude product (3.3 g) is dissolved in dry methylene chloride (45 cc). The solution, cooled to −10° C., is treated with N,N-dimethylacetamide (1.24 cc) and -1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.7 g) is obtained in the form of a brown powder.

Rf=0.68 [silica gel chromatographic phate; eluant: an 80:20 (by volume) mixture of ethyl acetate and methanol].

The crude product (3.35 g) obtained above is dissolved in dry methylene chloride (50 cc). N,N-dimethylacetamide (1.42 cc) is added, the mixture is then cooled to −10° C. and phosphorus trichloride (0.67 cc) is introduced. The reaction mixture is stirred for 1 hour at about −10° C. and then treated with N,N-dimethylacetamide (0.2 cc) and phosphorus trichloride (0.1 cc). After 20 minutes at −10° C., the reaction mixture is diluted with ethyl acetate (500 cc) and a saturated sodium bicarbonate solution (150 cc). The organic phase is decanted, washed with distilled water (2×50 cc) and with a saturated sodium chloride solution (100 cc), dried over magnesium sulphate and filtered. Evaporation of the solvent under reduced pressure (35 mm Hg; 4.7 kPa) at 40° C. gives a residue (3.6 g) which is chromatographed on a column (column diameter: 5 cm, height: 30 cm) of Merck silica gel (0.063–0.04 mm), elution being carried out, under a pressure of 40 kPa, with a 40:60 (by volume) mixture of cyclohexane and ethyl acetate (4 liters), and fractions of about 50 cc being collected. Fractions 38 to 76 are evaporated to dryness under reduced pressure (35 mm Hg; 4.7 kPa) at 40° C. 2-Benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isoner, E-form) (1.3 g) is obtained in the form of a light yellow powder.

Proton nuclear magnetic resonance spectrum (350 MHz, DMSO d$_6$, δ in ppm, J in Hz): 3.65 and 3.88 (AB, J=18, 2H, —SCH$_2$—); 3.84 (s, 3H, =NOCH$_3$); 4.10 and 4.32 (2t, J=5, 2×2H, >NCH$_2$CH$_2$OCHO); 5.21 (d, J=4, 1H, H in the 6-position); 5.75 (dd, J=4 and 9, 1H, H in the 7-position); 6.72 (s, 1H, H of the thiazole); 6.94 (s, 1H, —CH(C$_6$H$_5$)$_2$); 6.93 and 7.02 (AB, J=16, 2H, —CH=CH—S—); 7.1 to 7.5 (Mt, 25H, aromatics); 8.80 (s broad, 1H, (C$_6$H$_5$)$_3$CNH—); 9.60 (d, J=9, 1H, —CONH—C$_7$);

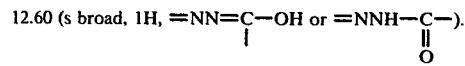

A solution of 2-benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.25 g) in formic acid (15 cc) is diluted with distilled water (4 cc) and heated for 25 minutes at 50° C., after which it is diluted with more distilled water (11 cc). After filtering off the insoluble matter, the filtrate is concentrated under reduced pressure (5 mm Hg; 0.67 kPa) at 30° C.; the residue is triturated in ethanol (50 cc), which is evaporated under reduced pressure (35 mm Hg; 4.7 kPa) at 40° C. This latter operation is repeated 4 times, after which the solid residue is taken up in ethanol (20 cc), filtered off, washed with diisopropyl ether (2×25 cc) and dried. The product is dissolved in pure formic acid (10 cc) and the solution is heated for 1 hour 30 minutes at 45° C. and then concentrated to dryness under reduced pressure (5 mm Hg; 0.67 kPa) at 40° C. The residue is triturated in anhydrous ethanol (30 cc) and the latter is then evaporated under reduced pressure (30 mm Hg; 4 kPa) at 40° C.; this operation is repeated twice more. 7-[2-(2-Amino-thiazol-4-yl)-2-methoxy imino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]-oct-2-ene (syn isomer, E-form) (0.54 g) is obtained in the form of a yellow powder.

Infra-red spectrum (KBr): characteristic bands in cm$^{-1}$ at 3400, 3200, 2200, 1775, 1710, 1680, 1530, 1040 and 945.

Proton nuclear magnetic resonance spectrum (350 MHz, DMSO d$_6$, δ in ppm, J in Hz): 3.62 and 3.82 (AB, J=18, 2H, —SCH$_2$—); 3.84 (s, 3H, =NOCH$_3$); 4.15 and 4.32 (2t, J=5, 2×2H, NCH$_2$CH$_2$—OCHO); 5.21 (d, J32 4, 1H, H in the 6-position); 5.78 (dd, J=4 and 9, 1H, H in the 7-position); 6.73 (s, 1H, H of the thiazole); 6.89 and 7.10 (2d, J=16, 2H, —CH=CH—S—); 7.16 (s, broad, 2H, —NH$_2$); 8.18 (s, 1H, HCOO—); 9.59 (d, J=9, 1H, —CONH—C$_7$);

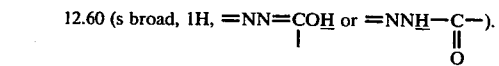

2-Benzhydryloxycarbonyl-3-{2-[5,6-dioxo-4-(2-hydroxyethyl)-1,4,5,6-tetrahydro-1,2,4-triazin-3-yl]-thiovinyl}-8-oxo-5-oxide-5-thia-1-aza-bicyclo[4.2.0]oct-2-ene (syn isomer, E-form) can be prepared in the following manner:

5,6-Dioxo-4-(2-hydroxyethyl)-perhydro-1,2,4-triazine (7 g) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (18 g) in dry N,N-dimethylformamide (490 cc) at 65° C., after which a solution of N,N-diisopropylethylamine (2.32 g) in dry N,N-dimethylformamide (160 cc) is introduced dropwise in the course of 10 minutes. The reaction mixture is stirred for 3 hours at 65° C. and then diluted with ethyl acetate (2 liters) and washed with distilled water (4×500 cc). The organic phase is dried over magnesium sulphate and concentrated under reduced pressure (35 mm Hg; 4.7 kPa) at 40° C. The residue is chromatographed on Merck silica gel (0.2–0.04 mm) (column diameter: 4 cm) (200 g), elution being carried out with a 20:80 (by volume) mixture of cyclohexane and ethyl acetate and fractions of about 250 cc being collected. Fractions 6 to 41 are concentrated to dryness under reduced pressure (35 mm Hg; 4.7 kPa) at 40° C. 2-Benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (17.16 g) is obtained in the form of a light brown powder.

Infra-red spectrum (KBr): characteristic bands in cm$^{-1}$ at 1800, 1720, 1685, 1525, 1495, 1450, 1045, 945, 755 and 700.

Proton nuclear magnetic resonance spectrum (350 MHz, DMSO d$_6$, δ in ppm, J in Hz): 3.60 and 4.28 (2d, J=17.5, 2×1H, —S(O)CH$_2$—); 3.57 and 3.88 (2 Mt, 2×2H, >NCH$_2$CH$_2$OH); 3.84 (s, 3H, =NOCH$_3$); 5.04 (d, J=4, 1H, H in the 6-position); 5.84 (dd, J=4 and 9, 1H, H in the 7-position); 6.77 (s, 1H, H of the thiazole);

nesium sulphate and filtered. After evaporation of the solvent under reduced pressure (30 mm Hg; 4 kPa) at 40° C., and drying, 2-benzhydryloxycarbonyl-3-{2-[4-(2-carbamyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.6 g) is obtained in the form of a yellow powder.

Infra-red spectrum (KBr): characteristic bands in cm$^{-1}$ at 3350, 2600, 1785, 1720, 1685, 1530, 1490, 1450, 755 and 700.

Proton nuclear magnetic resonance spectrum (350 MHz, DMSO d$_6$, δ in ppm, J in Hz): 3.30 and 3.64 (2d, J=18, 2H, —SCH$_2$—); 3.84 (s, 3H, =NOCH$_3$); 4.03 and 4.11 (2t, J=5, 2×2H, >NCH$_2$CH$_2$OCO—); 5.24 (d, J=4, 1H, H in the 6-position); 5.77 (dd, J=4 and 9, 1H, H in the 7-position); 6.71 (s, 1H, H of the thiazole); 6.94 (s, 1H, —CH(C$_6$H$_5$)$_2$); 6.93 and 7.02 (AB, J=16, 2H, —CH=CH—S—); 7.15 to 7.60 (Mt, 25H, aromatics); 8.25 to 8.80 (2s, 2H, —OCONH$_2$); 9.60 (d, J=9, 1H, —CONH—C$_7$); 12.60

(s, 1H, —N=C—OH or =N—NHC— of the triazine). 

A solution of 2-benzhydryloxycarbonyl-3-{-2-[4-(2-carbamyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.6 g) in formic acid (47 cc) is diluted with distilled water (20 cc) and the mixture is heated at 50° C. for 20 minutes and then diluted with a further amount of distilled water (27 cc); after filtering off the insoluble matter, the filtrate is concentrated to dryness under reduced pressure (5 mm Hg; 0.67 kPa) at 30° C. The residue is triturated with anhydrous ethanol (50 cc), which is then evaporated under reduced pressure (30 mm Hg; 4 kPa) at 40° C. This operation is repeated twice more, and the residue is then taken up in ethanol (40 cc), filtered off, washed with ether (2×50 cc) and dried. 7-[2-(2-Amino-thiazol-4-yl)-2-methoxyimino-acetamido]-3-{2-[4-(2-carbamyloxyethyl)-5,6-dioxo-1,4,5,6-tetrahydro-1,2,4-triazin-3-yl]-thiovinyl}-2-carboxy-8-oxo-5-thia-1-aza-bicyclo[4.2.0]oct-2-ene (syn isomer, E-form) (1.5 g) is obtained in the form of a cream-coloured powder.

Infra-red spectrum (KBr): characteristic bands in cm$^{-1}$ at 3550, 2200, 1770, 1710, 1680, 1050 and 940.

Proton nuclear magnetic resonance spectrum (350 MHz, DMSO d$_6$, δ in ppm, J in Hz): 3.62 and 3.82 (2d, J=18, 2H, —SCH$_2$—); 3.86 (s, 3H, =NOCH$_3$); 4.06 and 4.15 (2t, J=5, 2×2H, >NCH$_2$CH$_2$O—); 5.21 (d, J=9, 1H, H in the 6-position); 5.78 (dd, J=4 and 9, 1H, H in the 7-position); 6.50 (s broad, 2H, —OCONH$_2$); 6.75 (s, 1H, H of the thiazole); 6.92 and 7.08 (2d, J=16, 2H, —CH=CH—S—); 7 to 7.50 (s broad, 2H, —NH$_2$ of the thiazole); 9.66 (d, J=9, 1H, —CONH—C$_7$);

12.62 (s, 1H, —N=C—OH or =HNH—C—). 

2-Benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) can be obtained in the following manner:

A solution of N,N-diisopropylethylamine in dry N,N-dimethylformamide (50 cc) is added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (5.5 g) and of 5,6-dioxo-4-(2-hydroxyethyl)-3-thioxo-perhydro-1,2,4-triazine (2.08 g) in dry N,N-dimethylformamide (150 cc) in the course of 15 minutes, at 60° C. The reaction mixture is stirred for 3 hours at 60° C. and then diluted with ethyl acetate (600 cc). The organic phase is washed with a saturated sodium chloride solution (150 cc) and then with distilled water (3×150 cc), after which it is dried over magnesium sulphate. After filtration and concentration to dryness under reduced pressure (30 mm Hg; 4 kPa) at 40° C., the residue is chromatographed on Merck silica gel (0.04–0.06 mm) (column diameter: 6 cm, height: 30 cm), elution being carried out with a 15:85 (by volume) mixture of cyclohexane and ethyl acetate (7.5 liters) under a pressure of 40 kPa. The eluate is collected in fractions of about 100 cc. Fractions 24 to 70 are combined and concentrated to dryness under reduced pressure (30 mm Hg; 4 kPa) at 40° C. This gives 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.31 g) in the form of a light yellow solid.

Rf=0.33 [silica gel chromatographic plate, eluant: a 10:90 (by volume) mixture of cyclohexane and ethyl acetate].

Infra-red spectrum (CHBr$_3$): characteristic bands in cm$^{-1}$ at 3380, 1785, 1715, 1680, 1585, 1520, 1495, 1450, 1050, 940, 755 and 740.

Proton nuclear magnetic resonance spectrum (350 MHz, CDCl$_3$, δ in ppm, J in Hz): 3.44 and 3.60 (AB, J=18, 2H, —SCH$_2$—); 3.81 (mf, 2H, —CH$_2$OH); 4.00 (s, 3H, =NOCH$_3$); 5.00 (d, J=4, 1H, H in the 6-position); 5.90 (dd, J=4 and 9, 1H, H in the 7-position); 6.70 (s, 1H, H of the thiazole); 6.81 (d, J=15, 1H, —CH=CH—S—); 6.90 (s, 1H, —CH (C$_6$H$_5$)$_2$); 5.72 to 7.6 (mf, aromatics, —CONH—, —CH=CHS—, (C$_6$H$_5$)$_3$CNH—).

EXAMPLE 59

Triethylamine (0.38 cc) and 4-N,N-dimethylaminopyridine (0.05 g), followed by a solution of formic anhydride (4.9 millimols) in methylene chloride (10 cc) (prepared according to G. A. OLAH et al., Angew. Chem. 91 649 (1979)) are added to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in dry tetrahydrofurane (100 cc), cooled to −10° C. The reaction mixture is stirred for 3 hours at about 20° C. and is then filtered, diluted with ethyl acetate (450 cc) and washed successively with 0.2 N hydrochloric acid (50 cc), distilled water (100 cc), a saturated sodium bicarbonate solution (100 cc) and a saturated sodium chloride solution (100 cc). The organic phase is dried over magnesium sulphate, filtered and concentrated under reduced pressure (30 mm Hg; 4 kPa) at 40° C. Crude 2-benzhydryloxycarbonyl-3-{2-[5,6-dioxo-4-(2-formyloxyethyl)

Infra-red spectrum (KBr): characteristic bands (cm⁻¹) at 3410, 1795, 1720, 1500, 1160, 1050, 940, 755, 740 and 700.

Proton nuclear magnetic resonance spectrum (350 MHz, CDCl₃, δ in ppm, J in Hz): 1.50 (s, 9H, (CH₃)₃C—); 2.75 (s, 3H, —CH₃ Het);

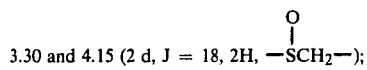

3.30 and 4.15 (2 d, J = 18, 2H, —SCH₂—);

4.55 (d, J=4, 1H, H in the 6-position); 5.7 to 5.9 (m, 2H, —CONH— and H in the 7-position); 6.97 (s, 1H, —COOCH<); 7.53 (d J=16, 1H, —CH=CHS—).

EXAMPLE 57

7-Amino-2-carboxy-3-[2-(1-methyl-tetrazol-5-yl)-thiovinyl]-8-oxo-5-thia-1-aza-bicyclo[4.2.0]oct-2-ene (E-form) (0.51 g) is dissolved in a mixture of water (10 cc), sodium bicarbonate (0.63 g) and acetone (7.5 cc). The solution is cooled to −8° C. and a solution of 4-bromo-2-methoxyimino-3-oxo-butyryl chloride, syn isomer (0.363 g) in acetone (5 cc) is added. The mixture is again stirred for 50 minutes whilst the temperature is allowed to rise from −8° C. to +5° C. The mixture is then filtered, the acetone is evaporated at 20° C. under 20 mm Hg (2.7 kPa), the residue is diluted with water (50 cc), this solution is washed with ethyl acetate (50 cc), the aqueous phase is diluted with water (100 cc), ethyl acetate (150 cc) is added and the mixture is acidified to pH 2.3 by means of a 4 N hydrochloric acid solution. The organic layer is washed with a half-saturated sodium chloride solution (100 cc), dried over sodium sulphate and concentrated to dryness at 20° C. under 20 mm Hg (2.7 kPa).

The solution of the product thus obtained, in ethanol (5 cc), is added, at 20° C., to a solution of thiourea (0.11 g) in ethanol (5 cc) and water (10 cc). The mixture is stirred for 35 minutes at 20° C., the pH is then adjusted to 6 by adding sodium bicarbonate, the mixture is acidified by adding formic acid (1 cc) and concentrated to dryness at 20° C. under 20 mm Hg (2.7 kPa), and the residue is taken up in ethanol (3×50 cc), the mixture being evaporated to dryness each time at 20° C. under 20 mm Hg. The residue is then extracted with ethanol (250 cc) under reflux, the mixture is filtered, the filtrate is concentrated to 25 cc at 20° C. under 20 mm Hg (2.7 kPa), this residue is left for 15 minutes at 5° C. and is then again filtered, and the solid is washed with ethanol (5 cc) and ether (2×10 cc). 7-[2-(2-Aminothiazol-4-yl)-2-methoxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, E-form) (0.28 g) is obtained in the form of a yellow powder, the characteristics of which are identical to those of the product described above in Example 48.

7-Amino-2-carboxy-3-[2-(1-methyl-tetrazol-5-yl)-thiovinyl]-8-oxo-5-thia-1-aza-bicyclo[4.2.0]oct-2-ene (E-form) can be obtained in the following manner:

A mixture of 7-amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) (3 g) in formic acid (105 cc) and water (40 cc) is treated at 50° C. for 30 minutes. It is then concentrated to dryness at 20° C. under 0.05 mm Hg (0.007 kPa), the residue is taken up in ethanol (2×100 cc), the mixture being concentrated to dryness each time at 20° C. under 20 mm Hg (2.7 kPa), and the solid obtained is triturated in ethanol (50 cc), filtered off and washed with diethyl ether (2×25 cc).

7-Amino-2-carboxy-3-[2-(1-methyl-tetrazol-5-yl)-thiovinyl]-8-oxo-5-thia-1-aza-bicyclo[4.2.0]oct-2-ene (E-form) is obtained as the formate (1.5 g).

Proton nuclear magnetic resonance spectrum (350 MHz, DMSO d₆, δ im ppm, J in Hz): 3.64 and 3.89 (2d, J=18, 2H, —SCH₂—); 4.02 (s, 3H, —CH₃); 5.15 (d, J=4, 1H, H in the 6-position); 5.77 (dd, J=4 and 9, 1H, H in the 7-position); 6.97 and 7.13 (2d, J=16, 2H, —CH=CH—); 9.07 (d, J=9, 1H, —CONH—).

7-Amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) can be obtained in the following manner:

2-Benzhydryloxycarbonyl-7-tert.-butoxycarbonylamino-3-[2-(1-methyl-tetrazol-5-yl)-thiovinyl]-8-oxo-5-thia-1-aza-bicyclo[4.2.0]oct-2-ene (E-form) (8 g), dissolved in acetonitrile (80 cc) is treated with p-toluenesulphonic acid hydrate (4.9 g) under the conditions described in Example 56. After this treatment, 7-amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) (5.7 g) is obtained in the form of a light brown solid.

Infra-red spectrum (KBr): characteristic bands (cm⁻¹) at 1775, 1710, 1495, 1455, 1210, 755 and 705.

A solution of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (13.8 g) in methylene chloride (250 cc) and dimethylacetamide (7.65 g) is treated with phosphorus tribromide (11.9 g) at −20° C. for 10 minutes. The mixture is poured into a saturated potassium bicarbonate solution (250 cc), with vigorous stirring, and the organic phase is washed with a saturated sodium chloride solution (100 cc), dried over sodium sulphate, filtered and concentrated to dryness at 20° C. under 20 mm Hg (2.7 kPa). The residue is chromatographed on a column (column diameter: 3 cm, height: 32 cm) of Merck silica gel (0.06–0.2 mm) (260 g). Elution is carried out with a 70:30 (by volume) mixture of cyclohexane and ethyl acetate (1.5 liters), 100 cc fractions being collected. Fractions 7 to 14 are concentrated to dryness at 20° C. under 20 mm Hg (2.7 kPa) and 2-benzhydryloxycarbonyl-7-tert.-butoxycarbonylamino-3-[2-(1-methyl-tetrazol-5-yl)-thiovinyl]-8-oxo-5-thia-1-aza-bicyclo[4.2.0]oct-2-ene (E-form) (8.5 g) is obtained in the form of a yellow powder.

Infra-red spectrum (KBr): characteristic bands (cm⁻¹) at 3340, 1790, 1705, 1690, 1510, 1160, 940, 730 and 700.

EXAMPLE 58

A solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form)(2.5 g), in dry tetrahydrofurane (250 cc) is cooled to −50° C. and treated with chlorosulphonyl isocyanate (11 cc). The mixture is stirred for 55 minutes, whilst allowing the temperature to rise slowly to −5° C., and a saturated sodium bicarbonate solution (150 cc) and ethyl acetate (250 cc) are then added. The aqueous phase is extracted with ethyl acetate (100 cc) and the combined organic extracts are washed with a saturated sodium chloride solution (2×100 cc) and then dried over mag- 7.01 (s, 1H, —COOCH—);

9.43 (d, J=9, 1H, —CONH—); 16.50 (s broad, 1H, =NOH).

A solution of bromine (5.79 g) in methylene chloride (3.53 cc) is added dropwise to a solution of diketene (3.04 g) in methylene chloride (3.53 cc) in the course of 35 minutes, at −30° C. The solution is then stirred at the same temperature for 30 minutes. One-tenth of this solution is taken and added dropwise to a stirred solution of 7-amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) (1.38 g) and bis-trimethylsilyl-acetamide (1.11 cc) in ethyl acetate (20 cc) in the course of 10 minutes at −15° C., and the solution is then stirred at the same temperature for 30 minutes. Thereafter, water (20 cc) is added and the organic phase is decanted, washed with a saturated sodium chloride solution (3×10 cc), dried over magnesium sulphate, filtered and concentrated to dryness under reduced pressure (20 mm Hg. 2.7 kPa). This gives 2-benzhydryloxycarbonyl-7-(4-bromo-3-oxo-butyramido)-3-[2-(2-methyl-1,3,4-thiadiazol-5-yl)-thiovinyl]-8-oxo-5-thia-1-aza-bicyclo[4.2.0]oct-2-ene (E isomer) (1.9 g) in the form of a brown solid.

Infra-red spectrum (KBr): characteristic bands (cm$^{-1}$) at 1780, 1720, 1680, 1535, 1490, 1450, 1250, 940, 760 and 700.

Proton nuclear magnetic resonance spectrum (350 MHz, CDCl$_3$, δ in ppm, J in Hz): 2.75 (s, 3H, —CH$_3$ of the heterocyclic ring); 3.58 and 3.84 (2 d, J=19, 2H, —SCH$_2$—); 3.75 (s, 2H, —COCH$_2$CO—); 4.03 (s, 2H, —CH$_2$Br); 5.04 (d, J=4, 1H, H in the 6-position); 5.85 (dd, J=4 and 9, 1H, H in the 7-position); 6.98 (s, 1H, —COOCH<).

7-Amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) can be prepared in the following manner:

A solution of p-toluenesulphonic acid monohydrate (8.43 g) in acetonitrile (46 cc) is added, in the course of 3 minutes, to a suspension of 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.2 g) in acetonitrile (138 cc) at 35° C. The mixture becomes homogeneous, and is kept at 38° C. for 40 minutes, after which it is poured into a solution of sodium bicarbonate (7.44 g) in water (600 cc). The mixture is extracted with ethyl acetate (300 cc, followed by 3×100 cc). The organic phases are combined, washed with a saturated sodium bicarbonate solution (100 cc) and then with a saturated sodium chloride solution (2×100 cc), dried over magnesium sulphate, filtered and concentrated to dryness under reduced pressure (20 mm Hg, 2.7 kPa). This gives 7-amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) (6.8 g) in the form of a brown gummy material.

Infra-red spectrum (KBr): characteristic bands (cm$^{-1}$) at 3400, 3340, 1780, 1720, 1670, 1560, 1500, 1455, 940, 760, 745 and 700.

Proton nuclear magnetic resonance spectrum (80 MHz, CDCl$_3$, δ in ppm, J in Hz): 2.72 (s, 3H, —CH$_3$ of the heterocyclic ring); 3.46 (s, broad, 2H, —SCH$_2$—); 4.77 (d, J=4, 1H, H in the 6-position); 5.00 (d, J=4, 1H, H in the 7-position); 7.00 (s, 1H, —COOCH<); 7.18 (s broad, 2H, —CH=CH—).

2-Benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) can be prepared as follows:

Phosphorus trichloride (4.7 cc) is added, in the course of 5 minutes, to a solution of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) (17 g) and dimethylacetamide (10.9 cc) in methylene chloride (170 cc) at −10° C., and the mixture is kept at this temperature for one hour. It is then diluted with ethyl acetate (2,000 cc) at 0° C., and this mixture is washed with a saturated sodium bicarbonate solution (three×250 cc) and a saturated sodium chloride solution (250 cc), dried over magnesium sulphate, filtered and evaporated to dryness under reduced pressure. The residue is chromatographed on a column (column diameter: 4.5 cm; height: 37 cm) of Merck silica gel (0.063–0.2 mm) (291 g), elution being carried out with a 92.5:7.5 (by volume) mixture of methylene chloride and ethyl acetate (3 liters) and 100 cc fractions being collected. Fractions 12 to 29, containing the product, are evaporated to dryness under reduced pressure (20 mm Hg, 2.7 kPa). This gives 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.25 g) in the form of a light yellow solid.

Infra-red spectrum (KBr): characteristic bands (cm$^{-1}$) at 3370, 1790, 1715, 1700, 1520, 1160, 945, 740 and 700.

Proton nuclear magnetic resonance spectrum (80 MHz, CDCl$_3$, δ in ppm, J in Hz): 1.50 (s, 9H, (CH$_3$)$_3$C—); 2.75 (s, 3H, —CH$_3$ of the heterocyclic ring); 3.68 (s broad, 2H, —SCH$_2$—); 5.03 (d, J=4, 1H, H in the 6-position); 5.28 (d, J=9, 1H, —CONH—); 5.65 (dd, J=4 and 9, 1H, H in the 7-position); 7.00 (1H, s, —COOCH<).

2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) can be prepared as follows:

A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E isomer) (20 g), 2-methyl-1,3,4-thiadiazoline-5-thione (4.87 g) and diisopropyl ethylamine (5.04 cc) in dimethylformamide (200 cc) is heated to 60° C. for 2 hours. The mixture is poured onto iced water (2,000 cc), the mixture is extracted with ethyl acetate (2,000 cc followed by 500 cc), and the organic phases are combined, washed with a saturated sodium bicarbonate solution (250 cc), distilled water (4×250 cc) and a saturated sodium chloride solution (250 cc), dried over magnesium sulphate, filtered in the presence of decolorising charcoal and concentrated to dryness under reduced pressure (30 mm Hg, 4 kPa) at 30° C. This gives 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]-oct-2-ene (E isomer) (17 g) in the form of a green-brown gummy material. This material is redissolved in ethyl acetate (60 cc), reprecipitated by means of isopropyl ether (600 cc), filtered off and dried. The expected product is thus obtained in the form of a yellow powder.

tritylamino-thiazol-4-yl)-acetamido]-8-oxo-5-oxide-5-thia-1-aza-bicyclo[4.2.0]oct-2-ene (syn isomer, E-form) (0.21 g) is obtained in the form of a brown froth.

On treating this product as described above in Example 28, 7-[2-(2-amino-thiazol-4-yl)-2-methoxyiminoa cetamido]-3-{2-[4-(2-aminoethyl)-5,6-dioxo-1,4,5,6-tetrahydro-1,2,4-triazin-3-yl]-thiovinyl}-2-carboxy-5-thia-1-aza-bicyclo[4.2.0]oct-2-ene (syn isomer, E-form) is obtained as the formate, the characteristics of which are identical to those of the product of Example 28.

The thiolo-ester used as the starting material can be prepared in the following manner:

N,N'-Dicyclohexylcarbodiimide (1.11 g) is added to a suspension, cooled to +4° C., of 2-methoxyimino-2-(2-tritylamino-thiazol-4-yl)-acetic acid, syn isomer (2.17 g) and 4-(2-tert.-butyoxycarbonylamino-ethyl)-5,6-dioxo-3-thioxo-perhydro-1,2,4-triazine (1.05 g) in ethyl acetate (50 cc). The mixture is stirred for 4 hours at 20° C., filtered and concentrated to dryness at 20° C. under 20 mm Hg (2.7 kPa). The residue is taken up in methylene chloride (20 cc) and the solution is poured into diisopropyl ether (250 cc). After filtration and drying, 4-(2-tert.-butoxycarbonylamino-ethyl)-5,6-dioxo-3-[2-methoxyimino-2-(2-tritylamino-thiazol-4-yl)-acetylthio]-1,4,5,6-tetrahydro-1,2,4-triazine (syn isomer) (0.73 g) is obtained in the form of a yellow powder.

Infra-red spectrum (CHBr$_3$): characteristic bands (cm$^{-1}$) at 3440, 3390, 2820, 1710, 1585, 1530, 1450, 1390, 1370, 1050, 955, 900 and 755.

EXAMPLE 56

Thiourea (0.18 g) is added to a solution of 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.4 g) in ethanol (25 cc), tetrahydrofurane (25 cc) and water (5 cc) and the solution is stirred for 4 hours at 20° C. It is then concentrated to dryness under reduced pressure (20 mm Hg, 2.7 kPa). The residue is triturated with water (10 cc), the mixture is brought to pH 7 with a sodium bicarbonate solution, and the precipitate is filtered off, washed with water (5 cc) and dried. A light beige solid (1.3 g) is obtained, which is dissolved in chloroform (10 cc). The solution obtained is added dropwise to isopropyl ether (100 cc), whilst stirring. The insoluble matter formed is filtered off and redissolved in tetrahydrofurane (25 cc), the solution formed is filtered in the presence of decolorising charcoal and the filtrate is concentrated to a volume of 5 cc under reduced pressure (20 mm Hg, 2.7 kPa). Ethyl acetate (25 cc) is added to this solution. The solid formed is filtered off, washed with ethyl acetate (10 cc) and dried. 2-Benzhydryloxycarbonyl-7[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.9 g) is thus obtained in the form of a beige solid.

Infra-red spectrum (KBr): characteristic bands (cm$^{-1}$) at 3380, 3200, 3100, 1785, 1720, 1685, 1630, 1535, 1500, 1445, 1210, 950, 760, 745 and 705.

Proton nuclear magnetic resonance spectrum (350 MHz, DMSO d$_6$, δ in ppm, J in Hz): 2.71 (s, 3H, —CH$_3$ Het); 3.72 and 3.98 (2 d, J=18, 2H, —SCH$_2$—); 5.28 (d, J=4, 1H, H in the 6-position); 5.90 (dd, J=4 and 9, 1H, H in the 7-position); 6.80 (1, 1H, H of the thiazole); 6.98 (s, 1H, —COOCH<); 7.05 (d, J=16, 1H, —CH=CHS—); 7.26 (d, J=16, 1H, —CH=CHS—); 9.65 (d, J=9, 1H, —CONH—); 11.85 (s broad, 1H, =NOH).

2-Benzhydryloxycarbonyl-7-[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.3 g) is dissolved in 98% strength formic acid (6 cc). Distilled water (6 cc) is added and the mixture is heated at 60° C. for 15 minutes. The cloudy solution is cooled and is filtered in the presence of decolorising charcoal, and the filtrate is evaporated to dryness under reduced pressure (20 mm Hg, 2.7 kPa). Ethanol (10 cc) is added to the residue, the mixture is concentrated to dryness under reduced pressure (20 mm Hg, 2.7 kPa), this operation is repeated twice, the suspension of the residue in ethanol (10 cc) is then heated under reflux and cooled, and the product is filtered off and dried under reduced pressure (0.5 mm Hg, 0.07 kPa). This gives 2-carboxy-7-[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.07 g) in the form of a yellow solid.

Infra-red spectrum (KBr): characteristic bands (cm$^{-1}$) at 3600, 2200, 1770, 1660, 1630, 1530, 1390 and 950.

Proton nuclear magnetic resonance spectrum (350 MHz, DMSO d$_6$, δ in ppm, J in Hz): 2.74 (s, 3H, —CH$_3$ Het); 3.64 and 3.90 (2 d, J=18, 2H, —SCH$_2$—); 5.20 (d, J=4, 1H, H in the 6-position); 5.80 (dd, J=4 and 9, 1H, H in the 7-position); 6.65 (s, 1H, H of the thiazole). 6.08 (s, broad, 2H, —NH$_2$); 7.10 and 7.20 (2 d, J=14, 2H, —CH=CH—S—); 9.46 (d, J=9, 1H, —CONH—); 11.28 (s broad, 1H, =NOH).

2-Benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) can be prepared in the following manner:

2-Benzhydryloxycarbonyl-7-(4-bromo-3-oxo-butyramido)-3-[2-(2-methyl-1,3,4-thiadiazol-5-yl)-thiovinyl]-8-oxo-5-thia-1-aza-bicyclo[4.2.0]oct-2-ene (E isomer) (1.8 g) is suspended in a mixture of tetrahydrofurane (23 cc) and water (4.7 cc) at 10° C. Acetic acid (7.8 cc) is then added, the mixture is cooled to 0° C. with ice, a solution of sodium nitrite (0.187 g) in water (2.3 cc) is added and the reaction mixture is allowed to return to 20° C. in the course of 4 hours. The resulting solution is diluted with iced water (150 cc). The precipitate is filtered off and dissolved in ethyl acetate (100 cc), and the organic phase is washed with a saturated sodium bicarbonate solution (2×25 cc) and a saturated sodium chloride solution (2×25 cc), dried over magnesium sulphate, filtered and concentrated to dryness under reduced pressure (20 mm Hg, 2.7 kPa). This gives 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.5 g) in the form of a brown solid.

Infra-red spectrum (KBr): characteristic bands (cm$^{-1}$) at 1785, 1715, 1685, 1540, 1495, 1455, 1205, 950, 760, 745 and 700.

Proton nuclear magnetic resonance spectrum (350 MHz, CDCl$_3$, δ in ppm, J in Hz): 2.76 (s, 3H, —CH$_3$ Het); 4.53 (s, 2H, —COCH$_2$Br); 5.12 (d, J=4, 1H, H in the 6-position); 5.85 (dd, J=4 and 9, 1H, H in the 7-position);

then filtered, and the filtrate is washed with water (2×200 cc), a half-saturated sodium bicarbonate solution (2×100 cc) and a saturated sodium chloride solution (100 cc), dried over sodium sulphate, filtered, concentrated to 20 cc at 20° C. under 20 mm Hg (2.7 kPa), and again filtered. The filtrate is diluted with petroleum ether (200 cc) and the mixture is filtered, a yellow powder (6.2 g), corresponding to a crude form of the expected product, being collected.

Purification is carried out in the following manner: the preceding product is treated with cyclohexane (200 cc) under reflux, the mixture is filtered hot, the filtrate is concentrated to 30 cc (at 20° C. under 20 mm Hg; 2.7 kPa), the concentrate is filtered and 5-[2-methoxyimino-2-(2-tritylamino-thiazol-4-yl)-acetylthio]-2-methyl-1,3,4-thiadiazole, syn isomer, (4.5 g) is collected.

Proton nuclear magnetic resonance spectrum (80 MHz, CDCl₃, δ in ppm, J in Hz): 2.85 (s, 3H, —CH₃); 4.08 (s, 3H, =NOCH₃); 6.60 (s, 1H, H of the thiazole).

Infra-red spectrum (CHBr₃): characteristic bands (cm⁻¹) at 1695, 1605, 1580, 1530, 1490, 1450, 1050 and 900.

EXAMPLE 54

A mixture of 7-amino-2-benzhydryloxycarbonyl-8-oxo-5-oxide-3-(2-tosyloxyvinyl)-5-thia-1-aza-bicyclo[4.2.0]oct-2-ene (E-form) (0.23 g), dimethylformamide (15 cc), 4-(2,2-dimethoxyethyl)-5,6-dioxo-3-[2-methoxyimino-2-(2-tritylamino-thiazol-4-yl)-acetylthio]-1,4,5,6-tetrahydro-1,2,4-triazine (syn isomer) (0.40 g) and N,N-diisopropylethylamine (0.07 cc) is stirred for 5 hours at 60° C. under nitrogen. It is diluted with ethyl acetate (60 cc) and the solution is washed with water (3×30 cc) and then with a half-saturated sodium chloride solution (2×30 cc), dried over sodium sulphate, filtered and concentrated to dryness at 20° C. under 20 mm Hg (2.7 kPa). The residue is taken up in methylene chloride (10 cc), Merck silica gel (0.06–0.2 mm) (2 g) is added and the mixture is concentrated to dryness at 20° C. under 20 mm Hg (2.7 kPa). The powder obtained is deposited on a column (column diameter: 1.2 cm) of Merck silica gel (0.06–0.2 mm) (8 g). Elution is carried out successively with the following mixtures of cyclohexane and ethyl acetate: 80:20 (by volume) (50 cc), 60:40 (by volume) (100 cc), 40:60 (by volume) (100 cc) and 20:80 (by volume) (200 cc) and with pure ethyl acetate (200 cc), 25 cc fractions being collected. Fractions 12 to 19 are concentrated to dryness at 20° C. under 20 mm Hg (2.7 kPa) and 2-benzhydryloxycarbonyl-3-{2-[4-(2,2-dimethoxyethyl)-5,6-dioxo-1,4-,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (0.19 g) is obtained in the form of a beige froth.

Infra-red spectrum (KBr): characteristic bands (cm⁻¹) at 3380, 3250, 1795, 1720, 1685, 1520, 1490, 1445, 1040, 940, 760 and 700.

Proton nuclear magnetic resonance spectrum (350 MHz, CDCl₃, δ in ppm, J in Hz): 3.34 and 4.12 (2d, J=18, 2H, —SCH₂—); 3.40 (s, 6H, —OCH₃); 3.94 to 4.06 (m, 5H, —OCH₃ and >NCH₂—); 4.60 to 4.68 (m, 2H, H in the 6-position and —CH(OCH₃)₂); 6.07 (dd, J=4 and 9, 1H, H in the 7-position); 6.70 (s, 1H, H of the thiazole); 6.82 (d, J=16, 1H, —CH=CHS—); 6.96 (s, 1H, —COOCH—).

The reduction of the sulphoxide and the removal of the protective radicals is carried out as described in Example 16. 7-[2-(2-Amino-thiazol-4-yl)-2-methoxyimino-acetamido]-2-carboxy-3-{2-[5,6-dioxo-4-formylmethyl-1,4,5,6-tetrahydro-1,2,4-triazin-3-yl]-thiovinyl}-8-oxo-5-thia-1-aza-bicyclo[4.2.0]oct-2-ene (syn isomer, E-form) is thus obtained; the characteristics of the product are identical to those of the product obtained in Example 16.

4-(2,2-Dimethoxyethyl)-5,6-dioxo-3-[2-methoxyimino-2-(2-tritylamino-thiazol-4-yl)-acetylthio]-1,4,5,6-tetrahydro-1,2,4-triazine (syn isomer) can be prepared in the following manner:

N,N'-Dicyclohexylcarbodiimide (0.50 g) is added, in a single shot, to a solution, cooled to 4° C., of [2-methoxyimino-2-(2-tritylamino-thiazol-4-yl)]-acetic acid (syn isomer) (0.89 g) and 4-(2,2-dimethoxyethyl)-5,6-dioxo-3-thioxo-perhydro-1,2,4-triazine (0.47 g) in dimethylformamide (20 cc); the mixture is stirred for 1 hour at 4° C. and then for 3 hours at 20° C. The reaction suspension is filtered, the filtrate is diluted with ethyl acetate (100 cc), and this mixture is washed with water (2×50 cc), a 1% strength sodium bicarbonate solution (2×50 cc) and a half-saturated sodium chloride solution (2×50 cc), dried over sodium sulphate, filtered and concentrated to dryness at 20° C. under 20 mm Hg (2.7 kPa). The residue is triturated in isopropyl ether (10 cc) and after filtration and drying 4-(2,2-dimethoxyethyl)-5,6-dioxo-3-[2-methoxyimino-2-(2-tritylamino-thiazol-4-yl)-acetamido]-1,4,5,6-tetrahydro-1,2,4-triazine (syn isomer) (0.91 g) is obtained in the form of a yellow powder.

Proton nuclear magnetic resonance spectrum (80 MHz, CDCl₃, δ in ppm, J in Hz): 3.30 (s, 6H, —OCH₃); 4.05 (s, 3H, =NOCH₃); 4.28 (d, J=5, 2H, >NCH₂—); 4.66 (t, J=5, 1H, —CH=); 6.68 (s, 1H, H of the thiazole).

Infra-red spectrum (CHBr₃): characteristic bands (cm⁻¹) at 3380, 1720, 1585, 1525, 1490, 1450, 1040, 900, 750 and 730.

EXAMPLE 55

A mixture of 7-amino-2-benzhydryloxycarbonyl-8-oxo-5-oxide-3-(2-tosyloxyvinyl)-5-thia-1-aza-bicyclo[4.2.0]oct-2-ene (E-form) (0.614 g), dimethylformamide (50 cc) and 4-(2-tert.-butoxycarbonylamino-ethyl)-5,6-dioxo-3-[2-methoxyimino-2-(2-tritylamino-thiazol-4-yl)-acetylthio]-1,4,5,6-tetrahydro-1,2,4-triazine (syn isomer) (0.70 g) is heated at 60° C. for 6 hours, under nitrogen. It is then diluted with ethyl acetate (150 cc), and this mixture is washed with water (2×120 cc), 1 N hydrochloric acid (2×100 cc), water (100 cc) and saturated aqueous sodium chloride (100 cc), dried over sodium sulphate, filtered and concentrated to dryness at 20° C. under 20 mm Hg (2.7 kPa). The residue is chromatographed on a column (column diameter: 2.5 cm, height: 29 cm) of Merck silica gel (0.06–0.2 mm) (40 g). Elution is carried out with ethyl acetate (1 liter), 60 cc fractions being collected. Fractions 3 to 6 are concentrated to dryness at 20° C. under 20 mm Hg (2.7 kPa). 2-Benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2- phate, filtered and concentrated to dryness at 20° C. under 20 mm Hg (2.7 kPa). The residue is taken up in methylene chloride (25 cc), Merck silica gel (0.06–0.2 mm) (5 g) is added, the mixture is concentrated to dryness at 20° C. under 20 mm Hg (2.7 kPa) and the powder is deposited on a column (column diameter: 2 cm) of Merck silica gel (0.06–0.2 mm) (35 g). Elution is carried out successively with the following mixtures of cyclohexane and ethyl acetate: 80:20 (by volume) (100 cc), 60:40 (by volume) (250 cc), 40:60 (by volume) (500 cc), and 20:80 (by volume) (500 cc) and with pure ethyl acetate (500 cc), 60 cc fractions being collected. Fractions 17 to 26 are concentrated to dryness at 20° C. under 20 mm Hg (2.7 kPa) and 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, E-form) (0.56 g) is obtained in the form of a pinkish froth.

Infra-red spectrum (CHBr$_3$): characteristic bands (cm$^{-1}$) at 3380, 1800, 1725, 1680, 1515, 1490, 1445, 1045, 935 and 750.

Proton nuclear magnetic resonance spectrum (350 MHz, CDCl$_3$, δ in ppm, J in Hz): 2.72 (s, 3H, —CH$_3$); 3.28 and 4.08 (2d, J=18, 2H, —SCH$_2$—); 4.07 (s, 3H, —OCH$_3$); 4.60 (d, J=4, 1H, H in the 6-position); 6.16 (dd, J=4 and 9, 1H, H in the 7-position); 6.71 (s, 1H, H of the thiazole);

6.95 (s, 1H, —COOCH—);

7.07 (s, 1H, —NH C(C$_6$H$_5$)$_3$); 7.23 and 7.33 (2d, J=16, —CH=CH—).

Phosphorus trichloride (0.93 cc) is added at −8° C., with stirring, to a solution of 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, E-form) (5.11 g) and dimethylacetamide (2.1 cc) in methylene chloride (50 cc). The mixture is stirred for 1 hour at −8° C. and is then diluted with ethyl acetate (1 liter), and this mixture is washed with a half-saturated sodium bicarbonate solution (2×250 cc) and a half-saturated sodium chloride solution (2×250 cc), dried over sodium sulphate and concentrated to dryness at 20° C. under 20 mm Hg (2.7 kPa). The product, dissolved in a 40:60 (by volume) mixture of cyclohexane and ethyl acetate (50 cc), is chromatographed on a column (column diameter: 5 cm) of Merck silica gel (0.04–0.06 mm) (150 g). Elution is carried out with the preceding mixture (3 liters) under a pressure of 4 kPa, 125 cc fractions being collected. Fractions 10 to 20 are concentrated to dryness at 20° C. under 20 mm Hg (2.7 kPa). 2-Benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (2.69 g) is obtained in the form of a yellow froth.

Infra-red spectrum (CHBr$_3$): characteristic bands (cm$^{-1}$) at 3390, 1785, 1720, 1685, 1515, 1495, 1445, 1045, 940 and 755.

Proton nuclear magnetic resonance spectrum (350 MHz, CDCl$_3$, δ in ppm, J in Hz): 2.75 (s, 3H —CH$_3$); 3.60 and 3.69 (2d, J=18, 2H, —SCH$_2$—); 4.09 (s, 3H, —OCH$_3$); 5.09 (d, J=4, 1H, H in the 6-position); 5.93 (dd, J=4 and 9, 1H, H in the 7-position); 6.75 (s, 1H, H of the thiazole);

6.98 (s, 1H, —COOCH—);

7.0 (s, 1H, —NH—C(C$_6$H$_5$)$_3$); 7.22 (d, J=14, 1H, —CH=CHS—).

A mixture of 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (2.37 g) in formic acid (30 cc) containing water (14 cc) is stirred at 50° C. for 15 minutes. It is allowed to cool, diluted with water (16 cc) and filtered. The filtrate is concentrated to dryness at 30° C. under 0.05 mm Hg (0.007 kPa) and the residue is taken up in ethanol (3×50 cc), the mixture being concentrated to dryness each time. The solid obtained is stirred in ethanol (35 cc) for 25 minutes at 50° C. and is then filtered off, washed with ethyl ether (2×20 cc) and dried. 7-[2-(2-Amino-thiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, E-form) (1.18 g) is obtained in the form of a yellow powder.

Infra-red spectrum (KBr): characteristic bands (cm$^{-1}$) at 3400, 3200, 3100, 2200, 1775, 1675, 1530, 1045 and 940.

Proton nuclear magnetic resonance spectrum (350 MHz, DMSO d$_6$, δ in ppm, J in Hz): 2.74 (s, 3H, —CH$_3$); 3.67 and 3.94 (2d, J=18, 2H, —SCH$_2$—); 3.86 (s, 3H, —OCH$_3$); 5.21 (d, J=4, 1H, H in the 6-position); 5.80 (2d, J=4 and 9, 1H, H in the 7-position); 6.75 (s, 1H, H of the thiazole); 7.12 and 7.17 (2d, J=16, 2H, —CH=CHS—); 7.20 (s, 2H, —NH$_2$); 9.63 (d, J=9, 1H, —CONH—).

7-Amino-2-benzhydryloxycarbonyl-8-oxo-5-oxide-3-(2-tosyloxyvinyl)-5-thia-1-aza-bicyclo[4.2.0]oct-2-ene (E-form) can be obtained in the following manner:

A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (54.3 g) and hydrated p-toluenesulphonic acid (30.4 g) in acetonitrile (1.4 liters) is stirred at 35° C. for 2 hours. It is then concentrated to dryness at 30° C. under 20 mm Hg (2.7 kPa), the residue is taken up in ethyl acetate (1 liter) and this solution is washed with a half-saturated sodium bicarbonate solution (2×500 cc) and a half-saturated sodium chloride solution (2×500 cc), dried over sodium sulphate and concentrated to dryness at 20° C. under 20 mm Hg (2.7 kPa). The residue is triturated in ether (200 cc). 7-Amino-2-benzhydryloxycarbonyl-8-oxo-5-oxide-3-(2-tosyloxyvinyl)-5-thia-1-aza-bicyclo[4.2.0]oct-2-ene (syn isomer, E-form) (28.13 g) is obtained in the form of a light brown powder.

Rf=0.32; silica gel chromatographic plate [using an 85:15 (by volume) mixture of methylene chloride and methanol].

5-[2-Methoxyimino-2-(2-tritylamino-thiazol-4-yl)-acetylthio]-2-methyl-1,3,4-thiadiazole (syn isomer) can be prepared in the following manner:

N,N'-Dicyclohexylcarbodiimide (4.96 g) is added as a single shot, with stirring, to a suspension, cooled to 4° C., of [2-methoxyimino-2-(2-tritylamino-thiazol-4-yl)]-acetic acid (syn isomer) (8.88 g) and 5-mercapto-2-methyl-1,3,4-thiadiazole (2.64 g) in ethyl acetate (200 cc). The suspension is stirred for 4 hours at 4° C. and is then diluted with methylene chloride (50 cc), and this mixture is washed with a saturated sodium bicarbonate solution (3×50 cc) and water (3×50 cc), dried over sodium sulphate, filtered and concentrated to dryness at 20° C. under 20 mm Hg (2.7 kPa). The residue is taken up in ethyl acetate (5 cc), the solution is added to diisopropyl ether (50 cc), and the supernatant liquor is decanted. The gummy material is taken up in methylene chloride (5 cc) and the solvent is driven off at 20° C. under 20 mm Hg (2.7 kPa). A pale yellow froth (2.4 g) is obtained, which consists principally of 2-benzhydryloxycarbonyl-7-tert.-butoxycarbonylamino-3-(2-ethoxymalonyloxyvinyl)-8-oxo-5-thia-1-aza-bicyclo[4.2.0]oct-2-ene (E-form).

Infra-red spectrum (KBr): characteristic bands (cm$^{-1}$) at 3380, 1785, 1720, 1635, 1510, 1500, 1455, 1395, 1370, 1160, 955, 760, 750 and 700.

Proton nuclear magnetic resonance spectrum (350 MHz, CDCl$_3$, δ in ppm, J in Hz): 1.29 (t, J=7, 3H, —OCH$_2$CH$_3$); 1.48 (s, 9H, —C(CH$_3$)$_3$); 3.46 (s, 2H, —COCH$_2$CO—); 4.23 (q, J=7, 2H, —OCH$_2$—); 5.02, (d, J=H, 1H, H in the 6-position); 5.22 (d, J=9, 1H, —CONH—); 5.64 (dd, J=4 and 9, 1H, H in the 7-position); 6.94 (s, 1H, —COOCH<); 7.05 and 7.60 (2 d, J=12, 1H, —CH═CHS—).

EXAMPLE 51

2-(2-Tritylamino-thiazol-4-yl)-2-vinyloxyiminoacetic acid, syn isomer, (3.8 g), prepared according to Belgian Pat. No. 869,079, 4-dimethylaminopyridine (0.10 g) and N,N'-dicyclohexylcarbodiimide (2.06 g) are added to a solution, cooled to +5° C., of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (4.37 g) in methylene chloride (100 cc). The mixture is stirred for 2 hours at 20° C. and is then diluted with ethyl acetate (500 cc), and this mixture is washed with 1 N hydrochloric acid (200 cc), a 5% strength sodium bicarbonate solution (2×200 cc) and water (200 cc), dried over sodium sulphate, filtered and concentrated to dryness at 20° C. under 20 mm Hg (2.7 kPa). The residue is chromatographed on a column (column diameter: 6 cm, height: 35 cm) of Merck silica gel (0.04-0.06 mm). Elution is carried out with a 50:50 (by volume) mixture (4 liters) and a 30:70 (by volume) mixture (2 liters) of cyclohexane and ethyl acetate under a pressure of 40 kPa, 120 cc fractions being collected. Fractions 32 to 39 are evaporated to dryness at 20° C. under 20 mm Hg (2.7 kPa) and 2-benzhydryloxycarbonyl-3-[2-(1-methyltetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (3 g) is obtained in the form of an orange-coloured froth.

On treating this product as described above in Example 45, 7-[2-(2-amino-thiazol-4-yl)-2-vinyloxyiminoacetamido]-2-carboxy-3-[2-(1-methyl-tetrazol-5-yl)-thiovinyl]-8-oxo-5-thia-1-aza-bicyclo[4.2.0]oct-2-ene (syn isomer, E-form), having characteristics identical to those described above in Example 45, is obtained.

EXAMPLE 52

Following the same procedure as in Example 45, 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (3.45 g) and 2-cyanomethoxyimino-2-(2-tritylamino-thiazol-4-yl)-acetic acid, syn isomer (3.1 g) (prepared according to German Patent Application No. 2,812,625) are condensed in methylene chloride (200 cc) in the presence of 4-dimethylaminopyridine (100 mg) and N,N'-dicyclohexylcarbodiimide (1.48 g). Purification is carried out analogously (to Example 45) and 2-benzhydryloxycarbonyl-7-[2-cyanomethoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form) (2.01 g) is obtained in the form of an orange-coloured froth.

Infra-red spectrum (KBr): characteristic bands (cm$^{-1}$) at 3330, 1800, 1720, 1685, 1625, 1525, 1495, 1450, 1210, 1040, 750 and 700.

Proton nuclear magnetic resonance spectrum (350 MHz, CDCl$_3$, δ in ppm, J in Hz): 3.27 and 4.10 (2 d, J=18, 2H, —SCH$_2$—); 3.90 (s, 3H, —CH$_3$); 4.62 (d, J=4, 1H, H in the 6-position); 4.86 (s, 2H, —OCH$_2$—); 6.08 (dd, J=4 and 9, 1H, H in the 7-position); 6.76 (s, 1H, H of the thiazole); 6.92 (s, 1H, —COOCH—); 6.99 (d, J=16, 1H, —C<u>H</u>═CHS—); 7.50 (d, J=16, ═CHS—); 7.58 (d, J=9, 1H, —CONH—).

2-Benzhydryloxycarbonyl-7-[2-cyanomethoxyimino-2-(2-tritylamino-thiazol-4-yl)-acetamido]-3-[2-(1-methyltetrazol-5-yl)-thiovinyl]-8-oxo-5-oxide-5-thia-1-aza-bicyclo[4.2.0]oct-2-ene (syn isomer, E-form) (2.01 g) in methylene chloride (21 cc) and dimethylacetamide (0.78 cc) is treated with phosphorus trichloride (0.365 cc), like in Example 45. The product is purified by chromatography analogously to Example 45 and 2-benzhydryloxycarbonyl-7-[2-cyanomethoxyimino-2-(2-tritylamino-thiazol-4-yl)-acetamido]-3-[2-(1-methyl-tetrazol-5-yl)-thiovinyl]-8-oxo-5-thia-1-aza-bicyclo[4.2.0]oct-2-ene (syn isomer, E-form) (1.14 g) is obtained in the form of a cream-coloured froth.

Rf=0.32 [silica gel chromatographic plate, eluant: a 50:50 (by volume) mixture of cyclohexane and ethyl acetate].

On using a procedure as in Example 45, starting from 2-benzhydryloxycarbonyl-7-[2-cyanomethoxyimino-2-tritylamino-thiazol-4-yl)-acetamido]-3-[2-(1-methyltetrazol-5-yl)-thiovinyl]-8-oxo-[5-thia-1-aza-bicyclo][4.2.0]oct-2-ene (syn isomer, E-form) (1.13 g), 7-[2-(2-amino-thiazol-4-yl)-2-cyanomethoxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, E-form) (0.53 g) is obtained in the form of a yellow powder.

Infra-red spectrum (KBr): characteristic bands (cm$^{-1}$) at 1770, 1680, 1620, 1530 and 1380.

Nuclear magnetic resonance spectrum (350 MHz, DMSO d$_6$, δ in ppm, J in Hz): 3.66 and 3.88 (2 d, J=18, 2H, —SCH$_2$—); 4.02 (s, 3H, —CH$_3$); 5.0 (s, 2H, —OCH$_2$—); 5.22 (d, J=4, 1H, H in the 6-position); 5.80 (dd, J=4 and 9, 1H, H in the 7-position); 6.89 (s, 1H, H of the thiazole); 6.99 (d, J=16, 1H, —C<u>H</u>═CHS—); 7.12 (d, J=16, 1H, ═CHS—); 9.82 (d, J=9, 1H, —CONH—).

EXAMPLE 53

A mixture of 7-amino-2-benzhydryloxycarbonyl-8-oxo-5-oxide-3-(2-tosyloxyvinyl)-5-thia-1-aza-bicyclo[4.2.0]oct-2-ene (E-form) (1.16 g), dimethylformamide (35 cc), 5-[2-methoxyimino-2-(2-tritylamino-thiazol-4-yl)-acetylthio]-2-methyl-1,3,4-thiadiazole (syn isomer) (1.67 g) and N,N-diisopropylethylamine (0.35 cc) is stirred for 1 hour at 60° C. under nitrogen. The mixture is diluted with ethyl acetate (140 cc) and the solution is washed with water (3×70 cc), dried over sodium suland ethyl acetate. Elution is carried out with 2 liters of the same mixture under a pressure of 40 kPa, 120 cc fractions being collected.

Fractions 6 to 21 are concentrated to dryness under reduced pressure (20 mm Hg) at 20° C.; 2-benzhydryloxycarbonyl-3-[2-(1-methyl-tetrazol-5-yl)-thiovinyl]-8-oxo-7-[2-(2-tritylamino-thiazol-4-yl)-2-trityloxyimino-acetamido]-5-thia-1-aza-bicyclo[4.2.0]oct-2-ene (syn isomer, E-form) (0.85 g) is obtained in the form of a cream-coloured powder.

Infra-red spectrum (CHBr$_3$): characteristic bands (cm$^{-1}$) at 3400, 1790, 1715, 1690, 1510, 1490, 1450, 950, 750 and 710.

Proton nuclear magnetic resonance spectrum (350 MHz, CDCl$_3$, δ in ppm, J in Hz): 3.43 and 3.50 (2d, J=18, 2H, —S—CH$_2$—); 3.94 (s, 3H, >NCH$_3$); 5.09 (d, J=4, 1H, H in the 6-position); 6.10 (dd, J=4 and 9, 1H, H in the 7-position); 6.41 (s, 1H, H in the 5-position of the thiazole); 6.71 (s, 1H, (C$_6$H$_5$)$_3$CN$\underline{H}$—);

6.95 (s, 1H, —COO$\underline{C}$H—);

6.97 (d, J=16, 1H, —C$\underline{H}$=CHS—).

A solution of 2-benzhydryloxycarbonyl-3-[2-(1-methyl-tetrazol-5-yl)-thiovinyl]-8-oxo-7-[2-(2-tritylamino-thiazol-4-yl)-2-trityloxyimino-acetamido]-5-thia-1-aza-bicyclo[4.2.0]oct-2-ene (syn isomer, E-form) (0.85 g) in tetrahydrofurane (10 cc) is treated with 50% strength by volume aqueous formic acid (10 cc) for 30 minutes at 50° C. The mixture is concentrated to dryness under reduced pressure (20 mm Hg) at 20° C., the residue is taken up in ethanol (20 cc) at 60° C., the solution is allowed to cool, and the crystals which have appeared are filtered off, washed with diethyl ether (2×10 cc) and dried. 7-[2-(2-Amino-thiazol-4-yl)-2-hydroxyimino-acetamido]-2-carboxy-3-[2-(1-methyl-tetrazol-5-yl)thiovinyl]-8-oxo-5-thia-1-aza-bicyclo[4.2.0]oct-2-ene (syn isomer, E-form) (0.24 g) is obtained in the form of a yellow powder.

Infra-red spectrum (KBr): characteristic bands (cm$^{-1}$) at 3440, 3360, 3200, 1785, 1720, 1680, 1610 and 1405.

Proton nuclear magnetic resonance spectrum (350 MHz, DMSO d$_6$, δ in ppm, J in Hz): 3.65 and 3.91 (2d, J=18, 2H, —S—CH$_2$—); 4.97 (s, 3H, >NCH$_3$); 5.25 (d, J=4, 1H, H in the 6-position); 5.90 (dd, J=4 and 9, 1H, H in the 7-position); 6.76 (s, 1H, H in the 5-position of the thiazole); 6.96 (d, J=14, 1H, —CH=CHS—); 7.07 (d, J=14, 1H, =CHS—); 9.50 (d, J=9, 1H, —CONH—).

7-Amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) can be obtained from 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) by proceeding as described above in Example 48.

2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) can be prepared in the following manner:

A mixture of 2-benzhydryloxycarbonyl-7-tert.-butoxycarbonylamino-3-(2-ethoxymalonyloxyvinyl)-8-oxo-5-oxide-5-thia-1-aza-bicyclo[4.2.0]oct-2-ene (E-form) (0.8 g), dimethylformamide (8 cc), 5-mercapto-1-methyltetrazole (0.3 g) and N,N-diisopropylethylamine (0.45 cc) is stirred at 25° C. for 3 hours. It is then diluted with ethyl acetate (200 cc) and this mixture is washed with water (2×100 cc), 0.1 N hydrochloric acid (100 cc), a 2% strength sodium bicarbonate solution (100 cc) and a saturated sodium chloride solution (100 cc), dried over sodium sulphate, filtered and concentrated to dryness at 20° C. under 20 mm Hg (2.7 kPa). The residue is chromatographed on a column (column diameter: 1.5 cm, height: 15 cm) of Merck silica gel (0.06-0.04 mm), elution being carried out with a 50:50 (by volume) mixture of cyclohexane and ethyl acetate (0.5 liter) under a pressure of 40 kPa, and 25 cc fractions being collected. Fractions 10 to 21 are concentrated to dryness at 20° C. under 20 mm Hg (2.7 kPa). 2-Benzhydryloxycarbonyl-7-tert.-butoxycarbonyl-3-[2-(1-methyl-tetrazol-5-yl)-thiovinyl-8-oxo-5-oxide-5-thia-1]-aza-bicyclo[4.2.0]oct-2-ene (E-form) (0.15 g) is obtained in the form of a cream-coloured powder.

2-Benzhydryloxycarbonyl-7-tert.-butoxycarbonylamino-3-(2-ethoxymalonyloxyvinyl)-8-oxo-5-oxide-5-thia-1-aza-bicyclo[4.2.0]oct-2-ene (E-form) may be obtained in the following manner:

A solution of 85% strength m-chloroperbenzoic acid (0.63 g) in methylene chloride (8 cc) is added dropwise in the course of 10 minutes, with stirring, to a solution, cooled to −10° C., of 2-benzhydryloxycarbonyl-7-tert.-butoxycarbonylamino-3-(2-ethoxymalonyloxyvinyl)-8-oxo-5-thia-1-aza-bicyclo[4.2.0]oct-2-ene (E-form) (1.65 g) in methylene chloride (8 cc). The mixture is stirred for 1 hour at between −10° C. and −15° C. and is then taken up in methylene chloride (50 cc), and this mixture is washed with a saturated sodium bicarbonate solution (2×50 cc) and a saturated sodium chloride solution (50 cc), dried over sodium sulphate, filtered and concentrated to dryness at 20° C. under 20 mm Hg. The residue is chromatographed on a column (column diameter: 1.5 cm, height: 15 cm) of Merck silica gel (0.04-0.06 mm). Elution is carried out with a 95:5 (by volume) mixture of methylene chloride and ethyl acetate (0.5 liter) under a pressure of 40 kPa, 20 cc fractions being collected. Fractions 5 to 10 are concentrated to dryness at 20° C. under 20 mm Hg and 2-benzhydryloxycarbonyl-7-tert.-butoxycarbonylamino-3-(2-ethoxymalonyloxyvinyl)-8-oxo-5-oxide-5-thia-1-aza-bicyclo[4.2.0]oct-2-ene (E-form) (0.8 g) is obtained in the form of a yellow powder.

Infra-red spectrum (KBr): characteristic bands (cm$^{-1}$) at 3420, 1795, 1725, 1640, 1500, 1460, 1395, 1370, 1160, 1050, 940, 760, 750 and 700.

Proton nuclear magnetic resonance spectrum (350 MHz, CDCl$_3$, δ in ppm, J in Hz): 1.29 (t, J=7, 3H, —CH$_2$C$\underline{H}$$_3$); 1.48 (s, 9H, —C(CH$_3$)$_3$); 3.24 and 3.95 (2 d, J=18, 2H, —SCH$_2$—); 3.45 (s, 2H, —OCOCH$_2$—); 4.23 (q, J=7, 2H, —OCH$_2$—); 4.55 (d, J=4, 1H, H in the 6-position); 5.76 (d, J=9, 1H, —CONH—); 5.83 (dd, J=4 and 9, 1H, H in the 7-position); 6.98 (s, 1H, —COOCH<); 7.61 (d, J=11, 1H, —CH=CHS—).

2-Benzhydryloxycarbonyl-7-tert.-butoxycarbonylamino-3-(2-ethoxymalonyloxyvinyl)-8-oxo-5-thia-1-aza-bicyclo[4.2.0]oct-2-ene (E-form) can be obtained in the following manner:

Triethylamine (1.4 cc) is added dropwise to a solution, cooled to −30° C. under nitrogen, of 2-benzhydryloxycarbonyl-7-tert.-butoxycarbonylamino-3-(2-oxo-ethyl)-8-oxo-5-thia-1-aza-bicyclo[4.2.0]oct-2-ene (5 g) in methylene chloride (50 cc), and a solution of ethoxymalonyl chloride (1.5 g) in methylene chloride (10 cc) is then added dropwise in the course of 10 minutes. The mixture is stirred for 1 hour at −30° C. and is clo[4.2.0]-oct-2-ene (syn isomer, E-form) (5.05 g) in the form of an orange-coloured solid.

Infra-red spectrum (CHCl₃): characteristic bands (cm⁻¹) at 3400, 2820, 1790, 1725, 1685, 1495, 1450, 1040 and 940.

Proton nuclear magnetic resonance spectrum (350 MHz, CDCl₃, δ in ppm, J in Hz): 3.59 and 3.70 (2 d, J=18, 2H, —SCH₂—); 4.07 (s, 3H, —OCH₃); 5.11 (d, J=4, 1H, H in the 6-position); 5.95 (dd, J=4 and 9, 1H, H in the 7-position); 6.74 (s, 1H, H of the thiazole); 6.98 (s, 1H, —COO CH<); 7.04 (s, 1H, —NHC(C₆H₅)₃); 9.04 (s, 1H, H of the thiazole).

Using the conditions described in Example 50, 2-benzhydryloxycarbonyl-7-[2-methoxyimino-2-(2-tritylaminothiazol-4-yl)-acetamido]-8-oxo-3-[2-(1,3,4-thiadiazol-2-yl)-thiovinyl]-5-thia-1-aza-bicyclo[4.2.-0]oct-2-ene (syn isomer, E-form) (4.9 g) is treated with a mixture of formic acid (70 cc) and water (13 cc). After this treatment, 7-[2-(2-amino-thiazol-4-yl)-2-methoxyiminoacetamido]-2-carboxy-8-oxo-3-[2-(1,3,4-thiadiazol-2-yl)thiovinyl]-5-thia-1-aza-bicyclo[4.2.-0]oct-2-ene (syn isomer, E-form) (1.5 g) is obtained in the form of a yellow powder.

Infra-red spectrum (KBr): characteristic bands (cm⁻¹) at 2820, 1775, 1675, 1630, 1530, 1490, 1450, 1370, 1040, 750 and 700.

Proton nuclear magnetic resonance spectrum (350 MHz, DMSO d₆, δ in ppm, J in Hz): 3.68 and 3.96 (2 d, J=18, 2H, —SCH₂—); 3.84 (s, 3H, —OCH₃); 5.21 (d, J=4, 1H, H in the 6-position); 5.80 (dd, J=4 and 9, 1H, H in the 7-position); 6.73 (s, 1H, H of the thiazole); 7.18 to 7.22 (hump, 4H, —NH₂ and —CH=CH—); 9.03 (d, J=9, 1H, —CONH—); 9.60 (s, 1H, H of the thiadiazole).

7-Amino-2-benzhydryloxycarbonyl-8-oxo-5-oxide-3-[2-(1,3,4-thiadiazol-2-yl)-thiovinyl]-5-thia-1-aza-bicyclo[4.2.0]oct-2-ene (E-form) is obtained by treating 2-benzhydryloxycarbonyl-7-tert.-butoxycarbonylamino-8-oxo-5-oxide-3-[2-(1,3,4-thiadiazol-2-yl)-thiovinyl]-5-thia-1-aza-bicyclo[4.2.0]oct-2-ene (E-form) with hydrated p-toluenesulphonic acid in acetonitrile at 35° C.

The crude product obtained is used, without purification, for the subsequent steps. Rf=0.32 [silica gel chromatographic plate; eluant: an 85:15 (by volume) mixture of 1,2-dichloroethane and methanol].

Using the conditions described in Example 46, 2-benzhydryloxycarbonyl-7-tert.-butoxycarbonylamino-8-oxo-5-oxide-3-(tosyloxyvinyl)-5-thia-1-aza-bicyclo[4.2.0]-oct-2-ene (syn isomer, E-form) (15.3 g) is treated with 2-mercapto-1,3,4-thiadiazole (2.66 g) in dimethylformamide (100 cc) in the presence of N,N-diisopropylethylamine (3.93 cc).

After this treatment, followed by chromatography on silica gel [eluant: a 20:80 (by volume) mixture of cyclohexane and ethyl acetate], 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (syn isomer, E-form) (7.2 g) is obtained in the form of an orange-coloured solid.

Rf=0.43 [silica gel chromatographic plate, eluant: a 20:80 (by volume) mixture of cyclohexane and ethyl acetate].

2-Benzhydryloxycarbonyl-7-tert.-butoxycarbonylamino-8-oxo-5-oxide-3-(tosyloxyvinyl)-5-thia-1-aza-bicyclo[4.2.0]oct-2-ene (syn isomer, E-form) can be obtained as described in Example 47.

EXAMPLE 50

2-(2-Tritylamino-thiazol-4-yl)-2-trityloxyiminoacetic acid (syn isomer) (6.2 g) is added to a solution of 7-amino-2-benzhydryloxycarbonyl-3-[2-(1-methyltetrazol-5-yl)-thiovinyl]-8-oxo-5-oxide-5-thia-1-aza-bicyclo[4.2.0]oct-2-ene (E-form) (4.4 g) in methylene chloride (100 cc), the mixture is cooled to 4° C. and 4-dimethylaminopyridine (0.1 g) and dicyclohexylcarbodiimide (1.89 g) are introduced successively, whilst stirring. The cooling bath is removed and the mixture is stirred for 1½ hours at 20° C. It is then filtered and the filtrate is concentrated at 20° C. under reduced pressure (20 mm Hg), the residue is taken up in ethyl acetate (500 cc) and the solution is washed with 1 N hydrochloric acid (250 cc), a 2% strength sodium bicarbonate solution (2×100 cc), water (2×100 cc) and a saturated sodium chloride solution (100 cc), dried over sodium sulphate and concentrated to dryness at 20° C. under reduced pressure (20 mm Hg). The residue is fixed on Merck silica gel (0.05–0.2 mm) (20 g) and the powder is charged onto a column (column diameter: 2.6 cm, height: 30 cm) of silica gel (70 g) which has been prepared with an 80:20 (by volume) mixture of cyclohexane and ethyl acetate; elution is carried out successively with the following mixtures of cyclohexane and ethyl acetate: 80:20 (by volume) (500 cc), 70:30 (1,000 cc) and 60:40 (1,200 cc), 60 cc fractions being collected.

Fractions 33 to 42 are evaporated to dryness under reduced pressure (20 mm Hg) at 20° C.; 2-benzhydryloxycarbonyl-3-[2-(1-methyl-tetrazol-5-yl)-thiovinyl]-8-oxo-5-oxide-7-[2-(2-tritylamino-thiazol-4-yl)-2-trityloxyimino-acetamido]-5-thia-1-aza-bicyclo[4.2.0]-oct-2-ene (syn isomer, E-form) (2 g) is obtained in the form of a cream-coloured powder.

Infra-red spectrum (CHBr₃): characteristic bands (cm⁻¹) at 3390, 1800, 1720, 1680, 1655, 1525, 1490, 1450, 750 and 700.

Proton nuclear magnetic resonance spectrum (350 MHz, CDCl₃, δ in ppm, J in Hz): 3.72 and 3 (2d, J=18, 2H, —S—CH₂—); 3.96 (s, 3H, >NCH₃); 4.44 (d, J=4, 1H, H in the 6-position); 5.35 (dd, J=4 and 9, 1H, H in the 7-position); 6.40 (s, 1H, H in the 5-position of the thiazole); 6.95 (d, J=16, 1H, —CH=CHS—);

6.97 (s, 1H, —COOCH—);
        |

7.60 (d, J=16, 1H, =CHS—).

Phosphorus trichloride (0.302 cc) is added, whilst stirring, to a solution, cooled to −10° C., of 2-benzhydryloxycarbonyl-3-[2-(1-methyl-tetrazol-5-yl)thiovinyl]-8-oxo-5-oxide-7-[2-(2-tritylamino-thiazol-4-yl)-2-trityloxyimino-acetamido]-5-thia-1-aza-bicyclo[4.2.0]oct-2-ene (syn isomer, E-form) (2 g) in methylene chloride (17 cc) and dimethylacetamide (0.64 cc). After 10 minutes at the same temperature, the mixture is diluted with ethyl acetate (500 cc) and the solution is washed with a 5% strength sodium bicarbonate solution (2×100 cc) and a saturated sodium chloride solution (2×100 cc), dried over sodium sulphate, filtered and concentrated to dryness at 20° C. under reduced pressure (20 mm Hg). The residue is taken up in methylene chloride (10 cc) and the solution is chromatographed on a column (column diameter: 4 cm, height: 20 cm) of silica gel (0.04–0.06 mm) (150 g), which has been prepared with a 65:35 (by volume) mixture of cyclohexane razol-5-yl)-thiovinyl]-8-oxo-5-thia-1-aza-bicyclo[4.2.-0]oct-2-ene (syn isomer, E-form) (9.32 g) is dissolved in trifluoroacetic acid (50 cc) and anisole (1 cc). The mixture is stirred for 1 hour at 4° C. and 30 minutes at 20° C. and is then concentrated at 20° C. under reduced pressure (0.05 mm Hg). The concentrate is taken up in ethyl acetate (2×200 cc), the mixture being evaporated each time at 20° C. under reduced pressure (20 mm Hg). The residue is triturated in diethyl ether (100 cc). After filtration and drying, a cream-coloured solid (4.87 g) containing 80% of the expected product and 20% of the N-tritylated product (the percentages being based on nuclear magnetic resonance measurements) is obtained.

The above solid is dissolved in trifluoroacetic acid (35 cc) and the solution obtained is poured, with stirring, into diethyl ether (175 cc). After filtration and drying, 7-[2-(2-amino-thiazol-4-yl)-2-methoxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, E-form) trifluoroacetate (4.57 g) is obtained.

Rf=0.49 [silica gel chromatographic plate, solvent: a 50:20:10:10 (by volume) mixture of ethyl acetate, acetone, acetic acid and water].

Infra-red spectrum (KBr): characteristic bands (cm$^{-1}$) at 3320, 1780, 1675, 1200, 1140, 1040 and 950.

Proton nuclear magnetic resonance spectrum (350 MHz, DMSO d$_6$, δ in ppm, J in Hz): 3.66 and 3.86 (2 d, J=17, 2H, —SCH$_2$—); 3.90 (s, 3H, >NCH$_3$); 4.0 (s, 3H, —OCH$_3$); 5.20 (d, J=4, 1H, H in the 6-position); 5.80 (dd, J=4 and 9, 1H, H in the 7-position); 6.83 (s, 1H, H in the 5-position of the thiazole); 7.0 (d, J=16, 1H, —C$\underline{H}$=CHS—); 7.1 (d, J=16, 1H, =CHS—); 9.7 (d, J=9, 1H, —CONH—).

7-Amino-2-benzhydryloxycarbonyl-3-[2-(1-methyl-tetrazol-5-yl)-thiovinyl]-8-oxo-5-oxide-5-thia-1-azabicyclo[4.2.0]oct-2-ene (E-form) can be prepared in the following manner:

A mixture of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (34.87 g), acetonitrile (560 cc) and p-toluenesulphonic acid monohydrate (21.31 g) is stirred for 16 hours at 25° C. The mixture is then concentrated at 20° C. under reduced pressure (20 mm Hg) and the residue is taken up in ethyl acetate (1 liter). The solution is neutralised by stirring with a 5% strength sodium bicarbonate solution (500 cc) and is decanted, washed with a half-saturated sodium chloride solution (3×500 cc), dried over sodium sulphate, filtered and concentrated to dryness under reduced pressure (20 mm Hg) at 20° C. 7-Amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (19.59 g) is obtained in the form of a crude brown froth.

Rf=0.27 [silica gel chromatographic plate, solvent: an 85:15 (by volume) mixture of dichloroethane and methanol].

2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) can be prepared in the following manner:

A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (40.73 g), dimethylformamide (300 cc), 1-methyl-5-mercapto-tetrazole (13.94 g) and N-ethyl-N,N-diisopropylamine (20.9 cc) is heated at 60° C. for 1½ hours, whilst stirring under nitrogen. It is then diluted with ethyl acetate (2 liters) and the mixture is washed successively with water (3×1 liter), 0.1 N hydrochloric acid (1 liter), a 1% strength sodium bicarbonate solution (1 liter) and a half-saturated sodium chloride solution (2×1 liter), dried over sodium sulphate, filtered and concentrated to dryness at 30° C. under reduced pressure (20 mm Hg). 2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (35.7 g) is obtained in the form of a brown froth.

Infra-red spectrum (CHBr$_3$): characteristic bands (cm$^{-1}$) at 3410, 1800, 1715, 1505, 1370, 1050, 945, 760 and 745.

Proton nuclear magnetic resonance spectrum (350 MHz, CDCl$_3$, δ in ppm, J in Hz): 1.47 (s, 9H, (CH$_3$)$_3$C—); 3.32 and 4.15 (2 d, J=17.5, 2H, —SCH$_2$—); 3.94 (s, 3H, >NCH$_3$); 4.56 (d, J=4, 1H, H in the 6-position); 5.72 (d, J=10, 1H, —CONH—); 5.83 (dd, J=4 and 10, 1H, H in the 7-position);

6.97 (s, 1H, —COOC$\underline{H}$—);

7.05 (d, J=16, 1H, —C$\underline{H}$=CHS—); 7.58 (d, J=16, 1H, =CHS—).

2-Benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) can be obtained according to the method described in Example 47.

EXAMPLE 49

The condensation of 2-methoxyimino-2-(2-tritylamino-thiazol-4-yl)-acetic acid (syn isomer) (8 g) and 7-amino-2-benzhydryloxycarbonyl-8-oxo-5-oxide-3-[2-(1,3,4-thiadiazol-2-yl)-thiovinyl]-5-thia-1-aza-bicyclo[4.2.0]oct-2-ene (E-form) (9.43 g) in the presence of N,N'-dicyclohexylcarbodiimide (4.12 g) in methylene chloride (150 cc) gives, after chromatography on silica gel [eluant: a 30:70 (by volume) mixture of cyclohexane and ethyl acetate], 2-benzhydryloxycarbonyl-7-[2-methoxyimino-2-(2-tritylamino-thiazol-4-yl)-acetamido]-8-oxo-5-oxide-3-[2-(1,3,4-thiadiazol-2-yl)-thiovinyl]-5-thia-1-aza-bicyclo[4.2.0]oct-2-ene (syn isomer, E-form) (6.7 g) in the form of an orange-coloured solid.

Infra-red spectrum (CHBr$_3$): characteristic bands (cm$^{-1}$) at 3380, 1800, 1725, 1680, 1595, 1580, 1515, 1495, 1450, 1210, 1050, 940 and 750.

Proton nuclear magnetic resonance spectrum (350 MHz, CDCl$_3$, δ in ppm, J in Hz): 3.31 and 4.09 (2 d, J=18, 2H, —SCH$_2$—); 4.08 (s, 3H, —OCH$_3$); 4.63 (d, J=4, 1H, H in the 6-position); 6.18 (dd, J=4 and 9, 1H, H in the 7-position); 6.72 (s, 1H, H of the thiazole); 6.97 (s, 1H, —COOCH—); 7.10 (s, 1H, —NHC(C$_6$H$_5$)$_3$); 7.57 (d, J=14, 1H, =CHS—); 9.05 (s, 1H, H of the thiadiazole).

The reduction of 2-benzhydryloxycarbonyl-7-[2-methoxyimino-2-(2-tritylamino-thiazol-4-yl)-acetamido]-8-oxo-5-oxide-3-[2-(1,3,4-thiadiazol-2-yl)-thiovinyl]-5-thia-1-aza-bicyclo[4.2.0]oct-2-ene (syn isomer, E-form) (6.7 g) with phosphorus trichloride (1.21 cc) in methylene chloride (100 cc) in the presence of dimethylacetamide (2.78 cc) under the conditions described in Example 48 gives, after chromatography on silica gel [eluant: a 30:70 (by volume) mixture of cyclohexane and ethyl acetate], 2-benzhydryloxycarbonyl-7-[2-methoxyimino-2-(2-tritylamino-thiazol-4-yl)-acetamido]-8-oxo-3-[2-(1,3,4-thiadiazol-2-yl)-thiovinyl]-5-thia-1-aza-bicyadded, and the mixture is heated under reflux and then allowed to cool. The crystals which have appeared are filtered off, washed with diethyl ether (3×250 cc) and then dried. 2-Benzhydryloxycarbonyl-7-tert.butoxycarbonylamino-3-methyl-8-oxo-5-thia-1-aza-bicyclo[4.2.0]oct-2-ene (191 g) is obtained in the form of white crystals (m.p.=179° C.). On concentrating the mother liquors to 500 cc, a second fraction of product (32.6 g, m.p.=178° C.) is obtained.

7-tert.-Butoxycarbonylamino-2-carboxy-3-methyl-8-oxo-5-thia-1-aza-bicyclo[4.2.0]oct-2-ene can be obtained in the following manner:

7-Amino-2-carboxy-3-methyl-8-oxo-5-thia-1-aza-bicyclo[4.2.0]oct-2-ene (371 g) is dissolved in a solution of sodium bicarbonate (307 g) in a mixture of distilled water (2 liters) and dioxane (2 liters). A solution of di-tert.-butyl-dicarbonate (421 g) in dioxane (2 liters) is added in the course of 10 minutes. The reaction mixture is stirred for 48 hours at 25° C. The suspension obtained is concentrated under reduced pressure (20 mm Hg) at 50° C. to a residual volume of about 2 liters and is then diluted with ethyl acetate (1 liter) and distilled water (2 liters). The aqueous phase is decanted, washed with ethyl acetate (500 cc) and acidified to pH 2 with 6 N hydrochloric acid in the presence of ethyl acetate (1,500 cc). The aqueous phase is extracted with ethyl acetate (2×1 liter). The combined organic phases are washed with a saturated sodium chloride solution (2×250 cc) and dried over sodium sulphate. After filtration, the solvent is evaporated under reduced pressure (20 mm Hg) at 50° C. 7-tert.-Butoxycarbonylamino-2-carboxy-3-methyl-8-oxo-5-thia-1-aza-bicyclo[4.2.0]oct-2-ene (486 g) is obtained in the form of yellow crystals (m.p.=190° C., with decomposition).

EXAMPLE 48

Dicyclohexylcarbodiimide (8.90 g) is added to a solution, cooled to 4° C., of syn-2-methoxyimino-2-(2-tritylamino-thiazol-4-yl)-acetic acid (36.59 g) in methylene chloride (135 cc). After stirring for 40 minutes at 4° C. and 30 minutes at 20° C., the solution is filtered.

To this filtered solution, cooled to −30° C., is added, with stirring, a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (19.59 g) in methylene chloride (165 cc) containing triethylamine (5.8 cc). The cooling bath is removed and stirring is continued for 1½ hours. The mixture is then concentrated at 20° C. under reduced pressure (20 mm Hg), the residue is taken up in ethyl acetate (1 liter) and the solution is washed successively with water (2×500 cc), 0.1 N hydrochloric acid (500 cc), a 2% strength sodium bicarbonate solution (2×250 cc) and a half-saturated sodium chloride solution (2×500 cc), dried over sodium sulphate and concentrated to dryness at 20° C. under reduced pressure (20 mm Hg). The residue is fixed on Merck silica gel (0.05–0.2 mm) (100 g) and the powder obtained is charged onto a column (column diameter: 6 cm, height: 61 cm) of Merck silica gel (0.05–0.2 mm) (700 g). Elution is carried out successively with the following mixtures of cyclohexane and ethyl acetate: 80:20 (by volume) (1.5 liters), 70:30 (by volume) (1.5 liters), 60:40 (by volume) (3 liters), 50:50 (by volume) (3 liters), 40:60 (by volume) (6 liters) and 30:70 (by volume) (7.5 liters), 600 cc fractions being collected. After evaporating fractions 27 to 37 to dryness at 20° C. under reduced pressure (20 mm Hg), and drying the residue, 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form) (15.52 g) is obtained.

Infra-red spectrum (CHBr$_3$): characteristic bands (cm$^{-1}$) at 3390, 1805, 1725, 1685, 1520, 1375, 1210, 1050, 945, 755 and 740.

Proton nuclear magnetic resonance spectrum (350 MHz, CDCl$_3$, δ in ppm, J in Hz): 3.28 and 4.06 (2 d, J=17.5, 2H, —SCH$_2$—); 3.91 (s, 3H, >NCH$_3$); 4.06 (s, 3H, —OCH$_3$); 4.60 (d, J=4, 1H, H in the 6-position); 6.14 (dd, J=4 and 10, 1H, H in the 7-position); 6.71 (s, 1H, H in the 5-position of the thiazole);

6.94 (s, 1H, —COOCH—);

6.99 (d, J=16, 1H, —C$\underline{H}$=CHS—); 7.56 (d, J=16, 1H, =CHS—).

Phosphorus trichloride (2.8 cc) is added to a solution, cooled to −10° C., of 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form) (15.17 g) in methylene chloride (160 cc) and dimethylacetamide (6.4 cc), and the mixture is stirred for 1 hour at the same temperature. It is then concentrated to about 20 cc (at 20° C. under 25 mm Hg), this material is diluted with ethyl acetate (1 liter and the solution is washed successively with a 5% strength sodium bicarbonate solution (2×500 cc) and a half-saturated sodium chloride solution (2×500 cc). After drying over sodium sulphate and filtering, the solution is concentrated at 20° C. under reduced pressure (20 mm Hg). The residue is fixed on Merck silica gel (0.05–0.2 mm) (50 g) and the powder obtained is charged onto a column (diameter: 6 cm, height: 37 cm) of Merck silica gel (0.05–0.2 mm) (250 g). Elution is carried out successively with the following mixtures of cyclohexane and ethyl acetate: 75:25 (by volume) (1 liter), 50:50 (by volume) (2 liters) and 25:75 (by volume) (2 liters), 600 cc fractions being collected. After evaporation of fractions 4 to 6 at 25° C. under reduced pressure (20 mm Hg), 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-thia-1-aza-bicyclo[4.2.0]oct-2-ene (syn isomer, E-form) is obtained in the form of a yellow froth.

Infra-red spectrum (CHBr$_3$): characteristic bands (cm$^{-1}$) at 3390, 1785, 1720, 1680, 1515, 1370, 1205, 1040, 940, 760 and 735.

Proton nuclear magnetic resonance spectrum (350 MHz, CDCl$_3$, δ ppm, J in Hz): 3.60 and 3.70 (AB, J=18, 2H, —SCH$_2$—); 3.95 (s, 3H, >NCH$_3$); 4.10 (s, 3H, —OCH$_3$); 5.10 (d, J=4, 1H, H in the 6-position); 5.95 (dd, J=4 and 10, 1H, H in the 7-position); 6.72 (s, 1H, H in the 5-position of the thiazole);

6.95 (s, 1H, —COOCH—);

7.02 (d, J=16, 1H, —C$\underline{H}$=CHS—); 7.04 (d, J=10, 1H, —CONH—); 7.05 (s, 1H, —NH—); 7.37 (d, J=16, =CHS—).

2-Benzhydryloxycarbonyl-7-[2-methoxyimino-2-(2-tritylamino-thiazol-4-yl)-acetamido]-3-[2-(1-methyl-tetand Z-forms) (180.56 g) in methylene chloride (1.4 liters). The mixture is washed with a 5% strength sodium bicarbonate solution (1.5 liters) and with water (2×1.5 liters), dried over sodium sulphate and concentrated to a volume of 300 cc at 20° C. under reduced pressure (20 mm Hg). This solution is chromatographed on a column (column diameter: 9.2 cm; height: 145 cm) of Merck silica gel (0.05–0.2 mm) (3 kg). Elution is carried out successively with the following mixtures of cyclohexane and ethyl acetate: 80:20 (by volume) (15 liters) and 70:30 (by volume) (32 liters), 600 cc fractions being collected. Fractions 27 and 28 are combined and concentrated to dryness; the Z-form of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (5.56 g) is obtained.

Infra-red spectrum (CHBr$_3$): characteristic bands (cm$^{-1}$) at 3420, 1800, 1720, 1505, 1380, 1370, 1195, 1180, 1050, 1010 and 730.

Proton nuclear magnetic resonance spectrum (350 MHz, CDCl$_3$, δ in ppm, J in Hz): 1.49 (s, 9H, —C(CH$_3$)$_3$); 2.44 (s, 3H, —CH$_3$); 3.36 and 4.04 (2 d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —C$\underline{H}$=CH OSO$_2$—); 6.46 (d, J=7, 1H, =CH OSO$_2$—);

6.89 (s, 1H, —COOCH—);
|

7.77 (d, J=9, 2H, H in the ortho-position of the tosyl group).

A mixture of the Z- and E-forms (26 g) is obtained from fractions 29 to 34.

Finally, the E-form of the product (43 g) is obtained from fractions 35 to 58:

Infra-red spectrum (CHBr$_3$): characteristic bands (cm$^{-1}$) at 3420, 1800, 1720, 1505, 1380, 1370, 1195, 1180, 1075, 935 and 745.

Proton nuclear magnetic resonance spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2 d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —C$\underline{H}$=CH OSO$_2$—);

6.83 (s, 1H, —COOCH—);
|

7.08 (d, J=13, 1H, =CH OSO$_2$—); 7.73 (d, J=9, 2H, H in the ortho-position of the tosyl group).

2-Benzhydryloxycarbonyl-7-tert.-butoxycarbonylamino-8-oxo-3-(2-tosyloxyvinyl)-5-thia-1-aza-bicyclo[4.2.0]oct-2-ene (mixture of the E- and Z-forms) can be obtained in the following manner:

A solution of formic acid (50 cc) in water (500 cc) is added to a solution of 2-benzhydryloxycarbonyl-7-tert.-butoxycarbonylamino-3-(2-dimethylaminovinyl)-8-oxo-5-thia-1-aza-bicyclo[4.2.0]oct-2-ene (E-form) (113.7 g) in tetrahydrofurane (1 liter). The homogeneous solution is stirred at 20° C. for 20 minutes and is then concentrated to a quarter of its volume under reduced pressure (20 mm Hg) at 20° C. The concentrate is taken up in ethyl acetate (2 liters) and this mixture is washed with a 5% strength sodium bicarbonate solution (2×500 cc), water (2×500 cc) and a saturated sodium chloride solution (2×500 cc), dried over sodium sulphate, filtered and evaporated to dryness at 20° C. under reduced pressure (20 mm Hg). A crude product (112.4 g) is obtained, which is dissolved in anhydrous pyridine (250 cc), and the solution is treated, at 5° C., with tosyl chloride (57.2 g). After 30 minutes at 5° C. and 1 hour at 20° C., the solution is poured into a mixture of water and crushed ice (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength sodium bicarbonate solution (2×750 cc) and water (4×750 cc), dried over sodium sulphate and concentrated to dryness under reduced pressure (20 mm Hg) at 20° C. A product (121 g) consisting principally of 2-benzhydryloxycarbonyl-7-tert.-butoxycarbonylamino-8-oxo-3-(2-tosyloxyvinyl)-5-thia-1-aza-bicyclo[4.2.0]oct-2-ene (a mixture of the E- and Z-forms) is obtained in the form of a crude brown froth.

2-Benzhydryloxycarbonyl-7-tert.-butoxycarbonylamino-3-(2-dimethylaminovinyl)-8-oxo-5-thia-1-aza-bicyclo[4.2.0]oct-2-ene (E-form) can be obtained in the following manner:

2-Benzhydryloxycarbonyl-7-tert.-butoxycarbonylamino-3-methyl-8-oxo-5-thia-1-aza-bicyclo[4.2.0]oct-2-ene (90.5 g) is dissolved in anhydrous N,N-dimethylformamide (400 cc). The solution obtained is heated at 80° C. under an atmosphere of nitrogen. A solution, preheated to 80° C., of bis-dimethylamino-tert.-butoxymethane (36.1 g) in anhydrous N,N-dimethylformamide (60 cc) is then added rapidly. The reaction mixture is kept at 80° C. for 5 minutes and then poured into ethyl acetate (3 liters). After addition of distilled water (1 liter), the organic phase is decanted, washed with distilled water (4×1 liter), dried over sodium sulphate and filtered in the presence of decolorising charcoal. The filtrate is concentrated to dryness under reduced pressure (20 mm Hg) at 30° C., and 2-benzhydryloxycarbonyl-7-tert.-butoxycarbonylamino-3-(2-dimethylaminovinyl)-8-oxo-5-thia-1-aza-bicyclo[4.2.0]oct-2-ene (E-form) (101 g) is obtained in the form of an orange-coloured froth.

Rf=0.29; silica gel chromatographic plate [using a 50:50 (by volume) mixture of cyclohexane and ethyl acetate].

2-Benzhydryloxycarbonyl-7-tert.-butoxycarbonylamino-3-methyl-8-oxo-5-thia-1-aza-bicyclo[4.2.0]oct-2-ene can be obtained in the following manner:

A solution of diphenyldiazomethane (116.5 g) in acetonitrile (800 cc) is added dropwise, in the course of 45 minutes, at a temperature of between 25° and 30° C., to a solution of 7-tert.-butoxycarbonylamino-2-carboxy-3-methyl-8-oxo-5-thia-1-aza-bicyclo[4.2.0]oct-2-ene (188.6 g) in acetonitrile (2,100 cc). The reaction mixture is stirred for 16 hours at 22° C. and then concentrated to dryness under reduced pressure (20 mm Hg) at 40° C. The residue is redissolved in ethyl acetate (2 liters) and the solution is washed with 2 N hydrochloric acid (700 cc) and then with a saturated aqueous sodium bicarbonate solution (700 cc) and a saturated aqueous sodium chloride solution (700 cc). The solution is dried over sodium sulphate, treated with decolorising charcoal, filtered and then concentrated to dryness under reduced pressure (20 mm Hg) at 40° C. The residue is dissolved in boiling ethyl acetate (600 cc). Cyclohexane (1 liter) is gel (0.05–0.2 mm) (15 g). Elution is carried out successively with the following mixtures of cyclohexane and ethyl acetate: 75:25 (by volume) (100 cc), 50:50 (by volume) (250 cc) and 25:75 (by volume) (250 cc), 60 cc fractions being collected. Fractions 3 to 7 are concentrated to dryness under reduced pressure (20 mm Hg) at 25° C. and 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-thia-1-aza-bicyclo[4.2.0]oct-2-ene (syn isomer, Z-form) (0.74 g) is obtained in the form of a yellow froth.

Infra-red spectrum (CHBr$_3$): characteristic bands (cm$^{-1}$) at 3400, 1790, 1725, 1685, 1515, 1370, 1050, 755 and 740.

Proton nuclear magnetic resonance spectrum (350 MHz, CDCl$_3$, δ in ppm, J in Hz): 3.56 and 3.69 (2 d, J=17.5, 2H, —SCH$_2$—); 3.81 (s, 3H, >NCH$_3$); 4.09 (s, 3H, —OCH$_3$); 5.13 (d, J=4, 1H, H in the 6-position); 5.99 (dd, J=4 and 10, 1H, H in the 7-position); 6.76 (AB, J=11, 2H, —CH=CH S—); 6.9 (d, J=10, 1H, —CONH—);

6.97 (s, 1H, —COOCH—);
|

7.01 (s, 1H, (C$_6$H$_5$)$_3$CNH—).

2-Benzhydryloxycarbonyl-7-[2-methoxyimino-2-(2-tritylamino-thiazol-4-yl)-acetamido]-3-[2-(1-methyl-tetrazol-5-yl)-thiovinyl[-8-oxo-5-thia-1-aza-bicyclo-[4.2.0]oct-2-ene (syn isomer, Z-form) (0.67 g) is dissolved in trifluoroacetic acid (3.6 cc) and anisole (0.07 cc). The mixture is stirred for 1 hour at 5° C. and then for 30 minutes at 20° C., and is concentrated to dryness under reduced pressure (20 mm Hg) at 20° C. The residue is redissolved in trifluoroacetic acid (2 cc) and the solution is poured, with stirring, into ethyl ether (10 cc). After filtering and drying, 7-[2-(2-amino-thiazol-4-yl)-2-methoxyimino-acetamido]-2-carboxy-3-[2-(1-methyl-tetrazol-5-yl)-thiovinyl]-8-oxo-5-thia-1-aza-bicyclo[4.2.-0]oct-2-ene (syn isomer, Z-form) trifluoroacetate (0.33 g) is obtained.

Rf=0.50 [silica gel chromatographic plate, solvent: a 50:20:10:10 (by volume) mixture of ethyl acetate, acetone, acetic acid and water].

Infra-red spectrum (KBr): characteristic bands (cm$^{-1}$) at 3300, 1785, 1675, 1180, 1140 and 1050.

Proton nuclear magnetic resonance spectrum (350 MHz, DMSO d$_6$, δ in ppm, J in Hz): 3.8 and 3.85 (AB, J=17.5, 2H, —SCH$_2$—); 3.93 (s, 3H, >NCH$_3$); 4.0 (s, 3H, —OCH$_3$); 5.26 (d, J=4, 1H, H in the 6-position); 5.85 (dd, J=4 and 10, H in the 7-position); 6.75 (d, J=11, 1H, =CH=CH—S—); 6.87 (s, 1H, H in the 5-position of the thiazole); 6.91 (d, J=11, 1H, =CH—S—); 9.34 (d, J=10, 1H, —CONH—).

7-Amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (Z-form) can be prepared in the following manner:

A mixture of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) (3.11 g), acetonitrile (50 cc) and p-toluenesulphonic acid monohydrate (1.9 g) is stirred for 16 hours at 25° C. The mixture is then concentrated under reduced pressure (20 mm Hg) at 20° C. and the residue is stirred with ethyl acetate (100 cc) and a 5% strength sodium bicarbonate solution (100 cc). The organic phase is decanted, washed with a 5% strength sodium bicarbonate solution (50 cc) and a half-saturated sodium chloride solution (2×50 cc), dried over sodium sulphate, filtered and concentrated to dryness under reduced pressure (20 mm Hg at 20° C.). This gives 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (Z-form) (1.55 g) in the form of a crude brown froth.

Rf=0.21 (silica gel chromatographic plate, solvent: an 85:15 (by volume) mixture of dichloroethane and methanol).

2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) can be prepared in the following manner:

A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (Z-form) (5.44 g), dimethylformamide (40 cc), 1-methyl-2-mercapto-tetrazole (1.88 g) and N-ethyl-N,N-diisopropylamine (2.8 cc) is heated at 60° C. for 1 hour, whilst stirring under nitrogen. The mixture is then diluted with ethyl acetate (250 cc) and this mixture is washed successively with water (3×100 cc), 0.1 N hydrochloric acid (100 cc), a 2% strength sodium bicarbonate solution (2×100 cc) and a half-saturated sodium chloride solution (2×100 cc), dried over sodium sulphate, filtered and concentrated to dryness under reduced pressure (20 mm Hg) at 20° C. The residue is fixed on silica gel (20 g) and is charged onto a column (column diameter: 3 cm, height: 12 cm) of Merck silica gel (0.05–0.2 mm) (80 g). Elution is carried out with the following mixtures of cyclohexane and ethyl acetate: 90:10 (by volume) (250 cc), 80:20 (by volume) (500 cc), 70:30 (by volume (1,000 cc), 60:40 (by volume (2,000 cc) and 40:60 (by volume) (2,000 cc), 125 cc fractions being collected. Fractions 34 to 45 are collected and concentrated to dryness and 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) (3.44 g) is obtained in the form of a light brown froth.

Infra-red spectrum (CHBr$_3$): characteristic bands (cm$^{-1}$) at 3410, 1800, 1720, 1500, 1370, 1230, 1045, 755 and 740.

Proton nuclear magnetic resonance spectrum (350 MHz, CDCl$_3$, δ in ppm, J in Hz): 1.48 (s, 9H, (CH$_3$)$_3$C—); 3.81 (s, 3H, >NCH$_3$); 3.38 and 4.03 (2 d, J=18, 2H, —SCH$_2$—); 4.58 (d, J=4.5, 1H, H in the 6-position); 5.75 (d, J=9, 1H, —CONH—); 5.85 (dd, J=4.5 and 9, 1H, H in the 7-position); 6.70 (d, J=9.5, 1H, —CH=CH—S—); 6.79 (d, J=9.5, 1H, =CHS—);

6.98 (s, 1H, —COOCH—).
|

2-Benzhydryloxycarbonyl-7-tert.-butoxycarbonyl-amino-8-oxo-5-oxide-3-(2-tosyloxyvinyl)-5-thia-1-aza-bicyclo[4.2.0]oct-2ene can be prepared in the following manner:

A solution of 85% strength m-chloroperbenzoic acid (55.22 g) in methylene chloride (600 cc) is added dropwise, in the course of 2 hours, to a solution, cooled to −10° C., of 2-benzhydryloxycarbonyl-7-tert.-butoxycarbonylamino-8-oxo-3-(2-tosyloxyvinyl)-5-thia-1-aza-bicyclo[4.2.0]oct-2ene (or oct-3-ene) (mixture of the E-

Rf=0.17 [silica gel chromatographic plate, eluant: 85:15 (by volume) mixture of dichloroethane and methanol].

2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) can be prepared in the following manner:

A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]-oct-2-ene (mixture of the E- and Z-forms) (13.58 g), dimethylformamide (40 cc), trimethylchlorosilane (0.13 cc), 2-methyl-5-mercapto-1,3,4-thiadiazole (2.91 g) and N-ethyl-N,N-diisopropylamine (3.85 cc) is stirred at 20° C., under nitrogen, for 17 hours. The mixture is diluted with ethyl acetate (500 cc) and this mixture is washed successively with water (4×250 cc), 0.1 N hydrochloric acid (250 cc), a 2% strength sodium bicarbonate solution (2×250 cc), water (500 cc) and saturated aqueous sodium chloride (2×250 cc), dried over sodium sulphate, filtered and concentrated to dryness under reduced pressure (20 mm Hg) at 20° C. The residue is fixed on Merck silica gel (0.05–0.2 mm) (50 g) and the powder is charged onto a column (column diameter: 4 cm, height: 47 cm) of Merck silica gel (0.05–0.2 mm) (200 g). Elution is carried out with the following mixtures of cyclohexane and ethyl acetate: 80:20 (by volume) (500 cc), 60:40 (by volume) (2,000 cc) and 40:60 (by volume) (8,000 cc), 124 cc fractions being collected. Fractions 38 to 80 are collected and concentrated to dryness at 20° C. under reduced pressure (20 mm Hg). 2-Benzhydryloxycarbonyl-7-tert.-butoxycarbonylamino-3-[2-(2-methyl-1,3,4-thiadiazol-5-yl)-thiovinyl[-8-oxo-5-oxide-5-thia-1-azabicyclo[4.2.0]oct-2-ene (mixture of the E- and Z-forms) (7.91 g) is obtained in the form of a light brown froth.

Infra-red spectrum (CHBr$_3$): characteristic bands (cm$^{-1}$) at 3420, 1805, 1720, 1505, 1370, 1050, 940, 760 and 745.

Proton nuclear magnetic resonance spectrum (350 MHz, CDCl$_3$, δ in ppm, J in Hz):

E-form: 1.5 (s, 9H, (CH$_3$)$_3$C—); 2.75 (s, 3H, —CH$_3$); 3.30 and 4.15 (2 d, J=18, 2H, —SCH$_2$—); 4.55 (d, J=4.5, 1H, H in the 6-position); 5.7 to 5.9 (mt, 2H, —CONH— and H in the 7-position);

6.97 (s, 1H, —COOCH—);

7.15 (d, J=16, 1H, —C$\underline{H}$=CHS—); 7.53 (d, J=16, 1H, =CHS—).

Z-form: 1.5 (s, 9H, (CH$_3$)$_3$C—); 2.74 (s, 3H, —CH$_3$); 3.45 and 4.11 (2 d, J=18, 2H, —SCH$_2$—); 4.55 (d, J=4.5, 1H, H in the 6-position); 5.7 to 5.9 (mt, 2H, —CONH— and H in the 7-position); 6.78 (d, J=10, 1H, —C$\underline{H}$=CHS—);

6.88 (d, J = 10, 1H, =CHS—); 6.95 (s, 1H, —COOCH—).

The mixture of the E- and Z-forms of 2-benzhydryloxycarbonyl-7-tert.-butoxycarbonylamino-8-oxo-5-oxide-3-(2-tosyloxyvinyl)-5-thia-1-aza-bicyclo[4.2.0]-oct-2-ene can be obtained according to the method described below, in Example 47.

EXAMPLE 47

Dicyclohexylcarbodiimide (0.71 g) is added to a solution, cooled to 4° C., of syn-2-methoxyimino-2-(2-tritylamino-thiazol-4-yl)-acetic acid (2.89 g) in methylene chloride (10 cc). The solution is stirred for 40 minutes at 4° C. and then for 30 minutes at 20° C., and is filtered.

To this filtered solution, cooled to −30° C., is added a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (Z-form) (1.55 g) in methylene chloride (13 cc) containing triethylamine (0.46 cc). The cooling bath is removed and the mixture is stirred for 1 hour 50 minutes at 20° C. It is then concentrated under reduced pressure (20 mm Hg) at 20° C. and the residue is taken up in ethyl acetate (100 cc). This organic phase is washed with water (3×50 cc), 0.05 N hydrochloric acid (50 cc), a 1% strength sodium bicarbonate solution (50 cc) and half-saturated aqueous sodium chloride (2×50 cc), dried over sodium sulphate, filtered and concentrated to dryness under reduced pressure (20 mm Hg) at 20° C. The concentrate is redissolved in a 10:90 (by volume) mixture of cyclohexane and ethyl acetate (25 cc) and the solution is chromatographed on a column (column diameter: 5 cm, height: 33 cm) of Merck silica gel (0.04–0.06 mm) (300 g). Elution is carried out with a 10:90 (by volume) mixture of cyclohexane and ethyl acetate (3 liters) under a nitrogen pressure of 0.4 bar, 110 cc fractions being collected. After concentrating fractions 9 to 17 to dryness, and drying this product, 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, Z-form) (0.98 g) is obtained in the form of a yellow froth.

Infra-red spectrum (CHBr$_3$): characteristic bands (cm$^{-1}$) at 3380, 1805, 1725, 1680, 1515, 1050, 755 and 740.

Proton nuclear magnetic resonance spectrum (350 MHz, CDCl$_3$, δ in ppm, J in Hz): 3.81 (s, 3H, >NCH$_3$); 3.89 and 4.01 (2 d, J=19, 2H, —S—CH$_2$—); 4.10 (s, 3H, —OCH$_3$); 4.66 (d, J=4, 1H, H in the 6-position); 6.24 (dd, J=4 and 10, 1H, H in the 7-position); 6.72 and 6.76 (2 d, J=10, 2H, —C$\underline{H}$=CHS—);

6.98 (s, 1H, —COOCH—);

6.72 (s, 1H, H in the 5-position of the thiazole); 7.07 (s, 1H, (C$_6$H$_5$)$_3$C—N$\underline{H}$—).

Phosphorus trichloride (0.17 cc) is added to a solution, cooled to −10° C., of 2-benzhydryloxycarbonyl-7-[2-methoxyimino-2-(2-tritylamino-thiazol-4-yl)-acetamido]-3-[2-(1-methyl-tetrazol-5-yl)-thiovinyl[-8-oxo-5-oxide-5-thia-1-aza-bicyclo[4.2.0]oct-2-ene (syn isomer, Z-form) (0.93 g) in methylene chloride (10 cc) and dimethylacetamide (0.39 cc) and the mixture is stirred for 45 minutes at the same temperature. It is then diluted with ethyl acetate (200 cc) and this mixture is washed with 2% strength sodium bicarbonate solution (2×50 cc) and a saturated sodium chloride solution (2×50 cc), dried over sodium sulphate, filtered and concentrated to dryness under reduced pressure (20 mm Hg) at 20° C. The residue is fixed on Merck silica gel (0.05–0.2 mm) (5 g) and the powder is charged onto a column (diameter: 2 cm, height: 8 cm) of Merck silica zole); 6.93 (s, 1H, —COOCH<); 7.0 (s, 1H, —NH—C(C₆H₅)₃).

2-(2-Tritylamino-thiazol-4-yl)-2-vinyloxyiminoacetic acid, syn isomer, is prepared according to Belgian Pat. No. 869,079.

EXAMPLE 46

Dicyclohexylcarbodiimide (1.90 g) is added to a solution, cooled at 5° C., of syn-2-methoxyimino-2-(2-tritylamino-thiazol-4-yl)-acetic acid (7.81 g) in methylene chloride (30 cc). The solution is stirred for 40 minutes at 5° C. and then for 30 minutes at 20° C.

To this filtered solution, cooled to −30° C., is added a solution of 7-amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) (4.32 g) in methylene chloride (25 cc) containing triethylamine (1.25 cc). The cooling bath is removed and the mixture is stirred for 1 hour 50 minutes at 60° C. It is then concentrated under reduced pressure (20 mm Hg) at 20° C., the residue is taken up in ethyl acetate (300 cc) and this solution is washed successively with water (3×100 cc), 0.1 N hydrochloric acid (100 cc), a 1% strength sodium bicarbonate solution (100 cc) and half-saturated aqueous sodium chloride (2×100 cc), dried over sodium sulphate and concentrated to dryness under reduced pressure (20 mm Hg) at 20° C. The residue is fixed on Merck silica gel (0.05–0.2 mm (30 g) and the powder is charged onto a column (column diameter: 3 cm, height: 54 cm) of Merck silica gel (0.05–0.2 mm) (130 g). Elution is carried out successively with the following mixtures of cyclohexane and ethyl acetate: 80:20 (by volume) (500 cc), 60:40 (by volume) (1,000 cc), 40:60 (by volume) (2,000 cc) and 20:80 (by volume) (3,000 cc), 125 cc fractions being collected. After evaporation of fractions 32 to 49 under reduced pressure (20 mm Hg at 20° C.), 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, mixture of the E- and Z-forms) (3.2 g) is obtained in the form of a light brown froth.

Infra-red spectrum (CHBr₃): characteristic bands (cm⁻¹) at 3390, 1805, 1725, 1685, 1520, 1375, 1050, 940, 755 and 740.

Proton nuclear magnetic resonance spectrum (350 MHz, CDCl₃, δ in ppm, J in Hz): the following principal signals are observed: 2.74 and 2.75 (2 s, total 3H, —CH₃); 4.09 (s, 3H, =NOCH₃); 6.73 (s, 1H, H in the 5-position of the thiazole).

Phosphorus trichloride (0.54 cc) is added to a solution, cooled to −10° C., of 2-benzhydryloxycarbonyl-7-[2-methoxyimino-2-(2-tritylamino-thiazol)-4-yl)-3-[2-(2-methyl-1,3,4-thiadiazol-5-yl)-thiovinyl]-8-oxo-5-oxide-5-thia-1-aza-bicyclo[4.2.0]oct-2-ene (syn isomer, mixture of the E- and Z-forms) (2.99 g) in methylene chloride (30 cc) and dimethylacetamide (1.25 cc), and the mixture is stirred for 30 minutes at the same temperature. It is then diluted with ethyl acetate (500 cc) and this mixture is washed successively with a 2% strength sodium bicarbonate solution (2×100 cc) and a half-saturated sodium chloride solution (2×200 cc), dried over sodium sulphate, filtered and concentrated under reduced pressure (20 mm Hg) at 20° C. The residue is fixed on Merck silica gel (0.05–0.2 mm (10 g) and the powder is charged onto a column (column diameter: 3 cm, height: 23 cm) of Merck silica gel (0.05–0.2 mm) (50 g). Elution is carried out successively with the following mixtures of cyclohexane and ethyl acetate: 75:25 (by volume) (500 cc), 50:50 (by volume) (750 cc) and 25:75 (by volume) (1,000 cc), 125 cc fractions being collected. Fractions 9 to 14 are concentrated to dryness under reduced pressure (20 mm Hg) at 20° C.; 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) (1.55 g) is obtained in the form of a yellow froth.

Infra-red spectrum (CHBr₃): characteristic bands (cm⁻¹) at 3400, 1790, 1720, 1685, 1515, 1370, 1045, 755 and 740.

Proton nuclear magnetic resonance spectrum (350 MHz, CDCl₃, δ in ppm, J in Hz): the following principal signals are observed: 2.77 (s, 3H, —CH₃); 4.09 (s, 3H, =NOCH₃); 6.77 (s, 1H, H in the 5-position of the thiazole).

2-Benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-azabicyclo[4.2.0]oct-2-ene (syn isomer, mixture of the E- and Z-forms) (1.47 g) is dissolved in trifluoroacetic acid (8 cc) and anisole (0.15 cc). The mixture is stirred for 1 hour at +5° C. and 30 minutes at 20° C. and is then poured, with stirring, into diethyl ether (35 cc). The product is filtered off and dried, and 7-[2-(2-amino-thiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) trifluoroacetate (1 g) is obtained.

Rf=0.50 [silica gel chromatographic plate, solvent: a 50:20:10:10 (by volume) mixture of ethyl acetate, acetone, acetic acid and water].

Infra-red spectrum (KBr): characteristic bands (cm⁻¹) at 3380, 3300, 1780, 1675, 1200, 1140, 1050 and 945.

Proton nuclear magnetic resonance spectrum (350 MHz, CDCl₃, δ in ppm, J in Hz):

E-form: 2.74 (s, 3H, —CH₃); 3.69 and 3.83 (2 d, J=17, 2H, —SCH₂—); 3.91 (s, 3H, —OCH₃); 5.23 (d, J=4, 1H, H in the 6-position); 5.83 (dd, J=4 and 10, 1H, H in the 7-position); 6.85 (s, 1H, H in the 5-position of the thiazole); 7.16 and 7.32 (2 d, J=16, 2H, —CH=C-HS—); 9.75 (d, J=10, 1H, —CONH—);

Z-form: 3.88 and 3.92 (2 d, J=17, 2H, —SCH₂—); 6.91 (AB limit, 2H, —CH=CH—).

7-Amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) can be prepared in the following manner.

A mixture of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) (7.67 g), acetonitrile (120 cc) and p-toluenesulphonic acid monohydrate (4.57 g) is stirred for 16 hours at 20° C. The mixture is diluted with ethyl acetate (300 cc) and this mixture is washed with a saturated sodium bicarbonate solution (200 cc) and a half-saturated sodium chloride solution (3×200 cc), dried over sodium sulphate, filtered and concentrated to dryness under reduced pressure (20 mm Hg) at 20° C. 7-Amino-2-benzhydryloxycarbonyl-3-[2-(2-methyl-1,3,4-thiadiazol-5-yl)-thio-vinyl]-8-oxo-5-oxide-5-thia-1-aza-bicyclo[4.2.0]oct-2-ene (4.32 g) is obtained in the form of a crude brown froth.

[2-(2-tritylamino-thiazol-4-yl)-2-vinyloxyiminoacetamido]-5-thia-1-aza-bicyclo[4.2.0]oct-2-ene and -oct-3-ene (a mixture of the E- and Z-forms).

Infra-red spectrum (KBr): characteristic bands (cm$^{-1}$) at 1790, 1725, 1690, 1640, 1525, 1495, 1450, 1195, 1180, 1075, 1005, 950, 755 and 705.

Proton nuclear magnetic resonance spectrum (350 MHz, CDCl$_3$, δ in ppm, J in Hz): 2.45 (s, 3H, —CH$_3$); 3.40 and 3.55 (2d, J=18, 2H, —SCH$_2$—);

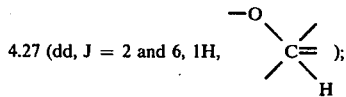

4.27 (dd, J = 2 and 6, 1H,

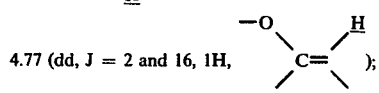

4.77 (dd, J = 2 and 16, 1H, 5.09 (d, J=4, 1H, H in the 6-position); 5.94 (dd, J=4 and 9, 1H, H in the 7-position); 6.81 (s, 1H, H of the thiazole); 6.91 (s, 1H, —COOCH<); 7.07 (dd, J=6 and 16, 1H, —CH=CH$_2$); 7.74 (d, J=8, 2H, H of the sulphonyl group.

2-Benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]oct-2-ene (syn isomer) can be prepared as follows:

A solution of 2-benzhydryloxycarbonyl-3-(2-dimethylaminovinyl)-8-oxo-7-[2-(2-tritylamino-thiazol-4-yl)-2-vinyloxyimino-acetamido]-5-thia-1-aza-bicyclo-[4.2.0]oct-2-ene (syn isomer, E-form) (2.5 g), in ethyl acetate (70 cc) is stirred in the presence of 1 N hydrochloric acid (50 cc) for 1 hour, at 25° C. The organic phase is decanted, washed with a half-saturated sodium bicarbonate solution (2×50 cc) and a half-saturated sodium chloride solution (50 cc), dried over sodium sulphate, filtered and concentrated to dryness under 20 mm Hg (2.7 kPg) at 20° C. A brown froth (2.4 g) is obtained, which consists principally of 2-benzhydryloxycarbonyl-3-(2-oxoethyl)-8-oxo-7-[2-(2-tritylamino-thiazol-4-yl)-2-vinyloxyimino-acetamido]-5-thia-1-azabicyclo[4.2.0]oct-2-ene (syn isomer).

Infra-red spectrum (KBr): characteristic bands (cm$^{-1}$) at 1785, 1725, 1685, 1640, 1530, 1495, 1450, 1000, 950, 755 and 700.

Proton nuclear magnetic resonance spectrum (350 MHz CDCl$_3$, δ in ppm, J in Hz); 3.26 and 3.58 (2d, J=18, 2H, —SCH$_2$—); 3.53 and 3.69 (2d, J=18, 2H, —CH$_2$—);

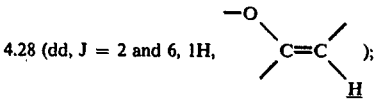

4.28 (dd, J = 2 and 6, 1H,

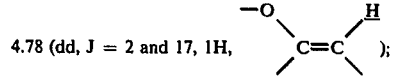

4.78 (dd, J = 2 and 17, 1H, 5.12 (d, J=4, 1H, H in the 6-position); 6.0 (dd, J=4 and 9, 1H, H in the 7-position); 6.8 (s, 1H, H of the thiazole); 6.90 (s, 1H, —COOCH<); 7.08 (dd, J=6 and 17, 1H, —CH=CH$_2$); 9.55 (s, 1H, —CHO).

2-Benzhydryloxycarbonyl-3-(2-dimethylaminovinyl)-8-oxo-7-[2-(2-tritylamino-thiazol-4-yl)-2-vinyloxyimino-acetamido]-5-thia-1-aza-bicyclo[4.2.0]oct-2-ene (syn isomer, E-form) can be prepared in the following manner:

tert.-Butoxy-bis-dimethylaminomethane (0.7 cc) is added to a solution of 2-benzhydryloxycarbonyl-3-metnyl-8-oxo-7-[2-(2-tritylamino-thiazol-4-yl)-2-vinyloxyimino-acetamido]-5-thia-1-aza-bicyclo[4.2.0]oct-2-ene (syn isomer) (2.5 g) in dimethylformamide (40 cc) at 80° C., under nitrogen, and the mixture is stirred for 10 minutes at 80° C. and then poured into ethyl acetate (250 cc) and iced water (250 cc). The organic phase is decanted, washed with water (3×150 cc) and saturated aqueous sodium chloride (150 cc), dried over sodium sulphate, filtered and concentrated to dryness under 20 mm Hg (2.7 kPa) at 30° C. A brown froth (2.5 g) consisting principally of 2-benzhydryloxycarbonyl-3-(2-dimethylaminovinyl)-8-oxo-7-[2-(2-tritylamino-thiazol-4-yl)-2-vinyloxyimino-acetamido]-5-thia-1-aza-bicyclo[4.2.0]oct-2-ene (syn isomer, E-form) is obtained.

Infra-red spectrum (KBr): characteristic bands (cm$^{-1}$) at 1770, 1670, 1635, 1610, 1530, 1495, 1450, 1000, 945, 755 and 700.

Proton nuclear magnetic resonance spectrum (350 MHz, CDCl$_3$, δ in ppm, J in Hz): 2.90 (s, 6H, —N(CH$_3$)$_2$);

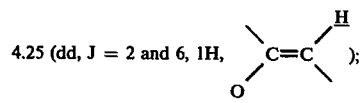

4.25 (dd, J = 2 and 6, 1H,

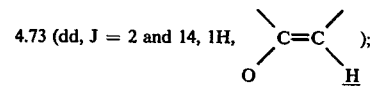

4.73 (dd, J = 2 and 14, 1H, 5.18 (d, J=4, 1H, H in the 6-position); 5.60 (dd, J=4 and 9, 1H, H in the 7-position); 6.53 and 6.75 (2d, J=16, 2H, —CH=CH—); 6.88 (s, 1H, —COOCH<); 7.10 (dd, J=6 and 14, 1H, =NOCH=).

2-Benzhydryloxycarbonyl-3-methyl-8-oxo-7-[2-(2-tritylamino-thiazol-4-yl)-2-vinyloxyimino-acetamido]-5-thia-1-aza-bicyclo[4.2.0]oct-2-ene (syn isomer) is prepared by condensing 2-(2-tritylamino-thiazol-4-yl)-2-vinyloxyimino-acetic acid, syn isomer (4.6 g) with the benzhydryl ester of 7-ADCA (3.8 g) in the presence of N,N'-dicyclohexylcarbodiimide (2.3 g) and of 4-dimethylaminopyridine (0.05 g) in methylene chloride (40 cc) for 4 hours at between 5° C. and 20° C. After chromatography on silica gel (200 g), using methylene chloride, the expected product (5 g) is obtained in the form of a yellow froth.

Infra-red spectrum (KBr): characteristic bands (cm$^{-1}$) at 3400, 1785, 1725, 1690, 1640, 1525, 1495, 1450, 1040, 1000, 940, 755 and 700.

Proton nuclear magnetic resonance spectrum (350 MHz, CDCl$_3$, δ in ppm, J in Hz): 2.12 (s, 3H, —CH$_3$); 3.22 and 3.49 (2d, J=18, 2H, —CH$_2$—);

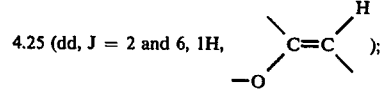

4.25 (dd, J = 2 and 6, 1H,

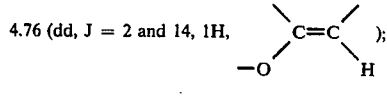

4.76 (dd, J = 2 and 14, 1H, 5.08 (d, J=4, 1H, H in the 6-position); 5.92 (dd, J=4 and 9, 1H, H in the 7-position); 6.83 (s, 1H, H of the thiature is poured into ethyl acetate (250 cc) and this mixture is washed with a saturated sodium bicarbonate solution (250 cc), water (250 cc) and a saturated sodium bicarbonate solution (250 cc), dried over sodium sulphate, filtered and concentrated to dryness under 20 mm Hg (2.7 kPa) at 20° C. The product is fixed on Merck silica gel (0.06–0.2 mm) (10 g) and is chromatographed on a column (column diameter: 1.5 cm) of Merck silica gel (0.06–0.2 mm) (30 g). Elution is carried out with an 80:20 (by volume) mixture (250 cc), a 70:30 (by volume) mixture (250 cc) and a 60:40 (by volume) mixture (250 cc) of cyclohexane and ethyl acetate, 60 cc fractions being collected. Fractions 5 to 10 are concentrated to dryness under 20 mm Hg (2.7 kPa) at 20° C., and 2-benzhydryloxycarbonyl-3-[2-(1-methyl-tetrazol-5-yl)-thiovinyl]-8-oxo-7-[2-(2-tritylamino-thiazol-4-yl)-2-vinyloxyimino-acetamido]-5-thia-1-aza-bicyclo[4.2.-0]oct-2-ene (syn isomer, E-form) (1.92 g) is obtained in the form of a cream-coloured froth.

Rf=0.58 [silica gel chromatographic plate, eluant: a 50:50 (by volume) mixture of cyclohexane and ethyl acetate].

A mixture of 2-benzhydryloxycarbonyl-3-[2-(1-methyl-tetrazol-5-yl)-thiovinyl]-8-oxo-7-[2-(2-tritylamino-thiazol-4-yl)-vinyloxyimino-acetamido]-5-thia-1-aza-bicyclo[4.2.0]oct-2-ene (syn isomer, E-form) (1.92 g), formic acid (15 cc) and water (7 cc) is stirred at 50° C. for 15 minutes. It is then filtered and concentrated to dryness under 0.05 mm Hg (0.007 kPa) at 30° C. The oil which remains is taken up in ethanol (100 cc), the solvent is driven off under 20 mm Hg (2.7 kPa) at 20° C., and this operation is repeated a second time. The residue is taken up in ethanol (100 cc), and the mixture is heated under reflux, whilst stirring, and is cooled and filtered. After drying, 7-[2-(2-amino-thiazol-4-yl)-2-vinyloxyimino-acetamido]-2-carboxy-3-[2-(1-methyltetrazol-5-yl)-thiovinyl]-8-oxo-5-thia-1-aza-bicyclo[4.2.-0]oct-2ene (syn isomer, E-form) (0.72 g) is obtained in the form of a yellow powder.

Infra-red spectrum (KBr): characteristic bands (cm$^{-1}$) at 3340, 1770, 1680, 1620, 1530 and 1380.

Proton nuclear magnetic resonance spectrum (350 MHz, DMSO, d$_6$, δ in ppm, J in Hz): 3.64 and 3.89 (2d, J=18, 2H, —SCH$_2$—); 4.0 (s, 3H, —CH$_3$);

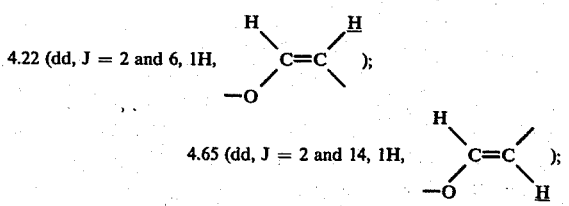

5.22 (d, J=4, 1H, H in the 6-position); 5.82 (dd, J=4 and 9, 1H, H in the 7-position); 6.75 (s, 1H, H of the thiazole); 6.95 (d, J=16, 1H, —CH=CHS—); 6.96 (dd, J=6 and 14, 1H, —OCH=CH$_2$); 7.13 (d, J=16, 1H, =CHS—); 9.83 (d, J=9, 1H, —CONH—).

2-Benzhydryloxycarbonyl-8-oxo-5-oxide-3-(2-tosyloxyvinyl)-7-[2-(2-tritylamino-thiazol-4-yl)-2-vinyloxyimino-acetamido]-5-thia-1-aza-bicyclo[4.2.-0]oct-2ene (syn isomer, E-form) can be prepared in the following manner:

A solution of 85% strength m-chloroperbenzoic acid (0.33 g) in methylene chloride (7 cc) is added dropwise, in the course of 10 minutes, to a solution, cooled to −10° C., of 2-benzhydryloxycarbonyl-8-oxo-3-(2-tosyloxyvinyl)-7-[2-(2-tritylamino-thiazol-4-yl)-2-vinyloxyimino-acetamido]-5-thia-1-aza-bicyclo[4.2.-0]oct-2-ene and oct-3-ene (syn isomer, mixture of the E- and Z-forms) in methylene chloride (5 cc). The mixture is stirred for 1 hour at −10° C. and is then diluted with methylene chloride (30 cc), and this mixture is washed with a saturated sodium bicarbonate solution (2×50 cc) and a half-saturated sodium chloride solution (50 cc), dried over sodium sulphate, filtered and concentrated to dryness under 20 mm Hg (2.7 kPa) at 30° C. The residue is chromatographed on a column (column diameter; 1 cm, height; 10 cm ) of Merck silica gel (0.06 –0.2 mm). Elution is carried out with methylene chloride (500 cc), a 97:3 (by volume) mixture (1 liter) and a 95:5 (by volume) mixture (1.5 liters) of methylene chloride and ethyl acetate, 25 cc fractions being collected. Fractions 14 to 24 are evaporated to dryness under 20 mm Hg (2.7 kPa) at 20° C. 2-Benzhydryloxycarbonyl-8-oxo-5-oxide-3-(2-tosyloxyvinyl)-7-[2-(2-tritylamino-thiazol-4-yl)-vinyloxyimino-acetamido]-5-thia-1-aza-bicyclo[4.2.-0]oct-2-ene (syn isomer, E-form (0.45 g) is obtained.

Infra-red spectrum (KBr): characteristic bands (cm$^{-1}$) at 1800, 1725, 1690, 1635, 1520, 1495, 1450, 1195, 1180, 1070, 1050, 1000, 945, 740 and 700.

Proton nuclear magnetic resonance spectrum (350 MHz, CDCl$_3$, δ in ppm, J in Hz): 2.45 (s, 3H, —CH$_3$); 3.19 and 3.77 (2d, J=18, 2H, —SCH$_2$—);

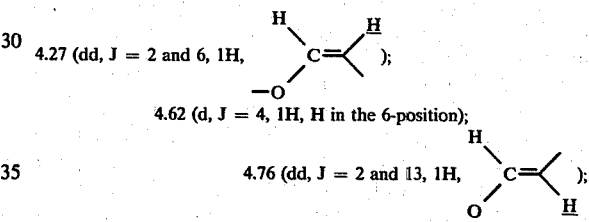

6.20 (dd, J=4 and 9, 1H, H in the 7-position); 6.80 (s, 1H, H of the thiazole); 6.90 L (s, 1H, —COOCH<); 6.92 and 7.10 (2d, J=12, 2H, —CH=CH—); 7.05 (dd, J=6 and 13, 1H, =NOCH=); 7.73 (d, J=8, 2H, H in the ortho-position of the —OSO$_2$— group).

2-Benzhydryloxycarbonyl-8-oxo-3-(2-tosyloxyvinyl)-7-[2-(2-tritylamino-thiazol-4-yl)-2-vinyloxyimino-acetamido]-5-thia-1-aza-bicyclo[4.2.0]oct-2-ene and -3-ene (a mixture of the E- and Z-forms) can be prepared in the following manner:

p-Toluenesulphonyl chloride (0.65 g) is added to a solution, cooled to −15° C., of 2-benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]-oct-2-ene (syn isomer) (2.4 g) in methylene chloride (30 cc), after which a solution of triethylamine (0.44 cc) in methylene chloride (5 cc) is added dropwise in the course of 10 minutes. The mixture is stirred for 30 minutes at −15° C., the temperature is allowed to return to +20° C. in the course of 1 hour, and the mixture is then diluted with methylene chloride (50 cc) washed with a saturated sodium bicarbonate solution (3×50 cc) and with water (3×50 cc), dried over sodium sulphate, filtered and concentrated to dryness under 20 mm Hg (2.7 kPa) at 30° C.

The residue is taken up in ethyl acetate (5 cc), and diisopropyl ether (50 cc) is added, the mixture is stirred for 10 minutes and filtered, and after drying, a beige powder (1.6 g) is obtained, which consists principally of 2-benzhydryloxycarbonyl-8-oxo-3-(2-tosyloxyvinyl)-7- graphed on a column (column diameter: 4 cm, height: 20 cm) of Merck silica gel (0.04–0.06 mm). Elution is carried out with a 50:50 (by volume) mixture of cyclohexane and ethyl acetate (1.8 liters), under a pressure of 40 kPa, 60 cc fractions being collected. Fractions 16 to 24 are evaporated to dryness and 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.1 g) is obtained in the form of a cream-coloured froth.

Infra-red spectrum (KBr): characteristic bands (cm$^{-1}$) at 3400, 1790, 1725, 1690, 1520, 1500, 1450, 1210, 1050, 1040, 945, 755 and 705.

Proton nuclear magnetic resonance spectrum (350 MHz, DMSO d$_6$, δ in ppm, J in Hz): 3.31 (s, 6H, >C(OCH$_3$)$_2$); 3.65 and 3.91 (2d, J=18, 2H, —SCH$_2$—); 3.83 (s, 3H, =NOCH$_3$); 4.48 (d, J=6, 2H, >NCH$_2$CH<); 4.70 (t, J=6, >NCH$_2$CH<); 5.23 (d, J=4, H$_6$); 5.78 (dd, J=4 and 9, H$_7$); 6.74 (s, H of the thiazole);

6.96 (s, —COOCH—);

7.02 and 7.08 (2d, J=16, 2H, —CH=CH—S—); 8.79 (s, —NH—); 9.60 (d, J=9, —NHCO—).

A solution of 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]8-oxo-5-thia-1-aza-bicyclo[4.2.0]oct-2-ene (syn isomer, E-form (1.06 g) in formic acid (42 cc) is heated for 30 minutes at 50° C. It is then concentrated to dryness under 0.05 mm Hg (0.007 kPa) at 30° C., the residue is taken up in acetone (100 cc), the mixture is again concentrated to dryness, under 20 mm Hg (2.7 kPa) at 20° C. and this operation is repeated 4 times. The yellow solid obtained is treated with acetone (30 cc) under reflux, and the mixture is allowed to cool and filtered. After drying the product, 7-[2-(2-amino-thiazol-4-yl)-2-methoxyimino-acetamido]-2-carboxy-3{2-[1-(2,2-dimethoxyethyl)-tetrazol-5-yl]-thiovinyl}-8-oxo-5-thia-1-aza-bicyclo[4.2.0]oct-2-ene (syn isomer, E-form) (0.43 g) is obtained in the form of a yellow powder.

Infra-red spectrum (KBr): characteristic bands (cm$^{-1}$) at 3350, 1780, 1680, 1655, 1620, 1530, 1120, 1040 and 940.

Proton nuclear magnetic resonance spectrum (350 MHz, CF$_3$CO$_2$D, δ in ppm, J in Hz): 3.61 (s, 6H, >C(OCH$_3$)$_2$); 3.92 (s broad, 2H, —SCH$_2$—); 4.31 (s, 3H, =NOCH$_3$); 4.73 (d, J=6, 2H >NCH$_2$—); 5.0 (t, J=6, 1H, —CH$_2$—CH<); 5.38 (d, J=4, H$_6$); 6.05 (dd, J=4 and 9, H$_7$); 7.16 and 7.88 (2d, J=16, —CH=CH—); 7.50 (s, H of the thiazole).

The sodium salt of 1-(2,2-dimethoxyethyl)-5-mercapto-tetrazole can be prepared in the following manner:

A solution of sodium azide (65 g) in 95% strength ethanol (1,680 cc) is heated under reflux. A solution of 2,2-dimethoxyethyl isothiocyanate (147.2 g) in 95% strength ethanol (320 cc) is added dropwise, with stirring, in the course of 1 hour 30 minutes, and the mixture is heated under reflux for 12 hours. It is then concentrated to dryness at 40° C. under 20 mm Hg (2.7 kPa), the residue is taken up in acetone (600 cc), the mixture is filtered and diethyl ether (1 liter) is added. The crystallisation is started, and a further amount of diethyl ether (2.5 liters) is added. The batch is left at 20° C. for 24 hours and is then filtered. After drying, the sodium salt of 1-(2,2-dimethoxyethyl)-5-mercapto-tetrazole, in the form of the hydrate (208.2 g), is obtained.

Infra-red spectrum (KBr): characteristic bands (cm$^{-1}$) at 3480, 3220, 2840, 1660, 1400, 1290, 1115, 1070, 1025 and 790.

EXAMPLE 45

A mixture of 2-benzhydryloxycarbonyl-8-oxo-5-oxide-3-(2-tosyloxyvinyl)-7-[2-(2-tritylamino-thiazol-4-yl)-2-vinyloxyimino-acetamido]-5-thia-1-aza-bicyclo[4.2.0]oct-2-ene (syn isomer, E-form) (0.4 g), dimethylformamide (5 cc), 5-mercapto-1-methyl-tetrazole (0.1 g) and N,N-diisopropylethylamine (0.15 cc) is heated at 60° C. for 4 hours. It is then taken up in ethyl acetate (50 cc) and the organic phase is washed with water (50 cc), 0.1 N hydrochloric acid (50 cc), a half-saturated sodium bicarbonate solution (50 cc) and a saturated sodium chloride solution (50 cc), dried over sodium sulphate, filtered and concentrated to dryness under 20 mm Hg (2.7 kPa) at 30° C. The residue is chromatographed on a column (column diameter: 1.5 cm, height: 15 cm) of Merck silica gel (0.06–0.2 mm) (50 g). Elution is carried out with a 90:10 (by volume) mixture of methylene chloride and ethyl acetate (2.5 liters) under a pressure of 40 kPa, 25 cc fractions being collected. Fractions 18 to 42 are concentrated to dryness under 20 mm Hg (2.7 kPa) at 20° C. This gives 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (0.15 g), having the following characteristics:

Infra-red spectrum (KBr): characteristic bands (cm$^{-1}$) at 3340, 2940, 2860, 1800, 1730, 1690, 1640, 1575, 1525, 1500, 1450, 1215, 1045, 1005, 950, 765 and 760.

Proton nuclear magnetic resonance spectrum (350 MHz, CDCl$_3$, δ in ppm, J in Hz): 3.31 and 4.05 (2d, J=18, 2H, —SCH$_2$—); 3.92 (s, 3H, —CH$_3$);

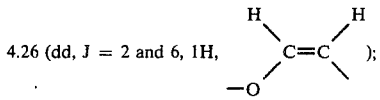

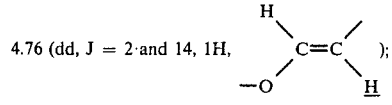

4.67 (d, J=4, 1H, H in the 6-position); 6.18 (dd, J=4 and 9, 1H, H in the 7-position); 6.78 (s, 3H, H of the thiazole); 6.95 (s, 1H, —COOCH<); 7.0 (d, J=15, 1H, —CH=CHS—); 7.05 (dd, J=4 and 6, 1H, —OCH=);

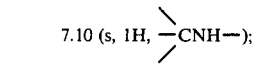

7.58 (d, J=15, 1H, —CH=CHS—).

A solution of 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (3 g) in methylene chloride (31.7 cc) and dimethylacetamide (1.22 cc) is treated with phosphorus trichloride (0.554 cc) at −10° C. for 20 minutes. The mix- 6.93 (s, 1H, —COOCH—);

7.00 (s, 1H, (C$_6$H$_5$)$_3$C—NH—).

3-{2-[1-(2-Acetamido-ethyl)-tetrazol-5-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.32 g) is dissolved in formic acid (60 cc), water (60 cc) is added and the mixture is heated at 50° C. for 15 minutes, whilst stirring. It is then cooled to about 20° C., filtered and concentrated to dryness at 50° C. under 0.05 mm Hg, and the residue is taken up in ethanol (3×150 cc), the solvent being driven off each time under reduced pressure (20 mm Hg) at 20° C. The residue is taken up in ethanol (50 cc), and the suspension is stirred at 40° C. for 1 hour, allowed to cool to 20° C. and filtered. This gives 3-{2-[1-(2-acetamido-ethyl)-tetrazol-5-yl]-thiovinyl}-7-[2-(2-amino-thiazol-4-yl)-2-methoxyimino-acetamido]-2-carboxy-8-oxo-5-thia-1-aza-bicyclo[4.2.0]-oct-2-ene (syn isomer, E-form) (0.86 g) in the form of a yellow powder.

Infra-red spectrum (KBr): characteristic bands (cm$^{-1}$) at 3500, 2500, 1775, 1660, 1540, 1040 and 945.

Proton nuclear magnetic resonance spectrum (350 MHz, DMSO d$_6$, δ in ppm, J in Hz): 1.90 (s, 3H, —CH$_3$); 3.44 (t, 2H, >N CH$_2$—); 3.60 (q, 2H, —CH$_2$NHCO—); 3.64 and 3.76 (2d, J=18, 2H, —S CH$_2$—); 4.0 (s, 3H, —OCH$_3$); 5.16 (d, J=4, 1H, H in the 6-position); 5.82 (dd, J=4 and 9, 1H, H in the 7-position); 6.60 (s, 3H, —NH$_3$+); 6.78 (s, 1H, H of the thiazole); 6.96 (d, J=16, 1H, —CH=CH—S—); 7.37 (d, J=16, 1H, =CHS—); 7.86 (t, J=5, 1H, —NHCOCH$_3$); 9.50 (d, J=9, 1H, —CONH—).

1-(2-Acetamido-ethyl)-5-mercapto-tetrazole can be prepared according to the method described in U.S. Pat. No. 4,117,123.

EXAMPLE 43

A solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (1.04 g) and of 1-(2-dimethylaminoethyl)-5-mercapto-tetrazole (0.35 g) (prepared according to German Patent Application No. 2,738,711) in dimethylformamide (15 cc) is stirred at 60° C. under nitrogen for 5 hours. After extraction with ethyl acetate as described in Example 42, and chromatography over silica gel, elution being carried out with a 20:80 (by volume) mixture of cyclohexane and ethyl acetate, 2-benzhydryloxycarbonyl-3-{2-[1-(2-dimethylaminoethyl)tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.3 g) is obtained in the form of a light brown froth.

Infra-red spectrum (CHBr$_3$): characteristic bands (cm$^{-1}$) at 3390, 2820, 2780, 1780, 1715, 1680, 1510, 1445, 1205, 1045, 940, 750 and 735.

Proton nuclear magnetic resonance spectrum (350 MHz, CDCl$_3$ d$_6$, δ in ppm, J in Hz): 2.25 (s, 6H, —N(CH$_3$)$_2$); 2.73 (t, J=7, 2H, —CH$_2$N(CH$_3$)$_2$); 3.61 and 3.68 (2d, J=18, 2H, —SCH$_2$—); 4.08 (s, 3H, =NOCH$_3$); 4.3 (t, J=7, 2H, —CH$_2$CH$_2$N(CH$_3$)$_2$); 5.11 (d, J=4, 1H, H in the 6-position); 5.95 (dd, J=4 and 9, 1H, H in the 7-position); 6.76 (s, 1H, H of the thiazole); 6.84 (d, J=9, 1H, —CONH—); 6.95 (s, 1H, —COOCH); 6.99 (s, 1H, —NHC(C$_6$H$_5$)$_3$); 7.07 (d, J=16, 1H, —CH=CHS—); 7.42 (d, J=16, 1H, =CHS—).

Following the procedure described in Example 42, 2-benzhydryloxycarbonyl-3-{2-[1-(2-dimethylaminoethyl)tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.59 g) is treated with a mixture of formic acid (30 cc) and water (30 cc), and 7-[2-(2-amino-thiazol-4-yl)-2-methoxyimino-acetamido]-2-carboxy-3-{2-[1-(2-dimethylaminoethyl)tetrazol-5-yl]-thiovinyl}-8-oxo-5-thia-1-aza-bicyclo[4.2.0]oct-2-ene (syn isomer, E-form) (0.38 g) is obtained, as the formate, in the form of a yellow powder.

Infra-red spectrum (KBr): characteristic bands (cm$^{-1}$) at 3400, 3200, 2000, 1770, 1670, 1615, 1530 and 1035.

Proton nuclear magnetic resonance spectrum (350 MHz, DMSO d$_6$, δ in ppm, J in Hz): 2.70 (s, 6H, —N(CH$_3$)$_2$); 2.75 (t, J=7, 2H, —CH$_2$N<); 3.85 (s, 3H, —OCH$_3$); 3.95 (t, J=7, 2H, —CH$_2$CH$_2$N(CH$_3$)$_2$); 5.16 (d, J=4, 1H, H in the 6-position); 5.85 (dd, J=4 and 9, 1H, H in the 7-position); 6.74 (s, 1H, H of the thiazole); 6.80 (d, J=16, 1H, —CH=CHS—); 6.90 (d, J=16, 1H, =CHS—); 7.20 (s, 2H, —NH$_2$); 9.63 (d, J=9, 1H, —CONH—).

EXAMPLE 44

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10 g), dimethylformamide (200 cc) and the sodium salt of 1-(2,2-dimethoxyethyl)-5-mercapto-tetrazole (5.75 g) is stirred for 24 hours at 50° C. under nitrogen. It is then diluted with ethyl acetate (200 cc) and water (200 cc), and the organic phase is decanted, washed with water (3×200 cc) and saturated aqueous sodium chloride (100 cc), filtered and concentrated to dryness under 20 mm Hg (2.7 kPa) at 20° C. The residue is chromatographed on a column (column diameter: 6 cm, height: 30 cm) of Merck silica gel (0.04–0.06 mm). Elution is carried out with a 50:50 (by volume) mixture (3.8 liters) and a 25:75 (by volume) mixture (4.6 liters) of cyclohexane and ethyl acetate, 120 cc fractions being collected. Fractions 40 to 69 are concentrated to dryness under 20 mm Hg (2.7 kPa) at 20° C., and 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.4 g) is obtained in the form of a brown froth, which is used, as obtained, in the subsequent operations.

A solution of 2-benzhydryloxycarbonyl-3--{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.37 g) in methylene chloride (25 cc) and dimethylacetamide (1.31 cc) is treated with phosphorus trichloride (0.58 cc) at −8° C. for 30 minutes, whilst stirring. The mixture is diluted with methylene chloride (75 cc), and this mixture is washed with a half-saturated sodium bicarbonate solution (2×50 cc) and water (2×50 cc), dried over sodium sulphate, filtered and concentrated to dryness under 20 mm Hg (2.7 kPa) at 20° C. The residue is chromatorazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.4 g) is obtained.

Infra-red spectrum (KBr): characteristic bands (cm$^{-1}$) at 3400, 1785, 1720, 1580, 1525, 1370, 1210, 1035, 940, 755 and 700.

Proton nuclear magnetic resonance spectrum (350 MHz, CDCl$_3$, δ in ppm, J in Hz): 3.57 and 3.67 (AB, J=18, 2H, —SCH$_2$—); 4.07 (s, 3H, —OCH$_3$); 4.1 and 4.35 (2 t, 4H, —CH$_2$CH$_2$O—); 5.09 (d, J=4, 1H, H in the 6-position); 5.94 (dd, J=4 and 9, 1H, H in the 7-position); 6.74 (s, 1H, H in the 5-position of the thiazole);

6.95 (s, 1H, —COOCH—);

6.97 (s, 1H, (C$_6$H$_5$)$_3$CNH—); 7.00 (d, J=16, 1H, —CH=CHS—).

2-Benzhydryloxycarbonyl-3-{2-[1-(2-hydroxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.39 g) is dissolved in formic acid (7 cc), and the solution is diluted with water (4 cc) and heated at 50° C. for 30 minutes. It is then allowed to cool, filtered and concentrated to dryness under reduced pressure (0.05 mm Hg) at 20° C. The residue is triturated in diisopropyl ether (10 cc), and after filtration and drying the formic acid solvate of 7-[2-(2-amino-thiazol-4-yl)-2-methoxyimino-acetamido]-2-carboxy-3-{2-[1-(2hydroxyethyl)tetrazol-5-yl]-thiovinyl}-8-oxo-5-thia-1-aza-bicyclo[4.2.0]oct-2-ene (syn isomer, E-form) (0.2 g) is obtained in the form of a pale yellow solid.

The above product (as the solvate) (0.9 g) is treated with ethanol (50 cc) under reflux, a slight amount of insoluble matter is removed by filtration, the filtrate is allowed to cool for 2 hours at 20° C. and 2 hours at 4° C., and the mixture is then filtered. The above product (0.41 g) is obtained in the form of its internal salt.

Infra-red spectrum (KBr): characteristic bands (cm$^{-1}$) at 3350, 1770, 1720, 1675, 1530, 1390, 1040 and 940.

Proton nuclear magnetic resonance spectrum (350 MHz, DMSO d$_6$, δ in ppm, J in Hz): 3.63 and 3.87 (AB, J=19, 2H, —SCH$_2$—); 3.77 and 4.41 (2 t, 4H, —CH$_2$CH$_2$O—); 3.84 (s, 3H, —OCH$_3$); 5.19 (d, J=4, 1H, H in the 6-position); 5.89 (dd, J=4 and 9, 1H, H in the 7-position); 6.73 (s, 1H, H in the 5-position of the thiazole); 6.94 (d, J=16, 1H, —CH=CHS—); 7.25 (d, J=16, 1H, =CHS—); 9.61 (d, J=9, 1H, —CONH—).

The internal salt (0.27 g) is suspended in distilled water (2 cc), sodium bicarbonate (0.042 g) is added and the mixture is stirred for 15 minutes at 20° C. After lyophilisation, the sodium salt of the product (0.27 g) is obtained.

2-Benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) can be obtained according to the method described in Example 3.

EXAMPLE 42

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.-0]oct-2-ene (syn isomer, E-form) (10.04 g), dimethylformamide (200 cc), 1-(acetamidoethyl)-5-mercapto-tetrazole (3.74 g) and diisopropylethylamine (3.5 cc) is stirred for 6 hours at 60° C. under nitrogen. It is diluted with ethyl acetate (800 cc) and this mixture is washed with water (3×400 cc), dried over sodium sulphate, filtered and concentrated to dryness at 20° C. under 20 mm Hg. The product, which is first fixed to Merck silica gel (0.05–0.2 mm) (50 g), is deposited on a column (column diameter: 3 cm) of the same silica gel (100 g). Elution is carried out successively with a 50:50 (by volume) mixture (500 cc) and a 25:75 (by volume) mixture (1 liter) of cyclohexane and ethyl acetate, and with ethyl acetate (3 liters), 125 cc fractions being collected. Fractions 19 to 30 are concentrated to dryness at 20° C. under 20 mm Hg. 3-{2-[1-(2-Acetamido-ethyl)-tetrazol-5-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (5.05 g) is obtained in the form of a brown froth.

Infra-red spectrum (CHBr$_3$): characteristic bands (cm$^{-1}$) at 3440, 3380, 1800, 1720, 1670, 1510, 1495, 1445, 1370, 1045, 940, 750 and 735.

Proton nuclear magnetic resonance spectrum (350 MHz, CDCl$_3$, δ in ppm, J in Hz): 1.84 (s, 3H, —COCH$_3$); 3.27 and 4 (2d, J=18, 2H, —SCH$_2$—); 3.62 (mt, 2H, —CH$_2$NHCO—); 4.05 (s, 3H, —OCH$_3$); 4.35 (t, 2H, >N CH$_2$—); 4.62 (d, J=4, 1H, H in the 6-position); 6.07 (dd, J=4 and 9, 1H, H in the 7-position); 6.50 (t, J=7, 1H, —NHCO—); 6.69 (s, 1H, H of the thiazole); 6.93 (s, 1H, —COOCH—); 6.96 (d, J=16, 1H, —CH=CH S—); 7.10 (s, 1H, —NHC(C$_6$H$_5$)$_3$).

Dimethylacetamide (1.95 cc) and phosphorus trichloride (0.86 cc) are added to a solution, cooled to −10° C., of 3-{2-[1-(2-acetamido-ethyl)-tetrazol-5-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (4.99 g) in methylene chloride (49 cc). The mixture is stirred for 2 hours at −10° C. and is diluted with ethyl acetate (300 cc), and this mixture is washed with a half-saturated sodium bicarbonate solution (200 cc) and a saturated sodium chloride solution (200 cc), dried over sodium sulphate, filtered and concentrated to dryness at 20° C. under 20 mm Hg. The material is chromatographed on a column (column diameter: 6 cm) of Merck silica gel (0.04–0.06 mm). Elution is carried out with a 20:80 (by volume) mixture of cyclohexane and ethyl acetate (5 liters) under a pressure of 40 kPa, 125 cc fractions being collected. Fractions 19 to 32 are evaporated to dryness at 20° C. under 20 mm Hg and 3-{2-[1-(2-acetamido-ethyl)-tetrazol-5-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.36 g) is obtained in the form of a yellow froth.

Infra-red spectrum (CHBr$_3$): characteristic bands (cm$^{-1}$) at 3440, 3400, 1785, 1720, 1680, 1515, 1495, 1450, 1370, 1040, 945, 755 and 740.

Proton nuclear magnetic resonance spectrum (350 MHz, CDCl$_3$, δ in ppm, J in Hz): 1.93 (s, 3H, —CH$_3$); 3.54 and 3.60 (2d, J=18, 2H, —SCH$_2$—); 3.70 (m, 2H, —CH$_2$NHCO—); 4.04 (s, 3H, —OCH$_3$); 4.35 (t, J=5, 2H, >NCH$_2$—); 5.10 (d, J=4, 1H, H in the 6-position); 5.94 (dd, J=4 and 9, 1H, H in the 7-position); 6.40 (t, J=5, 1H, —NHCOCH$_3$); 6.73 (s, 1H, H of the thiazole);

filtered, the filter cake is washed with distilled water (2×3 cc) and the filtrate is concentrated under reduced pressure (0.5 mm Hg; 0.07 kPa) at 30° C. The solid obtained is taken up in ethanol (40 cc) and the suspension obtained is concentrated under reduced pressure (0.5 mm Hg; 0.07 kPa) at 30° C. The operation is repeated twice. The solid obtained is triturated in a mixture of acetonitrile (10 cc) and ethanol (5 cc). It is then filtered off, washed with acetonitrile (2×5 cc) and dried under reduced pressure (0.2 mm Hg; 0.03 kPa) at 20° C. This gives 7-[2-(2-amino-thiazol-4-yl)-2-methoxyimino-acetamido]-2-carboxy-8-oxo-3-[2-(5-phenyl-1,3,4-oxadiazol-2-yl)-thiovinyl]-5-thia-1-aza-bicyclo[4.2.0]oct-2-ene (syn isomer, E-form) (0.25 g).

Infra-red spectrum (KBr): characteristic bands (cm$^{-1}$): 3400 to 2000, 3330, 1760, 1630, 1540, 1380, 1055, 750, 710 and 695.

Nuclear magnetic resonance spectrum (350 MHz, DMSO d$_6$, δ in ppm, J in Hz): 3.68 and 3.94 (2d, J=18, 2H, —SCH$_2$—); 3.86 (s, 3H, =NOCH$_3$); 5.22 (d, 1H, H in the 6-position); 5.82 (dd, 1H, H in the 7-position); 6.74 (s, 1H, H of the thiazole ring); 7.10 (d, J=16, 1H, —CH=CHS—); 7.18 (s, 2H, —NH$_2$); 7.26 (d, J=16, 1H, —CH=CHS—); 7.83 (mt, 3H, p- and m-protons of —C$_6$H$_5$); 8.0 (d, J=7, 2H, o-protons of —C$_6$H$_5$); 9.61 (d, J=9, 1H, —CONH—).

2-Mercapto-5-phenyl-1,3,4-oxadiazole can be prepared according to the method described by E. HOGGARTH, J. Chem. Soc. 4811 (1952).

EXAMPLE 40

N-Ethyl-N,N-diisopropylamine (1.4 cc) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4.0 g) and 2-mercapto-4-methyl-oxazole (0.92 g) in dimethylformamide (40 cc). The solution obtained is heated at 55° C. for 2 hours. After cooling, it is diluted with ethyl acetate (500 cc) and the mixture is then washed successively with 0.1 N hydrochloric acid (150 cc), a 3% strength sodium bicarbonate solution (2×150 cc) and finally a saturated sodium chloride solution (150 cc). The organic extract is dried with sodium sulphate, filtered and concentrated under reduced pressure (25 mm Hg; 3.3 kPa) at 20°-25° C. The product obtained is chromatographed on a column (column diameter: 3 cm) of Merck silica (0.02–0.063 mm) (150 g) under a pressure of 50 kPa. Elution is carried out with a 40:60 (by volume) mixture of cyclohexane and ethyl acetate (1.5 liters), 50 cc fractions being collected. Fractions 14 to 23 are combined and concentrated under reduced pressure (25 mm Hg; 3.3 kPa) at 40° C. Drying is completed under 0.2 mm Hg (0.03 kPa) at 20° C. This gives 2-benzhydryloxycarbonyl-7-[2-methoxyimino-2-(2-tritylamino-thiazol-4-yl)-acetamido]-3-[2-(4-methyl-oxazol-2-yl)-thiovinyl]-8-oxo-5-oxide-5-thia-1-aza-bicyclo[4.2.0]oct-2-ene (syn isomer, E-form) (1.15 g) in the form of a yellow froth.

Phosphorus trichloride (0.202 cc) is added to a solution, cooled to −12° C., of 2-benzhydryloxycarbonyl-7-[2-methoxyimino-2-(2-tritylamino-thiazol-4-yl)-acetamido]-3-[2-(4-methyl-oxazol-2-yl)-thiovinyl]-8-oxo-5-oxide-5-thia-1-aza-bicyclo[4.2.0]oct-2-ene (syn isomer, E-form) (1.1 g) in dry methylene chloride (10 cc) and N,N-dimethylacetamide (0.43 cc). The solution obtained is stirred for 1 hour 30 minutes at −15° C. and is then diluted with ethyl acetate (250 cc), and this mixture is washed successively with a 3% strength sodium bicarbonate solution (250 cc) and a saturated sodium chloride solution (250 cc). The organic extract is dried with sodium sulphate, filtered and then concentrated under reduced pressure (25 mm Hg; 3.3 kPa) at about 30° C. This gives 2-benzhydryloxycarbonyl-7-[2-methoxyimino-2-(2-tritylamino-thiazol-4-yl)-acetamido]-3-[2-(4-methyl-oxazol-2-yl)-thiovinyl]-8-oxo-5-thia-1-aza-bicyclo[4.2.0]-oct-2-ene (syn isomer, E-form) (1.08 g).

A solution of 2-benzhydryloxycarbonyl-7-[2-methoxyimino-2-(2-tritylamino-thiazol-4-yl)-acetamido]-3-[2-(4-methyl-oxazol-2-yl)-thiovinyl]-8-oxo-5-thia-1-aza-bicyclo[4.2.0]oct-2-ene (syn isomer, E-form) (1.08 g) in formic acid (10 cc) and distilled water (6 cc) is heated at 50° C. for 45 minutes. After cooling, the suspension is filtered and the solid is washed with distilled water (3 cc). The filtrate is concentrated to dryness under reduced pressure (0.5 mm Hg; 0.07 kPa) at 30° C. The solid obtained is taken up in ethanol (75 cc) and the suspension is concentrated under reduced pressure (0.5 mm Hg; 0.074 kPa) at 30° C. The operation is repeated twice. The solid obtained is triturated in acetonitrile (50 cc), filtered off, washed and then dried under reduced pressure (0.2 mm Hg; 0.03 kPa) at 20° C. This gives 7-[2-(2-amino-thiazol-4-yl)-2-methoxyimino-acetamido]-2-carboxy-3-[2-(4-methyl-oxazol-2-yl)-thiovinyl]-8-oxo-5-thia-1-aza-bicyclo[4.2.0]oct-2-ene (syn isomer, E-form) (0.41 g).

Infra-red spectrum (KBr): characteristic bands (cm$^{-1}$) at 3300, 2940, 1770, 1675, 1530, 1380, 1040, 940, 730 and 700.

Proton nuclear magnetic resonance spectrum (350 MHz, CDCl$_3$, δ in ppm, J in Hz): 2.10 (s, 3H, —CH$_3$); 3.66 and 3.90 (2d, J=18, 2H, —SCH$_2$—); 3.86 (s, 3H, =NOCH$_3$); 5.19 (d, 1H, H in the 6-position); 5.78 (dd, 1H, H in the 7-position); 6.74 (s, 1H, H of the thiazole ring); 7.0 (d, J=16, 1H, —CH=CHS—); 7.14 (d, J=16, 1H, —CH=CHS—); 7.20 (s, 2H, —NH$_2$); 7.94 (s, 1H, H of the oxazole ring); 9.72 (d, J=9, 1H, —CONH—).

2-Mercapto-4-methyl-oxazole can be prepared according to the method described by C. BRADSHER, J. Org. Chem. 32, 2079 (1967).

EXAMPLE 41

A mixture of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]-oct-2-ene (syn isomer, E-form) (0.57 g), dimethylformamide (15 cc) and 1-(2-hydroxyethyl)-5-mercapto-tetrazole (0.17 g) is heated to 60° C. under nitrogen. A solution of N-ethyl-N,N-diisopropylamine (0.1 cc) in dimethylformamide (5 cc) is added dropwise to this mixture in the course of 15 minutes, whilst stirring. After 3½ hours at 60° C., the mixture is diluted with ethyl acetate (100 cc) and this mixture is washed with distilled water (5×50 cc), dried over sodium sulphate, filtered and concentrated to dryness under reduced pressure (20 mm Hg) at 20° C. The residue is dissolved in methylene chloride (5 cc) and the solution is chromatographed on a column (column diameter: 2 cm, height: 15 cm) of Merck silica gel (0.04–0.06 mm) (80 g). Elution is carried out with a 25:75 (by volume) mixture of cyclohexane and ethyl acetate (300 cc) under a pressure of 40 kPa, 60 cc fractions being collected.

In fraction 1, some of the starting material (0.06 g) is obtained. Fractions 2 to 4 are concentrated to dryness under reduced pressure (20 mm Hg) at 20° C., and 2-benzhydryloxycarbonyl-3-{-2-[1-(2-hydroxyethy)tet- 3.29 and 4.07 (2d, J=18, 2H, —SCH₂—); 4.08 (s, 3H, —OCH₃); 4.61 (d, J=4, 1H, H in the 6-position); 6.18 (dd, J=4 and 9, 1H, H in the 7-position); 6.71 (s, 1H, H of the thiazole); 6.89 (s, 1H, —COOCH<); 7.05 (d, J=14, 1H, —CH=CHS—); 7.48 (d, J=9, 1H, —CONH—); 7.58 (d, J=14, 1H, =CHS—).

Phosphorus trichloride (0.35 cc) is added, as a single shot, to a solution, cooled to −10° C., of 2-benzhydryloxycarbonyl-7-[2-methoxyimino-2-(2-tritylaminothiazol-4-yl)-acetamido]-3-[2-(3-methyl-1,2,4-thiadiazol-5-yl)-thiovinyl]-8-oxo-5-oxide-5-thia-1-aza-bicyclo[4.2.0]oct-2-ene (syn isomer, E-form (1.75 g) and dimethylacetamide (0.72 cc) in methylene chloride (40 cc). The mixture is stirred for 1 hour at −10° C., a further amount of phosphorus trichloride (0.17 cc) is added, stirring is continued for 10 minutes, and the mixture is then treated as follows:

It is diluted with ethyl acetate (500 cc), and this mixture is washed with a 2% strength sodium bicarbonate solution (2×150 cc) and a half-saturated sodium chloride solution (2×150 cc), dried over sodium sulphate, filtered and concentrated to dryness at 20° C. under reduced pressure (20 mm Hg). The residue is taken up in a 30:70 (by volume) mixture of cyclohexane and ethyl acetate (15 cc) and the solution is chromatographed over a column (column diameter: 4 cm) of Merck silica gel (0.05–0.2 mm) (60 g). Elution is carried out with the same mixture as above (300 cc), 20 cc fractions being collected. Fractions 6 to 13 are combined and concentrated to dryness at 20° C. under reduced pressure (20 mm Hg). 2-Benzhydryloxycarbonyl-7-[2-methoxyimino-2-(2-tritylamino-thiazol-4-yl)-acetamido]-3-[2-(3-methyl-1,2,4-thiadiazol-5-yl)-thiovinyl]-8-oxo-5-thia-1-aza-bicyclo[4.2.0]oct-2-ene (syn isomer, E-form) (1.18 g) is obtained.

Proton nuclear magnetic resonance spectrum (350 MHz, CDCl₃, δ in ppm, J in Hz): 2.62 (s, 3H, —CH₃); 3.60 and 3.68 (2d, J=18, 2H, —SCH₂—); 4.07 (s, 3H, —OCH₃); 5.11 (d, J=4, 1H, H in the 6-position); 5.95 (dd, J=4 and 9, 1H, H in the 7-position); 6.75 (s, 1H, H of the thiazole); 6.88 (d, J=9, 1H, —CONH—); 6.98 (d, J=16, 1H, —CH=CHS—); 6.99 (s, 1H, —COOCH<); 7.0 (s, 1H, —NH—).

2-Benzhydryloxycarbonyl-7-[2-methoxyimino-2-(2-tritylamino-thiazol-4-yl)-acetamido]-3-[2-(3-methyl-1,2,4-thiadiazol-5-yl)-thiovinyl]-8-oxo-5-thia-1-aza-bicyclo[4.2.0]oct-2-ene (syn isomer, E-form) (1.1 g) is dissolved in formic acid (30 cc), distilled water (13 cc) is added and the mixture is heated at 50° C. for 30 minutes. The suspension is cooled to about 20° C. and filtered, and the filtrate is concentrated at 20° C. under reduced pressure (0.05 mm Hg). The residue is taken up in ethanol (30 cc), the mixture is concentrated under reduced pressure at 20° C., and this operation is repeated 3 times. The solid which remains is treated with ethanol (100 cc) under reflux, a slight amount of insoluble matter is removed by filtration, the filtrate is then concentrated to 5 cc and diluted with diethyl ether (20 cc), and the mixture is cooled to +4° C. After filtration and drying, 7-[2-(2-amino-thiazol-4-yl)-2-methoxyimino-acetamido]-2-carboxy-3-[2-(3-methyl-1,2,4-thiadiazol-5-yl)-thiovinyl]-8-oxo-5-thia-1-aza-bicyclo[4.2.0]oct-2-ene (syn isomer, E-form) (0.44 g) is obtained in the form of a yellow powder.

Proton nuclear magnetic resonance spectrum (350 MHz, DMSO d₆, δ in ppm, J in Hz): 2.57 (s, 3H, —CH₃); 3.65 and 3.95 (2d, J=18, 2H, —SCH₂—); 3.86 (s, 3H, —OCH₃); 5.23 (d, J=4, 1H, H in the 6-position); 5.82 (dd, J=4 and 9, 1H, H in the 7-position); 6.75 (s, 1H, H of the thiazole); 7.04 (d, J=16, 1H, —CH=CHS—); 7.36 (d, J=16, 1H, =CHS—); 9.63 (d, J=9, 1H, —CONH—).

5-Mercapto-3-methyl-1,2,4-thiadiazole can be prepared according to the method described in Chem. Ber. 90, 184 (1957).

EXAMPLE 39

N-Ethyl-N,N-diisopropylamine (1.4 cc) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4.0 g) and 2-mercapto-5-phenyl-1,3,4-oxadiazole (1.4 g) in dry dimethylformamide (40 cc). The solution obtained is heated at 60° C. for 6 hours. After cooling, it is diluted with ethyl acetate (500 cc) and this mixture is then washed successively with 0.1 N hydrochloric acid (150 cc), distilled water (150 cc), a 3% strength sodium bicarbonate solution (150 cc) and finally a saturated sodium chloride solution (150 cc). The organic extract is dried over magnesium sulphate, filtered and concentrated under reduced pressure (25 mm Hg; 3.3 kPa) at 30° C. The product obtained is chromatographed over a column (column diameter 45 mm; height 300 mm) of Merck silica (0.020–0.063 mm) under a pressure of 50 kPa. Elution is carried out with a 50:50 (by volume) mixture of cyclohexane and ethyl acetate (3 liters), 50 cc fractions being collected. Fractions 43 to 59 are combined and concentrated under reduced pressure (25 mm Hg; 3.3 kPa). This gives 2-benzhydryloxycarbonyl-7-[2-methoxyimino-2-(2-tritylamino-thiazol-4-yl)-acetamido]-8-oxo-5-oxide-3-[2-(5-phenyl-1,3,4-oxadiazol-2-yl)-thiovinyl]-5-thia-1-aza-bicyclo[4.2.0]oct-2-ene (syn isomer, E-form) (1.0 g).

Phosphorus trichloride (0.36 cc) is added to a solution, cooled to −15° C., of 2-benzhydryloxycarbonyl-7-[2-methoxyimino-2-(2-tritylamino-thiazol-4-yl)-acetamido]-8-oxo-5-oxide-3-[2-(5-phenyl-1,3,4-oxadiazol-2-yl)-thiovinyl]-5-thia-1-aza-bicyclo[4.2.0]oct-2-ene (syn isomer, E-form) (2.1 g) in dry methylene chloride (20 cc) and N,N-dimethylacetamide (0.76 cc). The solution obtained is stirred for 1 hour at between −10° and −15° C. and is then diluted with ethyl acetate (500 cc). The mixture is washed successively with a 5% strength sodium bicarbonate solution (2×200 cc) and a saturated sodium chloride solution (2×200 cc). The organic extract is dried over magnesium sulphate, filtered and concentrated under reduced pressure (25 mm Hg; 3.3 kPa). The product is chromatographed on a column (column diameter 15 mm, height 200 mm) of Merck silica (0.020–0.063 mm) under a pressure of 50 kPa, elution being carried out with a 95:5 (by volume) mixture of methylene chloride and ethyl acetate (1 liter) and 50 cc fractions being collected. Fractions 5 to 16 are combined and concentrated under reduced pressure (25 mm Hg; 3.3 kPa). This gives 2-benzhydryloxycarbonyl-7-[2-methoxyimino-2-(2-tritylamino-thiazol-4-yl)-acetamido]-8-oxo-3-[2-(5-phenyl-1,3,4-oxadiazol-2-yl)-thiovinyl]-5-thia-1-aza-bicyclo[4.2.0]oct-2-ene (syn isomer, E-form) (1.2 g).

A solution of 2-benzhydryloxycarbonyl-7-[2-methoxyimino-2-(2-tritylamino-thiazol-4-yl)-acetamido]-8-oxo-3-[2-(5-phenyl-1,3,4-oxadiazol-2-yl)-thiovinyl]-5-thia-1-aza-bicyclo[4.2.0]oct-2-ene (syn isomer, E-form) (1.2 g) in formic acid (10 cc) and distilled water (3 cc) is heated at 50° C. for 30 minutes. After cooling, the suspension is yl)-2-methoxyimino-acetamido]-2-carboxy-8-oxo-5-thia-1-aza-bicyclo[4.2.0]oct-2-ene (syn isomer, E-form) (0.74 g) is obtained in the form of a yellow powder.

Infra-red spectrum (KBr): characteristic bands (cm$^{-1}$) at 3320, 3200, 3100, 2820, 2000, 1770, 1670, 1610, 1380, 1040 and 940.

Proton nuclear magnetic resonance spectrum (350 MHz, DMSO d$_6$, δ in ppm, J in Hz): 3.83 (s, 3H, —OCH$_3$); 5.12 (d, J=4, 1H, H in the 6-position); 5.76 (dd, J=4 and 9, 1H, H in the 7-position); 6.74 (s, 1H, H of the thiazole); 6.95 (d, J=16, 1H, —C$\underline{H}$=CHS—); 7.02 (d, J=16, 1H, =CHS—); 7.18 (s broad, 2H, —NH$_2$ of the thiazole; 7.48 (s broad, 2H, —NH$_2$ of the thiadiazole); 9.60 (d, J=9, 1H, —CONH—).

2-tert.-Butoxycarbonylamino-5-mercapto-1,3,4-thiadiazole is prepared by condensation of tert.-butyl dicarbonate with 2-amino-5-mercapto-1,3,4-thiadiazole, obtained according to V. PETROW, J. Chem. Soc. 1508 (1958), in a water/dioxane mixture, in the presence of sodium carbonate, for 24 hours at 25° C.

The product is recrystallised from acetonitrile.

Instantaneous m.p. (Kofler)=200° C.

Infra-red spectrum (KBr): characteristic bands (cm$^{-1}$) at 1725, 1390, 1370, 1240, 1170 and 1070.

Proton nuclear magnetic resonance spectrum (60 MHz, DMSO d$_6$, δ in ppm, J in Hz): 1.53 (s, 9H, —C(CH$_3$)$_3$).

EXAMPLE 37

Using the conditions described in Example 35, 2-dimethylaminomethyl-5-mercapto-1,3,4-thiadiazole (1.3 g) is reacted with 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (6.02 g) in dimethylformamide (60 cc) in the presence of N,N-diisopropylethylamine (1.15 cc). After chromatography on silica gel [eluant: a 20:80 (by volume) mixture of cyclohexane and ethyl acetate], 2-benzhydryloxycarbonyl-3-[2-(2-dimethylaminomethyl-1,3,4-thiadiazol-5-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.7 g) is obtained in the form of an orange-coloured froth.

Infra-red spectrum (CHBr$_3$): characteristic bands (cm$^{-1}$) at 3380, 2820, 2780, 1790, 1715, 1665, 1515, 1445, 1200, 1040, 940, 750 and 735.

Proton nuclear magnetic resonance spectrum (350 MHz, CDCl$_3$, δ in ppm, J in Hz): 2.34 (s, 6H, —N(CH$_3$)$_2$); 3.28 and 3.98 (2d, J=18, 2H, —SCH$_2$—); 3.85 (s, 2H, >NCH$_2$—); 4.07 (s, 3H, —OCH$_3$); 4.62 (d, J=4, 1H, H in the 6-position); 6.15 (dd, J=4 and 9, 1H, H in the 7-position); 6.71 (s, 1H, H of the thiazole); 6.96 (s, 1H, —COOCH<).

The reduction of a 2-benzhydryloxycarbonyl-3-[2-(2-dimethylaminomethyl-1,3,4-thiadiazol-5-yl)-thiovinyl]-7-[2-methoxyimino-2-(2-tritylamino-thiazol-4-yl)-8-oxo-5-oxide-5-thia-1-aza-bicyclo[4.2.0]oct-2-ene (syn isomer, E-form) (2.7 g), under the conditions described in Example 35, with phosphorus trichloride (0.468 cc) in methylene chloride (27 cc) in the presence of dimethylacetamide (0.995 cc) results, after chromatography on silica gel [eluant: a 30:70 (by volume) mixture of cyclhexane and ethyl acetate], in 2-benzhydryloxycarbonyl-3-[2-(2-dimethylaminomethyl-1,3,4-thiadiazol-5-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.6 g), in the form of a pinkish froth.

Infra-red spectrum (CHBr$_3$): characteristic bands (cm$^{-1}$) at 3400, 2820, 2780, 1780, 1715, 1685, 1515, 1450, 1205, 1040, 755 and 740.

Proton nuclear magnetic resonance spectrum (350 MHz, CDCl$_3$, δ in ppm, J in Hz): 2.35 (s, 6H, —N(CH$_3$)$_2$); 3.62 and 3.72 (2d, J=18, 2H, —SCH$_2$—); 3.86 (s, 2H, >NCH$_2$—); 4.09 (s, 3H, —OCH$_3$); 5.12 (d, J=4, 1H, H in the 6-position); 5.95 (dd, J=4 and 9, 1H, H in the 7-position); 6.76 (s, 1H, H of the thiazole); 6.88 (s, 1H, —COOCH<); 6.88 (d, J=9, 1H, —CONH—); 7.22 (d, J=16, 1H, —C$\underline{H}$=CHS—); 7.42 (d, J=16, 1H, =CHS—).

Using the conditions described in Example 35, 2-benzhydryloxycarbonyl-3-[2-(2-dimethylaminomethyl-1,3,4-thiadiazol-5-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.6 g) is treated with a mixture of formic acid (16 cc) and water (8 cc). 7-[2-(2-Amino-thiazol-4-yl)-2-methoxyimino-acetamido]-2-carboxy-3-[2-(2-dimethylaminomethyl-1,3,4-thiadiazol-5-yl)-thiovinyl]-8-oxo-5-thia-1-aza-bicyclo[4.2.0]-oct-2-ene (syn isomer, E-form) (0.92 g) is obtained, as the formate, in the form of a yellow powder.

Infra-red spectrum (KBr): characteristic bands (cm$^{-1}$) at 3400, 3330, 3250, 2000, 1765, 1665, 1600, 1530, 1035 and 960.

Proton nuclear magnetic resonance spectrum (350 MHz, DMSO d$_6$, δ in ppm, J in Hz): 2.36 (s, 6H, —N(CH$_3$)$_2$); 3.67 and 3.92 (2d, J=18, 2H, —SCH$_2$—); 3.88 (s, 3H, —OCH$_3$); 5.28 (d, J=4, 1H, H in the 6-position); 5.80 (dd, J=4 and 9, 1H, H in the 7-position); 6.76 (s, 1H, H of the thiazole); 7.10 (d, J=16, 1H, —CH=CHS—); 7.20 (s, 2H, —NH$_2$); 7.25 (d, J=16, 1H, =CHS—); 9.60 (d, J=9, 1H, —CONH—).

EXAMPLE 38

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4 g), 5-mercapto-3-methyl-1,2,4-thiadiazole (1.05 g), N,N-diisopropylethylamine (0.83 cc) and dimethylformamide (50 cc) is stirred at 60° C. under nitrogen for 2 hours. The mixture is cooled to about 20° C. and diluted with ethyl acetate (600 cc), and the organic phase is washed with distilled water (100 cc), 0.1 N hydrochloric acid (150 cc), a 5% strength sodium bicarbonate solution (2×150 cc) and a saturated sodium chloride solution (2×150 cc), dried over sodium sulphate, filtered and concentrated to dryness at 20° C. under reduced pressure (20 mm Hg). The brown residue is taken up in a 40:60 (by volume) mixture of cyclohexane and ethyl acetate (10 cc) and the solution is chromatographed on a column (column diameter: 4 cm) of Merck silica gel (0.04–0.06 mm) (150 g). Elution is carried out with a 40:60 (by volume) mixture of cyclohexane and ethyl acetate under a pressure of 40 kPa, 50 cc fractions being collected. Fractions 24 to 60 are evaporated to dryness at 20° C. under reduced pressure (20 mm Hg) and 2-benzhydryloxycarbonyl-7-[2-methoxyimino-2-(2-tritylamino-thiazol-4-yl)-acetamido]-3-[2-(3-methyl-1,2,4-thiadiazol-5-yl)-thiovinyl]-8-oxo-5-oxide-5-thia-1-aza-bicyclo[4.2.0]oct-2-ene (syn isomer, E-form) (1.8 g) is obtained.

Proton nuclear magnetic resonance spectrum (350 MHz, CDCl$_3$, δ in ppm, J in Hz): 2.63 (s, 3H, —CH$_3$);

Dimethylacetamide (1.1 cc) and phosphorus trichloride (0.519 cc) are added to a solution, cooled to −10° C., of 3-[2-(2-acetamidomethyl-1,3,4-thiadiazol-5-yl)thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) in methylene chloride (29 cc), and the mixture is then stirred for 1 hour at −10° C. Thereafter it is poured into ethyl acetate (250 cc) and this mixture is washed with a saturated sodium bicarbonate solution (250 cc) and with water (2×100 cc), dried over sodium sulphate, filtered and concentrated to dryness at 20° C. under reduced pressure (20 mm Hg). The residue is dissolved in methylene chloride (10 cc) and the solution is chromatographed on a column (column diameter: 4 cm) of Merck silica gel (0.04–0.06 mm). Elution is carried out with a 80:20 (by volume) mixture of ethyl acetate and cyclohexane (2.5 liters) under a pressure of 40 kPa, 100 cc fractions being collected. Fractions 11 to 21 are evaporated to dryness at 20° C. under reduced pressure (20 mm Hg) and 3-[2-(2-acetamido-1,3,4-thiadiazol-5-yl]-thiovinyl]-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is obtained in the form of a yellow froth.

Infra-red spectrum (KBr): characteristic bands (cm$^{-1}$) at 3400, 3280, 1785, 1720, 1670, 1530, 1495, 1450, 1370, 1040, 945, 755 and 700.

Proton nuclear magnetic resonance spectrum (350 MHz, CDCl$_3$, δ in ppm, J in Hz): 2.0 (s, 3H, —COCH$_3$); 3.58 and 3.68 (2d, J=18, 2H, —SCH$_2$—); 4.08 (s, 3H, —OCH$_3$); 4.75 (d, J=5, 2H, —C$\underline{H}_2$NHCO—); 5.10 (d, J=4, 1H, H in the 6-position); 5.97 (dd, J=4 and 9, 1H, H in the 7-position); 6.55 (t, J=5, 1H, —NHCO—); 6.76 (s, 1H, H of the thiazole); 7.0 (s, 1H, —COOCH<); 7.05 (s, 1H, —NH—C(C$_6$H$_5$)$_3$); 7.18 (d, J=16, 1H, —C$\underline{H}$=CHS—).

3-[2-(2-Acetamidomethyl-1,3,4-thiadiazol-5-yl)thiovinyl]-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is dissolved in formic acid (21 cc), water (12 cc) is added and the mixture is heated at 50° C. for 30 minutes. It is then cooled to about 20° C., filtered and concentrated to dryness at 50° C. under reduced pressure (0.05 mm Hg), the residue is taken up in ethanol (50 cc) and the solvent is driven off at 20° C. under reduced pressure (20 mm Hg); this operation is repeated twice, after which the residue is taken up in ethanol (50 cc) under reflux. The mixture is filtered hot to remove a small amount of insoluble matter, and the filtrate is concentrated to 20 cc under reduced pressure (20 mm Hg) at 20° C. and filtered. After drying, 3-[2-(2-acetamidomethyl-1,3,4-thiadiazol-5-yl)-thiovinyl]-7-[2-(2-aminothiazol-4-yl)-2-methoxyimino-acetamido]-2-carboxy-8-oxo-5-thia-1-aza-bicyclo[4.2.0]oct-2-ene (syn isomer, E-form) (0.75 g) is obtained in the form of a cream-coloured powder.

Infra-red spectrum (KBr): characteristic bands (cm$^{-1}$) at 3320, 1770, 1660, 1540, 1380 and 1040.

Proton nuclear magnetic resonance spectrum (350 MHz, DMSO d$_6$, δ in ppm, J in Hz): 1.90 (s, 3H, —COCH$_3$); 3.68 and 3.92 (2d, J=18, 2H, —S—CH$_2$—); 3.87 (s, 3H, —OCH$_3$); 4.22 (d, J=4, 1H, H in the 6-position); 4.60 (AB limit, 2H, —CH$_2$NHCO—); 5.82 (dd, J=4 and 9, 1H, H in the 7-position); 6.75 (s, 1H, —OCH$_3$); 7.15 (d, J=16, 1H, —CH=CHS—); 7.20 (s, 3H, —NH$_3{}^+$); 7.25 (d, J=16, 1H, =CHS—); 9.63 (d, J=9, 1H, —CONH—).

2-Acetamidomethyl-5-mercapto-1,3,4-thiadiazole can be prepared by application of the method described in Japanese Patent Application 51/80,857 (Derwent 65961 X).

EXAMPLE 36

Following the procedure described in Example 35, 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4 g) is treated with 2-tert.butoxycarbonylamino-5-mercapto-1,3,4-thiadiazole (1.86 g) in dimethylformamide (50 cc) in the presence of N,N-diisopropylethylamine (0.83 cc). After chromatography over silica gel [eluant: a 40:60 (by volume) mixture of cyclohexane and ethyl acetate], 2-benzhydryloxycarbonyl-3-[2-(2-tert.-butoxycarbonylamino-1,3,4-thiadiazol-5-yl)-thiovinyl]-7-[2-methoxyimino-2-(2-tritylaminothiazol-4-yl)-acetamido]-8-oxo-5-oxide-5-thia-1-azabicyclo[4.2.0]oct-2-ene (syn isomer, E-form) (2.6 g) is obtained in the form of a cream-coloured froth.

Infra-red spectrum (CHBr$_3$): characteristic bands (cm$^{-1}$) at 3380, 2820, 1800, 1720, 1530, 1490, 1445, 1390, 1370, 1050, 940, 760 and 605.

Proton nuclear magnetic resonance spectrum (350 MHz, CDCl$_3$, δ in ppm, J in Hz): 1.43 (s, 9H, —C(CH$_3$)$_3$); 3.24 and 4.46 (2d, J=19, 2H, —SCH$_2$—); 4.04 (s, 3H, —OCH$_3$); 4.64 (d, J=4, 1H, H in the 6-position); 6.14 (dd, J=4 and 9, 1H, H in the 7-position); 6.70 (s, 1H, H of the thiazole); 6.94 (s, 1H, —COOCH—); 7.11 (d, J=16, 1H, —C$\underline{H}$=CHS—); 7.34 (d, J=9, 1H, —CONH—); 7.37 (d, J=16, 1H, =CHS—).

Using the conditions described in Example 35, 2-benzhydryloxycarbonyl-3-[2-(2-tert.-butoxycarbonylamino-1,3,4-thiadiazol-5-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.55 g) is treated with phosphorus trichloride (0.46 cc) in the presence of dimethylacetamide (0.95 cc) in methylene chloride (50 cc). After chromatography over silica gel [using a 30:70 (by volume) mixture of cyclohexane and ethyl acetate as the eluant], 2-benzhydryloxycarbonyl-3-[2-(2-tert.-butoxycarbonylamino-1,3,4-thiadiazol-5-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is obtained in the form of a cream-coloured froth.

Infra-red spectrum (CHBr$_3$): characteristic bands (cm$^{-1}$) at 3400, 1785, 1725, 1685, 1530, 1495, 1450, 1250, 1210, 1050, 940, 755 and 740.

Proton nuclear magnetic resonance spectrum (350 MHz, CDCl$_3$, δ in ppm, J in Hz): 1.53 (s, 9H, —C(CH$_3$)$_3$); 3.52 and 3.62 (2d, J=18, 2H, —SCH$_2$—); 4.06 (s, 3H, —OCH$_3$); 5.06 (d, J=4, 1H, H in the 6-position); 5.92 (dd, J=4 and 9, 1H, H in the 7-position); 6.72 (s, 1H, H of the thiazole); 7.03 (d, J=16, 1H, —CH=C-HS—); 7.07 (d, J=9, 1H, —CONH—).

Using the conditions described in Example 35, 2-benzhydryloxycarbonyl-3-[2-(2-tert.-butoxycarbonylamino-1,3,4-thiadiazol-5-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2 g) is treated with a mixture of formic acid (40 cc) and water (15 cc). 3-[2-(2-Amino-1,3,4-thiadiazol-5-yl)-thiovinyl]-7-[2-(2-amino-thiazol-4- pressure (30 mm Hg; 4 kPa) at 40° C. This gives some of the unchanged tosylate starting material (2.1 g). Fractions 17 to 42 are combined and concentrated to dryness under reduced pressure (30 mm Hg; 4 kPa) at 40° C. This gives 2-benzhydryloxycarbonyl-3-{2-[3-methoxycarbonyl-1-methyl-1,2,4-triazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form), (3 g) in the form of a yellow froth.

Infra-red spectrum (CHBr$_3$, characteristic bands in cm$^{-1}$) at 3380, 1800, 1730, 1670, 1515, 1495, 1450, 1210, 1040, 950, 755 and 740.

Proton nuclear magnetic resonance spectrum (350 MHz, CDCl$_3$, δ in ppm, J in Hz): 3.30 and 4 (2d, J=18, 2H, —S(O)CH$_2$—); 3.84 (s, 3H, >NCH$_3$ of the triazole); 3.97 (s, 3H, —CO$_2$CH$_3$); 4.07 (s, 3H, =NOCH$_3$); 4.63 (d, J=9, 1H, H in the 6-position); 6.13 (dd, J=4 and 9, 1H, H in the 7-position); 6.72 (s, 1H, —CH(C$_6$H$_5$)$_2$); 7.0 and 7.50 (2d, J=16, 2H, =CH=CH—S—); 7.09 (s, 1H, (C$_6$H$_5$)$_3$CNH—); 7.15 to 7.45 (Mt, 26 H, aromatics and —CONH—C$_7$).

A solution of 2-benzhydryloxycarbonyl-3-{2-[3-methoxycarbonyl-1-methyl-1,2,4-triazol-4-yl]-thiovinyl}-7-[2-methoxyimino-2-(2-tritylamino-thiazol-4-yl)-acetamide]-8-oxo-5-oxide-5-thia-1-aza-bicyclo[4.2.0]oct-2-ene (syn isomer, E-form) (3 g) in a mixture of dry methylene chloride (30 cc) and N,N-dimethylacetamide (1.2 cc) is cooled to —25° C. and treated with phosphorus trichloride (0.57 cc). After having been stirred for 30 minutes at a temperature of between —25° and —10° C., the reaction mixture is diluted with ethyl acetate (150 cc) and washed with a saturated sodium bicarbonate solution (100 cc) and then with a saturated sodium chloride solution (100 cc). The organic phase is dried over magnesium sulphate, filtered and concentrated to dryness under reduced pressure (30 mm Hg; 4 kPa) at 40° C. The residue is filtered over a column (height=25 cm, diameter=4 cm) of silica gel (0.02–0.04 mm), elution being carried out under a pressure of 40 kPa with a 50:50 (by volume) mixture of cyclohexane and ethyl acetate (2.5 liters), and 100 cc fractions being collected. Fractions 9 to 24 are combined and concentrated under reduced pressure (30 mm Hg; 4 kPa) at 40° C. 2-Benzhydryloxycarbonyl-3-{2-[3-methoxycarbonyl-1-methyl-1,2,4-triazol-5-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (2.35 g) is obtained in the form of a yellow froth.

Infra-red spectrum (CHBr$_3$, characteristic bands in cm$^{-1}$) at 3490, 1785, 1735, 1685, 1515, 1495, 1450, 1210, 1040, 755 and 740.

Proton nuclear magnetic resonance spectrum (350 MHz, CDCl$_3$, δ in ppm, J in Hz): 3.62 and 3.72 (2d, J=18, 2H, —SCH$_2$—); 3.87 (s, 3H, —COOCH$_3$); 4.0 (s, 3H, >NCH$_3$ of the triazole); 4.08 (s, 3H, =NOCH$_3$); 5.12 (d, J=9, 1H, H in the 6-position); 5.98 (dd, J=4 and 9, 1H, H in the 7-position); 6.78 (s, 1H, H of the thiazole); 6.96 (s, 1H, —CH(C$_6$H$_5$)$_2$); 6.94 and 7.03 (2d, J=14, 2H, —CH=CH—S—); 7.15 to 7.50 (Mt, 27 H, aromatic+—CONH—C$_7$+(C$_6$H$_5$)$_3$CNH—).

A solution of 2-benzhydryloxycarbonyl-3-{2-[3-methoxycarbonyl-1-methyl-1,2,4-triazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.3 g) in formic acid (40 cc) is diluted with distilled water (25 cc) and heated for 20 minutes at 50° C., and then diluted again with distilled water (15 cc). After filtering off the insoluble matter, the reaction mixture is concentrated under reduced pressure (5 mm Hg; 0.67 kPa) at 40° C. The residue is triturated with ethanol (50 cc), which is subsequently evaporated under reduced pressure (30 mm Hg; 4 kPa) at 40° C.; this operation is repeated twice, and the residue is then taken up in ethanol (50 cc). The solid is filtered off and washed with ethanol (10 cc) and with isopropyl ether (2×25 cc). After drying, 7-[2-(2-amino-thiazol-4-yl)-2-methoxyimino-acetamido]-2-carboxy-3-{2-[3-methoxycarbonyl-1-methyl-1,2,4-triazol-5-yl]thiovinyl}-8-oxo-5-thia-1-aza-bicyclo[4.2.0]oct-2-ene (syn isomer, E-form) (1.1 g) is obtained in the form of a cream-coloured powder.

Infra-red spectrum (KBr, characteristic bands in cm$^{-1}$) at 3450, 3320, 2200, 1770, 1735, 1660, 1630, 1535, 1385, 1220, 1040 and 945.

Proton nuclear magnetic resonance spectrum (350 MHz, DMSO d$_6$, δ in ppm, J in Hz): 3.66 and 3.90 (2d, J=18, 2H, —SCH$_2$—); 3.85 (s, 3H, =NOCH$_3$); 3.87 (s, 3H, —CO$_2$CH$_3$); 3.90 (s, 3H, >NCH$_3$ of the triazole); 5.20 (d, J=9, 1H, H in the 6-position); 5.79 (dd, J=4 and 9, 1H, H in the 7-position); 6.74 (s, 1H, H of the thiazole); 6.98 and 7.03 (AB, J=14, 2H, —CH=CH—S—); 7.20 (s broad, 2H, —NH$_2$); 9.63 (d, J=9, 1H, —CONH—C$_7$).

EXAMPLE 35

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2ene (syn isomer, E-form) (6.02 g), dimethylformamide (60 cc), 2-acetamidomethyl-5-mercapto-1,3,4-thiadiazole (2.27 g) and diisopropylethylamine (1.15 cc) is stirred for 2 hours 30 minutes at 60° C. under nitrogen. The cooled mixture is diluted with ethyl acetate (250 cc), and this mixture is washed with water (150 cc), 0.1 N hydrochloric acid (100 cc), a saturated sodium bicarbonate solution (100 cc) and water (2×100 cc), dried over sodium sulphate, filtered and concentrated to dryness at 20° C. under reduced pressure (20 mm Hg). The residue, fixed on Merck silica gel (0.05–0.2 mm) (20 g), is deposited on a column (column diameter: 2.5 cm) of silica gel (0.05–0.2 mm) (70 g). Elution is carried out with ethyl acetate (2.5 liters), 100 cc fractions being collected. Fractions 9 to 23 are evaporated to dryness at 20° C. under reduced pressure (20 mm Hg) and 3-[2-(2-acetamidomethyl-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) is obtained in the form of a brown froth.

Infra-red spectrum (KBr): characteristic bands (cm$^{-1}$) at 3400, 1795, 1720, 1670, 1525, 1495, 1450, 1370, 1040, 940, 750 and 700.

Proton nuclear magnetic resonance spectrum (350 MHz, CDCl$_3$, δ in ppm, J in Hz): 1.97 (s, 3H, —COCH$_3$); 3.30 and 4.15 (2d, J=18, 2H, —SCH$_2$—); 4.08 (s, 3H, —OCH$_3$); 4.64 (d, J=4, 1H, H in the 6-position); 4.72 (AB, 2H, —CH$_2$NHCO—); 6.14 (dd, J=4 and 9, 1H, H in the 7-position); 6.72 (s, 1H, H of the thiazole);

6.97 (s, 1H, —COOCH—).

kPa, 125 cc fractions being collected. Fractions 17 to 25 are concentrated to dryness at 20° C. under 20 mm Hg (2.7 kPa). 2-Benzhydryloxycarbonyl-3[2-(5,6-dioxo-2-methyl-1,2,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (0.50 g) is obtained in the form of a cream-coloured froth.

Infra-red spectrum (CHBr₃): characteristic bands (cm⁻¹) at 1800, 1725, 1685, 1595, 1515, 1495, 1450, 1040, 750 and 700.

Proton nuclear magnetic resonance spectrum (350 MHz, CDCl₃, δ in ppm, J in Hz): 3.24 and 3.88 (2d, J=18, 2H, —SCH₂—); 3.80 (s, 3H, —CH₃); 4.09 (s, 3H, —OCH₃); 4.60 (d, J=4, 1H, H in the 6-position); 6.15 (dd, J=4 and 9, 1H, H in the 7-position); 6.74 (s, 1H, H of the thiazole); 6.95 (s, 1H, —COOCH>); 7.73 (d, J=9, 1H, —CONH—).

A solution of 2-benzhydryloxycarbonyl-3-[2-(5,6-dioxo-2-methyl-1,2,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (0.5 g) in methylene chloride (30 cc) and dimethylacetamide (0.192 cc) is treated with phosphorus trichloride (0.176 cc) at −9° C. for 1 hour 40 minutes. The mixture is diluted with ethyl acetate (250 cc), and this mixture is washed with water (2×100 cc), a saturated sodium bicarbonate solution (100 cc) and water (100 cc), dried over sodium sulphate, filtered and concentrated to dryness at 20° C. under 20 mm Hg (2.7 kPa). The product is purified by chromatography on a column (column diameter: 2.5 cm, height: 15 cm) of Merck silica gel (0.06-0.2 mm) (50 g). Elution is carried out with ethyl acetate (50 cc), 30 cc fractions being collected, fractions 6 to 10 are concentrated to dryness at 20° C. under 20 mm Hg (2.7 kPa) and 2-benzhydryloxycarbonyl-3-[2-(5,6-dioxo-2-methyl-1,2,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.4 g) is obtained in the form of a orange-yellow froth.

Infra-red spectrum (CHBr₃): characteristic bands (cm⁻¹) at 3400, 1780, 1725, 1680, 1595, 1520, 1495, 1450, 1040 and 755.

Proton nuclear magnetic resonance spectrum (350 MHz, CDCl₃, δ in ppm, J in Hz): 3.52 and 3.61 (2d, J=18, 2H, —SCH₂—); 3.84 (s, 3H, —CH₃); 4.08 (s, 3H, —OCH₃); 5.12 (d, J=4, 1H, H in the 6-position); 5.84 (dd, J=4 and 9, 1H, H in the 7-position); 6.78 (s, 1H, H of the thiazole); 6.81 (d, J=9, 1H, —CONH—); 6.98 (s, 1H, —COOCH<); 7.18 (d, J=16, 1H, —C$\underline{H}$=CHS—); 7.20 (s, 1H, —NHC(C₆H₅)₃).

A mixture of 2-benzhydryloxycarbonyl-3-[2-(-5,6-dioxo-2-methyl-1,2,5,6-tetrahydro-1,2,4-triazin-3-yl)-thiovinyl]-7-[2-methoxyimino-2-(2-tritylamino-thiazol-4-yl)-acetamido]-8-oxo-5thia-1-aza-bicyclo[4.2.0]oct-2-ene (syn isomer, E-form) (0.18 g), formic acid (15 cc) and water (15 cc) is treated at 50° C. for 30 minutes. The mixture is filtered and concentrated to dryness at 30° C. under 0.05 mm Hg (0.007 kPa), the residue is taken up in ethanol (4×25 cc), the mixture being evaporated to dryness each time (at 20° C. under 20 mm Hg; 2.7 kPa), and the residue is triturated in ethanol (10 cc) at 60° C., allowed to cool and filtered off. After drying, 7-[2-(2-amino-thiazol-4-yl)-2-methoxyimino-acetamido]-2-carboxy-3-[2-(5,6-dioxo-2-methyl-1,2,5,6-tetrahydro-1,2,4-triazin-3-yl)-thiovinyl]-8-oxo-5-thia-1-aza-bicyclo-[4.2.0]oct-2-ene (syn isomer, E-form) (0.062 g) is obtained in the form of a yellow powder.

Infra-red spectrum (KBr): characteristic bands (cm⁻¹) at 3600, 2300, 1765, 1720, 1670, 1600, 1525, 1280, 1075, 1040 and 930.

Proton nuclear magnetic resonance spectrum (350 MHz, CF₃COOD, δ in ppm, J in Hz): 3.77 and 3.88 (2d, J=18, 2H, —SCH₂—); 4.0 (s, 3H, —CH₃); 4.30 (s, 3H, —OCH₃); 5.41 (d, J=4, 1H, H in the 6-position); 6.0 (d, J=4, 1H, H in the 7-position); 7.50 (s, 1H, H of the thiazole).

5,6-Dioxo-2-methyl-3-thioxo-perhydro-1,2,4-triazine can be prepared in the following manner:

A solution of sodium (4.6 g) in methanol (200 cc) is prepared under nitrogen and 2-methyl-thiosemicarbazide (21.03 g) is added to this solution at 40° C., followed by diethyl oxalate (27.1 cc) added dropwise in the course of 10 minutes. The mixture is then heated under reflux, with stirring, for 5 hours, and is cooled at 5° C. for 1 hour. It is filtered and the white crystals obtained are washed with methanol (25 cc) and ether (3×25 cc). The sodium salt thus obtained is stirred in the presence of 2 N hydrochloric acid (50 cc) for 15 minutes at 20° C. and then for 1 hour at 5° C. The mixture is filtered and a white solid (10.7 g) consisting of the expected product, of the thiosemicarbazide starting material and of 5-mercapto-3-methoxycarbonyl-1-methyl-1,2,4-triazole is obtained. After dissolving the product in methylene chloride (200 cc) under reflux, cooling the solution and filtering, a mixture (9.63 g) of the expected product and 2-methyl-thiosemicarbazide is obtained. The final purification of the product is carried out by converting it to the sodium salt (by adding to the product, in methanol (200 cc) 4 N sodium 2-ethylhexanoate solution (10 cc) and filtering), and then acidifying (in water (10 cc), with 2 N hydrochloric acid (20 cc)). 5,6-Dioxo-2-methyl-3-thioxo-perhydro-1,2,4-triazine (5.5 g) is obtained in the form of a white powder melting at 185° C.

2-Methyl-thiosemicarbazide is prepared according to K. A. JENSEN, Acta Chem. Scand. 22, 1–50 (1968).

EXAMPLE 34

A solution of N,N-diisopropylethylamine (1.21 cc) and of an equimolecular mixture (2.2 g) of 3-methoxycarbonyl-1-methyl-5-thioxo-1,2,4-triazoline and of 5,6-dioxo-2-methyl-3-thioxo-perhydro-1,2,4-triazine [prepared according to M. PESSON and M. ANTOINE, C.R. Acad. Sci., Ser. C, 267, 25, 1726 (1968)] in dry N,N-dimethylformamide (35 cc) is added dropwise, in the course of 40 minutes, under nitrogen, to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (6.92 g) at 65° C. The reaction mixture is stirred for 5 hours 30 minutes at 65° C. and is then diluted with ethyl acetate (200 cc) and washed with distilled water (2×100 cc.). After having been dried over magnesium sulphate and filtered, the organic phase is concentrated to dryness under reduced pressure (30 mm Hg; 4 kPa) at 40° C. The residue is chromatographed on a column (height=35 cm, diameter=4 cm) of silica gel (0.02-0.04 mm), elution being carried out, under a pressure of 40 kPa, with a 30:70 (by volume) mixture of cyclohexane and ethyl acetate (4.5 liters), and 100 cc fractions being collected. Fractions 2, 3 and 4 are combined and concentrated under reduced =NOCH$_3$); 5.18 (d, J=4, 1H, H in the 6-position); 5.82 (dd, J=4 and 9, 1H, H in the 7-position); 6.74 (s, 1H, H of the thiazole); 6.95 and 7.14 (2d, J=16, 2H, —CH=CH—S—); 7.18 (s broad, 2H, —NH$_2$); 9.64 (d, J=9, 1H, —CONH—). anti isomer:

3.35 and 3.48 (2s, 2×3H, 2—CH$_3$ of the triazine); 3.66 and 3.90 (2d, J=18, 2H, —SCH$_2$—); 3.98 (s, 3H, =NOCH$_3$); 5.19 (d, J=4, 1H, H in the 6-position); 5.81 (dd, J=4 and 9, 1H, H in the 7-position); 6.95 and 7.15 (2d, J=16, 2H, —CH=CH—S—); 7.09 (s broad, 2H, —NH$_2$); 9.48 (d, J=9, 1H, —CONH—).

1,4-Dimethyl-5,6-dioxo-3-thioxo-perhydro-1,2,4-triazine can be prepared according to the method described in Belgian Pat. No. 830,455.

EXAMPLE 32

A mixture of 2-benzhydryloxycarbonyl-7-[2-methoxyimino-2-(2-tritylamino-thiazol-4-yl)-acetamideo]-8-oxo-3-(2tosyloxyvinyl)-5-thia-1-aza-bicyclo[4.2.0]-oct-2-ene (syn isomer, E-form) (1 g), dimethylformamide (10 cc), 5,6-dioxo-1-ethyl-3-thioxo-perhydro-1,2,4-triazine (0.345 g) and N,N-diisopropylethylamine (0.35 cc) is stirred at 23° C. under nitrogen for 1 hour 20 minutes. It is then poured into a 2% strength sodium bicarbonate solution (100 cc), this mixture is extracted with ethyl acetate (2×30 cc), and the organic phase is washed with 0.05 N hydrochloric acid (50 cc) and a half-saturated sodium chloride solution (50 cc), dried over sodium sulphate, filtered and concentrated to dryness at 20° C. under 20 mm Hg (2.7 kPa). The residue is chromatographed over a column (column diameter: 1.5 cm, height: 30 cm) of Merck silica gel (0.04–0.06 mm). Elution is carried out with ethyl acetate (0.5 liter) under a pressure of 40 kPa, 25 cc fractions being collected. Fractions 4 to 15 are evaporated to dryness at 20° C. under 20 mm Hg (2.7 kPa) and 2-benzhydryloxycarbonyl-3-[2-(5,6-dioxo-1-ethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.75 g) is obtained in the form of a yellow froth.

Infra-red spectrum (CHBr$_3$): characteristic bands (cm$^{-1}$) at 3410, 1795, 1720, 1625, 1605, 1560, 1505, 1455, 1245, 1205, 1045, 940, 760 and 745.

Proton nuclear magnetic resonance spectrum (350 MHz, DMSO d$_6$, δ in ppm, J in Hz): 1.25 (t, J=7, —CH$_2$CH$_3$); 3.68 and 3.88 (2d, J=18, 2H, —SCH$_2$—): 3.80–3.90 (hump, 5H, —CH$_2$CH$_3$ and —OCH$_3$); 5.22 (d, J=4, 1H, H in the 6-position); 5.74 (dd, J=4 and 9, 1H, H in the 7-position); 6.75 (s, 1H, H of the thiazole); 6.94 (s, 1H, —COOCH—); 6.95 (d, J=16, 1H, —CH=CHS—); 8.80 (s, 1H, —NHC(C$_6$H$_5$)$_3$); 9.60 (d, J=9, 1H, —CONH—).

A mixture of 2-benzhydryloxycarbonyl-3-[2-(-5,6-dioxo-1-ethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (0.72 g), formic acid (12 cc) and water (6 cc) is treated at 50° C. for 45 minutes. The cooled mixture is filtered and concentrated to dryness at 35° C. under 0.05 mm Hg (0.007 kPa), and the residue is taken up in ethanol (2×20 cc), the mixture being evaporated to dryness each time at 20° C. under 20 mm Hg (2.7 kPa). The solid residue is triturated in ethanol (10 cc) at 60° C. for 10 minutes, the cooled suspension is filtered, and the filter residue is washed with diethyl ether (2×5 cc) and dried. 7-[2-(2-Amino-thiazol-4-yl)-2-methoxyimino-acetamido]-2-carboxy-3-[2-(5,6-dioxo-1-ethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.39 g) is obtained in the form of a yellow powder.

Infra-red spectrum (KBr): characteristic bands (cm$^{-1}$) at 3700, 2200, 1770, 1720, 1665, 1630, 1590, 1040 and 945.

Proton nuclear magnetic resonance spectrum (350 MHz, DMSO d$_6$, δ in ppm, J in Hz): 1.25 (t, J=7, 3H, —CH$_2$CH$_3$); 3.71 and 3.88 (2d, J=18, 2H, —SCH$_2$—); 3.80 to 3.90 (hump, 5H, —CH$_2$CH$_3$ and —OCH$_3$); 5.19 (d, J=4, 1H, H in the 6-position); 5.75 (dd, J=4 and 9, 1H, H in the 7-position); 6.77 (s, 1H, H of the thiazole); 7.10 (s, broad, 2H, —CH=CH—); 7.20 (s, 2H, —NH$_2$); 9.62 (d, J=9, 1H, —CONH—).

1-Ethyl-5,6-dioxo-3-thioxo-perhydro-1,2,4-triazine can be prepared in the following manner:

A solution of sodium (1.15 g) in methanol (25 cc) is prepared, 1-ethyl-1-ethoxalyl-thiosemicarbazide (11 g) is added and the reaction mixture is heated under reflux for 1 hour. It is then concentrated to dryness at 20° C. under 20 mm Hg (2.7 kPa), and the residue is triturated in diethyl ether (50 cc) and filtered off. The yellow solid obtained is dissolved in water (15 cc), the solution is acidified to pH 2 by adding 2 N hydrochloric acid, crystallisation is started by scratching, and the mixture is left for 1 hour at 4° C. and filtered. 1-Ethyl-5,6-dioxo-3-thioxo-perhydro-1,2,4-triazine (5 g) is obtained in the form of a pale yellow sold melting at 214°–216° C.

1-Ethyl-1-ethoxalyl-thiosemicarbazide can be prepared in the following manner:

Ethoxalyl chloride (10.6 cc) is added dropwise, in the course of 10 minutes, to a solution, at 20° C., of 1-ethyl-thiosemicarbazide (11.9 g) in acetone (200 cc). The temperature rises to 43° C., the mixture is stirred for 1 hour without heating and is concentrated to dryness at 20° C. under 20 mm Hg (2.7 kPa), the residue is taken up in methanol (30 cc) and the crystallisation is started. After filtration and drying, 1-ethyl-1-ethoxalyl-thiosemicarbazide (13.2 g) is obtained in the form of a white solid melting at 170° C.

1-Ethyl-thiosemicarbazide is prepared by reduction of acetaldehyde thiosemicarbazone (52 g) in ethanol (2 liters) by means of sodium borohydride (26 g). The product obtained melts at 143° C.

Acetaldehyde thiosemicarbazone (52.2 g) is obtained by condensing thiosemicarbazide (45.5 g) and acetaldehyde (42.4 cc) in ethanol (1 liter). The product crystallises on partially concentrating the reaction mixture, and melts at 153° C.

EXAMPLE 33

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (7.03 g), dimethylformamide (70 cc), 5,6-dioxo-2-methyl-3-thioxo-perhydro-1,2,4-triazine (1.23 g) and N,N-diisopropylethylamine (1.34 cc) is heated at 60° C. under nitrogen, whilst stirring, for 20 hours. It is then poured into ethyl acetate (300 cc) and this mixture is washed with water (4×150 cc), dried over sodium sulphate, filtered and concentrated to dryness at 20° C. under 20 mm Hg (2.7 kPa). The product is purified by chromatography over a column (column diameter: 6 cm, height: 30 cm) of Merck silica gel (0.04–0.06 mm) (200 g). Elution is carried out with a 20:80 (by volume) mixture of cyclohexane and ethyl acetate (3.5 liters) under a pressure of 40

4-yl)-acetamido]-8-oxo-5-thia-1-aza-bicyclo[4.2.0]oct-2-ene (syn isomer, E-form)(3.3 g) in formic acid (100 cc) is stirred at 50° C. for 40 minutes. It is then concentrated to dryness at 30° C. under 0.05 mm Hg (0.007 kPa), the residue is taken up in acetone (60 cc), the mixture is again concentrated to dryness, at 20° C. under 20 mm Hg (2.7 kPa), and this operation is repeated twice. The solid which remains is treated with acetone (15 cc) at 40° C. and the mixture is allowed to cool and is filtered. After filtration and drying, 7-[2-(2-amino-thiazol--4-yl)-2-methoxyimino-acetamido]-2-carboxy-3-{2-[1-(2,2dimethoxyethyl)-2-methoxycarbonyl-1,3,4-triazol-5-yl]-thiovinyl}-8-oxo-5-thia-1-aza-bicyclo[4.2.0]oct-2-ene (syn isomer, E-form) (0.65 g) is obtained in the form of a cream-coloured powder.

Infra-red spectrum (KBr): characteristic bands (cm$^{-1}$) at 3200, 1775, 1735, 1680, 1620, 1535, 1385, 1050 and 945.

Proton nuclear magentic resonance spectrum (350 MHz, CF$_3$COOD, δ in ppm, J in Hz): 3.65 (s, 6H, >CH(OC$\underline{H}_3$)$_2$); 4.21 (s, 3H, —COOC$\underline{H}_3$); 4.29 (s, 3H, =NOC$\underline{H}_3$); 5.38 (d, J=4, 1H, H in the 6-position); 6.08 (d, J=4, 1H, H in the 7-position); 7.07 and 7.95 (2d, J=16, 2H, —C$\underline{H}$=C$\underline{H}$S—); 7.48 (s, 1H, H of the thiazole).

1-(2,2-Dimethoxyethyl)-5-mercapto-2-methoxy-carbonyl-1,3,4-triazole is obtained as a by-product of the preparation of 4-(2,2-dimethoxyethyl)-5,6-dioxo-3-thioxo-perhydro-1,2,4-triazine, described previously, in Example 16, that is to say in the course of the condensation of ethyl oxalate (81.6 g) with 4-(2,2-dimethoxyethyl)-thiosemicarbazide (100 g) in the presence of sodium methylate (44 g) in methanol (440 cc). At the end of the reaction, the mixture is filtered and the sodium salt of the triazine (46.8 g) is collected. The filtrate is concentrated to dryness at 20° C. under 20 mm Hg (2.7 kPa), the residue is taken up in ethyl acetate (300 cc) and the mixture is acidified by stirring with 1 N hydrochloric acid (200 cc). The organic phase is decanted, washed with saturated aqueous sodium chloride (3×100 cc), dried over sodium sulphate, filtered and concentrated to dryness at 20° C. under 20 mm Hg (2.7 kPa). The residue is chromatographed on Merck silica gel (0.06–0.2 mm) (200 g) (column diameter: 4.5 cm, height: 25 cm). Elution is carried out with a 30:70 (by volume) mixture of cyclohexane and ethyl acetate (1 liter), 100 cc fractions being collected. Fractions 2 to 9 are concentrated to dryness at 20° C. under 20 mm Hg (2.7 kPa) and a crystalline white solid (14.3 g) melting at 123° C. is obtained.

Infra-red spectrum (CHBr$_3$): characteristic bands (cm$^{-1}$) at 3420, 3200, 2840, 2600, 1745, 1450, 1085, 1065 and 980.

EXAMPLE 31

1,4-Dimethyl-5,6-dioxo-3-thioxo-perhydro-1,2,4-triazine (0.75 g) is added to a solution of 2-benzhydryloxycarbonyl-7-[2-methoxy-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (2.37 g) in dry N,N-dimethylformamide (75 cc) heated to 60° C., and a solution of N,N-diisopropylethylamine (0.42 cc) in dry N,N-dimethylformamide (25 cc) is then introduced dropwise in the course of 15 minutes. The reaction mixture is stirred for 25 minutes at 60° C. and then diluted with ethyl acetate (400 cc) and washed with distilled water (3×200 cc), with a saturated sodium bicarboanate solution (100 cc) and with a saturated sodium chloride solution (200 cc). After drying over magnesium sulphate, the organic phase is concentrated to dryness under reduced pressure (30 mm Hg; 4 kPa) at 40° C. An orange-coloured froth (2 g) is obtained, which is purified by chromatography on a column (column diameter: 4 cm, height: 30 cm) of Merck silica gel (0.04–0.06 mm), elution being carried out with a 30:70 (by volume) mixture of cyclohexane and ethyl acetate (2 liters), and 50 cc fractions being collected. Fractions 15 to 40 are combined and concentrated under reduced pressure (30 mm Hg; 4 kPa) at 40° C. 2-Benzhydryloxycarbonyl-3-[2-(1,4-dimethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo-[4.2.0]-oct-2-ene (a 50:50 mixture of the syn and anti isomers of the E-form) (0.85 g) is obtained.

Infra-red spectrum (KBr): characteristic bands (cm$^{-1}$) at 3400, 1790, 1720, 1680, 1585, 1520, 1506, 1450, 1035, 1025, 945 and 760.

Proton nuclear magnetic resonance spectrum (350 MHz, CDCl$_3$, δ in ppm, J in Hz):

syn isomer:

3.43 and 3.58 (2s, 2×3H, 2CH$_3$ of the triazine); 3.61 and 3.70 (2d, J=18, 2H, —SCH$_2$—); 4.08 (s, 3H, =NOCH$_3$); 5.12 (d, J=4, 1H, H in the 6-position); 5.95 (dd, J=4 and 9, 1H, H in the 7-position); 6.77 (s, 1H, H of the thiazole); 6.81 (d, J=16, 1H, —C$\underline{H}$=CH—S—); 6.98 (s, 1H, —CO$_2$C$\underline{H}$(C$_6$H$_5$)$_2$); 7.0 (s broad, 1H, >N$\underline{H}$ of the trityl); 7.2 to 7.50 (hump, 27H, aromatics, —CON$\underline{H}$—C$_7$, —CH=CH—S—).

anti isomer:

3.43 and 3.50 (2s, 2×3H, 2CH$_3$ of the triazine); 3.50 and 3.58 (2d, J=18, 2H, —SCH$_2$—); 4.12 (s, 3H, =NOCH$_3$); 5.13 (d, J=4, 1H, H in the 6-position); 6.08 (dd, J=4 and 9, 1H, H in the 7-position); 6.75 (d, J=16, 1H, —C$\underline{H}$=CH—S—); 6.98 (s, 1H, —CO$_2$C$\underline{H}$(C$_6$H$_5$)$_2$); 7.18 (s, broad, 1H, —N$\underline{H}$—of the trityl); 7.2 to 7.50 (hump, 26H, aromatics, —CH=CH—S—); 7.42 (s, 1H, H of the thiazole); 9.60 (d, J=9, —CONH—C$_7$).

Distilled water (10 cc) is added to a solution of 2-benz hydryloxycarbonyl-3-[2-(1,4-dimethyl-5,6-dioxo-1,4,5,6-tetrahydro-1,2,4-triazin-3yl)-thiovinyl]-7-[2-methoxyimino-2-(2-tritylamino-thiazol-4-yl)-acetamido]-8-oxo-5-thia-1-aza-bicyclo[4.2.0]oct-2-ene (a 50:50 mixture of the syn and anti isomers of the E-form) (0.8 g) in 98% strength formic acid (20 cc), and the reaction mixture is then heated at 60° C. for 25 minutes. After concentration under reduced pressure (10 mm Hg; 1.44 kPa) at 40° C., the residue is triturated with absolute ethanol (25 cc) and the mixture is concentrated to dryness under reduced pressure (30 mm Hg; 4 kPa) at 40° C. This operation is repeated twice more and the solid residue is then taken up in boiling ethanol (20 cc). The solid is filtered off hot and dried under reduced pressure (10 mm Hg; 1.33 kPa) at 25° C. 7-[2-(2-Amino-thiazol-4-yl)-2-methoxyimino-acetamido]-2-carboxy-3-[2-(1,4-dimethyl-5,6-dioxo-1,4,5,6-tetrahydro-1,2,4-triazin-3-yl)-thiovinyl]-8-oxo-5-thia-1-aza-bicyclo-[4.2.0]oct-2-ene (a 50:50 mixture of the syn and anti isomers of the E-form) (0.345 g) is obtained.

Infra-red spectrum (KBr): characteristic bands (cm$^{-1}$) at 3500, 2300, 1770, 1710, 1670, 1575, 1530, 1030 and 940.

Proton nuclear magnetic resonance spectrum (350 MHz, DMSO d$_6$, δ in ppm, J in Hz):

syn isomer:

3.35 and 3.48 (2s, 2×3H, 2—CH$_3$ of the triazine); 3.66 and 3.90 (2d, J=18, 2H, —SCH$_2$—); 3.87 (s, 3H, J=18, 2H, —SCH₂—); 4.0 (s, 3H, —OCH₃); 5.15 (d, J=4, 1H, H in the 6-position); 5.82 (dd, J=4 and 9, 1H, H in the 7-position); 6.78(s, 1H, H of the thiazole); 6.86 (d, J=16, 1H, —C$\underline{H}$=CHS—); 7.31 (d, J=16, 1H, =CHS—); 7.73 (s, 3H, —NH₃⁺); 9.50 (d, J=9, 1H, —CONH—);

12.54 (s broad, 1H, —CONHN= or —C=N—N=).
                                          |
                                         OH A portion of the preceding product (0.128 g) is dissolved in an 0.1 M sodium bicarbonate solution (2 cc), and the resulting solution is filtered and lyophilised. The sodium salt of 3-{2-[4-(acetamidoethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (synisomer, E-form) (0.127 g) is obtained.

4-(2-Acetamidoethyl)-5,6-dioxo-3-thioxo-perhydro-1,2,4-triazine (3.61 g) is obtained from 4-(2-acetamidoethyl)-thiosemicarbazide (4.41 g) and ethyl oxalate (3.4 cc) in the presence of sodium methylate, by application of the method described by M. PESSON and M. ANTOINE, Bull. Soc. Chim. France 1590 (1970). The product has the following properties: instantaneous m.p. [Kofler]>260° C.; infra-red spectrum (KBr): characteristic bands (cm⁻¹) at 3365, 3050, 2000, 1710, 1630, 1600–1580, 1545, 1350, 1330 and 1200; proton nuclear magnetic resonance spectrum (80 MHz, DMSO d₆, δ in ppm, J in Hz): 1.7 (s, 3H, —CH₃); 3 to 3.7 (mt, —C$\underline{H}_2$NHCO—and H₂O); 4.3 (t, 2H, >N CH₂—); 7.85 (t, 1H, —NHCO—); 12.5 (m, 2H, —NH— of the ring).

The thiosemicarbazide starting material can be obtained in the following manner:

A solution of methyl N-(2-acetamidoethyl)-dithiocarbamate (57.7 g) and hydrazine hydrate (14.6 cc) in absolute ethanol (300 cc) is heated under reflux for 2 hours. The mixture is then cooled to 4° C. and is filtered, and the insoluble matter is dried at 30° C. under 0.05 mm Hg. 4-(2-Acetamidoethyl)-thiosemicarbazide (39.5 g) is obtained in the form of white crystals (instantaneous m.p. [Kofler]=171° C.).

Infra-red spectrum (KBr): characteristic bands (cm⁻¹) at 3280, 3180, 1650, 1560 to 1535, 1360 and 1280;

EXAMPLE 30

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (10.04 g), dimethylformamide (50 cc), 1-(2,2-dimethoxyethyl)-5-mercapto-2-methoxycarbonyl-1,3,4-triazole (3.95 g) and N,N-diisopropylethylamine (1.91 cc) is stirred at 60° C. for 6 hours and at 20° C. for 8 hours. It is then poured into ethyl acetate (700 cc), and this mixture is washed with water (2×125 cc), 0.1 N hydrochloric acid (150 cc), a half-saturated sodium bicarbonate solution (2×150 cc) and half-saturated aqueous sodium chloride (2×150 cc), dried over sodium sulphate, filtered and concentrated to dryness at 20° C. under 20 mm Hg (2.7 kPa). The product is fixed on Merck silica gel (0.06–0.2 mm) (50 g) and is chromatographed on a column (column diameter: 4 cm, height: 46 cm) of Merck silica gel (0.06–0.2 mm) (200 g). Elution is carried out with ethyl acetate (3.5 liters), 250 cc fractions being collected. Fractions 5 to 14 are evaporated to dryness at 30° C. under 20 mm Hg (2.7 kPa) and 2-benzhydryloxycarbonyl-3-{2-[1-(2,2-dimethoxyethyl)-2-methoxycarbonyl-1,3,4-triazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (4.35 g) is obtained in the form of an orange-coloured solid.

Infra-red spectrum (KBr): characteristic bands (cm⁻¹) at 3400, 1800, 1730, 1685, 1515, 1495, 1450, 1210, 1050, 945, 755 and 700.

Proton nuclear magnetic resonance spectrum (350 MHz, DMSO d₆, δ in ppm, J in Hz): 3.30 (s, 6H, >C(OC$\underline{H}_3$)₂; 3.86 (s, 3H, C$\underline{H}_3$ON=); 3.94 (s, 3H, C$\underline{H}_3$OCO—); 3.64 and 4.35 (2d, J=18, 2H, —SCH₂—); 4.35 (d, J=6, 2H, >CH—CH₂N<); 4.58 (t, J=6, 1H, >C$\underline{H}$—CH₂—N<); 5.05 (d, J=4, 1H, H in the 6-position); 5.86 (dd, J=4 and 9, H₇); 6.80 (s, 1H, H of the thiazole); 6.98 (s, 1H, —COOCH<); 7.06 (d, J=16, —C$\underline{H}$=CH—S—); 7.17 (d, J=16, 1H, —CH=CH—S—); 8.72 (s, 1H, —N$\underline{H}$—of the thiazolyl group); 9.0 (d, J=9, 1H, —CONH—).

A solution of 2-benzhydryloxycarbonyl-3-{2-[1-(2,2-dimethoxyethyl)-2-methoxycarbonyl-1,3,4-triazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (4.15 g) in methylene chloride (60 cc) and dimethylacetamide (1.46 cc) is treated with phosphorus trichloride (0.67 cc) at −6° C. for 1 hour 20 minutes. The mixture is then diluted with ethyl acetate (700 cc), and this mixture is washed with water (150 cc), a saturated sodium bicarbonate solution (150 cc) and a saturated sodium chloride solution (150 cc), dried over sodium sulphate, filtered and concentrated to dryness at 20° C. under 20 mm Hg (2.7 kPa). The residue is chromatographed on a column (column diameter: 4.5 cm, height: 28 cm) of Merck silica gel (0.06–0.2 mm) (150 g). Elution is carried out with ethyl acetate (1.7 liters), 250 cc fractions being collected. Fractions 2 to 6 are evaporated to dryness at 20° C. under 20 mm Hg (2.7 kPa). An orange-coloured froth (4 g) is obtained. This product is dissolved in ethyl acetate (70 cc), diisopropyl ether (450 cc) is added, whilst stirring, and the product is filtered off and dried. 2-Benzhydryloxycarbonyl-3-{2-[1-(2,2-dimethoxyethyl)-2-methoxycarbonyl-1,3,4-triazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.4 g) is obtained in the form of a beige solid.

Infra-red spectrum (KBr): characteristic bands (cm⁻¹) at 3400, 1790, 1730, 1690, 1520, 1495, 1450, 1210, 1090, 1050, 945, 755 and 705.

Proton nuclear magnetic resonance spectrum (350 MHz, DMSO d₆, δ in ppm, J in Hz):

3.29 (s, 6H, —C(OC$\underline{H}_3$)₂;
       |

3.65 and 3.87 (2d, J=18, 2H, —SCH₂—); 3.86 (s, 3H, =N—OC$\underline{H}_3$); 3.94 (s, 3H, C$\underline{H}_3$OCO—); 4.35 (d, J=6, 2H, >NC$\underline{H}_2$CH<); 4.57 (t, J=6, 1H, >NCH₂C$\underline{H}$—); 5.23 (d, J=4, 1H, H₆); 5.77 (dd, J=4 and 9, 1H, H₇); 6.73 (s, 1H, H of the thiazole); 6.94 (s, 1H, —COOCH<); 7.0 (d, J=12, 1H, —C$\underline{H}$=CH—S—); 7.10 (d, J=12, 1H, —CH=C$\underline{H}$—S); 8.77 (s, 1H>NH); 9.57 (d, J=9, 1H, —CONH—).

A solution of 2-benzhydryloxycarbonyl-3-{2-[1-(2,2-dimethoxyethyl)-2-methoxycarbonyl-1,3,4-triazol-5-yl]-thiovinyl}-7-[2-methoxyimino-2-(2- tritylamino-thiazol- 2-tert.-Butoxycarbonylamino-ethylamine is prepared by hydrazinolysis of N-tert.-butoxycarbonyl-phthalimidoethylamine:

Hydrazine hydrate (10.8 cc) is added to a suspension of 2-N-tert.-butoxycarbonyl-phthalimidoethylamine (53.7 g) in ethanol (540 cc), and the mixture is heated under reflux for 25 minutes. It is then cooled to 0° C. and filtered. The filtrate is concentrated to dryness under reduced pressure (20 mm Hg; 2.7 kPa). This gives 2N-tert.-butoxycarbonylamino-ethylamine (19.6 g) in the form of a yellow oil.

Infra-red spectrum (CHCl₃): characteristic bands (cm$^{-1}$) at 3460, 3380, 3320, 1700, 1585, 1500, 1390, 1370, 1160 and 490.

Proton nuclear magnetic resonance spectrum (60 MHz, CDCl₃, δ in ppm, J in Hz): 1.48 (s, 9H, —C(C$\underline{H}$₃)₃); 2.20 (s broad, 2H, —NH₂); 2.80 (t, J=5, 2H, H₂N—C$\underline{H}$₂—CH₂—); 3.18 (t, J=5, 2H, H₂NCH₂C$\underline{H}$₂—); 5.50 (s broad, 1H, —NHCO—).

EXAMPLE 29

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]-oct-2-ene (syn isomer, E-form) (10.04 g), dimethylformamide (200 cc), 4-(2-acetamidoethyl)-5,6-dioxo-3-thioxoperhydro-1,2,4-triazine (2.76 g) and diisopropylethylamine (2.1 cc) is stirred at 60° C. for 3 hours, under nitrogen. The cooled mixture is then diluted with ethyl acetate (800 cc) and the organic phase is washed with water (1.2 liters), dried over sodium sulphate, filtered and concentrated to dryness under reduced pressure (20 mm Hg) at 20° C. The residue is triturated in ether (150 cc), the insoluble matter is filtered off, and after drying 3-{2-[4-(2-acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (9.5 g) is obtained in the form of a light brown solid.

Infra-red spectrum (CHBr₃): characteristic bands (cm$^{-1}$) at 3370, 1795, 1710, 1680, 1520, 1495, 1445, 750 and 735.

Proton nuclear magnetic resonance spectrum (350 MHz, DMSO d₆, δ in ppm, J in Hz): 1.75 (s, 3H, —COCH₃); 3.65 and 3.90 (2d, J=18, 2H, —SCH₂—); 3.86 (s, 3H, —OCH₃); 3.88 (t, 2H, >NCH₂—); 5.26 (d, J=4, 1H, H in the 6-position); 5.78 (dd, J=4 and 9, 1H, H in the 7-position); 6.73 (s, 1H, H of the thiazole); 6.92 (d, J=16, 1H, —C$\underline{H}$=CHS—);

6.95 (s, 1H, —COOC$\underline{H}$—);

7.0 (d, J=16, 1H, =CHS—); 7.78 (t, J=6, —N$\underline{H}$-COCH₃); 8.81 (s, 1H, —NHC(C₆H₅)₃); 9.60 (d, J=9, 1H, —CONH—);

12.60 (s, 1H, =N—NHCO— or =N—C—).
                                    |
                                    OH

Dimethylacetamide (3.4 cc) followed by phosphorus trichloride (1.49 cc) is added to a solution, cooled to −10° C., of 3-{2-[4-(2-acetamidoethyl)-5,6-dioxo-1,4,5,6-tetrahydro-1,2,4-triazin-3yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form (9.03 g) in methylene chloride (85 cc). The mixture is stirred for 2 hours at −10° C. and is then diluted with methylene chloride (500 cc), and this mixture is washed with a half-saturated sodium bicarbonate solution (250 cc) and a saturated sodium chloride solution (250 cc), dried over sodium sulphate and concentrated to dryness under reduced pressure (20 mm Hg) at 20° C. The chestnut-coloured solid obtained is dissolved in a mixture of ethyl acetate, methylene chloride and methanol (120:120:80 cc) and the solution is chromatographed over a column (column diameter: 4 cm) of Merck silica gel (0.04–0.06 mm). Elution is carried out with a 95:5 (by volume) mixture of ethyl acetate and methanol (1.5 liters) under a pressure of 40 kPa, 125 cc fractions being collected. Fractions 6 to 10 are concentrated to dryness under reduced pressure (20 mm Hg) at 20° C. 3-{2-[4-(2-Acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.33 g) is obtained in the form of a beige solid.

Infra-red spectrum (CHBr₃): characteristic bands (cm$^{-1}$) at 3380, 1785, 1710, 1680, 1520, 1495, 1445, 755 and 740.

Proton nuclear magnetic resonance spectrum (350 MHz, DMSO d₆, δ in ppm, J in Hz): 1.75 (s, 3H, —COCH₃); 3.32 (mt, 2H, —C$\underline{H}$₂NHCO—); 3.62 and 4.30 (2d, J=18, 2H, —SCH₂—); 3.86 (t, 2H,>NCH₂—); 3.86 (s, 3H, —OCH₃); 5.05 (d, J=4, 1H, H in the 6-position); 5.85 (dd, J=4 and 9, 1H, H in the 7-position); 6.80 (s, 1H, H of the thiazole); 6.96 (d, J=16, 1H, —C$\underline{H}$=CHS—); 6.97 (s, 1H, —COOC$\underline{H}$—); 7.12 (d, J=16, 1H, =CHS—); 7.98 (t, J=6, 1H, —NHCOCH₃); 8.75 (s, 1H, —NHC(C₆H₅)₃); 9.04 (d, J=9, 1H, —CONH—);

12.60 (s, 1H, =N—NHCO— or =N—N=C—).
                                        |
                                        OH 3-2-[4-(2-acetamidoethyl)-5,6-dioxo-1,4,5,6-tetrahydro-1,2,4-triazin-3-yl]-thiovinyl -2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.15 g) is dissolved in formic acid (80 cc), water (30 cc) is added and the mixture is heated at 60° C. for 30 minutes, whilst stirring. It is then cooled, filtered and concentrated to dryness under reduced pressure (0.05 mm Hg) at 50° C. The residue is taken up in ethanol (250 cc), the mixture is concentrated to dryness under reduced pressure (20 mm Hg) at 30° C., the operation is repeated and the solid is then taken up in ethanol (40 cc) whilst stirring at 40° C. After cooling, filtering and drying, 3-{2-[4-(2-acetamidoethyl)-5,6-dioxo-1,4,5,6-tetrahydro-1,2,4-triazin-3-yl]-thiovinyl}-7-[2-(2-amino-thiazol-4-yl)-2-methoxyiminoacetamido]-2-carboxy-8-oxo-5-thia-1-aza-bicyclo-[4.2.0]oct-2-ene (syn isomer, E-form ) (1.56 g) is obtained in the form of a yellow powder.

Infra-red spectrum (KBr): characteristic bands (cm$^{-1}$) at 3500, 2500, 1775, 1710, 1685 to 1630, 1540, 1045 and 950.

Proton nuclear magnetic resonance spectrum (350 MHz, DMSO d₆, δ in ppm, J in Hz): 1.90 (s, 3H, —CH₃); 3.48 (m, 2H, —C$\underline{H}$₂NH—); 3.62 and 3.73 (2d, whilst stirring. The mixture is then diluted with ethyl acetate (250 cc) and this mixture is washed with a 2% strength sodium bicarbonate solution (150 cc) and with half-saturated aqueous sodium chloride (2×100 cc), dried over sodium sulphate, filtered and concentrated to dryness at 20° C. under 20 mm Hg (2.7 kPa). The product is fixed on Merck silica gel (0.06-0.2 mm) (5 g) and chromatographed on a column (column diameter: 3 cm, height: 15 cm) of Merck silica gel (0.06-0.2 mm) (50 g). Elution is carried out with ethyl acetate (6 liters), 600 cc fractions being collected. Fractions 2 to 7 are concentrated to dryness at 20° C. under 20 mm Hg (2.7 kPa) and 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.97 g) is obtained in the form of a yellow froth.

Infra-red spectrum (KBr): characteristic bands (cm$^{-1}$) at 3400, 3280, 1790, 1715, 1695, 1590, 1520, 1495, 1450, 1040, 945, 755 and 700.

Proton nuclear magnetic resonance spectrum (350 MHz, DMSO, δ in ppm, J in Hz): 1.33 (s, 9H, —C(CH$_3$)$_3$; 3.20 (m, 2H, —CH$_2$CH$_2$N<); 3.64 and 3.86 (2d, J=18, 2H, —SCH$_2$—); 3.83 (2, J=6, 2H, —CH$_2$—CH$_2$N<); 3.84 (s, 3H, =NOCH$_3$); 5.25 (d, J=4, 1H, H$_6$); 5.77 (dd, J=4 and 9, 1H, H$_7$); 6.72 (s, 1H, H of the thiazole); 6.92 (s, 1H, —COOCH<); 9.93 and 7.02 (2d, J=12, 2H, —CH=CH—S—); 8.82 (s, 1H, —NH—); 9.58 (d, J=9, 1H, —NHCO—); 12.55 (s, 1H, —NH— of the triazine).

A mixture of 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.88 g), formic acid (35 cc) and water (15 cc) is heated at 50° C. for 30 minutes. Water (20 cc) is then added and the mixture is allowed to cool to 20° C., filtered and concentrated to dryness at 50° C. under 0.05 mm Hg (0.007 kPa). The residue is taken up in ethanol (2×100 cc), and the mixture is in each case concentrated to dryness at 20° C. under 20 mm Hg (2.7 kPa). The residue is treated with ethanol (50 cc) at 45° C. for 15 minutes, the mixture is filtered and the solid is washed with ether (2×20 cc) and dried. 7-[2-(2-Amino-thiazol-4-yl)-2-methoxyimino-acetamido]-3-{2-[4-(2-aminoethyl)-5,6-dioxo-1,4,5,6-tetrahydro-1,2,4-triazin-3-yl]-thiovinyl}-2-carboxy-8-oxo-5-thia-1-aza-bicyclo[4.2.0]oct-2-ene (syn isomer, E-form) (1.08 g) is obtained, as the formate, in the form of a yellow powder.

Infra-red spectrum (KBr): characteristic bands (cm$^{-1}$) at 3500, 2200, 1770, 1710, 1680, 1630, 1530, 1380, 1040 and 930.

Proton nuclear magnetic resonance spectrum (350 MHz, DMSO, δ in ppm, J in Hz): 3.12 (m, 2H, —CH$_2$—CH$_2$—NH$_2$); 3.51 and 3.60 (2d, J=18, 2H, —SCH$_2$—); 3.85 (s, 3H, CH$_3$ON=); 4.12 (t, J=6, 2H, >NCH$_2$—CH$_2$—NH$_2$); 5.12 (d, J=4, 1H, H$_6$); 5.67 (dd, J=4 and 9, 1H, H$_7$); 6.44 (d, J=8, 1H, —CH=CHS—); 6.73 (s, 1H, H of the thiazole); 7.2 (s broad, 2H, —NH$_2$); 8.18 (s, 1H, H of the formate); 9.55 (d, J=9, 1H, —NHCO—).

4-(2-tert.-Butoxycarbonylamino-ethyl)-5,6-dioxo-3-thioxo-perhydro-1,2,4-triazine can be prepared in the following manner:

4-(2-tert.-Butoxycarbonylamino-ethyl)-thiosemicarbazide (9.37 g) is added to a solution of sodium (0.92 g) in methanol (40 cc) at 20° C., and diethyl oxalate (5.4 g) is then introduced dropwise in the course of 10 minutes. The mixture is heated under reflux for 3 hours. It is allowed to cool, water (100 cc) is added, concentrated hydrochloric acid (3 cc) is introduced dropwise, the mixture is extracted with ethyl acetate (2×100 cc) and the extract is washed with a saturated sodium chloride solution (2×50 cc), dried ocer sodium sulphate, filtered and concentrated to dryness at 20° C. under 20 mm Hg (2.7 kPa). The residue is taken up in methylene chloride (65 cc), the crystallisation is started, the batch is left for 2 hours at 20° C. and then filtered, and white crystals (4.59 g) of 4-(2-tert.-butoxycarbonylamino-ethyl)-5,6-dioxo-3-thioxoperhydro-1,2,4-triazine, melting at 160° C., are obtained.

Infra-red spectrum (KBr): characteristic bands (cm$^{-1}$) at 3380, 3150, 1685, 1640, 1545 and 1370.

Proton nuclear magnetic resonance spectrum (80 MHz, DMSO, δ in ppm, J in Hz): 1.45 (s, 9H, —C(CH$_3$)$_3$); 3.32 (q, J=5, 2H, —CH$_2$CH$_2$NH—); 4.38 (t, J=5, 2H, —CH$_2$—CH$_2$—NH—); 6.72 (d, J=5, 1H, CH$_2$CH$_2$NH—); 12.3 (s broad, 1H, —NH— of the triazine).

4-(2-tert.-Butoxycarbonylamino-ethyl)-thiosemicarbazide can be prepared as follows:

A mixture of methyl N-(2-tert.-butoxycarbonylamino-ethyl)-dithiocarbamate (22.53 g), ethanol (90 cc) and hydrazine hydrate (4.4 cc) is heated under reflux for 1 hour 30 minutes. The solution is concentrated to dryness at 30° C. under 20 mm Hg (2.7 kPa) and the residue is triturated in the presence of diethyl ether (100 cc). Crystallisation starts in 5 minutes. The mixture is left for 1 hour at 20° C. and the product is then filtered off and dried. Pinkish white crystals (11.3 g) of 4-(2-tert.-butoxycarbonylamino-ethyl)-thiosemicarbazide, melting at 85° C., are obtained.

Infra-red spectrum (CHBr$_3$): characteristic bands (cm$^{-1}$) at 3450, 3350, 1700, 1620, 1545, 1510, 1390, 1370, 1250, 1225 and 1160.

Proton nuclear magnetic resonance spectrum (80 MHz, CDCl$_3$, δ in ppm, J in Hz): 1.48 (s, 9H, —C(CH$_3$)$_3$); 3.45 and 3.80 (2t, J=5, 4H, —CH$_2$CH$_2$—).

Triethylamine (15.5 cc) is added to a solution of 2-tert.-butoxycarbonylamino-ethylamine (17.62 g) in 95% strength ethanol (110 cc), and carbon disulphide (6.65 cc) is introduced dropwise in the course of 10 minutes, whilst maintaining the temperature at between 20° C. and 25° C. The mixture is stirred for 1 hour 30 minutes at 22° C. Methyl iodide (6.85 cc) is then added and the mixture is stirred for 1 hour 30 minutes at 22° C. It is then concentrated to dryness at 20° C. under 20 mm Hg (2.7 kPa), the residue is taken up in ethyl acetate (200 cc), and the organic phase is washed with water (3×100 cc), dried over sodium sulphate, filtered and concentrated to dryness at 20° C. under 20 mm Hg (2.7 kPa). Methyl N-(2-tert.-butoxycarbonylaminoethyl)-dithiocarbamate (23.2 g) is obtained in the form of a yellow oil.

Infra-red spectrum (CHBr$_3$): characteristic bands (cm$^{-1}$) at 3440, 3370, 1700, 1505, 1430, 1380, 1370 and 945.

Proton nuclear magnetic resonance spectrum (60 MHz, CDCl$_3$, δ in ppm, J in Hz): 1.50 (s, 9H, —C(CH$_3$)$_3$); 2.65 (s, 3H, —CH$_3$); 3.50 and 3.80 (2t, J=5, 4H, —CH$_2$—CH$_2$—).

nol (1 liter). After concentration under reduced pressure (5 mm Hg) at 30° C., and drying, 7-[2-(2-aminothiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.2 g) is obtained in the form of light yellow crystals.

Proton nuclear magnetic resonance spectrum (350 MHz, DMSO d$_6$, δ in ppm, J in Hz): 3.60 (t, J=5, 2H, N—CH$_2$—CH$_2$OH); 3.84 (s, 3H, =NOCH$_3$); 3.92 (t, J=5, 2H, >N—CH$_2$CH$_2$OH); 5.10 (d, J=4, 1H, H in the 6-position); 5.65 (dd, J=4 and 9, 1H, H in the 7-position); 6.39 (d, J=16, 1H, —CH=CH—S—); 6.73 (s, 1H, H in the 5-position of the thiazole); 7.17 (s broad, 2H, —NH$_2$); 7.37 (d, J=16, 1H, —CH=CH—S—); 9.54 (d, J=9, 1H, —CONH—C$_7$).

7-[2-(2-Amino-thiazol-4-yl)-2-methoxy-imino-acetamido]-2-carboxy-3-{2-[5,6-dioxo-4-(2-hydroxyethyl)-1,4,5,6-tetrahydro-1,2,4-triazin-3-yl]-thiovinyl}8-oxo-5-thia-1-aza-bicyclo[4.2.0]oct-2-ene (syn isomer, E-form) (0.13 g) is dissolved in a N/100 sodium bicarbonate solution (21 cc). The solution is frozen at −80° C. and lyophilised. The sodium salt of 7-[2-(2-amino-1,3-thiazol-4-yl)-2-methoxyimino-acetamido]-2-carboxy-3-2-[5,6-dioxo-4-(2-hydroxyethyl)-1,4,5,6-tetrahydro-1,2,4-triazin-3-yl]-thiovinyl-8-oxo-5-thia-1-aza-bicyclo[4.2.0]oct-2-ene (syn isomer, E-form) (0.145 g) is obtained in the form of a white lyophilisate.

Rf=0.28; silica gel chromatographic plate; eluant: a 60:20:20 (by volume) mixture of ethyl acetate: acetic acid and water.

Proton nuclear magnetic resonance spectrum (350 MHz, DMSO d$_6$, δ in ppm, J in Hz): 3.50 (AB not resolved, 2H, —SCH$_2$—); 3.60 (t, J=6, 2H, >NCH$_2$CH$_2$OH); 3.91 (t, J=6, 2H, >N—CH$_2$CH$_2$OH); 3.87 (s, 3H, =NOCH$_3$); 5.07 (d, J=4, 1H, H in the 6-position); 5.60 (dd, J=4 and 9, 1H, H in the 7-position); 6.31 (d, J=16, 1H, —CH=CH—S—); 6.71 (s, 1H, H in the 5-position of the thiazole); 7.17 (s broad, 2H, —NH$_2$); 7.36 (d, J=16, 1H, —CH=CHS—); 9.54 (d, J=9, 1H, —CONH—).

5,6-Dioxo-4-(2-hydroxyethyl)-3-thioxo-perhydro-1,2,4-triazine can be prepared by applying the method described by M. PESSON and M. ANTOINE, Bull. Soc. Chim. France 1590 (1970), and working as follows:

4-(Hydroxyethyl)-thiosemicarbazide (5 g) and ethyl oxalate (5.5 cc) are added to a solution of sodium methylate (prepared from sodium (0.85 g) and methanol (37 cc), and the mixture is heated under reflux for 3 hours. After it has cooled, the precipitate is filtered off and washed with methanol (2×5 cc). The crude sodium salt is obtained, and is then taken up in distilled water (25 cc); the solution is filtered, and acidified to pH 2 with 1 N hydrochloric acid. The precipitate is filtered off, washed with water and dried in air. 5,6-Dioxo-4-(2-hydroxyethyl)-3-thioxo-perhydro-1,2,4-triazine (2.4 g) (m.p.=230° C.) is obtained.

The sodium salt can be prepared by treating 5,6-dioxo-4-(2-hydroxyethyl)-3-thioxo-perhydro-1,2,4-triazine (4.73 g), in anhydrous methanol, with sodium 2-ethyl-hexanoate. This gives 4.7 g of the sodium salt.

Infra-red spectrum (KBr): principal bands (cm$^{-1}$) at 3420, 3200, 3070, 1655, 1575, 1560, 1395, 1205, 1080, 1045 and 835.

4-(2-Hydroxyethyl)-thiosemicarbazide can be obtained according to the method described by Y. KAZAKOV and I. Y. POTOVSKII, Doklady Acad. Nauk. SSSR, 134, 824 (1960).

7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) can be prepared in the following manner:

A solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]-oct-2-ene (syn isomer, E-form) (5.93 g) in a mixture of pure formic acid (80 cc) and water (25 cc) is heated at 50° C. for 30 minutes. The mixture is then cooled to 20° C., filtered and concentrated to dryness at 30° C. under 20 mm Hg (2.7 kPa). The residue is taken up in acetone (150 cc), the mixture is concentrated to dryness at 20° C. under 20 mm Hg (2.7 kPa), the operation is repeated twice more and the residue is then triturated in ether (75 cc) and filtered off. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (3.4 g) is obtained in the form of a yellow powder.

EXAMPLE 28

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10.04 g), dimethylformamide (200 cc), 4-(2-tert.-butoxycarbonylamino-ethyl)-5,6-dioxo-3-thioxo-perhydro-1,2,4-triazine (3.46 g) and N,N-diisopropylethylamine (2.1 cc) is stirred at 60° C. for 3 hours 30 minutes. It is then diluted with ethyl acetate (800 cc) and this mixture is washed with a half-saturated sodium chloride solution (400 cc), dried over sodium sulphate, filtered and concentrated to dryness at 30° C. under 20 mm Hg (2.7 kPa). The product, dissolved in methylene chloride (50 cc), is chromatographed on a column (column diameter: 3 cm, height: 30 cm) of Merck silica gel (0.06–0.2 mm) (100 g). Elution is carried out with a 50:50 (by volume) mixture of cyclohexane and ethyl acetate (500 cc), a 25:75 (by volume) mixture of cyclohexane and ethyl acetate (500 cc) and ethyl acetate alone (1.5 liters), 125 cc fractions being collected. Fractions 9 to 21 are concentrated to dryness (under 20 mm Hg; 2.7 kPa, at 20° C.) and 2-benzhydryloxycarbonyl-3-{2-[4-(2-tert.-butoxycarbonyl amino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (7.69 g) is obtained in the form of a brown froth.

Infra-red spectrum (KBr): characteristic bands (cm$^{-1}$) at 3380, 1795, 1715, 1690, 1590, 1520, 1495, 1445, 1205, 1160, 1040, 940, 750 and 700.

Proton nuclear magnetic resonance spectrum (350 MHz, CDCl$_3$, δ in ppm, J in Hz): 1.36 (s, 9H, —C(CH$_3$)$_3$); 3.30 and 4.65 (2d, J=18, 2H, —SCH$_2$—); 3.38 (m, 2H, —CH$_2$NHCO—); 3.95 (m, 2H, —CH$_2$—CH$_2$NH—); 4.0 (s, 3H, CH$_3$ON=); 5.20 (d, J=4, H$_6$); 6.03 (dd, J=4 and 9, H$_7$); 6.70 (s, H of the thiazole); 6.86 (d, J=16, —CH=CHS—); 6.94 (s, —COOCH<); 11.7 (s broad, —NH— of the triazine).

A solution of 2-benzhydryloxycarbonyl-3-{2-[4-(2-tert.-butoxycarbonylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.36 g) in methylene chloride (30 cc) and dimethylformamide (1.2 cc) is treated with phosphorus trichloride (1.04 cc) at −10° C. for 1 hour 30 minutes, (0.06–0.2 mm) (40 g). Elution is carried out with methylene chloride (500 cc), 60 cc fractions being collected. Fractions 2 to 7 are combined and concentrated to dryness at 20° C. under 20 mm Hg, and 2-benzhydryloxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.4 g) is obtained in the form of a yellow froth.

A mixture of 2-benzhydryloxycarbonyl-3-{2-[4-(2,2-dimethyl-dioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.4 g), formic acid (13 cc) and water (6.5 cc) is heated at 50° C. for 30 minutes. It is then cooled to 20° C., filtered and concentrated to dryness at 30° C. under 0.05 mm Hg (0.007 kPa). The residue is taken up in ethanol (100 cc), the solvent is driven off at 20° C. under 20 mm Hg (2.7 kPa) and the operation is repeated twice. The yellow solid is taken up in boiling ethanol (100 cc), the mixture is filtered, the filtrate is concentrated to 50 cc at 20° C. (20 mm Hg; 2.7 kPa) and then filtered, and the solid is washed with diethyl ether (20 cc) and dried. 7-[2-(2-Amino-thiazol-4-yl)-2-methoxyimino-acetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-aza-bicyclo[4.2.0]oct-2-ene (syn isomer, E-form) (0.49 g) is obtained.

The nuclear magnetic resonance shows that this product contains about 25% of formic acid ester of one or other of the alcohol groups.

Infra-red spectrum (KBr): characteristic bands (cm$^{-1}$) at 3650–2200, 1770, 1710, 1680, 1590, 1530, 1045 and 945.

Proton nuclear magnetic resonance spectrum (350 MHz, DMSO d$_6$+D$_2$O, δ in ppm, J in Hz):

diol: 3.87 (s, 3H, =NOCH$_3$); 5.20 (d, J=4, 1H, H in the 6-position); 5.75 (d, J=4, H in the 7-position); 6.74 (s, 1H, H of the thiazole); 6.95 and 7.10 (2d, J=16, 2H, —CH=CH—S—);

formic acid ester: 3.87 (s, 3H, =NOCH$_3$); 5.18 (d, J=4, 1H, H in the 6-position); 5.75 (d, J=4, 1H, H in the 7-position); 6.74 (s, 1H, H of the thiazole); 6.93 and 7.08 (2d, J=16, 2H, —CH=CHS—); 8.22 (s, 1H, HCOO—).

4-(2,2-Dimethyl-dioxolan-4-yl-methyl)-5,6-dioxo-3-thioxo-perhydro-1,2,4-triazine can be prepared in the following manner:

A solution of sodium (1.12 g) in anhydrous methanol (50 cc) is prepared, 4-(2,2-dimethyl-dioxolan-4-yl-methyl)-thiosemicarbazide (10 g) is added under nitrogen, whilst stirring at 25° C., diethyl oxalate (6.6 cc) is then introduced dropwise in the course of 10 minutes, and the mixture is heated under reflux for 2 hours. It is then allowed to cool to 20° C., diluted with diethyl ether (1 liter) and filtered, and after drying a white solid (3.7 g) is obtained. The product is taken up in methylene chloride (200 cc) and the mixture is stirred in the presence of 1 N hydrochloric acid (10 cc). The organic phase is decanted, washed with saturated aqueous sodium chloride (2×50 cc), dried over sodium sulphate and concentrated to dryness at 20° C. under 20 mm Hg (2.7 kPa). The oil which remains is taken up in methylene chloride (50 cc), crystallisation is started by scratching, and the mixture is left at 4° C. for 3 hours. After filtration and drying, 4-(2,2-dimethyl-dioxolan-4-yl-methyl)-5,6-dioxo-3-thioxo-perhydro-1,2,4-triazine (1.5 g) is obtained in the form of white crystals.

Infra-red spectrum (KBr): characteristic bands (cm$^{-1}$) at 3600–3100, 1680, 1575, 1535, 1210 and 1060.

Proton nuclear magnetic resonance spectrum (80 MHz, DMSO d$_6$, δ in ppm, J in Hz): 1.30 and 1.42 (2s, 6H, >C(CH$_3$)$_2$); 3.95 (m, 2H, —CH$_2$O—);

4.50 (m, 3H, —CHO— and —N—CH$_2$—).

4-(2,2-Dimethyl-dioxolan-4-yl-methyl)-thiosemicarbazide can be prepared in the following manner:

A mixture of methyl N-(2,2-dimethyl-dioxolan-4-yl-methyl)-dithiocarbamate (23,6 g) prepared according to U.S. Pat. No. 4,064,242, absolute ethanol (500 cc) and hydrazine hydrate (5.6 g) is heated under reflux for 2 hours 30 minutes. It is then concentrated to dryness at 20° C. under 20 mm Hg (2.7 kPa) and the residue is taken up in diethyl ether (100 cc). After filtration and drying, 4-(2,2-dimethyl-dioxolan-4-yl-methyl)-thiosemicarbazide (15.2 g) is obtained in the form of a cream-coloured solid melting at 145° C.

Infra-red spectrum (KBr): characteristic bands (cm$^{-1}$) at 3340, 3200, 1630, 1555, 1510, 1380, 1370, 1240, 1210 and 1060.

Proton nuclear magnetic resonance spectrum (80 MHz, CDCl$_3$, δ in ppm, J in Hz): 1.38 and 1.48 (2s, 6H, >(CH$_3$)$_2$); 3.72 (dd, J=5 and 6, 2H, —CH$_2$N<); 3.90 (s, 2H, —NH$_2$); 4.10 (dd, J=6 and 7, 2H, —CH$_2$O—); 4.38 (m, 1H, >CHO—); 7.78 (t, J=5, 1H, —CH$_2$NH—);

7.98 (s, 1H, —NH—N).

EXAMPLE 27

A solution of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.58 g) and of the sodium salt of 5,6-dioxo-4-(2-hydroxyethyl)-3-thioxo-perhydro-1,2,4-triazine (0.31 g) in N,N-dimethylformamide (10 cc) is heated for 4 hours at 30°–60° C. The reaction mixture is cooled and diluted with ethyl ether (150 cc) and the precipitate is filtered off, washed with ether (2×25 cc) and dried. Crude 7-[2-(2-amino-thiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.6 g) is obtained in the form of an amorphous beige powder.

Rf=0.42; silica gel chromatographic plate; eluant: a 60:20:20 (by volume) mixture of ethyl acetate, acetic acid and water.

The product can be purified as follows: it is redissolved in a dilute sodium hydroxide solution (50 cc) (pH=8) and the mixture is then brought to pH 5 by means of dilute hydrochloric acid; after filtering off a small amount of insoluble matter, the solution obtained is chromatographed on a column (diameter: 2.4 cm) of XAD-2 resin, with successive elution of the impurities with distilled water (1 liter) and then of the pure product with a 95:5 (by volume) mixture of water and ethagel (0.05–0.2 mm) (10 g) and deposited on a column (column diameter: 1.4 cm) of silica gel (30 g). Elution is carried out with a 20:80 (by volume) mixture of cyclohexane and ethyl acetate (500 cc), 60 cc fractions being collected. Fractions 2 to 4 are evaporated to dryness at 20° C. under reduced pressure (20 mm Hg). 3-{2-[4-(all-3-yl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido-]8-oxo-5-thia-1-aza-bicyclo[4.2.0]oct-2ene (syn isomer, E-form) (1.34 g) is obtained in the form of a yellow froth.

Infra-red spectrum (CHBr3): characteristic bands (cm$^{-1}$) at 3380, 1780, 1720, 1680, 1515, 1490, 1445, 1040, 940, 750 and 735.

Proton nuclear magnetic resonance spectrum (350 MHz, CDCl3, δ in ppm, J in Hz): 3.57 and 3.66 (2d, J=18, 2H, —SCH2—); 4.03 (s, 3H, —OCH3); 4.52 (d, J=4, 2H, >NCH2—); 5.09 (d, J=4, 1H, H in the 6-position); 5.26 to 5.38 (2d, 2H, =CH2); 5.78 to 5.88 (mt, 1H, —CH=CH2); 5.92 (dd, J=4 and 9, 1H, H in the 7-position); 6.74 (s, 1H, H of the thiazole); 6.86 (d, J=16, —CH=CHS—); 6.96 (s, 1H, —COOCH<); 7.05 (d, J=9, 1H, —CONH—);

11.68 (s, 1H, =NNHCO— or =N—N=C—).
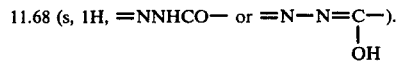
OH

3-{2-[4-(all-3-yl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido-]8-oxo-5-thia-1-aza-bicyclo[4.2.0]oct-2-ene (syn isomer, E-form (1.34 g) is dissolved in formic acid (13 cc), water (6.5 cc) is added and the mixture is heated at 50° C. for 30 minutes, whilst stirring. After cooling, the mixture is filtered and the solution is concentrated to dryness at 30° C. under reduced pressure (0.05 mm Hg). The residue is taken up in ethanol (50 cc), the solvent is driven off under reduced pressure (20 mm Hg) at 20° C. and this operation is repeated 3 times. The residue is treated with ethanol (100 cc) under reflux, a slight amount of insoluble matter is removed by filtration, and the filtrate is concentrated to 50 cc at 30° C. under reduced pressure (20 mm Hg) and then cooled for 1 hour at +4° C. After filtering off and drying the precipitate, 3-{2-[4-(all-3-yl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form) is obtained in the form of a yellow powder.

Infra-red spectrum (KBr): characteristic bands (cm$^{-1}$) at 3600, 2300, 1775, 1710, 1680, 1535, 1040 and 945.

Proton nuclear magnetic resonance spectrum (350 MHz, DMSO d6, δ in ppm, J in Hz): 3.63 and 3.80 (2d, J=18, 2H, —SCH2—); 3.88 (s, 3H, —OCH3); 4.48 (d, J=4, 2H, >NCH2—); 5.19 to 5.27 (mt, 3H, =CH2 and H in the 6-position); 5.74 to 5.92 (mt, 2H, —CH=CH2 and H in the 7-position); 6.74 (s, 1H, H of the thiazole); 6.91 (d, J=16, 1H, —CH=CHS—); 7.09 (d, J=16, 1H, =CHS—); 7.18 (s, —NH3+); 9.60 (d, J=9, 1H, —CONH—);

12.61 (s, 1H, =N—NHCO— or =N—N=C—).
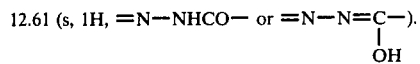
OH

4-Allyl-5,6-dioxo-3-thioxo-perhydro-1,2,4-triazine can be prepared according to the method described in Belgian Pat. No. 830,455.

EXAMPLE 26

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.02 g), dimethylformamide (93 cc), 4-(2,2-dimethyl-dioxolan-4-yl-methyl) -5,6-dioxo-3-thioxo-perhydro-1,2,4-triazine (1.5 g) and N,N-diisopropylethylamine (1.05 cc) is stirred at 60° C., under nitrogen, for 3 hours. It is then diluted with ethyl acetate (200 cc) and this mixture is washed with water (4×200 cc), dried over sodium sulphate, filtered and concentrated to dryness at 20° C. under 20 mm Hg (2.7 kPa). The residue is fixed on Merck silica gel (0.06–0.2 mm) (10 g) and the powder is deposited on a column (column diameter: 2.5 cm, height: 40 cm) of Merck silica gel (0.06–0.2 mm) (100 g). Elution is carried out with ethyl acetate (1.3 liters), 60 cc fractions being collected. Fractions 6 to 20 are concentrated to dryness at 20° C. under 20 mm Hg (2.7 kPa) and 2-benzhydryloxycarbonyl-3-{2-[4-(2,2-dimethyl-dioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-oxide-5-thia-1-aza-bicyclo[4.2.0]oct-2-ene (syn isomer, E-form) (2.48 g) is obtained in the form of a yellow froth.

Proton nuclear magnetic resonance spectrum (350 MHz, CDCl3, δ in ppm, J in Hz): 1.32 and 1.43 (2s, 6H, —C(CH3)2);

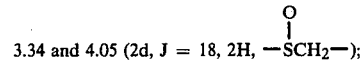
3.34 and 4.05 (2d, J = 18, 2H, —SCH2—);

3.74 (t, J=6, 2H, —CH2O—); 3.84 (s, 3H, =NOCH3); 3.95 (t, J=6, 2H, >N—CH2—); 4.38 (quintuplet, J=6, 1H, >CH—O—); 4.65 (d, J=4, 1H, H in the 6-position); 6.06 (dd, J=4 and 9, 1H, H in the 7-position); 6.71 (s, 1H, H of the thiazole); 6.84.(d, J=16, 1H, —CH=CHS—); 6.96 (s, 1H, —COOCH<); 11.60 (s, 1H, =N—NHCO—).

A solution of 2-benzhydryloxycarbonyl-3-2-[4-(2,2-dimethyl-dioxolan-4-yl-methyl)-5,6-dioxo-1,4,5,6-tetrahydro-1,2,4-triazin-3-yl]-thiovinyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form (2.48 g) in methylene chloride (22.9 g) and dimethylacetamide (0.85 cc) is treated with phosphorus trichloride (0.4 cc) at −10° C. for 40 minutes. The mixture is poured into ethyl acetate (250 cc) and this mixture is washed successively with saturated sodium bicarbonate solution (200 cc), water (2×100 cc) and a saturated sodium chloride solution (100 cc), dried over sodium sulphate, filtered and concentrated to dryness at 20° C. under 20 mm Hg (2.7 kPa). The residue is taken up in methylene chloride (20 cc), Merck silica gel (0.06–0.2 mm) (10 g) is added, the mixture is concentrated to dryness at 20° C. under 20 mm Hg and the powder obtained is deposited on a column (column diameter: 1.5 cm, height: 15 cm) of Merck silica gel (30 cc) is heated at 50° C. for 15 minutes. The mixture is cooled, diluted with water (70 cc) and filtered, and the filtrate is concentrated to dryness under reduced pressure (20 mm Hg; 2.7 kPa). The residue is taken up in ethanol (3×50 cc) and is each time concentrated to dryness under reduced pressure (20 mm Hg; 2.7 kPa); the solid obtained is then suspended in refluxing ethanol (50 cc), cooled, filtered off and dried in vacuo (20 mm Hg; 2.7 kPa). This gives 7-[2-(2-amino-thiazol-4-yl)-2-methoxyimino-acetamido]-2-carboxy-3-[2-(5,6-dioxo-4-ethoxycarbonylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1.9 g) in the form of a yellow solid.

Infra-red spectrum (KBr): characteristic bands (cm$^{-1}$) at 3340, 3220, 3130, 1780, 1725, 1690, 1590, 1530, 1040 and 945.

Proton nuclear magnetic resonance spectrum (350 MHz, DMSO d$_6$, δ in ppm, J in Hz): 1.22 (t, J=7, 3H, C$\underline{H}_3$—CH$_2$—); 3.60 and 3.85 (2d, J=18, 2H, —SCH$_2$—); 3.85 (s, 3H, —OCH$_3$); 4.15 (q, J=7, 2H, —OC$\underline{H}_2$—CH$_3$); 4.66 (s, 2H, >N—CH$_2$CO—); 5.18 (d, J=4, 1H, H in the 6-position); 5.77 (dd, J=4 and 9, 1H, H in the 7-position); 6.72 (s, 1H, H of the thiazole); 6.87 (d, J=16, 1H, —C$\underline{H}$=CHS—); 7.08 (d, J=16, 1H, —CH=C$\underline{H}$S—) 7.15 (s broad, 2H, —NH$_2$); 9.58 (d, J=9, 1H, —CONH—);

12.80 (s, 1H, =NNHCO— or =N—N=C—).
OH 5,6-Dioxo-4-ethoxycarbonylmethyl-3-thioxo-perhydro-1,2,4-triazine can be obtained as follows:

A solution of ethyl isothiocyanoacetate in anhydrous ethanol (185 cc) is added, in the course of 5 minutes, to a suspension of ethyl hydrazino-oxalate (24.4 g) in anhydrous ethanol (185 cc) at 25° C. The mixture dissolves, after which a white precipitate again forms. The mixture is kept stirred for 20 hours under nitrogen, after which a solution prepared from sodium (8.5 g) in ethanol (185 cc) is added in the course of 15 minutes and the mixture is heated under reflux for 4 hours. The red-brown suspension obtained is concentrated to dryness under reduced pressure (20 mm Hg; 2.7 kPa) and the residue is dissolved by adding 4 N hydrochloric acid (100 cc) and ethyl acetate (2,000 cc). The insoluble matter is filtered off and the organic phase is washed with a saturated sodium chloride solution (4×250 cc), dried over magnesium sulphate, filtered and concentrated to dryness under reduced pressure (20 mm Hg; 2.7 kPa). This gives a red-brown gum (43 g) which is dissolved in a saturated sodium bicarbonate solution (300 cc). The brown solution obtained is washed with isopropyl ether (3×100 cc) and brought to pH 1 with the requisite amount of 1 N hydrochloric acid, and is extracted with ethyl acetate (500 cc). The organic phase is washed with a saturated sodium chloride solution (2×50 cc), dried over magnesium sulphate, filtered in the presence of decolorising charcoal and concentrated to dryness under reduced pressure (20 mm Hg; 2.7 kPa). This gives 5,6-dioxo-4-ethoxycarbonylmethyl-3-thioxo-perhydro-1,2,4-triazine (9.5 g) in the form of a brown solid.

Infra-red spectrum (KBr): characteristic bands (cm$^{-1}$) at 3500-2800, 1740, 1700, 1645, 1380, 1235 and 1200.

Proton nuclear magnetic resonance spectrum (80 MHz, DMSO d$_6$, δ in ppm, J in Hz): 1.38 (t, J=7, 3H, —CH$_2$C$\underline{H}_3$); 4.30 (q, J=7, 2H, —C$\underline{H}_2$CH$_3$); 5.03 (s, 2H, >N—CH$_2$CO—); 12.50 (s, 1H, —NHCO—).

Ethyl isothiocyanoacetate can be prepared according to D. HOPPE and R. FOLLMANN, Chem. Ber. 109 3047 (1976).

EXAMPLE 25

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (10.04 g), dimethylformamide (200 cc), 4-allyl-5,6-dioxo-3-thioxo-perhydro-1,2,4-triazine (2.22 g) and N,N-diisopropylethylamine (2.1 cc) is stirred for 3 hours under nitrogen at 60° C. The mixture is then diluted with ethyl acetate (600 cc), and this mixture is washed with water (2×200 cc) and half-saturated aqueous sodium chloride (2×100 cc), dried over sodium sulphate, filtered and concentrated to dryness at 20° C. under 20 mm Hg. The residue is taken up in methylene chloride (50 cc), Merck silica gel (0.05-0.2 mm) (20 g) is added and the mixture is concentrated to dryness at 20° C. under 20 mm Hg. The powder is deposited on a column (column diameter: 6.1 cm) of Merck silica gel (0.05-0.2 mm) (200 g). Elution is carried out with a 20:80 (by volume) mixture of cyclohexane and ethyl acetate (2 liters), a 10:90 (by volume) mixture of cyclohexane and ethyl acetate (1 liter) and then with ethyl acetate (2 liters), 120 cc fractions being collected. Fractions 8 to 28 are concentrated to dryness at 20° C. under 20 mm Hg. 3-[2-(4-Allyl-5,6-dioxo-1,4,5,6-tetrahydro-1,2,4-triazin-3-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.7 g) is obtained in the form of an orange-coloured froth.

Infra-red spectrum (CHBr$_3$): characteristic bands (cm$^{-1}$) at 3380, 1800, 1720, 1670, 1515, 1045 and 940.

Proton nuclear magnetic resonance spectrum (350 MHz, DMSO d$_6$, δ in ppm, J in Hz): 3.60 and 4.29 (2d, J=18, 2H, —SCH$_2$—); 3.85 (s, 3H, —OCH$_3$); 4.45 (d, J=5, 2H, >NCH$_2$—); 5.05 (d, J=4, 1H, H in the 6-position); 5.17 to 5.27 (Mt, 2H, =CH$_2$); 5.78 to 5.92 (2 Mt, 2H, H in the 7-position and —C$\underline{H}$=CH$_2$); 6.78 (s, 1H, H of the thiazole); 6.95 (d, J=16, 1H, —C$\underline{H}$=CHS—); 6.97 (s, 1H, —COOCH<); 7.09 (d, J=16, 1H, =CHS—); 8.78 (s, 1H, —NHC(C$_6$H$_5$)$_3$); 9.04 (d, J=9, 1H, —CONH—)

12.62 (s, 1H, =N—NH—CO— or =N—N=C—).
OH

Phosphorus trichloride (0.40 cc) is added to a mixture, cooled to −10° C., of 3-{2-[4-(all-3-yl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.34 g) and dimethylacetamide (0.85 cc) in methylene chloride (23 cc), and the mixture is stirred for 30 minutes at −10° C. It is then poured into ethyl acetate (250 cc) and this mixture is washed with water (50 cc), a saturated sodium bicarbonate solution (50 cc) and a saturated sodium chloride solution (2×50 cc), dried over sodium sulphate, filtered and concentrated to dryness at 30° C. under 20 mm Hg. The residue, dissolved in methylene chloride (10 cc), is fixed on Merck silica insoluble matter, the solution is concentrated to dryness under reduced pressure (10 mm Hg; 1.33 kPa) at 40° C. The residue is taken up, and triturated, in ethanol (20 cc), which is then concentrated under reduced pressure (30 mm Hg; 4 kPa) at 30° C. The solid is taken up in ethanol (25 cc) and filtered off, after which it is washed successively with ethanol (3×5 cc) and ethyl ether (3×10 cc) and dried. 7-[2-(2-Amino-thiazol-4-yl)--2-methoxyimino-acetamido]-2-carboxy-3-{2-[4-N,N-dimethylcarbamylmethyl)-5,6-dioxo-1,4,5,6-tetrahydro-1,2,4-triazin-5-yl]-thiovinyl}-5-thia-1-aza-bicyclo[4.2.-0]oct-2-ene (syn isomer, E-form) (0.62 g) is obtained.

Infra-red spectrum (KBr): characteristic bands (cm⁻¹) at 3420, 3320, 3210, 1780, 1720, 1690, 1660, 1530, 1040 and 945.

Proton nuclear magnetic resonance spectrum (350 MHz, DMSO d₆, δ in ppm, J in Hz): 2.88 and 3.08 (2s, 2×3H, —CON(CH₃)₂); 3.61 and 3.82 (2d, J=18, 2H, —SCH₂—); 3.85 (s, 3H, =NOCH₃); 4.80 (s broad, 2H, —CH₂CON<); 5.21 (d, J=4, 1H, H in the 6-position); 5.79 (dd, J=4 and 9, 1H, H in the 7-position); 6.75 (s, 1H, H of the thiazole); 6.88 and 7.10 (2d, J=16, 2H, —CH=CH—S—); 7.19 (s broad, 2H, —NH₂); 9.60 (d, J=9, 1H, —CONH—C₇);

12.73 (s, 1H, —N=C—OH or —NH—C— of the triazine). 

The sodium salt of 4-(N,N-dimethylcarbamylmethyl)-5,6-dioxo-4-thioxo-perhydro-1,2,4-triazine can be obtained by the method of M. PESSON and M. ANTOINE, Bull. Soc. Chim. Fr. (1970) 1590, by the action of ethyl oxalate on 4-(N,N-dimethylcarbamylmethyl)-thiosemicarbazide in methanol in the presence of sodium methylate.

Infra-red spectrum (KBr): characteristic bands (cm⁻¹) at 3200, 1696, 1640, 1580 and 1530.

EXAMPLE 24

A solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.-0]oct-2-ene (syn isomer, E-form) (18.2 g), 5,6-dioxo-4-ethoxycarbonylmethyl-3-thioxo-perhydro-1,2,4-triazine (8.4 g) and diisopropylethylamine (3.11 cc) in dimethylformamide (182 cc) is heated at 80° C. for 1 hour 20 minutes. The mixture is then cooled, diluted with ethyl acetate (2,000 cc) and washed with a saturated sodium bicarbonate solution (3×100 cc) and a saturated sodium chloride solution (2×100 cc), dried over magnesium sulphate, filtered and concentrated to dryness under reduced pressure (20 mm Hg; 2.7 kPa). The residue is chromatographed on a column (column diameter: 4.9 cm, height: 31 cm) of Merck silica gel (0.06–0.2 mm) (313 g) and elution is carried out with a 20:80 (by volume) mixture of cyclohexane and ethyl acetate (2,000 cc) and then with ethyl acetate (2,200 cc), 100 cc fractions being collected. Fractions 10 to 40 are concentrated to dryness under reduced pressure (20 mm Hg; 2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (6.15 g) is thus obtained in the form of a yellow froth.

Infra-red spectrum (KBr): characteristic bands (cm⁻¹) at 3400, 1795, 1720, 1685, 1590, 1515, 1490, 1445, 1210, 1040, 935, 750 and 700.

Proton nuclear magnetic resonance spectrum (350 MHz, CDCl₃, δ in ppm, J in Hz): 1.28 (t, J=7, 3H, —CH₂CH₃);

3.32 and 4.50 (2d, J = 18, 2H, SCH₂—); 

4.02 (s, 3H, —OCH₃); 4.23 (q, J=7, 2H, —O—CH₂CH₃); 4.60 (s, 2H, >NCH₂COO—); 4.63 (d, J=4, 1H, H in the 6-position); 6.05 (dd, J=4 and 9, 1H, H in the 7-position); 6.70 (s, 1H, H of the thiazole); 6.76 (d, J=16, 1H, —CH=CHS—); 6.95 (s, 1H, —COOCH<);

11.54 (s, 1H, =N—NHCO— or =N—N=C—).
                                                                    |
                                                                   OH

Phosphorus trichloride (1 cc) is added to a solution, cooled to −10° C., of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (6 g) and dimethylacetamide (2.27 cc) in methylene chloride (60 cc), and the mixture is kept at −10° C. for 1 hour 20 minutes. It is then diluted with ethyl acetate (750 cc) and this mixture is washed with a saturated sodium bicarbonate solution (3×100 cc) and a saturated sodium chloride solution (2×100 cc) and evaporated to dryness under reduced pressure (20 mm Hg; 2.7 kPa). The residue is chromatographed over a column (column diameter: 2.1 cm, height: 18 cm) of Merck silica gel (0.06–0.2 mm) (35 g) and elution is carried out with ethyl acetate (0.5 liter), 30 cc fractions being collected. Fractions 2 to 7 are concentrated to dryness under 20 mm Hg (2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.2 g) is thus obtained in the form of a yellow froth.

Infra-red spectrum (KBr): characteristic bands (cm⁻¹) at 3400, 1780, 1720, 1685, 1590, 1525, 1490, 1445, 1210, 1035, 940, 750 and 700.

Proton nuclear magnetic resonance spectrum (350 MHz, CDCl₃, δ in ppm, J in Hz): 1.28 (t, J=7, 3H, —CH₂CH₃); 3.55 and 3.64 (2d, J=18, 2H, —SCH₂—); 4.06 (s, 3H, —OCH₃); 4.26 (q, J=7, 2H, —OCH₂CH₃); 4.63 (s, 2H, >N—CH₂COO—); 5.09 (d, J=4, 1H, H in the 6-position); 5.94 (dd, J=4 and 9, 1H, H in the 7-position); 6.72 (s, 1H, H of the thiazole); 6.75 (d, J=16, 1H, —CH=CHS—); 6.94 (s, 1H, —COOCH<);

11.05 (s, 1H, =N—NHCO— or =N—N=C—). 
                                                                    |
                                                                   OH A solution of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5 g) in 98% strength formic acid (100 cc) and distilled water cc). The insoluble matter is filtered off and washed with anhydrous ethanol (25 cc) and ether (2×50 cc) and then dried under reduced pressure (5 mm Hg; 0.67 kPa) at 20° C. This gives 7-[2-(2-amino-thiazol-4-yl)-2-methoxyiminoacetamido]-3-[2-(4-carbamyl-methyl-5,6-dioxo-1,4,5,6-tetrahydro-1,2,4-triazin-3-yl)-thiovinyl]-2-carboxy-8-oxo-5-thia-1-aza-bicyclo[4.2.0]oct-2-ene (syn isomer, E-form) (1.3 g) in the form of a beige powder.

Infra-red spectrum (KBr): characteristic bands in cm$^{-1}$ at 3410, 3320, 3200, 3100, 2000, 1770, 1710, 1680, 1630, 1590, 1380, 1040 and 945.

Proton nuclear magnetic resonance spectrum (350 MHz, DMSO d$_6$, δ in ppm, J in Hz): 3.63 and 3.83 (AB, J=18, 2H, —SCH$_2$—); 3.87 (s, 3H, =NOCH$_3$); 4.45 (s broad, 2H, —CH$_2$—CONH$_2$); 5.20 (d, J=4, 1H, H in the 6-position); 5.78 (dd, J=4 and 9, 1H, H in the 7-position); 6.75 (s, 1H, H of the thiazole); 6.90 and 7.08 (2d, J=16, 2×1H, —CH=CH—S—); 7.32 (s broad, 2H, —NH$_2$ of the thiazole); 7.70 (s broad, 2H, —CONH$_2$); 9.60 (d, J=9, 1H, —CONH—C$_7$);

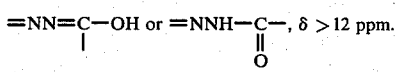

4-Carbamylmethyl-5,6-dioxo-3-thioxo-perhydro-1,2,4-triazine can be prepared in the following manner:

4-Ethoxycarbonylmethyl-thiosemicarbazide (8.33 g) (GANTE and LANTSCH, Chem. Ber., 97, 989 (1964)) are suspended in a saturated solution (250 cc) of ammonia in ethanol, and the reaction mixture is stirred at 25° C. for 22 hours. The insoluble matter is filtered off and washed with alcohol (2×25 cc) and ether (2×50 cc); after drying, 4-carbamylmethyl-thiosemicarbazide (6.2 g), m.p.=188° C., is obtained.

4-Carbamylmethyl-5,6-dioxo-3-thioxo-perhydro-1,2,4-triazine (3.8 g) is obtained by condensing 4-carbamylmethyl-thiosemicarbazide (6.8 g) and ethyl oxalate (6.7 g) in accordance with the method of M. PESSON and M. ANTOINE, Bull. Soc. Chim. France 1590 (1970).

Infra-red spectrum (KBr): characteristic bands in cm$^{-1}$ at 3350, 3480, 3430, 3270, 3100, 2000, 1710, 1690, 1670, 1365 and 1200.

EXAMPLE 23

A solution of the sodium salt of 4-N,N-dimethylcarbamylmethyl-5,6-dioxo-3-thioxo-perhydro-1,2,4-triazine (4 g) in N,N-dimethylformamide (240 cc) is treated with formic acid (0.60 cc) and then heated to 60° C. under nitrogen. 2-Benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (8 g) is then added, followed by a solution of N,N-diisopropylethylamine (2.8 cc) in N,N-dimethylformamide (20 cc) added dropwise in the course of 10 minutes. The mixture is stirred for 2 hours 20 minutes at 60° C. and is then diluted with distilled water (600 cc) and extracted with ethyl acetate (2×250 cc). The organic extracts are washed successively with an 0.1 N hydrochloric acid solution (200 cc), a half-saturated sodium bicarbonate solution (200 cc) and a half-saturated sodium chloride solution (200 cc) and are then dried over magnesium sulphate. The residue obtained by concentrating to dryness under reduced pressure (30 mm Hg; 4 kPa) at 30° C. is chromatographed on a column (height: 30 cm, diameter: 5 cm) of silica gel (0.04–0.06 mm), elution being carried out under 50 kPa with ethyl acetate (2.5 liters) and then with a 95:5 (by volume) mixture of ethyl acetate and methanol (1.5 liters). Fractions 32 to 37 (each of 100 cc) are combined and concentrated to dryness. This gives 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in the form of a salmon-coloured solid.

Infra-red spectrum (CHBr$_3$): characteristic bands (cm$^{-1}$) at 3380, 3200, 1800, 1725, 1685, 1670, 1590, 1520, 1495, 1450, 1040, 945, 755 and 740.

A solution, cooled to −10° C., of 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.4 g) in methylene chloride (48 cc) is treated with N,N-dimethylacetamide (1.47 cc) and then with phosphorus trichloride (0.44 cc), after which the mixture is stirred for 3 hours at about −10° C. The reaction mixture is then diluted with methylene chloride (100 cc) and poured into a half-saturated sodium bicarbonate solution (100 cc). The organic phase is washed with a half-saturated sodium chloride solution (100 cc), dried over magnesium sulphate and then concentrated to dryness under reduced pressure (30 mm Hg; 4 kPa) at 30° C. The residue is chromatographed over a column (column diameter: 2.2 cm, height: 30 cm) of silica gel (0.04–0.06 mm), elution being carried out with ethyl acetate (600 cc) and 25 cc fractions being collected. Fractions 10 to 21 are combined and concentrated to dryness. 2-Benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.3 g) is obtained.

Infra-red spectrum (CHBr$_3$): characteristic bands (cm$^{-1}$) at 3400, 1790, 1730, 1690, 1670, 1590, 1520, 1500, 1460, 1050, 760 and 740.

Proton nuclear magnetic resonance spectrum (350 MHz, CDCl$_3$, δ in ppm, J in Hz): 2.97 and 3.40 (2s, 2×3H, —CON(CH$_3$)$_2$); 3.60 and 3.75 (2d, J=18, 2H, —SCH$_2$—); 4.08 (s, 3H, =NOCH$_3$); 4.73 (s broad, 2H, —CH$_2$CON<); 5.08 (d, J=4, 1H, H in the 6-position); 5.93 (dd, J=4 and 9, 1H, H in the 7-position); 6.77 (s, 1H, H in the 5-position of the thiazole); 6.88 (d, J=16, 1H, —CH=CH—S—); 6.92 (s, 1H, —CO$_2$CH(C$_6$H$_5$)$_2$); 7.0 to 7.6 (hump, 27H, aromatics, —CONH— and —CH=CHS—); 7.81 (s broad, 1H, —NH— of the trityl);

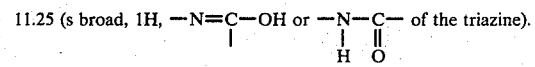

Distilled water (9 cc) is added to a solution of 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0-oct-2]-ene (syn isomer, E-form) (1.3 g) in 98% strength formic acid (15 cc) and the reaction mixture is heated at 50° C. for 45 minutes. After filtration to remove the 4-Bromo-2-methoxyimino-3-oxo-butyryl chloride (syn isomer) can be prepared in the following manner:

2 drops of dimethylformamide are added to a solution, at 20° C., of 2-methoxyimino-3-oxo-butyric acid (syn isomer) (4.08 g) in diethyl ether (50 cc), and oxalyl chloride (2 cc) dissolved in ethyl ether (5 cc) is then added dropwise in the course of 15 minutes. The mixture is stirred for 1 hour at 20° C., a further drop of dimethylformamide is added, and the reaction is continued for 15 minutes. The mixture is then concentrated to dryness at 20° C. under 20 mm Hg (2.7 kPa) and the residue is taken up in petroleum ether (2×30 cc), the solvent being evaporated off, each time, at 20° C. under 20 mm Hg (2.7 kPa). The 2-methoxyimino-3-oxo-butanoyl chloride (syn isomer) thus obtained is dissolved in methylene chloride (50 cc), and a 5.4 N solution of hydrogen chloride in ether (0.2 cc), and bromine (1.14 cc) are added to this solution at 20° C. The mixture is stirred for 20 hours at 20° C. and is then concentrated to dryness at 20° C. under 20 mm Hg (2.7 kPa), and a brown oil consisting principally of 4-bromo-2-methoxyimino-3-oxo-butyryl chloride (syn isomer) (5.42 g) is obtained.

Proton nuclear magnetic resonance spectrum (60 MHz, CDCl$_3$, δ in ppm, J in Hz): 4.25 (s, 3H, —OCH$_3$); 4.34 (s, 2H, —CH$_2$—).

2-Methoxyimino-3-oxo-butyric acid (syn isomer) can be prepared in the following manner:

A mixture of ethyl 2-methoxyimino-3-oxo-butyrate (syn isomer) (52 g), ethanol (300 cc) and 1 N sodium hydroxide solution (330 cc) is heated under reflux for 15 hours. The ethanol is evaporated at 20° C. under a pressure of 20 mm Hg (2.7 kPa) and the residue is extracted with methylene chloride (150 cc). The aqueous phase is treated with animal charcoal (1 g), filtered, saturated with sodium chloride, cooled to 4° C. and acidified to pH 2 by means of 2 N hydrochloric acid in the presence of methylene chloride (200 cc). The aqueous phase is re-extracted with the same solvent (2×100 cc) and then with ethyl acetate (6×200 cc). The organic phases are dried over sodium sulphate and concentrated to dryness separately at 20° C. under 20 mm Hg (2.7 kPa). The residues are combined and treated with diisopropyl ether (80 cc) for 4 hours, with very vigorous stirring. The crystals obtained are filtered off and dried; this gives 2-methoxyimino-3-oxo-butyric acid (syn isomer) (8.9 g).

Infra-red spectrum (CHCl$_3$): characteristic bands (cm$^{-1}$) at 3400, 2830, 2300, 1730, 1695, 1370 and 1035.

Proton nuclear magnetic resonance spectrum (60 MHz, CDCl$_3$, δ in ppm, J in Hz): 2.48 (s, 3H, CH$_3$CO—); 4.18 (s, 3H, —OCH$_3$); 11.2 (s, 1H, —COOH).

Ethyl 2-methoxyimino-3-oxo-butyrate (syn isomer) is prepared according to R. BUCOURT et al., Tetrahedron 34, 2233 (1978).

EXAMPLE 21

A solution of 7-[2-(2-amino-thiazol-4-yl)-2-methoxyimino-acetamido]-2-carboxy-3-{2-[4-(2,2-dimethoxyethyl)-5,6-dioxo-1,4,5,6-tetrahydro-1,2,4-triazin-3-yl]-thiovinyl}-8-oxo-5-thia-1-aza-bicyclo[4.2.0]oct-2-ene (syn isomer, E-form) (0.1 g) in pure formic acid (10 cc) is stirred at 50° C. for 30 minutes. It is then concentrated to dryness at 50° C. under 30 mm Hg (4 kPa), the residue is taken up in acetone (10 cc), the mixture is concentrated to dryness at 20° C. under 20 mm Hg (2.7 kPa), the residue is treated with acetone (20 cc) under reflux and the mixture is allowed to cool and is filtered. 7-[2-(2-Amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.088 g) is obtained in the form of a yellow powder, of which the characteristics are identical to those of the product obtained in Example 16 (1-a).

EXAMPLE 22

4-Carbamylmethyl-5,6-dioxo-3-thioxo-perhydro-1,2,4-triazine (1.5 g) and N,N-diisopropylethylamine (0.65 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (3.7 g) in dry N,N-dimethylformamide (70 cc). The reaction mixture is heated for 3 hours at 60°-65° C. under nitrogen, then diluted with ethyl acetate (300 cc), and washed with distilled water (3×100 cc). After drying over magnesium sulphate and filtration, the solvent is evaporated under reduced pressure (35 mm Hg; 4.4 kPa) at 40° C., and the expected crude product (3.1 g) is obtained.

The crude product (3.7 g) obtained in accordance with the working method described above is chromatographed on a column (column diameter: 4 cm, height: 30 cm) of Merck silica gel (0.04–0.06 mm), elution being carried out under a pressure of 40 kPa with ethyl acetate, and 200 cc fractions being collected. Fractions 11 to 32 are evaporated to dryness under reduced pressure (35 mm Hg; 4.4 kPa) at 40° C. This gives 2-benzhydryloxycarbonyl-3-[2-(4-carbamylmethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g).

Infra-red spectrum (CHBr$_3$): characteristic bands in cm$^{-1}$ at 3450, 3390, 3190, 2820, 1780, 1720, 1685, 1590, 1475, 1450, 1050, 945, 755 and 700.

Proton nuclear magnetic resonance spectrum (350 MHz, CDCl$_3$, δ in ppm, J in Hz): 3.62 and 3.88 (AB, J=16, 2H, —SCH$_2$—); 3.83 (s, 3H, =NOCH$_3$); 4.41 (s broad, 2H, —CH$_2$CONH$_2$); 5.22 (d, J=5, 1H, H in the 6-position); 5.75 (dd, J=5 and 9, 1H, H in the 7-position); 6.71 (s, 1H, H of the thiazole); 6.85 and 6.95 (AB, J=16, —CH=CH—S—); 6.94 (s, 1H, —CH(C$_6$H$_5$)$_2$); 7.15 to 7.50 (Mt. 25H, aromatics); 7.71 and 8.80 (2s, 2×1H, —CONH$_2$); 9.58 (d, J=9, 1H, —CONH—C$_7$);

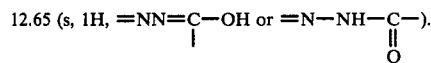

12.65 (s, 1H, =NN=C—OH or =N—NH—C—).

2-Benzhydryloxycarbonyl-3-[2-(4-carbamylmethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g) is dissolved in formic acid (47 cc). After addition of distilled water (30 cc), the reaction mixture is heated for 30 minutes at 50° C. and then diluted with distilled water (17 cc) and filtered. The filtrate is concentrated under reduced pressure (5 mm Hg; 0.67 kPa) at 40° C. The residue is triturated with anhydrous ethanol (50 cc), which is evaporated under reduced pressure (30 mm Hg; 4 kPa) at 40° C.; this operation is repeated twice more. The residue is taken up in anhydrous ethanol (50

1-azabicyclo[4.2.0]oct-2-ene (syn isomer, E-form) can be prepared as follows:

A mixture of 7-[2-(2-amino-thiazol-4-yl)-2-methoxyimino-acetamido]-2-benzhydryloxycarbonyl-8-oxo-3-(2-tosyloxyvinyl)-5-thia-1-aza-bicyclo[4.2.0]oct-2-ene (syn isomer, E-form) (0.35 g), formic acid (10 cc) and water (3 cc) is stirred at 50° C. for 30 minutes. Water (8 cc) is then added, and the mixture is filtered and concentrated to dryness at 30° C. under 0.05 mm Hg (0.007 kPa). The residue is taken up in ethanol (2×20 cc), and in each case the mixture is concentrated to dryness at 20° C. under 20 mm Hg (2.7 kPa). The solid obtained is triturated in diethyl ether (20 cc). After filtration and drying, 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.12 g) is obtained in the form of a yellow powder.

Infra-red spectrum (KBr): characteristic bands (cm$^{-1}$) at 3360, 3200, 3100, 2000, 1770, 1670, 1630, 1530, 1370, 1190, 1175, 1070, 1045, 925 and 810.

Proton nuclear magnetic resonance spectrum (350 MHz, DMSO d$_6$, δ in ppm, J in Hz): 2.45 (s, 3H, —CH$_3$); 3.58 and 3.80 (2d, J=18, 2H, —SCH$_2$—); 3.88 (s, 3H, —OCH$_3$); 5.18 (d, J=4, 1H, H in the 6-position); 5.78 (dd, J=4 and 9, 1H, H in the 7-position); 6.68 and 7.20 (2d, J=12, 2H, —CH=CH—); 6.74 (s, 1H, H of the thiazole); 7.20 (s, 2H, —NH$_2$); 7.51 and 7.88 (2d, J=8, 4H, tosyl group); 9.58 (d, J=9, 1H, —CONH—).

7-[2-(2-Amino-thiazol-4-yl)-2-methoxyimino-acetamido]-2-benzhydryloxycarbonyl-8-oxo-3-(2-tosyloxyvinyl)-5-thia-1-aza-bicyclo[4.2.0]oct-2-ene (syn isomer, E-form) can be prepared as follows:

A solution of 4-bromo-2-methoxyimino-3-oxo-butyryl chloride (syn isomer) (2 g) in acetone (10 cc) is added, in the course of 7 minutes, to a solution, cooled to −10° C., of 7-amino-2-benzhydryloxycarbonyl-8-oxo-3-(2-tosyloxyvinyl)-5-thia-1-aza-bicyclo[4.2.0]oct-2-ene (E-form) (4.7 g) in acetone (50 cc), water (5 cc) and sodium bicarbonate (2.8 g). The mixture is stirred for 1 hour at −10° C. and is then concentrated to dryness at 20° C. under 20 mm Hg (2.7 kPa). This gives a chestnut-coloured solid A (11 g). A portion (6 g) of this solid A is chromatographed on a column (column diameter: 5 cm, height: 25 cm) of Merck silica gel (0.04–0.06 mm). Elution is carried out with a 65:35 (by volume) mixture of cyclohexane and ethyl acetate (2.5 liters) under a pressure of 40 kPa, 125 cc fractions being collected. Fractions 10 to 14 are concentrated to dryness at 20° C. under 20 mm Hg (2.7 kPa) and 2-benzhydryloxycarbonyl-7-(4-bromo-2-methoxyimino-3-oxobutyrylamino)-8-oxo-3-(2-tosyloxyvinyl)-5-thia-1-aza-bicyclo[4.2.0]oct-2-ene (syn isomer, E-form) (1 g) is collected in the form of a yellow froth.

Infra-red spectrum (CHBr$_3$): characteristic bands (cm$^{-1}$) at 3390, 1785, 1720, 1685, 1515, 1495, 1455, 1375, 1190, 1180, 1075, 1045, 950, 810, 760 and 740.

Proton nuclear magnetic resonance spectrum (CDCl$_3$, 350 MHz, δ in ppm, J in Hz): 2.43 (s, 3H, —C$_6$H$_4$CH$_3$); 3.35 (AB, J=17, 2H, —SCH$_2$—); 4.14 (s, 3H, =NOCH$_3$); 4.35 (s, 2H, BrCH$_2$CO—); 5.02 (d, J=4, 1H, H in the 6-position); 5.34 (dd, J=4 and 9, 1H, H in the 6-position); 6.89 (s, 1H, —CH(C$_6$H$_5$)$_2$); 6.86 and 6.92 (2d, J=12, 2H, —CH=CH—); 7.17 (d, J=9, 1H, —CONH—); 7.2 to 7.4 (hump, 12H, —CH(C$_6$H$_5$)$_2$ and 2H in the meta-position of the tosyl group); 7.74 (d, J=8, 2H, 2H in the ortho-position of the tosyl group).

A solution of the crude product A (5 g) obtained above, in tetrahydrofurane (25 cc) is poured, in the course of 5 minutes, into a solution of thiourea (0.5 g), water (50 cc) and ethanol (25 cc) at 20° C. The mixture is stirred for 30 minutes at 20° C. and is then concentrated to dryness at 20° C. under 20 mm Hg (2.7 kPa). The residue is taken up in ethyl acetate (150 cc) and a saturated sodium chloride solution (50 cc), the phases are separated and the organic phase is washed with water (2×100 cc) and a saturated sodium chloride solution (100 cc), dried over sodium sulphate, filtered and concentrated to dryness at 20° C. under 20 mm Hg (2.7 kPa). The product obtained is chromatographed over a column (column diameter: 4 cm, height: 20 cm) of Merck silica gel (0.04–0.06 mm) (120 g). Elution is carried out with a 30:70 (by volume) mixture of cyclohexane and ethyl acetate (2 liters) under a pressure of 40 kPa 50 cc fractions being collected. Fractions 16 to 38 are concentrated to dryness at 20° C. under 20 mm Hg (2.7 kPa) and 7-[2-(2-amino-thiazol-4-yl)-2-methoxyimino-acetamido]-2-benzhydryloxycarbonyl-8-oxo-3-(2-tosyloxyvinyl)-5-thia-1-aza-bicyclo[4.2.0]oct-2-ene (syn isomer, E-form) (0.75 g) is collected in the form of a cream-coloured solid.

7-Amino-2-benzhydryloxycarbonyl-8-oxo-3-(2-tosyloxyvinyl)-5-thia-1-aza-bicyclo[4.2.0]oct-2-ene (E-form) can be prepared in the following manner:

A solution of p-toluenesulphonic acid hydrate (3.49 g) in acetonitrile (25 cc) is added dropwise, in the course of 25 minutes, to a solution, at 35° C., of 2-benzhydryloxycarbonyl-7-tert.-butoxycarbonylamino-8-oxo-3-(2-tosyloxyvinyl)-5-thia-1-aza-bicyclo[4.2.0]oct-2-ene (E-form) (6.1 g) in acetonitrile (75 cc). The mixture is stirred for 45 minutes at 35° C. and is then poured into a saturated sodium bicarbonate solution (500 cc). After 30 minutes' contact, with stirring, the mixture is extracted with ethyl acetate (500 cc) and the organic phase is washed with water (100 cc), dried over sodium sulphate, filtered and concentrated to dryness at 20° C. under 20 mm Hg (2.7 kPa). 7-Amino-2-benzhydryloxycarbonyl-8-oxo-3-(2-tosyloxyvinyl)-5-thia-1-aza-bicyclo[4.2.0]oct-2-ene (E-form) (4.7 g) is obtained in the form of a brown froth.

Rf=0.18 [silica gel chromatographic plate, 50:50 (by volume) mixture of cyclohexane and ethyl acetate].

2-Benzhydryloxycarbonyl-7-tert.-butoxycarbonylamino-8-oxo-3-(2-tosyloxyvinyl)-5-thia-1-aza-bicyclo[4.2.0]oct-2-ene (E-form) can be prepared in the following manner:

2-Benzhydryloxycarbonyl-7-tert.-butoxycarbonylamino-8-oxo-5-oxide-3-(2-tosyloxyvinyl)-5-thia-1-azabicyclo[4.2.0]oct-2-ene (E-form) (7.1 g), dissolved in methylene chloride (75 cc) and dimethylacetamide (4.62 cc), is reduced with phosphorus trichloride (2.03 cc) as described in Example 19. After chromatography on silica gel [eluant: 50:50 (by volume) cyclohexane/ethyl acetate], 2-benzhydryloxycarbonyl-7-tert.-butoxycarbonylamino-8-oxo-3-(2-tosyloxyvinyl)-5-thia-1-aza-bicyclo[4.2.0]oct-2-ene (E-form) (6.1 g) is obtained.

Infra-red spectrum (CHBr$_3$): characteristic bands (cm$^{-1}$) at 3425, 1780, 1720, 1505, 1370, 1190, 1180, 1075 and 760.

Proton nuclear magnetic resonance spectrum (350 MMHz, CDCl$_3$, δ in ppm, J in Hz): 1.50 (s, 9H, —C(CH$_3$)$_3$); 2.42 (s, 3H, —CH$_3$); 3.35 and 3.42 (2d, J=18, 2H, —SCH$_2$—); 4.92 (d, J=4, 1H, H in the 6-position); 5.59 (dd, J=5 and 9, 1H, H in the 7-position); 6.84 (d, J=12, 1H, —CH=CHS—); 6.88 (s, 1H, —COOCH<); 6.90 (d, J=12, 1H, =CHS—).

being collected. Fractions 5 to 12 are concentrated to dryness at 20° C. under 30 mm Hg (4 kPa) and 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, Z-form) (18.5 g) is obtained in the form of a cream-coloured powder.

Infra-red spectrum (KBr): characteristic bands (cm$^{-1}$) at 3380, 3200, 1800, 1725, 1685, 1585, 1515, 1495, 1445, 1080, 1040, 750 and 740.

A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, Z-form) (18.5 g) in methylene chloride (137 cc) and dimethylacetamide (6.43 cc) is treated with phosphorus trichloride (3.03 cc) for 45 minutes at −8° C., whilst stirring. The mixture is then poured into ethyl acetate (400 cc), and this mixture is washed with a saturated sodium bicarbonate solution (150 cc) and with water (2×100 cc), dried over sodium sulphate, filtered and concentrated to dryness at 20° C. under 20 mm Hg (2.7 kPa). The product is fixed on Merck silica gel (0.06–0.2 mm) (40 g) and is chromatographed on a column (column diameter: 4.5 cm, height: 80 cm) of Merck silica gel (0.06–0.2 mm) (400 g). Elution is carried out with ethyl acetate (2 liters), 360 cc fractions being collected. Fractions 2 to 5 are evaporated to dryness at 30° C. under 20 mm Hg (2.7 kPa). The residue is taken up in ethyl acetate (100 cc) and diisopropyl ether (1 liter) is added, whilst stirring. After filtering and drying, 2-benzhydryloxy carbonyl-3-{2-[4-(2,2-dimethoxyethyl)-5,6-dioxo-1,4,5,-6-tetrahydro-1,2,4-triazin-3-yl]-thiovinyl}-7-2-methoxyimino-2-(2-tritylamino-thiazol-4-yl)-acetamido]-8-oxo-5-thia-1-aza-bicyclo[4.2.0]oct-2-ene (syn isomer, Z-form) (6.8 g) is obtained in the form of a cream-coloured powder.

Infra-red spectrum (CHBr$_3$): characteristic bands (cm$^{-1}$) at 3400, 1790, 1720, 1685, 1585, 1515, 1495, 1450, 1220, 1080, 1050, 1040, 750 and 740.

Proton nuclear magnetic resonance spectrum (350 MHz, DMSO d$_6$, δ in ppm, J in Hz): 2.30 (s, 6H, >C(OCH$_3$)$_2$); 3.22 and 3.78 (2d, J=18, 2H, —SCH$_2$—); 3.85 (s, 3H, =NOCH$_3$); 3.88 (d, J=5, 2H, >NCH$_2$—); 4.50 (t, J=5, 1H, —CH(OCH$_3$)$_2$); 5.23 (d, J=4, 1H, H in the 6-position); 5.78 (d d, J=4 and 9, 1H, H in the 7-position); 6.58 and 6.70 (2d, J=10, 2H, —CH=CHS—); 6.72 (d, 1H, H of the thiazole); 6.88 (s, 1H, —COOCH<); 8.75 (s, broad, 1H, —NHC(C$_6$H$_5$)$_3$); 9.58 (d, J=9, 1H, —CONH—); 12.63 (s broad, 1H, >N—NHCO—).

A solution of 2-benzhydryloxycarbonyl-3-2-[4-(2,2-dimethoxyethyl)-5,6-dioxo-1,4,5,6-tetrahydro-1,2,4-triazin-3-yl]-thiovinyl-7-[2-methoxyimino-2-(2-tritylamino-thiazol-4-yl)-acetamido]-8-oxo-5-thia-1-aza-bicyclo[4.2.0]oct-2-ene (syn isomer, Z-form) (5 g) in formic acid (200 cc) is heated at 50° C. for 30 minutes. It is then concentrated to dryness at 30° C. under 0.05 mm Hg (0.007 kPa), the residue is taken up in acetone (200 cc), the mixture is concentrated to dryness at 20° C. under 20 mm Hg (2.7 kPa) and this operation is repeated a second time. The solid which remains is heated in acetone under reflux (200 cc), the mixture is allowed to cool and the solid is filtered off and washed with diethyl ether (100 cc). The expected product (2.8 g) is obtained. The final purification of the product can be carried out as follows: the preceding product (1 g) is suspended in water (31 cc), sodium bicarbonate (0.15 g) dissolved in water (9 cc) is added, with gentle warming to 30° C. and vigorous stirring, the pH is brought to 6.2 by supplementary addition of sodium bicarbonate, and the mixture is treated with decolorising charcoal, filtered and acidified to pH 3.2 by addition of acetic acid. The suspension obtained is heated to 80° C., treated with carbon black, filtered and left for 3 hours at 4° C. After filtration and drying, 7-[2-(2-aminothiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo-[4.2.0]oct-2-ene (syn isomer, Z-form) (0.4 g) is obtained in the form of a white powder.

Infra-red spectrum (KBr): characteristic bands (cm$^{-1}$) at 3700–2200, 1770, 1715, 1680, 1590, 1530 and 1045.

Proton nuclear magnetic resonance spectrum (350 MHz, CF$_3$COOD, δ in ppm, J in Hz): 3.77 and 3.84 (2d, J=18, 2H, —SCH$_2$); 5.18 (s, 2H, >N—CH$_2$—); 5.38 (d, J=4, 1H, H in the 6-position); 6.02 (d, J=4, 1H, H in the 7-position); 6.84 and 7.05 (2d, J=10, 2H, —CH=CHS—); 7.48 (s, 1H, H of the thiazole); 9.72 (s, 1H, —CHO).

EXAMPLE 20

A mixture of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (1 g), dimethylformamide (20 cc) and the sodium salt of 5,6-dioxo-4-(2,2-dimethoxyethyl)-3-thioxo-perhydro-1,2,4-triazine (0.44 g) is stirred for 5 hours at 60° C. It is then concentrated to dryness at 30° C. under 0.05 mm Hg (0.007 kPa), the residue is taken up in water (30 cc) and the product is filtered off and dried. A crude product (0.9 g) is obtained.

The purification can be effected in the following manner:

The preceding crude product (0.5 g) is treated with boiling isopropanol (2×10 cc) and the mixture is filtered and allowed to cool. After filtration and drying, 7-[2-(2-amino-thiazol-4-yl)-2-methoxyimino-acetamido]-2-carboxy-3-{2-[4-(2,2-dimethoxyethyl)-5,6-dioxo-1,4,5,6-tetrahydro-1,2,4-triazin-3-yl]-thiovinyl}-8-oxo-5-thia-1-aza-bicyclo[4.2.0]oct-2-ene (syn isomer, E-form) (0.215 g) is obtained in the form of a yellow powder.

Infra-red spectrum (KBr): characteristic bands in cm$^{-1}$ at 3500, 3300, 1780, 1715, 1680, 1590, 1535, 1050 and 950.

Proton nuclear magnetic resonance spectrum (350 MHz, DMSO d$_6$, δ in ppm, J in Hz): 3.62 and 3.81 (2d, J=18, —SCH$_2$—); 3.84 (s, 3H, —OCH$_3$); 3.97 (d, J=3, 2H, >NCH$_2$—); 4.58 (t, J=3, 1H, —CH(OCH$_3$)$_2$); 5.20 (d, J=4, 1H, H in the 6-position); 5.77 (dd, J=4 and 9, 1H, H in the 7-position); 6.74 (s, 1H, H of the thiazole); 6.91 (d, J=16, 1H, —CH=CHS—); 7.09 (d, J=16, 1H, =CHS—); 7.17 (s, 3H, —NH$_3$+); 9.60 (d, J=9, 1H, —COHN—);

12.64 (s, 1H, =N NHCO— or =N N=C—).
　　　　　　　　　　　　　　　　　　　　|
　　　　　　　　　　　　　　　　　　　　OH

7-[2-(2-Amino-thiazol-4-yl)-2-methoxyimino-acetamido]-2-carboxy-8-oxo-3-(2-tosyloxyvinyl)-5-thia- 120 cc) are concentrated to dryness at 30° C. under 20 mm Hg (2.7 kPa). The residue is dissolved in ethyl acetate (50 cc) and diisopropyl ether (200 cc) is added, whilst stirring. After filtration and drying, 2-benzhydryloxycarbonyl-3-{2-[4-(2,2-dimethoxyethyl-)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (anti isomer, E-form) (3.8 g) is obtained in the form of a white solid.

Infra-red spectrum (KBr): characteristic bands (cm⁻¹) at 3400, 1785, 1720, 1695, 1585, 1510, 1490, 1445, 1205, 1075, 1020, 940, 750 and 700.

Proton nuclear magnetic resonance spectrum (350 MHz, CDCl₃, δ in ppm, J in Hz): 3.41 (s, 6H, —OCH₃); 3.50 and 3.57 (2d, J=18, 2H, —SCH₂—); 4.00 (d, J=6, 2H, >NCH₂—); 4.10 (s, 3H, ═NOCH₃); 4.66 (t, J=6, 1H, >C<u>H</u>—CH₂—); 5.08 (d, J=4, 1H, H in the 6-position); 6.02 (dd, J=4 and 9, 1H, H in the 7-position); 6.77 (d, J=16, 1H, —C<u>H</u>═CH—S—); 6.96 (s, 1H, —COO-CH<); 9.55 (d, J=9, 1H, —CONH—);

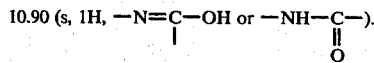

A solution of 2-benzhydryloxycarbonyl-3-2-[4-(2,2-dimethoxyethyl)-5,6-dioxo-1,4,5,6-tetrahydro-1,2,4-triazin-3-yl]-thiovinyl-7-[2-methoxyimino-2-(2-tritylamino-thiazol-4-yl)-acetamido]-8-oxo-5-thia-1-azabicyclo[4.2.0]oct-2-ene (anti isomer, E-form) (3.5 g) in formic acid (300 cc) is stirred at 50° C. for 30 minutes. It is then concentrated to dryness at 30° C. under 0.05 mm Hg (0.0067 kPa), the residue is taken up in acetone (250 cc), this mixture is concentrated to dryness at 20° C. under 20 mm Hg (2.7 kPa) and this operation is repeated a second time. The solid obtained is refluxed in acetone (100 cc), the mixture is allowed to cool and the product is filtered off and washed with diethyl ether (50 cc). The expected product (2.1 g) is obtained, and can be purified as follows: the preceding product (2 g) is suspended in water (62 cc), sodium bicarbonate (0.3 g) dissolved in water (16.5 cc) is added under nitrogen, with very vigorous stirring, and the mixture is warmed to 30° C., treated with animal charcoal and filtered. The filtrate is at pH 5.4; it is acidified to pH 3.2 by adding acetic acid, heated to 80° C., treated with charcoal, filtered and allowed to cool to 4° C. for 1 hour. After filtration and drying, 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (anti isomer, E-form) (1.2 g) is obtained in the form of a cream-coloured powder.

Infra-red spectrum (KBr): characteristic bands (cm⁻¹) at 3700-2300, 1770, 1715, 1685, 1630, 1590, 1525, 1060, 1030 and 940.

Proton nuclear magnetic resonance spectrum (350 MHz, CF₃COOD, δ in ppm, J in Hz): 3.86 (s broad, 2H, —SCH₂—); 4.43 (s, 3H, —NOCH₃); 5.18 (s broad, 2H, >N-CH₂—); 5.35 (d, J=4, 1H, H in the 6-position); 5.88 (d, J=4, 1H, H in the 7-position); 7.24 and 7.74 (2d, J=16, 2H, —CH═CHS—); 8.14 (s, 1H, H of the thiazole); 9.77 (s, 1H, —CHO).

2-Benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (anti isomer, E-form) can be prepared as follows:

7-Amino-2-benzhydryloxycarbonyl-3-(2-tosyloxyvinyl)-8-oxo-5-oxide-5-thia-1-aza-bicyclo[4.2.0]oct-2-ene (E isomer) (8.5 g) is dissolved in methylene chloride (100 cc), 2-methoxyimino-2-(2-tritylamino-thiazol-4-yl)-acetic acid (anti isomer) (7.1 g) prepared according to R. BUCOURT, Tetrahedron 34, 2233-2243 (1978) and 4-dimethylaminopyridine (0.1 g) are added, the mixture is cooled to 5° C. and a solution of N,N'-dicyclohexylcarbodiimide in methylene chloride (50 cc) is added dropwise in the course of 25 minutes. The mixture is stirred for 2 hours at 20° C. and is concentrated to dryness at 20° C. under 20 mm Hg (2.7 kPa), the residue is taken up in ethylacetate (300 cc) and the solution is filtered, wased with water (100 cc) and saturated sodium chloridesolution (100 cc), dried over sodium sulphate, agan filtered and concentrated to dryness at 20° C. under 20 mm Hg (2.7 kPa). The product is fixed on Merck silica gel (0.06-0.2 mm) (50 g) and is chromatographed over a column (column diameter: 4 cm, height: 60 cm) of Merck silica gel (0.06-0.2 mm) (200 g). Elution is carried out successively with the following mixtures of cyclohexane and ethyl acetate: a 70:30 (by volume) mixture (0.5 liter), a 60:40 (by volume) mixture (0.5 liter) and a 50:50 (by volume) mixture (4 liters), 120 cc fractions being collected. Fractions 17 to 32 are concentrated to dryness at 20° C. under 20 mm Hg (2.7 kPa) and 2-benzhydryloxycarbonyl-7-[2-methoxyimino-2-(2-tritylaminothiazol-4-yl)-acetamido]-8-oxo-5-oxide-3-(2-tosyloxyvinyl)-5-thia-1-aza-bicyclo[4.2.0]oct-2-ene (syn isomer, E-form) (7.33 g) is obtained.

Infra-red spectrum (CHBr₃): characteristic bands (cm⁻¹): 3400, 3280, 1805, 1730, 1680, 1555, 1520, 1495, 1450, 1375, 1190, 1180, 1070, 1035, 1025 and 935.

Proton nuclear magnetic resonance spectrum (350 MHz, CDCl₃, δ in ppm, J in Hz): 2.44 (s, 3H, —C₆H₄C<u>H</u>₃);

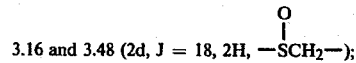

4.14 (s, 3H, ═NOCH₃); 4.59 (d, J=4, 1H, H in the 6-position); 6.34 (dd, J=4 and 9, 1H, H in the 7-position); 6.90 (s, 1H, —COOCH<); 6.92 and 7.15 (2d, J=12, 2H, —CH═CH—); 7.47 (s, 1H, H in the 5-position of the thiazole); 7.43 and 7.77 (2d, J=8, 4H, —OSO₂C₆H₄CH₃).

EXAMPLE 19

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, Z-form) (22.59 g), dimethylformamide (112 cc), 4-(2,2-dimethoxyethyl)-5,6-dioxo-3-thioxo-perhydro-1,2,4-triazine (6.29 g) and N,N-diisopropylethylamine (4.27 cc) is stirred for 5 hours under nitrogen at 50° C. It is then poured into water (500 cc) in the presence of ethyl acetate (500 cc), and the organic phase is decanted, washed with water (2×250 cc), 0.1 N hydrochloric acid (100 cc) and saturated aqueous sodium chloride (200 cc), dried over sodium sulphate, filtered and concentrated to dryness at 20° C. under 20 mm Hg (2.7 kPa). The product is fixed on Merck silica gel (0.06-0.2 mm) (75 g) and is chromatographed on a column (column diameter: 4 cm, height: 80 cm) of Merck silica gel (0.06-0.2 mm) (500 g). Elution is carried out with ethyl acetate (4 liters), 300 cc fractions tion); 6.75 (s, 1H, H of the thiazole); 6.85 (d, J=16, 1H, —C<u>H</u>=CHS—); 6.92 (d, J=9, 1H, —CONH—);

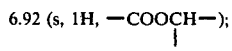

A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (1 g) in pure formic acid (25 cc) is heated at 50° C. for 30 minutes. It is then concentrated to dryness at 40° C. under 20 mm Hg (2.7 kPa), the residue is taken up in acetone (20 cc), the mixture is concentrated to dryness at 20° C. under 20 mm Hg (2.7 kPa), the operation is repeated twice, the residue is triturated in acetone (40 cc), this mixture is heated under reflux for 10 minutes, whilst stirring, and the suspension is cooled and filtered. A yellow powder (0.6 g) is obtained, which is purified as follows:

The preceding product (50 mg) is dissolved in pure formic acid (5 cc), Merck silica gel (0.05–0.2 mm) (2.5 g) is added and the mixture is concentrated to dryness at 30° C. under 0.05 mm Hg (0.007 kPa). The powder is deposited on a column (column diameter: 2.5 cm, height: 3 cm) of silica gel (5 g) and elution is carried out with a 3:2:2 (by volume) mixture of ethyl acetate/acetic acid/water (100 cc), 10 cc fractions being collected. Fractions 2 to 7 are concentrated to dryness (30° C., under 0.05 mm Hg; 0.007 kPa) and 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (30 mg) is obtained in the form of a cream-coloured powder, of which the infra-red characteristics and nuclear magnetic resonance characteristics are identical to those of the product of Example 16, variant 1(a).

4-(2,2-Diethoxyethyl)-5,6-dioxo-3-thioxo-perhydro-1,2,4-triazine can be prepared as follows:

4-(2,2-Diethoxyethyl)-thiosemicarbazide (18.6 g) and diethyl oxalate (13.15 g) are added successively to a solution of sodium (2.07 g) in dry methanol (70 cc) and the mixture is refluxed under nitrogen for 4 hours. The cooled mixture is diluted with water (300 cc) and ethyl acetate (150 cc) and then acidified to pH=2 with concentrated hydrochloric acid whilst cooling to 4° C. The mixture is allowed to settle out, the aqueous phase is extracted with ethyl acetate (3×100 cc), and the organic phase is washed with a saturated sodium chloride solution (3×100 cc), dried over sodium sulphate, filtered and concentrated to dryness at 20° C. under 20 mm Hg (2.7 kPa). A thick yellow oil (22.6 g) consisting principally of 4-(2,2-diethoxyethyl)-5,6-dioxo-3-thioxoperhydro-1,2,4-triazine is obtained.

4-(2,2-Diethoxyethyl)-thiosemicarbazide can be prepared as follows:

Hydrazine hydrate (27.3 cc) is added over the course of 1 hour to a solution of 2,2-diethoxyethyl isothiocyanate (94 g) in ethanol (150 cc), at 4° C. The mixture is stirred for a further 20 minutes at 4° C. and is then filtered; the desired product (86 g) is obtained as a white solid, m.p.=96° C.

EXAMPLE 18

A mixture of 2-benzhydryloxycarbonyl-7-[2-methoxyimino-2-(2-tritylamino-thiazol-4-yl)-acetamido]8-oxo-5-oxide-3-(2-tosyloxyvinyl)-5-thia-1-aza-bicyclo-[4.2.0]oct-2-ene (anti isomer, E-form) (7.33 g), dimethylformamide (37 cc), 4-(2,2-dimethoxyethyl)-5,6-dioxo-3-thioxo-perhydro-1,2,4-triazine (2.04 g) and N,N-diisopropylethylamine (1.39 cc) is stirred for 2 hours 30 minutes at 50° C., under nitrogen. The mixture is poured into water (250 cc) and this mixture is extracted with ethyl acetate (250 cc); the extract is washed with water (2×200 cc), 0.1 N hydrochloric acid (100 cc), water (100 cc) and a saturated sodium chloride solution (100 cc), dried over sodium sulphate, filtered and concentrated to dryness at 20° C. under 20 mm Hg (2.7 kPa). The residue is taken up in diethyl ether (100 cc) and the insoluble matter is filtered off. After drying, 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)acetamido]-8-oxo-5-oxide-5-thia-1-aza-bicyclo[4.2.0]oct-2-ene (anti isomer, E-form) (6.7 g) is obtained in the form of a cream-coloured powder.

Infra-red spectrum (KBr): characteristic bands (cm$^{-1}$) at 3400–3250, 1800, 1725, 1696, 1590, 1555, 1520, 1495, 1450, 1210, 1080, 1060, 1035, 1025, 940, 755, 745 and 700.

Proton nuclear magnetic resonance spectrum (350 MHz, DMSO, δ in ppm, J in Hz): 3.35 (s, 6H, —OCH₃);

3.98 (hump, 5H, =NOCH₃ and —NCH₂—); 3.76 and 4.23 (2d,

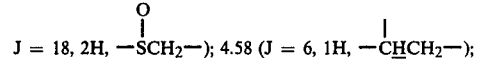

5.14 (d, J=4, 1H, H in the 6-position); 6.08 (dd, J=4 and 9, 1H, H in the 7-position); 6.98 (s, 1H, —CO₂CH(C₆H₅)₂; 7.03 and 7.17 (2d, J=16, 2H, —CH=CH—); 8.62 (s, 1H, —N<u>H</u>— of the thiazole); 9.57 (d, J=9, 1H, —CONH— in the 7-position);

12.72 (s, 1H, —N=C—OH or —NH—C—).
  |  ‖
  |  O

A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (anti isomer, E-form) (6.7 g) in methylene chloride (70 cc) and dimethylacetamide (2.3 cc) is treated with phosphorus trichloride (1.1 cc) at −8° C. for 35 minutes. The mixture is diluted with ethyl acetate (200 cc) and this mixture is washed with a saturated sodium bicarbonate solution (200 cc) and water (2×100 cc), dried over sodium sulphate, filtered and concentrated to dryness at 20° C. under 20 mm Hg (2.7 kPa). The residue is fixed on Merck silica gel (0.06–0.2 mm) (20 g) and is chromatographed on a column (column diameter: 3.5 cm, height: 60 cm) of Merck silica gel (0.06–0.2 mm) (140 g). Elution is carried out with a 20:80 (by volume) mixture of cyclohexane and ethyl acetate (1 liter) and then with ethyl acetate (1 liter). Fractions 5 to 12 (volume of the fractions:

Infra-red spectrum (KBr): characteristic bands in cm$^{-1}$ at 3420, 3200, 1760, 1710, 1670, 1600, 1530, 1040 and 945.

Proton nuclear magnetic resonance spectrum (350 MHz, DMSO d$_6$+D$_2$O, δ in ppm, J in Hz): 3.54 (AB limit, 2H, —SCH$_2$—); 5.06 (d, J=4, 1H, H in the 6-position); 5.08 (s, 1H, —C<u>H</u>(OH)$_2$); 5.63 (d, J=4, 1H, H in the 7-position); 6.44 (d, J=16, 1H, —C<u>H</u>=CHS—); 6.76 (s, 1H, H of the thiazole); 7.24 (d, J=16, 1H, =CHS—); 9.60 (s, 0.05 H, —CHO).

The nuclear magnetic resonance spectrum of this sodium salt, as the aldehyde hydrate, recorded in CF$_3$COOD, shows that in solution in this solvent the product is in the aldehyde form [spectrum identical to that described in 1. (a)].

3. A solution of L-lysine (0.233 g) in distilled water (2.8 cc) is saturated with carbon dioxide by bubbling the latter through the solution. The resulting solution is added to a suspension of 7-[2-(2-aminothiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1 g) in distilled water (2.8 cc). After stirring for 25 minutes at 20° C., the solution is filtered and the filtrate is lyophilised. This gives the lysine salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]-oct-2-ene (syn isomer, E-form), as the aldehyde hydrate (1.23 g), in the form of a cream-coloured lyophilisate.

Infra-red spectrum (KBr): characteristic bands (cm$^{-1}$) at 3420, 3200, 1765, 1710, 1660, 1600, 1530, 1040 and 945.

4-(2,2-Dimethoxyethyl)-5,6-dioxo-3-thioxo-perhydro-1,2,4-triazine can be prepared as follows:

A solution of sodium methylate is prepared by dissolving sodium (4.15 g) in methanol (140 cc), and 4-(2,2-dimethoxyethyl)-thiosemicarbazide (32.3 g) and ethyl oxalate (26.3 g) are added. The mixture is refluxed, with stirring, for 4 hours and is then allowed to cool. After standing overnight, the suspension obtained is filtered and the precipitate is washed with ether (3×25 cc). The solid is dissolved in water (40 cc) and after cooling to about 4° C. the solution is acidified to pH 3 by means of 4 N hydrochloric acid and left at 4° C. for 30 minutes. After filtering and drying, 4-(2,2-dimethoxyethyl)-5,6-dioxo-3-thioxo-perhydro-1,2,4-triazine (12 g) is obtained in the form of a white solid. Instantaneous m.p. (Kofler)=172° C. (with decomposition).

Infra-red spectrum (KBr): characteristic bands in cm$^{-1}$ at 3280, 3250, 1695, 1380, 1130 and 1050.

Proton nuclear magnetic resonance spectrum (80 MHz, DMSO d$_6$, δ in ppm, J in Hz): 3.30 (s, 6H, —CH(OC<u>H</u>$_3$)$_2$); 4.38 (d, J=5.5, 2H, >NCH$_2$—); 4.94 (t, J=5.5, 1H, —C<u>H</u>(OCH$_3$)$_2$).

4-(2,2-Dimethoxyethyl)-thiosemicarbazide can be prepared as follows:

2,2-Dimethoxyethyl isothiocyanate (37.7 g) is added in the course of 1 hour to a solution of hydrazine hydrate (14.35 g) in ethanol (40 cc), whilst stirring at a temperature of between 5° and 9° C. After 12 hours at 4° C., the mixture is concentrated to dryness at 20° C. under reduced pressure (20 mm Hg; 2.7 kPa). The yellow syrup obtained crystallises after seeding. The solid is dissolved in hot methanol (50 cc) and the solution is filtered and diluted with diethyl ether (200 cc). After about ten hours at 4° C., the mixture is filtered and 4-(2,2-dimethoxyethyl)-thiosemicarbazide (32.3 g) is obtained in the form of a white solid.

Instantaneous m.p. (Kofler)=69° C.

EXAMPLE 17

2-Benzhydryloxycarbonyl-3-{2-[4-(2,2-diethoxyethyl)-5,6-dioxo-1,4,5,6-tetrahydro-1,2,4-triazin-3-yl]thiovinyl}-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) is prepared as described in Example 16 from the tosylate (15.06 g) and 4-(2,2-diethoxyethyl)-5,6-dioxo-3-thioxo-perhydro-1,2,4-triazine (8 g) in the presence of N,N-diisopropylethylamine (2.85 cc) in dimethylformamide (75 cc). Chromatography is carried out on a column (column diameter: 5 cm, height: 40 cm) of Merck silica gel (0.05–0.2 mm) (250 g), elution being effected with a 30:70 (by volume) mixture of cyclohexane and ethyl acetate (5 liters). The expected product (8.35 g) is obtained in the form of a brown-red froth.

Proton nuclear magnetic resonance spectrum (350 MHz, CDCl$_3$, δ in ppm, J in Hz): 1.15 (t, J=7, 6H, —CH$_3$); 3.38 (d, J=18, 1H, —SCH—); 3.50 and 3.72 (2 q AB, J=9 and 7, 4H, —OCH$_2$—); 3.90 to 4.20 (hump, 6H, >NCH$_2$—, —OCH$_3$ and —SCH—); 4.65 (d, J=4, 1H, H in the 6-position); 4.72 (t, J=5, 1H, —CH(O Et)$_2$); 6.04 (dd, J=4 and 9, 1H, H in the 7-position); 6.70 (s, 1H, H of the thiazole); 6.85 (d, J=16, 1H, —CH=CHS—);

6.97 (s, 1H, —COOC<u>H</u>—);
|

11.94 (s broad, 1H, =NNHCO— or =N N=C—).
                                         |
                                         OH A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.30 g) in methylene chloride (100 cc) and dimethylacetamide (2.88 cc) is treated with phosphorus trichloride (1.33 cc) at −10° C. for 2 hours. The product is treated as described in Example 16, by chromatography on a column (column diameter: 4 cm, height: 44 cm) of Merck silica gel (0.05–0.2 mm) (200 g) and elution with a 30:70 (by volume) mixture of cyclohexane and ethyl acetate (2 liters). 2-Benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (5.3 g) is obtained in the form of a yellow-orange froth. The product is purified by dissolving it in ethyl acetate (20 cc) and adding isopropyl ether (100 cc); this gives a cream-coloured solid (4.5 g).

Infra-red spectrum (CHBr$_3$): characteristic bands in cm$^{-1}$ at 3390, 1785, 1720, 1685, 1585, 1515, 1495, 1050, 940, 750 and 740.

Proton nuclear magnetic resonance spectrum (350 MHz, CDCl$_3$, δ in ppm, J in Hz): 1.18 (t, J=7, 6H, —CH$_3$); 3.52 and 3.75 (2 q AB, J=7 and 10, 4H, —OCH$_2$—); 3.60 (d, J=18, 1H, —SCH=); 3.97 to 4.06 (hump, 6H, —OCH$_3$, >NCH$_2$—, —SCH=); 4.76 (t, J=5, 1H, —C<u>H</u>(O Et)$_2$); 5.09 (d, J=4, 1H, H in the 6-position); 5.92 (dd, J=4 and 9, 1H, H in the 7-posi- Infra-red spectrum (KBr): characteristic bands in cm$^{-1}$ at 3380, 3250, 1795, 1720, 1685, 1520, 1490, 1445, 1040, 940, 760 and 700.

Proton nuclear magnetic resonance spectrum (350 MHz, CDCl$_3$, δ in ppm, J in Hz): 3.34 and 4.12 (2d, J=18, 2H, —SCH$_2$—); 3.40 (s, 6H, —CH(OCH$_3$)$_2$); 3.94 to 4.06 (m, 5H, —OCH$_3$ and >NCH$_2$—); 4.60 to 4.68 (m, 2H, H in the 6-position and —CH(OCH$_3$)$_2$); 6.07 (dd, J=4 and 9, 1H, H in the 7-position); 6.70 (s, 1H, H of the thiazole); 6.82 (d, J=16, 1H, —CH=C-HS—);

6.96 (s, 1H, —COOCH—).

A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form (8.5 g) and dimethylacetamide (3 cc) in methylene chloride (100 cc) is treated with phosphorus trichloride (1.40 cc) at −10° C., whilst stirring; phosphorus trichloride (0.7 cc) is added after 1 hour 30 minutes and the same amount is added again after a further 2 hours. The mixture is diluted with ethyl acetate (600 cc) and this mixture is washed with a 2% strength sodium bicarbonate solution (2×150 cc) and a half-saturated sodium chloride solution (2×150 cc), dried over sodium sulphate, filtered and concentrated to dryness at 20° C. under a pressure of 20 mm Hg (2.7 kPa). The residue is taken up in ethyl acetate (50 cc) and the solution is chromatographed over a column (column diameter: 3 cm, height: 25 cm) of Merck silica gel (0.05–0.2 mm) (100 g). Elution is carried out with ethyl acetate (1 liter), 200 cc fractions being collected. Fractions 3, 4 and 5 are concentrated to dryness (20 mm Hg; 2.7 kPa) at 20° C. 2-Benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (7.5 g) is obtained in the form of an orange-coloured froth.

Infra-red spectrum (CHBr$_3$): characteristic bands in cm$^{-1}$ at 3380, 1780, 1720, 1680, 1515, 1490, 1445, 755 and 740.

Proton nuclear magnetic resonance spectrum (350 MHz, CDCl$_3$, δ in ppm, J in Hz): 3.40 (s, 6H, —CH(OCH$_3$)$_2$); 3.54 and 3.66 (2d, J=18, 2H, —SCH$_2$—); 3.98 (d, J=5, 2H, >NCH$_2$—); 4.02 (s, 3H, =NOCH$_3$); 4.65 (t, J=5, 1H, —CH(OCH$_3$)$_2$); 5.08 (d, J=4, 1H, H in the 6-position); 5.92 (dd, J=4 and 9, 1H, H in the 7-position); 6.73 (s, 1H, H of the thiazole); 6.83 (d, J=16, 1H, —CH=CHS—);

6.95 (s, 1H, —COOCH—).

1. (a) A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.05 g) in 98% strength formic acid (20 cc) is kept at 50° C. for 30 minutes. The mixture is then concentrated to dryness at 50° C. under a pressure of 0.05 mm Hg (0.007 kPa), the residue is taken up in acetone (50 cc), this mixture is concentrated to dryness at 30° C. under reduced pressure (20 mm Hg; 2.7 kPa) and this operation is repeated a second time.

The solid obtained is treated with acetone (50 cc) at 60° C. for 10 minutes whilst stirring, the cooled suspension is filtered and the residue is dried, giving 7-[2-(2-a mino-thiazol-4-yl)-2-methoxyimino-acetamido]-2-carboxy-3-{2-[5,6-dioxo-4-formylmethyl-1,4,5,6-tetrahydro-1,2,4-triazin-3-yl]-thiovinyl}-8-oxo-5-thia-1-azabicyclo[4.2.0]oct-2ene (syn isomer, E-form) (0.51 g).

Infra-red spectrum (KBr): characteristic bands in cm$^{-1}$ at 3500, 2300, 1770, 1715, 1680, 1540, 1050 and 950.

Proton nuclear magnetic resonance spectrum (350 MHz, CF$_3$COOD, δ in ppm, J in Hz): 3.87 (AB limit, 2H, —SCH$_2$—); 4.30 (s, 3H, —OCH$_3$); 5.20 (s broad, 2H, >NCH$_2$—); 5.38 (d, J=4, 1H, H in the 6-position); 6.03 (d, J=4 1H, H in the 7-position); 7.22 (d, J=16, 1H, —CH=CHS—); b 7.50 (s, 1H, H of the thiazole); 7.72 (d, J=16, 1H, =CHS—); 9.74 (s broad, 1H, —CHO).

Proton nuclear magnetic resonance spectrum (350 MHz, CF$_3$COOD+D$_2$O, δ in ppm, J in Hz): 3.82 (AB limit, 2H, —SCH$_2$—); 4.26 (s, 1H, —OCH$_3$); 5.10 (s broad, 2H, >NCH$_2$—); 5.31 (d, J=4, 1H, H in the 6-position); 5.96 (d, J=4, 1H, H in the 7-position); 7.06 (d, J=16, 1H, —CH=CHS—); 7.43 (s, 1H, H of the thiazole); 7.56 (d, J=16, 1H, =CHS—); 9.67 (s broad, 1H, —CHO).

(b) It is also possible to proceed as follows.

A mixture of 2-benzhydryloxycarbonyl-3-{2-[4-(2,2-d imethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1 g), pure formic acid (40 cc), water (1.27 cc) and Merck silica gel (0.05–0.2 mm) (6 g) is heated at 50° C. for 30 minutes, whilst stirring. The mixture is concentrated to dryness at 30° C. under 20 mm Hg (2.7 kPa) and the powder obtained is deposited on a column (column diameter: 2 cm, height: 17 cm) of Merck silica gel (0.05–0.2 mm) (20 g). Elution is carried out with a 3:1:1 (by volume) mixture of ethyl acetate/formic acid/water, 10 cc fractions being collected. Fractions 3 to 26 are concentrated to dryness at 27° C. under 0.05 mm Hg (0.007 kPa). The yellow solid obtained is triturated in ether (60 cc), the mixture is filtered, the residue is dried and 7-[2-(2-a mino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (syn isomer, E-form) (0.4 g) is obtained, the nuclear magnetic resonance characteristics and infra-red characteristics of this product being identical to those of the product described in (a).

2. A mixture of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.297 g), water (10 cc) and sodium bicarbonate (0.042 g) is stirred under nitrogen until all has dissolved, and the solution is filtered and lyophilised. The sodium salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.-0]oct-2-ene (syn isomer, E-form) as the aldehyde hydrate (0.28 g) is obtained.

6.94 (s, 1H, —COOCH—);

11.87 (s broad, 1H, =N—NHCO— or =N—N=C—).
                                              |
                                              OH A solution of 2-benzhydryloxycarbonyl-3-[2-(4-benzyl-5,6-dioxo-1,4,5,6-tetrahydro-1,2,4-triazin-3-yl)thiovinyl]-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (2.68 g) in a mixture of methylene chloride (25 cc) and dimethylacetamide (0.95 cc) is treated with phosphorus trichloride (0.44 cc) at −10° C. for 30 minutes, whilst stirring. The mixture is diluted with ethyl acetate (200 cc) and this mixture is washed with a 5% strength sodium bicarbonate solution (50 cc), water (2×50 cc) and a saturated sodium chloride solution (50 cc), dried over sodium sulphate, filtered and concentrated to dryness at 20° C. under 20 mm Hg (2.7 kPa). The product is first fixed to Merck silica gel (0.05–0.2 mm) (20 g) and is then deposited on a column (column diameter: 1.4 cm, height: 15 cm) of silica gel (40 g). Elution is carried out with a 20:80 (by volume) mixture of cyclohexane and ethyl acetate (1 liter), 60 cc fractions being collected. Fractions 2 to 13 are evaporated to dryness at 20° C. under 20 mm Hg (2.7 kPa). 2-Benzhydryloxycarbonyl-3-[2-(-4-benzyl-5,6-dioxo-1,4,5,6-tetrahydro-1,2,4-triazin-3-yl)-thiovinyl]-7-[2-methoxyimino-2-(2-tritylamino-thiazol-4-yl)acetamido]-8-oxo-5-thia-1-aza-bicyclo[4.2.0]oct-2-ene (syn isomer, E-form) (1.78 g) is obtained in the form of a cream-coloured froth.

Infra-red spectrum (CHBr₃): characteristic bands in cm⁻¹ at 3390, 1785, 1720, 1680, 1520, 1495, 1450, 1045 and 940.

Proton nuclear magnetic resonance spectrum (350 MHz, CDCl₃, δ in ppm, J in Hz): 3.54 and 3.64 (2d, J=18, 2H, —SCH₂—); 4.02 (s, 3H, —OCH₃); 5.06 (d, J=4, 1H, H in the 6-position); 5.10 (s, 2H, >NCH₂—); 5.92 (dd, J=4 and 9, 1H, H in the 7-position); 6.74 (s, 1H, H of the thiazole); 6.82 (d, J=16, 1H, —CH=C-HS—); 6.95 (s, 1H, —COOCH—); 7.03 (d, J=9, 1H, —CONH—); 11.60

(s, 1H, =NNH—CO— or =N—N=C—).
                                 |
                                 OH

A solution of 2-benzhydryloxycarbonyl-3-[2-(-4-benzyl-5,6-dioxo-1,4,5,6-tetrahydro-1,2,4-triazin-3-yl)thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) in a mixture of formic acid (16 cc) and water (8 cc) is stirred at 50° C. for 30 minutes. The cooled solution is filtered and concentrated to dryness at 50° C. under 20 mm Hg (2.7 kPa). The residue is taken up in ethanol (50 cc), the mixture is evaporated to dryness at 20° C. under 20 mm Hg (2.7 kPa) and this operation is repeated twice. The yellow solid obtained is treated with ethanol (100 cc) under reflux. A slight amount of insoluble matter is filtered off and the solution is concentrated to 50 cc (20° C., 20 mm Hg; 2.7 kPa). After cooling this residue for 3 hours at 4° C., it is filtered and the precipitate is dried, giving 7-[2-(2-amino-thiazol-4-yl)-2-methoxyimino-acetamido]-3-[2-(4-benzyl-5,6-dioxo-1,4,5,6-tetrahydro-1,2,4-triazin-3-yl)-thiovinyl]-2-carboxy-8-oxo-5-thia-1-aza-bicyclo[4.2.0]oct-2-ene (syn isomer, E-form) (0.69 g) in the form of a yellow powder.

Infra-red spectrum (KBr): characteristic bands in cm⁻¹ at 3500, 2300, 1770, 1710, 1680, 1585, 1530, 1045 and 945.

Proton nuclear magnetic resonance spectrum (350 MHz, DMSO d₆, δ in ppm, J in Hz): 3.58 and 3.78 (2d, J=18, 2H, —SCH₂—); 3.88 (s, 3H, —OCH₃); 5.10 (s, 2H, >NCH₂—); 5.18 (d, J=4, 1H, H in the 6-position); 5.78 (dd, J=4 and 9, 1H, H in the 7-position); 6.75 (s, 1H, H of the thiazole); 6.86 (d, J=16, 1H, —CH=C-HS—); 7.05 (d, J=16, 1H, =CHS—); 7.20 (s, 3H, —NH₃⁺); 9.60 (d, J=9, 1H, —CONH—);

12.69 (s, 1H, =NNHCO— or =N N=C—).
                                      |
                                      OH

The triazine starting material can be prepared as follows:

4-Benzyl-thiosemicarbazide (9.06 g), prepared in accordance with W. BAIRD et al., J. Chem. Soc. 2527 (1927), followed by diethyl oxalate (6.76 cc) is added to a solution, at 20° C., of sodium (1.15 g) in methanol (50 cc). The mixture is heated under reflux for 2 hours and cooled at 4° C. for 3 hours, and the precipitate is filtered off. The sodium salt thus obtained is dissolved in water (50 cc) and the solution is acidified to pH=2 by adding 1 N hydrochloric acid whilst cooling to 4° C. After one hour, the product is filtered off and dried, and 4-benzyl-5,6-dioxo-3-thioxo-perhydro-1,2,4-triazine (9.2 g) is obtained.

Infra-red spectrum (KBr): characteristic bands in cm⁻¹ at 3440, 3320, 1680, 1625, 1495, 1450, 1350, 730 and 695.

EXAMPLE 16

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]-oct-2-ene (syn isomer, E-form) (10 g), dimethylformamide (50 cc), 4-(2,2-dimethoxyethyl)-5,6-dioxo-3-thioxo-perhydro-1,2,4-triazine (2.56 g) and N,N-diisopropylethylamine (1.9 cc) is stirred at 60° C. under nitrogen for 2 hours 30 minutes. It is then diluted with ethyl acetate (600 cc) and this mixture is washed with water (2×125 cc), 1 N hydrochloric acid (150 cc), a half-saturated sodium bicarbonate solution (2×150 cc) and a half-saturated sodium chloride solution (2×150 cc), dried over sodium sulphate, filtered and concentrated to dryness under reduced pressure (20° C., 20 mm Hg; 2.7 kPa). The residue, dissolved in methylene chloride (30 cc), is chromatographed over a column (column diameter: 7 cm, height: 35 cm) of Merck silica gel (0.02–0.06 mm). Elution is carried out with a 40:60 (by volume) mixture of cyclohexane ethyl acetate (7 liters) under a pressure of 40 kPa, 100 cc fractions being collected. Fractions 27 to 46 are concentrated to dryness at 20° C. under reduced pressure (20 mm Hg; 2.7 kPa). 2-Benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.5 g) is obtained in the form of a beige-coloured froth.

The product is fixed to Merck silica gel (0.05–0.2 mm) (15 g) and the powder is placed in a column (column diameter: 3 cm, height: 30 cm) of silica gel (100 g). Elution is carried out with a 20:80 (by volume) mixture of cyclohexane and ethyl acetate (1.5 liters), 60 cc fractions being collected. Fractions 3 to 18 are concentrated to dryness at 20° C. under 20 mm Hg (2.7 kPa). 2-B enzhydryloxycarbonyl-3-{2-[5,6-dioxo-4-(2-methylthioethyl)-1,4,5,6-tetrahydro-1,2,4-triazin-3-yl]-thiovinyl}7-[2-methoxyimino-2-(2-tritylamino-thiazol-4-yl)-acetamido]-8-oxo-5-thia-1-aza-bicyclo[4.2.0]oct-2-ene (syn isomer, E-form) (4.16 g) is obtained in the form of a yellow froth.

Infra-red spectrum (KBr): characteristic bands in cm$^{-1}$ at 1785, 1715, 1680, 1525, 1490, 1445, 1040, 940, 750 and 700.

Proton nuclear magnetic resonance spectrum (350 MHz, CDCl$_3$, δ in ppm, J in Hz): 2.18 (s, 3H, —SCH$_3$); 2.78 (t, J=6, 2H, —CH$_2$S—); 3.58 and 3.67 (d, J=18, 2H, —SCH$_2$—); 3.95 to 4.05 (m, 5H, —OCH$_3$ and >NCH$_2$—); 5.08 (d, J=4, 1H, H in the 6-position); 5.93 (dd, J=4 and 9, 1H, H in the 7-position); 6.74 (s, 1H, H of the thiazole); 6.82 (d, J=16, 1H, —C$\underline{H}$=CHS—);

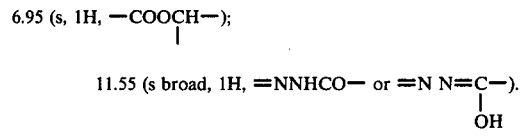

A solution of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (4.16 g) in a mixture of formic acid (40 cc) and water (20 cc) is stirred at 50° C. for 30 minutes. The cooled mixture is then filtered and concentrated to dryness under reduced pressure (40° C., 20 mm Hg; 2.7 kPa). The residue is taken up in ethanol (100 cc) and the mixture is concentrated to dryness at 20° C. under 20 mm Hg 2.7 kPa). This operation is repeated twice, the solid is then dissolved in boiling ethanol (250 cc) and the solution is filtered hot and concentrated to 20 cc (20° C., 20 mm Hg; 2.,7 kPa). The precipitate is filtered off and dried, giving 7-[2-(2-amino-thiazol-4-yl)-2-methoxyimino-acetamido]-2-carboxy-3- 2-[5,6-dioxo-4-(2-methylthioethyl)-1,4,5,6-tetrahydro-1,2,4-triazin-3-yl]-thiovinyl -8-oxo-5-thia-1-aza-bicyclo[4.2.0]oct-2-ene (syn isomer, E-form) (1.95 g).

Infra-red spectrum (KBr): characteristic bands in cm$^{-1}$ at 3600, 2200, 1770, 1710, 1680, 1585, 1535, 1040 and 945.

Proton nuclear magnetic resonance spectrum (350 MHz, DMSO d$_6$, δ in ppm, J in Hz): 2.12 (s, 3H, —SCH$_3$); 2.73 (t, J=7, 2H, —C$\underline{H}_2$S—CH$_3$); 3.64 and 3.82 (2d, J=18, 2H, —SCH$_2$—); 3.85 (s, 3H, —OCH$_3$); 4.0 (t, J=7, 2H, >NCH$_2$—); 5.20 (d, J=4, 1H, H in the 6-position); 5.78 (dd, J=4 and 9, 1H, H in the 7-position); 6.73 (s, 1H, H of the thiazole); 6.92 (d, J=16, 1H, —CH=CHS—); 7.12 (d, J=16, 1H, =CHS—); 7.15 (s, 3H, —NH$_3$+); 9.66 (d, J=9, 1H, —CONH—);

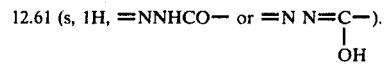

5,6-Dioxo-4-(2-methylthioethyl)-3-thioxo-perhydro-1,2,4-triazine can be prepared as follows:

4-(2-methylthioethyl)-thiosemicarbazide (13.6 g) is added to a solution of sodium (1.83 g) in methanol (80 cc), after which diethyl oxalate (10.8 cc) is added dropwise over 15 minutes. The mixture is heated under reflux for 3 hours and allowed to cool, and diethyl ether (1 liter) is added whilst stirring. The precipitate is filtered off. The yellow solid obtained is dissolved in water (100 cc), and the pH of the solution is brought to 2 by adding 1 N hydrochloric acid whilst cooling in an ice-bath.

After filtration and drying, a white solid (3 g) is obtained, which is purified by 2 successive crystallisations from boiling water (50 cc). 5,6-Dioxo-4-(2-methylthioethyl)-3-thioxo-perhydro-1,2,4-triazine (2.4 g) is obtained.

Infra-red spectrum (KBr): characteristic bands in cm$^{-1}$ at 3550, 3490, 3280, 3220 and 1690.

4-(2-Methylthioethyl)-thiosemicarbazide can be prepared by adding hydrazine hydrate (6.8 cc) to a solution of methyl N-(2-methylthioethyl)-dithiocarbamate (26 g) in ethanol (500 cc) and heating under reflux for 3 hours. After concentrating the mixture to dryness at 20° C. under 20 mm Hg (2.7 kPa), the oil obtained is triturated in diethyl ether (100 cc). The crystals formed are filtered off and dried. The thiosemicarbazide (18.16 g), m.p. 70° C., is obtained.

Infra-red spectrum (KBr): characteristic bands in cm$^{-1}$ at 3320, 3200, 3160, 1635, 1550 and 1260.

EXAMPLE 15

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10.04 g), dimethylformamide (200 cc), 4-benzyl-5,6-dioxo-3-thioxoperhydro-1,2,4-triazine (2.82 g) and diisopropylethylamine (2.1 cc) is stirred at 60° C. for 3 hours. It is then poured into ethyl acetate (500 cc) and this mixture is washed with water (2×250 cc) and a saturated sodium chloride solution (2×200 cc), dried over sodium sulphate, filtered and concentrated to dryness at 20° C. under 20 mm Hg (2.7 kPa). The residue is dissolved in a 20:80 (by volume) mixture of cyclohexane and ethyl acetate (30 cc) and this solution is chromatographed over a column (column diameter: 8 cm, height: 30 cm) of Merck silica gel (0.04–0.06 mm) (200 g). Elution is carried out with a 20:80 (by volume) mixture of cyclohexane and ethyl acetate (2 liters), a 10:90 (by volume) mixture of cyclohexane and ethyl acetate (2 liters) and ethyl acetate (2 liters) under a pressure of 40 kPa, 100 cc fractions being collected. Fractions 45 to 60 are evaporated to dryness at 20° C. under 20 mm Hg (2.7 kPa), giving 2-benzhydryloxycarbonyl-3-[2-(4-benzyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.68 g) in the form of a cream-coloured froth.

Infra-red spectrum (CHBr$_3$): characteristic bands in cm$^{-1}$ at 3380, 1800, 1720, 1670, 1520, 1495, 1450, 1045, 940 and 755.

Proton nuclear magnetic resonance spectrum (350 MHz, CDCl$_3$, δ in ppm, J in Hz): 3.32 and 4 (2d, J=18, 2H, —SCH$_2$—); 3.97 (s, 3H, —OCH$_3$); 4.60 (d, J=4, 1H, H in the 6-position); 5.0 (s, 2H, >NCH$_2$—); 6.02 (dd, J=4 and 9, 1H, H in the 7-position); 6.70 (s, 1H, H of the thiazole); 6.80 (d, J=16, 1H, —C$\underline{H}$=CHS—);